US012590168B2

(12) United States Patent
DiLillo et al.

(10) Patent No.: US 12,590,168 B2
(45) Date of Patent: Mar. 31, 2026

(54) ANTIGEN-BINDING MOLECULES THAT BIND CD38 AND/OR CD28, AND USES THEREOF

(71) Applicant: REGENERON PHARMACEUTICALS, INC., Tarrytown, NY (US)

(72) Inventors: David DiLillo, New York, NY (US); Aynur Hermann, New York, NY (US); Jessica Kirshner, New York, NY (US); Kara Olson, White Plains, NY (US); Olga Sineshchekova, Pleasantville, NY (US); Eric Smith, New York, NY (US); Erica Ullman, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/420,588

(22) Filed: Jan. 23, 2024

(65) Prior Publication Data

US 2024/0158529 A1    May 16, 2024

Related U.S. Application Data

(62) Division of application No. 17/477,870, filed on Sep. 17, 2021, now Pat. No. 11,905,332.

(60) Provisional application No. 63/080,172, filed on Sep. 18, 2020.

(51) Int. Cl.
| | |
|---|---|
| *C07K 16/28* | (2006.01) |
| *A61K 39/00* | (2006.01) |
| *A61K 39/395* | (2006.01) |
| *A61K 45/06* | (2006.01) |
| *A61P 35/00* | (2006.01) |

(52) U.S. Cl.
CPC ...... *C07K 16/2896* (2013.01); *A61K 39/3955* (2013.01); *A61K 45/06* (2013.01); *A61P 35/00* (2018.01); *C07K 16/2809* (2013.01); *C07K 16/2818* (2013.01); *C07K 16/2878* (2013.01); *C07K 16/2887* (2013.01); *A61K 2039/507* (2013.01); *C07K 2317/31* (2013.01); *C07K 2317/33* (2013.01); *C07K 2317/565* (2013.01); *C07K 2317/73* (2013.01); *C07K 2317/92* (2013.01)

(58) Field of Classification Search
CPC ............ C07K 16/2818; C07K 16/2878; C07K 2317/565; C07K 2317/31; A61K 2039/505
See application file for complete search history.

(56) References Cited

U.S. PATENT DOCUMENTS

| | | | |
|---|---|---|---|
| 5,500,362 | A | 3/1996 | Robinson et al. |
| 5,821,337 | A | 10/1998 | Carter et al. |
| 8,586,713 | B2 | 11/2013 | Davis et al. |
| 9,657,102 | B2 | 5/2017 | Smith et al. |
| 9,987,500 | B2 | 6/2018 | Papadopoulos et al. |
| 11,905,332 | B2 | 2/2024 | Dilillo et al. |
| 2007/0280945 | A1 | 12/2007 | Stevens et al. |
| 2011/0195454 | A1 | 8/2011 | Mcwhirter et al. |
| 2014/0243504 | A1 | 8/2014 | Davis et al. |
| 2017/0355756 | A1 | 12/2017 | Julien et al. |
| 2019/0106504 | A1 | 4/2019 | Wu et al. |
| 2019/0389951 | A1 | 12/2019 | Murphy et al. |
| 2020/0024356 | A1 | 1/2020 | Smith et al. |
| 2020/0179511 | A1 | 6/2020 | Daley |
| 2020/0199233 | A1 | 6/2020 | Murphy et al. |
| 2020/0199234 | A1 | 6/2020 | Georges et al. |

FOREIGN PATENT DOCUMENTS

| | | | | |
|---|---|---|---|---|
| WO | WO 2008/068048 | | 6/2008 | |
| WO | WO-2008068048 A2 | * | 6/2008 | .............. A61P 31/10 |
| WO | WO 2017/180913 | | 10/2017 | |
| WO | WO-2017180913 A2 | * | 10/2017 | ......... A61K 39/3955 |
| WO | WO 2018/083204 A1 | | 5/2018 | |
| WO | WO 2019/074973 A2 | | 4/2019 | |
| WO | WO2019246514 A1 | | 12/2019 | |
| WO | WO2020127618 A1 | | 6/2020 | |

(Continued)

OTHER PUBLICATIONS

Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79): 18294-18302, 2011) (Year: 2011).*
Jansen (https://clinicaltrials.gov/ct2/show/NCT04557098) (Year: 2024).*
El-Murr (https://aacrjournals.org/cancerres/article/80/16_Supplement/5641/644015/Abstract-5641-CD28-expression-on-multiple-myeloma) (Year: 2020).*

(Continued)

*Primary Examiner* — Gregory S Emch
*Assistant Examiner* — Ashley H. Gao
(74) *Attorney, Agent, or Firm* — FisherBroyles, LLP; Cara L. Crowley-Weber; Aparna G. Patankar

(57) ABSTRACT

CD38 is expressed on malignant plasma cells. CD28 is a costimulatory molecule required for T-cell activation and survival. Provided herein are novel anti-CD38 antibodies, anti-CD28 antibodies, and bispecific antibodies (bsAbs) that bind to both CD38 and CD28 and act as costimulatory agents to activate T cells via binding CD80 and/or CD86. In certain embodiments, the bispecific antigen-binding molecules of the present invention are capable of inhibiting the growth of tumors expressing CD38. The bispecific antigen-binding molecules of the invention are useful for the treatment of diseases and disorders in which an upregulated or induced CD38-targeted immune response is desired and/or therapeutically beneficial. For example, the bispecific antibodies of the invention are useful for the treatment of various cancers, including multiple myeloma, lymphoma, and leukemia.

35 Claims, 12 Drawing Sheets

Specification includes a Sequence Listing.

(56)                    References Cited

FOREIGN PATENT DOCUMENTS

WO          WO2020132066 A1          6/2020

OTHER PUBLICATIONS

Al Qaraghuli et al (2020, Nature Scientific Reports 10:13969) (Year: 2020).*

Rabia, et al (2018, Biochemical Engineering Journal 137:365-374) (Year: 2018).*

Tiller et al (2017, J. Biol. Chem. (2017) 292(40) 16638-16652) (Year: 2017).*

Tsuji et al (2022, J Virol 96:e00071-22) (Year: 2022).*

Accession No. NM_001775.3 Nucleotide [Internet]. Bethesda (MD): National Library of Medicine (US), National Center for Biotechnology Information; [2018]—Accession No. NM_001775.3, "*Homo sapiens* CD38 molecule (CD38), transcript variant 1, mRNA", cited on Oct. 28, 2018, [online], [retrieved on Dec. 17, 2021]. Retrieved from: https://www.ncbi.nlm.nihm.gov/nuccore/NM_001775.3, 5 pages.

Accession No. NM_006139.3 Nucleotide [Internet]. Bethesda (MD): National Library of Medicine (US), National Center for Biotechnology Information; [2018]—Accession No. NM_006139.3, "*Homo sapiens* CD28 molecule (CD28), transcript variant 1, mRNA", cited on Nov. 18, 2018, [online], [retrieved on Dec. 17, 2021]. Retrieved from: https://www.ncbi.nlm.nihm.gov/nuccore/NM_006139.3, 5 pages.

Accession No. NP_001766.2 Protein [Internet]. Bethesda (MD): National Library of Medicine (US), National Center for Biotechnology Information; [2021]—Accession No. NP_001766.2, "ADP-ribosyl cyclase/cyclic ADP-ribose hydrolase 1 [*Homo sapiens*]", cited on Oct. 31, 2021, [online], [retrieved on Dec. 17, 2021]. Retrieved from: https://www.ncbi.nlm.nihm.gov/protein/NP_001766.2, 3 pages.

Altschul et al. (1990) "Basic Local Alignment Search Tool," J. Mol. Biol., 215: 403-410.

Altschul et al. (1997) "Gapped BLAST and PSI-BLAST: a New Generation of Protein Database Search Programs," Nucleic Acids Res., 25: 3389-3402.

Angal et al. (1993) "A Single Amino Acid Substitution Abolishes the Heterogeneity of Chimeric Mouse/Human (IgG4) Antibody," Molecular Immunology, 30(1): 105-108.

Attarwala (2010) "TGN1412: From Discovery to Disaster," J Young Pharm., 2(3): 332-336.

Azad et al. (2016) "A Fully Human CXCR4 Antibody Demonstrates Diagnostic Utility and Therapeutic Efficacy in Solid Tumor Xenografts," Oncotarget, 7(11): 12344-12358.

Benedict et al. (1997) "Determination of the Binding Affinity of an Anti-CD34 Single-Chain Antibody Using a Novel, Flow Cytometry Based Assay," J Immunol Methods., 201(2): 223-231.

Cagnetta et al. (2013) "Intracellular NAD (+) Depletion Enhances Bortezomib-Induced Anti-Myeloma Activity," Blood, 122: 1243-1255.

Chillemi et al. (2017) "Roles and Modalities of Ectonucleotidases in Remodeling the Multiple Myeloma Niche," Front Immunol., 8: 305.

Clynes et al. (1998) "Fc Receptors are Required in Passive and Active Immunity to Melanoma," Proc. Natl. Acad. Sci. (USA), 95: 652-656.

Ehring (1999) "Hydrogen Exchange/Electrospray Ionization Mass Spectrometry Studies of Structural Features of Proteins and Protein/Protein Interactions," Analytical Biochemistry, 267(2): 252-259.

El-Murr et al. (2020) "Abstract 5641: CD28 Expression on Multiple Myeloma Cells Enhances the Cytotoxic Activity of CD38/CD28xCD3 Trispecific T Cell Engager," Cancer Res., 80 (16_Supplement): 5641, https://doi.org/10.1158/158-7445.AM2020-5641.

Engen and Smith (2001) "The Basics of Ion Chromatography," Anal. Chem., 73: 256A-265A.

Francisco et al. (2010) "The PD-1 Pathway in Tolerance and Autoimmunity," Immunol Rev., 236: 219-242.

Geuijen et al. (2005) "Affinity Ranking of Antibodies Using Flow Cytometry: Application in Antibody Phage Display-Based Target Discovery," J Immunol Methods., 302(1-2): 68-77.

Gonnet et al. (1992) "Exhaustive Matching of the Entire Protein Sequence Database," Science, 256: 1443-1445.

Harding et al. (1992) "CD28-Mediated Signaling Co-Stimulates Murine T Cells and Prevents Induction of Anergy In T-Cell Clones," Nature, 356(6370): 607-609.

Howard et al. (1993) "Formation and Hydrolysis of Cyclic ADP-Ribose Catalyzed by Lymphocyte Antigen CD38," Science, 262: 1056-1059.

Hui et al. (2017) "T Cell Costimulatory Receptor CD28 Is a Primary Target For PD-1-Mediated Inhibition," Science, 355(6332): 1428-1433.

International Search Report and Written Opinion for International Application No. PCT/US2021/050850 mailed Jan. 18, 2022, 20 pages.

Jansen (2020) "A Study of Teclistamab in Participants with Relapsed or Refractory Multiple Myeloma (Majes TEC-1)," Clinical Trials, https://clinicaltrialsgov/ct2/show/NCT045570998.

June et al. (1987) "T-cell Proliferation Involving the CD28 Pathway is Associated with Cyclosporine-Resistant Interleukin 2 Gene Expression," Molecular and Cellular Biology, 7(12): 4472-4481.

Junghans et al. (1990) "Anti-Tac-H, a Humanized Antibody to the Interleukin 2 Receptor with New Features for Immunotherapy in Malignant and Immune Disorders," Cancer Res., 50:1495-1502.

Klein et al. (2012) "Progress in Overcoming the Chain Association Issue in Bispecific Heterodimeric IgG Antibodies," mAbs, 4(6): 653-663.

Kufer et al. (2004) "A Revival of Bispecific Antibodies," Trends Biotechnol., 22: 238-244.

Langer and Wise (1984) "Medical Applications of Controlled Release," CRC Pres., Boca Raton, Florida, vol. 2, pp. 115-138.

Langer (1990) "New Methods of Drug Delivery," Science, 249: 1527-1533.

Lin et al. (2011) "Improved Affinity of a Chicken Single-Chain Antibody to Avian Infectious Bronchitis Virus by Site-Directed Mutagenesis of Complementarity-Determining Region H3," African Journal of Biotechnology, 10(79): 18294-18302.

Mariuzza et al. (1987) "The Structural Basis of Antigen-Antibody Recognition," Annual Review of Biophysics and Biophysical Chemistry, 16:139-159.

Martin et al. (1986) "A 44 Kilodalton Cell Surface Homodimer Regulates Interleukin 2 Production by Activated Human T Lymphocytes," Journal of immunology, 136(9): 3282-3287.

McCarthy et al. (2001) "Altering the Fine Specificity of an Anti-Legionella Single Chain Antibody by a Single Amino Acid Insertion," J. Immunol. Methods, 251(1-2): 137-49.

Mordenti et al. (1991) "Interspecies Scaling of Clearance and Volume of Distribution Data for Five Therapeutic Proteins," Pharmaceut. Res., 8(11): 1351-1359.

Pearson (1994) "Using the FASTA Program to Search Protein and DNA Sequence Databases," Methods Mol. Biol., 24: 307-331.

Pearson (2000) "Flexible Sequence Similarity Searching with the FASTA3 Program Package," Methods in Molecular Biology, 132: 185-219.

Powell et al. (1998) "Compendium of Excipients for Parenteral Formulations," PDA, J Pharm Sci Technol., 52: 238-311.

Reineke (2004) "Antibody Epitope Mapping Using Arrays of Synthetic Peptides," Methods Mol Biol., 248: 443-463.

Sefton (1987) "Implantable Pumps," CRC Crit. Ref. Biomed. Eng., 14(3): 201-240.

Shield et al. (2002) "Lack of Fucose on Human IgG1 N-Linked Oligosaccharide Improves Binding to Human FcyRIII and Antibody-dependent Cellular Toxicity," JBC, 277: 26733-26740.

Tavare et al. (2016) "An Effective Immuno-PET Imaging Method to Monitor CD8-Dependent Responses to Immunotherapy," Cancer Res., 76(1):73-82.

Taylor et al. (1992) "A Transgenic Mouse that Expresses a Diversity of Human Sequence Heavy and Light Chain Immunoglobulins," Nucl. Acids Res., 20(23): 6287-6295.

Tomer (2000) "Characterization of a Discontinuous Epitope of the Humban Immunodeficiency Virus (HIV) Core Protein p24 by

(56) References Cited

OTHER PUBLICATIONS

Epitope Excision and Differential Chemical Modification Followed by Mass Spectrometric Peptide Mapping Analysis," Protein Science, 9: 487-496.

Tutt et al. (1991) "Trispecific F(ab')3 Derivatives that use Cooperative Signaling Via the TCR/CD3 Complex and CD2 to Activate and Redirect Resting Cytotoxic T Cells," J. Immunol., 147: 60-69.

Wu et al. (1987) "Receptor-Mediated in Vitro Gene Transformation by a Soluble DNA Carrier System," J. Biol. Chem., 262: 4429-4432.

Wu et al. (2020) "Trispecific Antibodies Enhance the Therapeutic Efficacy of Tumor-Directed T Cells Through T Cell Receptor Co-Stimulation," Nature Cancer, 1(1): 86-98.

Zou and Chen (2008) "Inhibitory B7-Family Molecules in the Tumour Microenvironment," Nature Reviews Immunology, 8: 467-477.

* cited by examiner

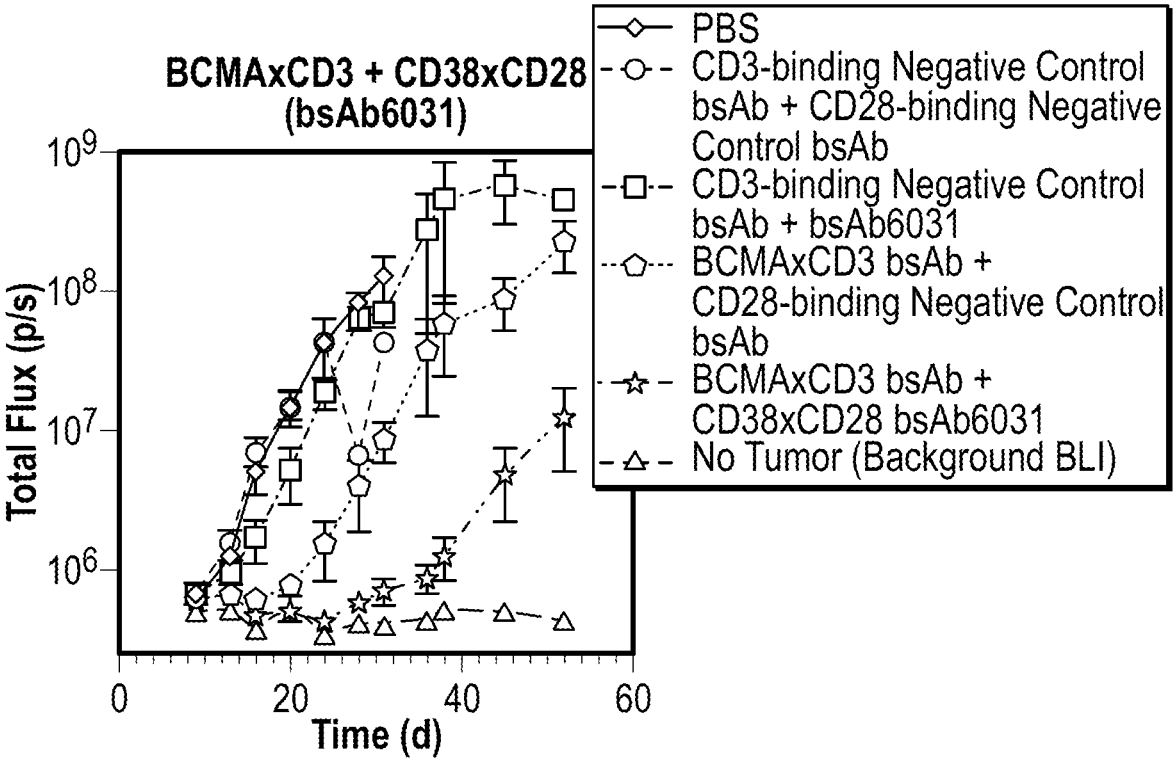
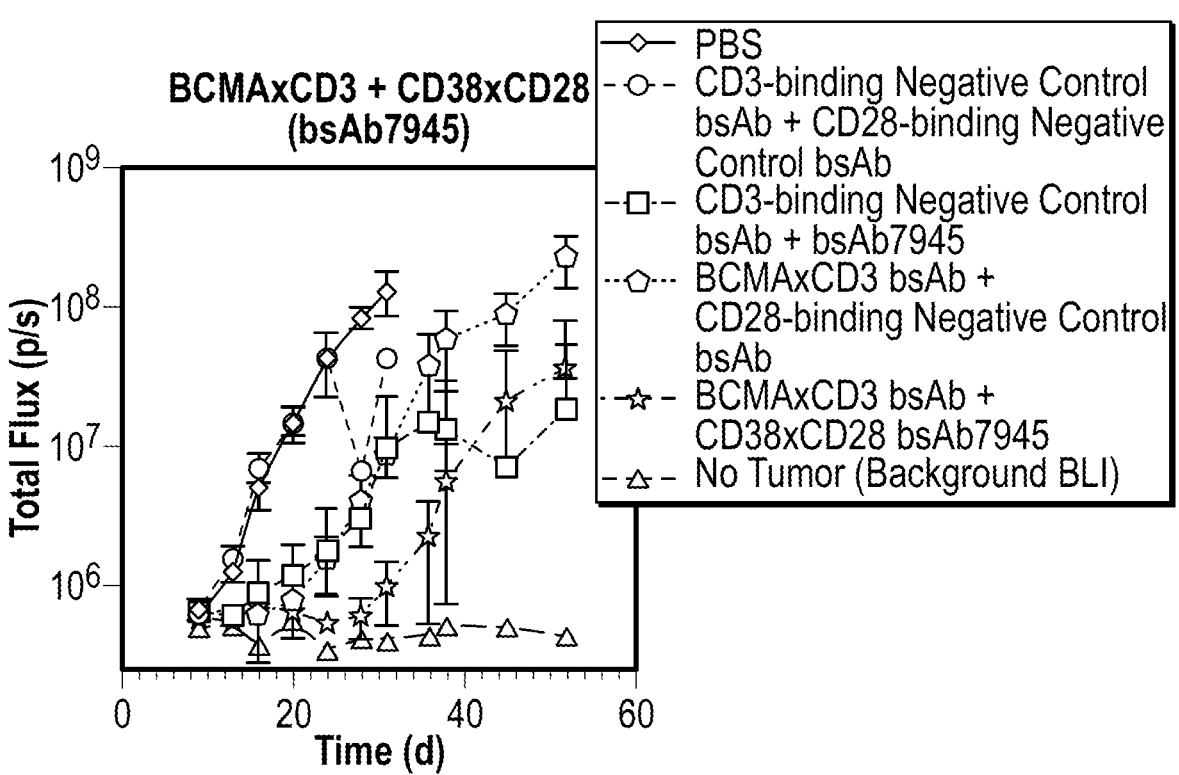
FIG. 5

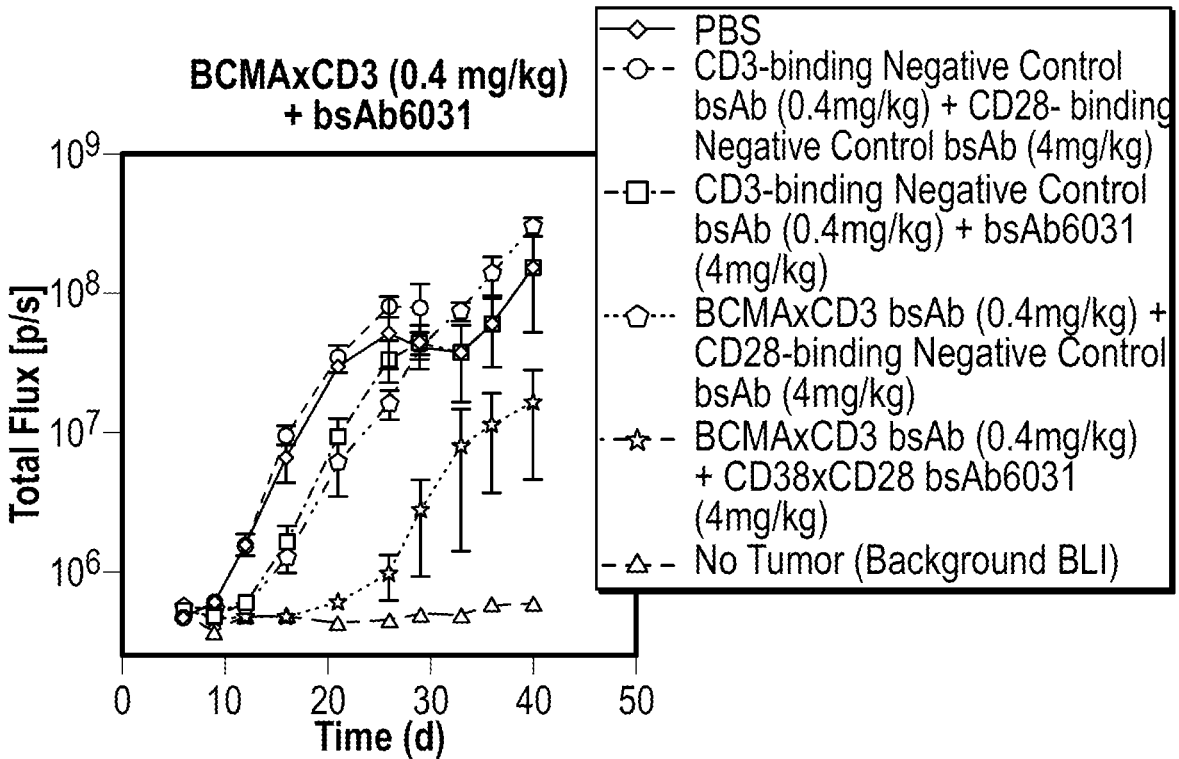
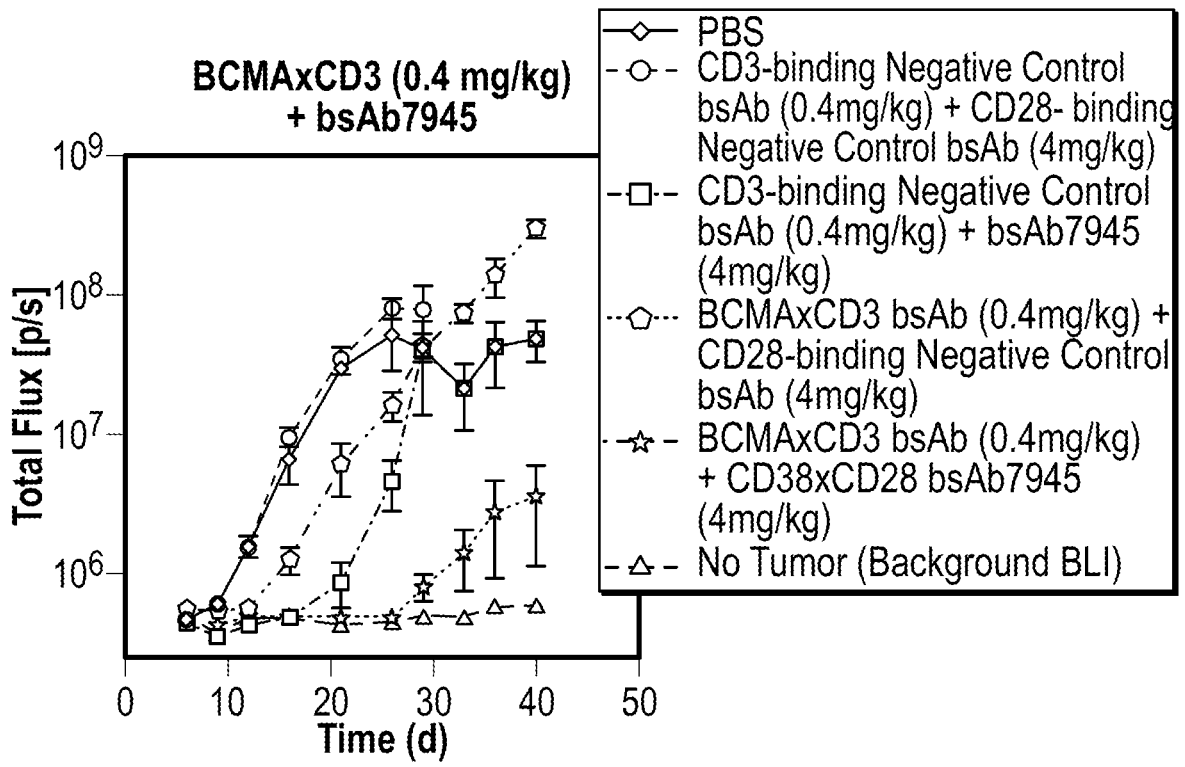
FIG. 6

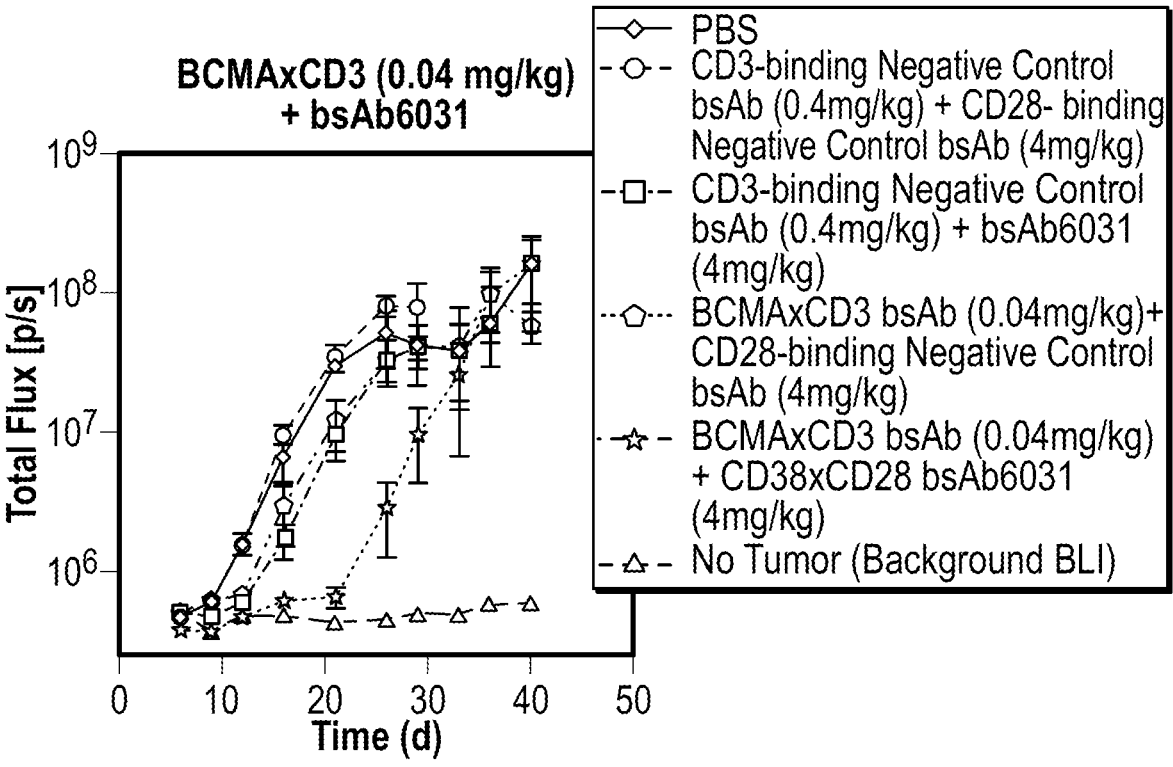
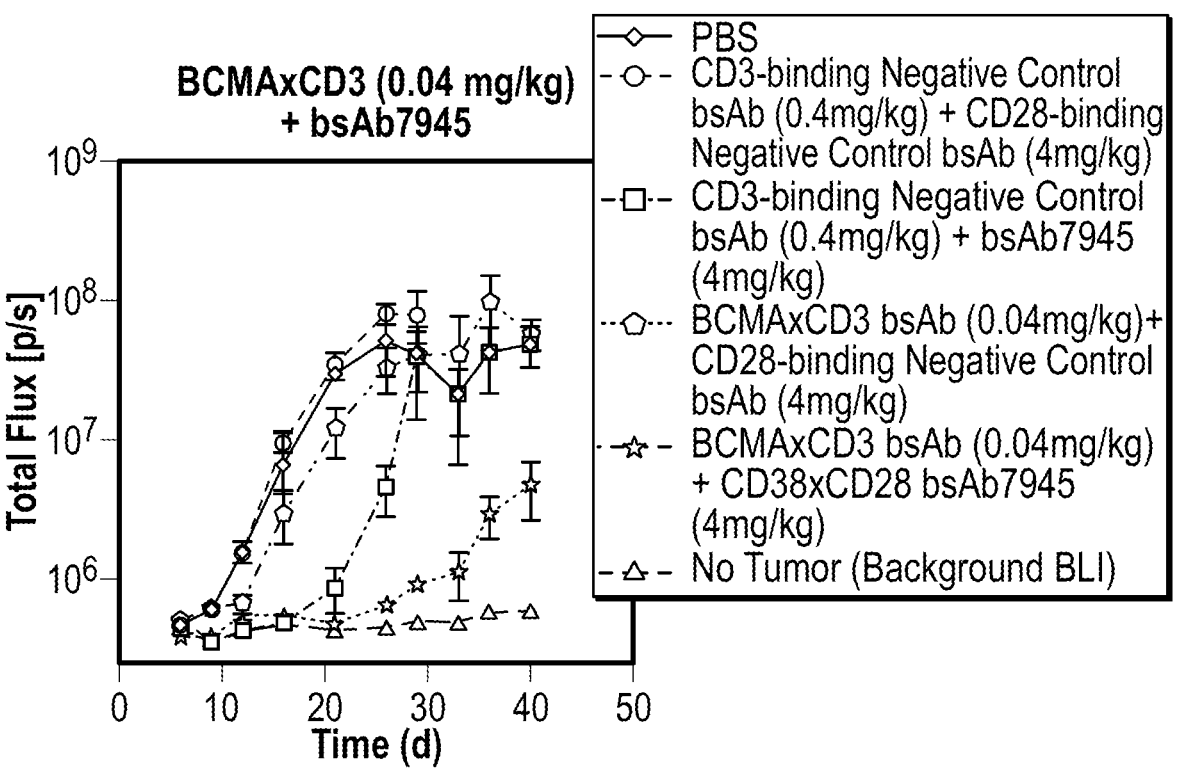
FIG. 6 (Continued)

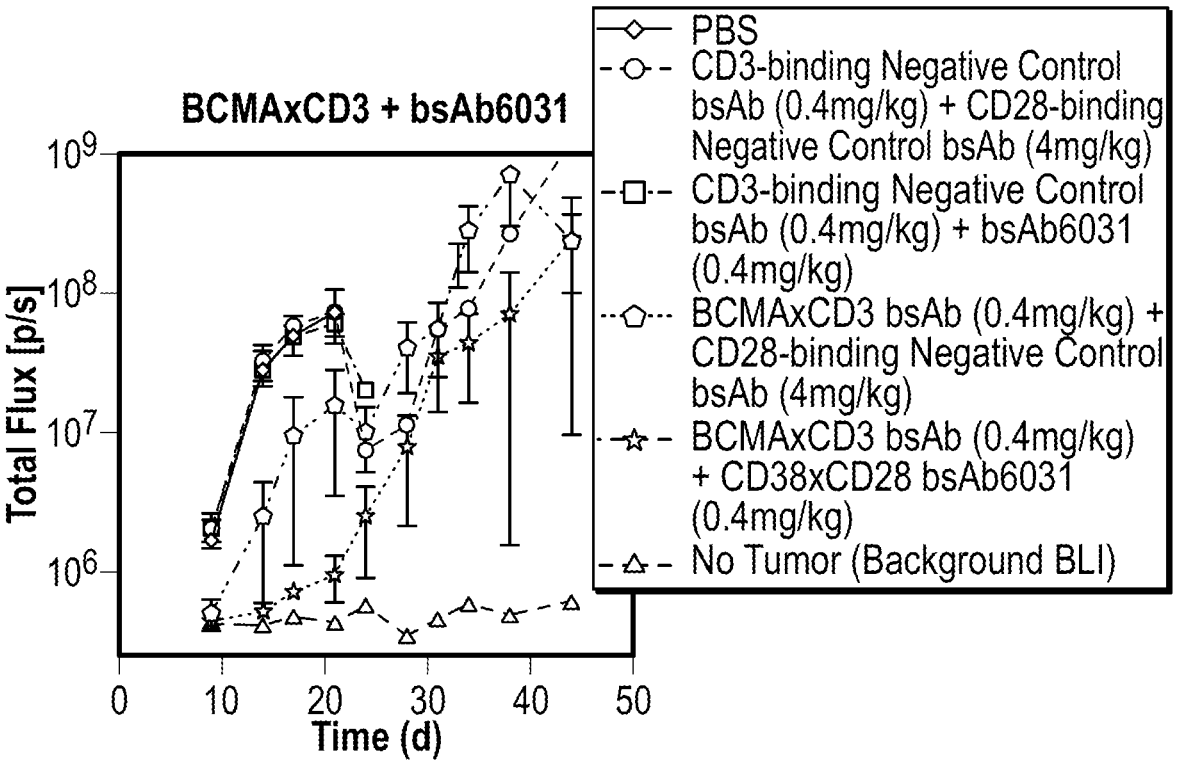
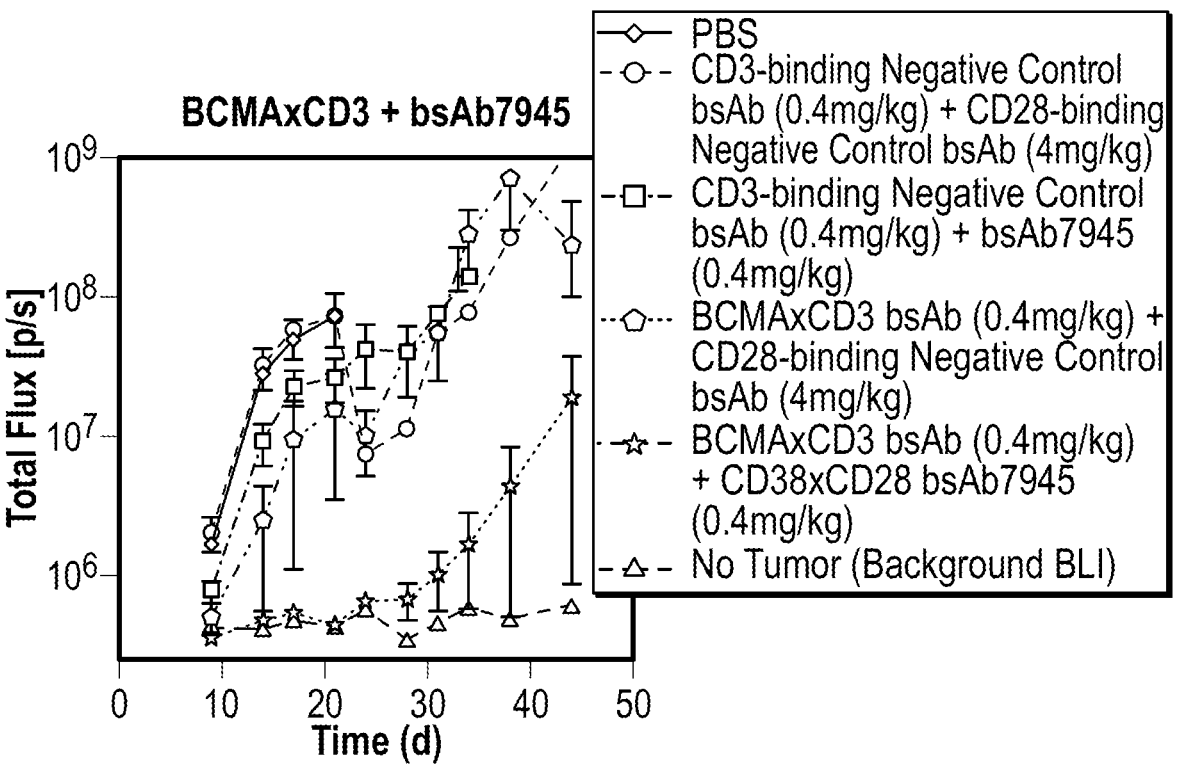
FIG. 8

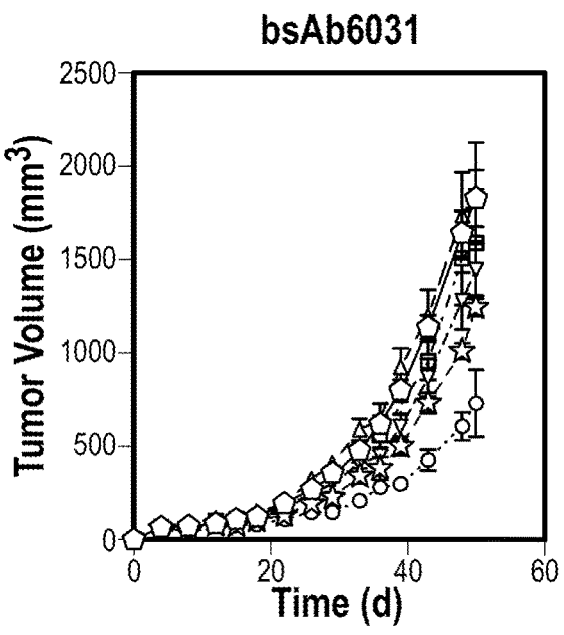

bsAb6031

- ⬠ CD3-binding control bsAb (4mg/kg) + CD28-binding Control bsAb (4mg/kg)
- ☆ BCMAxCD3 bsAb (0.4mg/kg) + CD28-binding Control bsAb (4mg/kg)
- ▽ CD3-binding Control bsAb (4mg/kg) +CD38xCD28 bsAb6031 (4mg/kg)
- ○ BCMAxCD3 bsAb (0.4mg/kg) + CD38xCD28 bsAb6031 (4mg/kg)
- □ BCMAxCD3 bsAb (0.4mg/kg) + CD38xCD28 bsAb6031 (0.4mg/kg)
- △ BCMAxCD3 bsAb (0.4mg/kg) + CD38xCD28 bsAb6031 (0.04mg/kg)

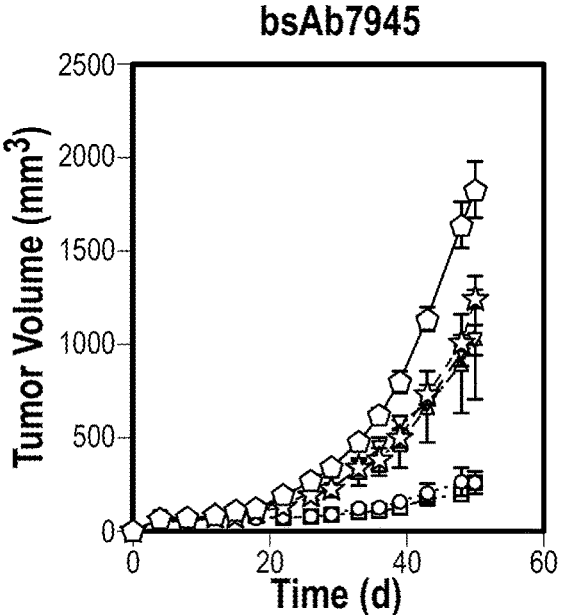

bsAb7945

- ⬠ CD3-binding control bsAb (0.4mg/kg) + CD28-binding Control bsAb (4mg/kg)
- ☆ BCMAxCD3 bsAb (0.4mg/kg) + CD28-binding Control bsAb (4mg/kg)
- ▽ CD3-binding Control bsAb (0.4mg/kg) +CD38xCD28 bsAb7945 (4mg/kg)
- ○ BCMAxCD3 bsAb (0.4mg/kg) + CD38xCD28 bsAb7945 (4mg/kg)
- □ BCMAxCD3 bsAb (0.4mg/kg) + CD38xCD28 bsAb7945 (0.4mg/kg)
- △ BCMAxCD3 bsAb (0.4mg/kg) + CD38xCD28 bsAb7945 (0.04mg/kg)

FIG. 9

ANTIGEN-BINDING MOLECULES THAT BIND CD38 AND/OR CD28, AND USES THEREOF

FIELD OF THE INVENTION

This application is a divisional application of U.S. patent application Ser. No. 17/477,870, filed on Sep. 17, 2021, which claims the benefit of U.S. Provisional Patent Application No. 63/080,172, filed Sep. 18, 2020, which is herein incorporated by reference in its entirety.

The present invention relates to antigen-binding molecules, including antibodies and antigen-binding fragments thereof, and bispecific antigen-binding molecules (e.g., bispecific antibodies), which are specific for CD38 and/or CD28, and methods of use thereof.

SEQUENCE LISTING

A copy of the sequence listing is submitted concurrently with the specification electronically via Patent Center. The content of the electronic sequence listing (10786US02_Sequence_Listing_ST26.xml; Size 90,112 bytes; and Date of Creation: Jan. 22, 2024) is herein incorporated by reference in its entirety.

BACKGROUND

Multiple Myeloma (MM) is the second most common blood cancer after non-Hodgkin lymphoma, with a prevalence of ~120,000, and roughly 30,000 new cases and 13,000 deaths each year in the US. MM is characterized by a clonal expansion of malignant plasma cells which secrete cytokines in an unregulated manner. The production of cytokines, especially IL-6, causes localized organ and tissue damage responsible for many of the symptoms associated with myeloma. Subjects with MM suffer from bone pain and osteoporosis, anemia, impaired kidney function and kidney failure, bacterial infections, and neurological impairments. MM is rarely curable with a median life expectancy of 4-5 years. While progress has been made in treating MM, new therapies have disproportionately benefited younger patients. Prognosis of relapsed MM patients is poor, and novel therapeutic approaches are urgently needed.

CD38, also known as cyclic ADP ribose hydrolase, is a 45 KDa surface glycoprotein expressed on thymocytes, some activated peripheral blood T cells and B cells, plasma cells, and dendritic cells. CD38 functions as an ectoenzyme involved in the metabolism of extracellular nicotinamide adenine dinucleotide ($NAD^+$) and cytoplasmic nicotinamide adenine dinucleotide phosphate (NADP) (Howard, et al. Formation and hydrolysis of cyclic ADP-ribose catalyzed by lymphocyte antigen CD38. Science (1993) 262:1056-9), resulting in the production of $Ca^{2+}$-mobilizing compounds, such as cyclic adenosine diphosphate (ADP) ribose, ADP ribose (ADPR) and nicotinic acid adenine dinucleotide phosphate. Calcium regulation results in the activation of signaling pathways that control a wide range of physiological functions, including lymphocyte proliferation, insulin release by the pancreas, cardiac muscle contraction, neutrophil chemotaxis and T cell activation. CD38 enzymatic activities regulate NAD+ levels and improve the function of proteasome inhibitors (Cagnetta, et al. Intracellular NAD (+) depletion enhances bortezomib-induced anti-myeloma activity. Blood (2013) 122:1243-55). In addition, ADPR can be metabolized by CD203a/PC-1 and CD73 to produce the immunosuppressive molecule adenosine (ADO), facilitating the escape of tumor cells from the control of the immune system (Chillemi et al. Roles and modalities of ectonucleotidases in remodeling the multiple myeloma niche. Front Immunol. (2017) 8:305). CD38 appears to contribute to the proliferative potential of B-chronic leukemia/small lymphocytic lymphoma; malignant plasma cells in the bone marrow express high and uniform levels of CD38. Anti-CD38 mAbs are thought to deplete CD38+immunosuppressive cells, such as myeloid-derived suppressor cells, regulatory T cells, and regulatory B cells, leading to increased anti-tumor activity of immune effector cells. Daratumumab, an anti-CD38 antibody, has been approved for multiple myeloma patients who are refractory to conventional therapy.

T cell activation involves stimulation of a highly specific T cell receptor (TCR) by an antigen-presenting cell (such as a dendritic cell) presenting its specific antigen on its class II major histocompatibility (MHC) complex, and can be facilitated by costimulatory molecules such as CD28. CD28 is a 44 KDa disulfide-linked homodimer receptor that is glycosylated at five different sites. CD28 is expressed on T-cells (95% of resting CD4+ cells and 50% of resting CD8+ T-cells in human peripheral blood), and plasmablasts, and provides costimulatory signalling required for T-cell activation and survival. Costimulation occurs when CD28 on the surface of the T-cell binds with CD80 (B7-1) and CD86 (B7-2) on the antigen presenting cell. CD80 expression is upregulated in antigen-presenting cells (APCs) when activated, and CD86 is constitutively expressed on APCs. CD28 costimulation of T helper cells enhances the transcription of IL-2R and IL-2 (leading to T-cell proliferation), induces expression of Bcl-XL (enhancing T-cell survival), and increases production of IL-4 (leading to Th2 differentiation), IFNγ, IL-1, TNF, IL-5, various chemokines, and their receptors. In addition, CD28 induces expression or upregulation of several other costimulatory and regulatory molecules, including ICOS, 4-1BB, and CTLA-4, along with the CD40L molecules necessary for T-B cell interaction. Mak and Saunders, The Immune Response, Basic and Clinical Principles, Academic Press, 2006. TGN1412 is a CD28 superagonist monoclonal antibody that preferentially activates regulatory T ($T_{Reg}$) cells in the absence of costimulation of the TCR. Attarwala, TGN1412: From Discovery to Disaster. J Young Pharm. 2010, 2 (3): 332-6. Unfortunately, a phase I clinical trial resulted in rapid multiple-organ failure a severe cytokine release syndrome (cytokine storm) of all six volunteers. Id.

Thus, a need exists in the art for alternative approaches to treating cancer.

BRIEF SUMMARY OF THE INVENTION

The present invention relates, in part, to monospecific antibodies that bind CD38, or CD28 and bispecific antibodies that bind both CD38 and CD28 and their use in treating various diseases, including cancer.

The antibodies or bispecific antibodies can be used alone or in combination with other agents for treating cancers that express CD38.

Anti-CD38 Antibodies and Antigen-Binding Fragments Thereof

In a one aspect, provided herein are antibodies and antigen-binding fragments thereof that bind human CD38. The antibodies may be useful, inter alia, for targeting cells expressing CD38 and/or inducing apoptosis. In certain embodiments, the antibodies may be useful for mediating antibody-dependent cellular cytotoxicity (ADCC), and/or complement-mediated cytotoxicity (CDC) against CD38+ cancer cells. The anti-CD38 antibodies provided herein, or antigen-binding portions thereof, may be included as part of a bispecific antibody that facilitates CD38-targeted cytotoxicity of specific cell types such as tumor cells.

Exemplary anti-CD38 antibodies provided herein are listed in Tables 1 and 2. Table 1 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-CD38 antibodies. Table 2 sets forth the sequence identifiers of the nucleic acid molecules encoding the HCVRs, LCVRs, HCDR1, HCDR2, HCDR3, LCDR1, LCDR2 and LCDR3 of the exemplary anti-CD38 antibodies.

Provided herein are anti-CD38 antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

Also provided herein are anti-CD38 antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

Provided herein are anti-CD38 antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-CD38 antibodies listed in Table 1. In certain embodiments, the HCVR/LCVR amino acid sequence pair is selected from the group consisting of SEQ ID NOs: 2/18 (e.g., mAb1) and 32/48 (e.g., mAb2).

Provided herein are anti-CD38 antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Provided herein are anti-CD38 antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the antibodies, or antigen-binding fragments thereof, comprise an HCDR3/LCDR3 amino acid sequence pair contained within any of the exemplary anti-CD38 antibodies listed in Table 1. In certain embodiments, the HCDR3/LCDR3 amino acid sequence pair is selected from the group consisting of SEQ ID NOs: 8/24 (e.g., mAb1); 38/54 (e.g., mAb2).

Provided herein are antibodies, or antigen-binding fragments thereof, comprising a set of six CDRs (i.e., HCDR1-HCDR2-HCDR3-LCDR1-LCDR2-LCDR3) contained within any of the exemplary anti-CD38 antibodies listed in Table 1. In certain embodiments, the HCDR1-HCDR2-HCDR3-LCDR1-LCDR2-LCDR3 amino acid sequences set is selected from the group consisting of SEQ ID NOs: 4-6-8-20-AAS-24 (e.g., mAb1) and 34-36-38-50-GAS-54 (e.g., mAb2).

In a related embodiment, provided herein are antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD38 antibodies listed in Table 1. For example, provided herein are antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/18 (e.g., mAb1) and 32/48 (e.g., mAb2).

In an embodiment provided herein, the anti-CD38 antibody or antigen-binding fragment thereof includes:
an HCDR1 that comprises the amino acid sequence: GFTFDDYA (SEQ ID NO: 4; or a variant thereof); an HCDR2 that comprises the amino acid sequence: ISWKSDNI (SEQ ID NO: 6; or a variant thereof); and an HCDR3 that comprises the amino acid sequence: AKALGGWKFDYYYGMDV (SEQ ID NO: 8; or a variant thereof); and
an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTPPIT (SEQ ID NO: 24; or a variant thereof).

In an embodiment provided herein, the anti-CD38 antibody or antigen-binding fragment thereof includes:
an HCDR1 that comprises the amino acid sequence: GGPFRSSS (SEQ ID NO: 34; or a variant thereof); an HCDR2 that comprises the amino acid sequence: IIPILGKT (SEQ ID NO: 36; or a variant thereof); and an HCDR3 that comprises the amino acid sequence: VRGSSLFDY (SEQ ID NO: 38; or a variant thereof); and an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof).

In an embodiment provided herein, the anti-CD38 antibody or antigen-binding fragment thereof includes:

an HCVR1 that comprises the amino acid sequence: EVOLVESGGGLVQPGRSLRLSCAASGFTFDDY-AMHWVRQAPGKGLEWVSGISWKSDNIGYA DSVKGRFTISRDNAKNSLYLQMNSLRAED-TALYYCAKAL-GGWKFDYYYGMDVWGQGTTVTVS S (SEQ ID NO: 2; or a variant thereof); and an LCVR1 that comprises the amino acid sequence: DIQMTQSPSSLSASVGDRVTITCRASQSIS-SYLNWYQQKPGKAPKLLI-YAASSLQSGVPSRFSG SGSGTDFTLTISSLQPED-FATYYCQQSYSTPPITFGQGTRLEIK (SEQ ID NO: 18; or a variant thereof).

In an embodiment provided herein, the anti-CD38 antibody or antigen-binding fragment thereof includes:

an HCVR1 that comprises the amino acid sequence: QVQLVQSGAEVKKPGSSVKVSCKASGGP-FRSSSFSWVRQAPGQGLEWMGGIIPILGKTNYAQ KFQGRITIVTDESTTTVYMELSSLRSED-TAVFYCVRGSSLFDYWGQGTLVTVSS (SEQ ID NO: 32; or a variant thereof); and an LCVR1 that comprises the amino acid sequence: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIK (SEQ ID NO: 48; or a variant thereof).

Also provided herein are nucleic acid molecules encoding anti-CD38 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

Provided herein are nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

Provided herein are nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

Provided herein are nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

Provided herein are nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

Provided herein are nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

Provided herein are nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

Provided herein are nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

Provided herein are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD38 antibodies listed in Table 1.

Provided herein are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CD38 antibodies listed in Table 1.

Provided herein are nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CD38 antibody listed in Table 1.

Provided herein are recombinant expression vectors capable of expressing a polypeptide comprising a heavy or light chain variable region of an anti-CD38 antibody. For example, provided herein are recombinant expression vectors comprising any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are anti-CD38 antibodies having a modified glycosylation pattern. In some embodiments, modification to remove undesirable glycosylation sites may be useful, or an antibody lacking a fucose moiety present on the oligosaccharide chain, for example, to increase anti-tumor activity such as antibody dependent cellular cytotoxicity (ADCC) function (see Shield et al. JBC 277:26733 2002). In other applications, modification of galactosylation can be made in order to modify complement dependent cytotoxicity (CDC).

In another aspect, provided herein is a pharmaceutical composition comprising a recombinant human antibody or fragment thereof which specifically binds CD38 and a pharmaceutically acceptable carrier. In a related aspect, the invention features a composition which is a combination of an anti-CD38 antibody and a second therapeutic agent. In one embodiment, the second therapeutic agent is any agent that is advantageously combined with an anti-CD38 antibody. Exemplary agents that may be advantageously combined with an anti-CD38 antibody include, without limitation, agents that bind and/or inactivate CD38 signaling (including other antibodies or antigen-binding fragments thereof, etc.) and/or agents which do not directly bind CD38 but nonetheless activate or stimulate immune cell activation. Additional combination therapies and co-formulations involving the anti-CD38 antibodies of the present invention are disclosed elsewhere herein.

In yet another aspect, provided herein are therapeutic methods for facilitating treatment of cancer using an anti-CD38 antibody or antigen-binding portion of an anti-CD38 antibody disclosed herein, wherein the therapeutic methods comprise administering a therapeutically effective amount of a pharmaceutical composition comprising an antibody or antigen-binding fragment of an anti-CD38 antibody to a subject in need thereof. The disorder treated is any disease or condition which is improved, ameliorated, inhibited or prevented by inhibition of CD38 activity or signaling.

Anti-CD28 Antibodies and Antigen-Binding Fragments Thereof

In another aspect, provided herein are antibodies and antigen-binding fragments thereof that bind human CD28. The antibodies according to this aspect of the invention are useful, inter alia, for binding immune cells expressing CD28, including CD4+, CD8+, plasma cells and natural killer cells, and for costimulating T cell activation, e.g., under circumstances where T cell-mediated killing is beneficial or desirable. The anti-CD28 antibodies of the invention, or antigen-binding portions thereof, may be included as part of a bispecific antibody that directs T cell activation to specific cell types such as tumor cells.

Exemplary anti-CD28 antibodies provided herein are listed in Tables 4 and 5 herein. Table 4 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-CD28 antibodies. Table 5 sets forth the sequence identifiers of the nucleic acid molecules encoding the HCVRs, LCVRs, HCDR1, HCDR2 HCDR3, LCDR1, LCDR2 and LCDR3 of the exemplary anti-CD28 antibodies.

Provided herein are anti-CD28 antibodies, or antigen-binding fragments thereof, comprising an HCVR comprising an amino acid sequence selected from any of the HCVR amino acid sequences listed in Table 4, or a substantially similar sequence thereof having at least 90%, at least 95%, at least 98% or at least 99% sequence identity thereto.

Provided herein are anti-CD28 antibodies, or antigen-binding fragments thereof, comprising an LCVR comprising an amino acid sequence selected from any of the LCVR amino acid sequences listed in Table 4, or a substantially similar sequence thereof having at least 90%, at least 95%, at least 98% or at least 99% sequence identity thereto.

Provided herein are anti-CD28 antibodies, or antigen-binding fragments thereof, comprising an HCVR and an LCVR amino acid sequence pair (HCVR/LCVR) comprising any of the HCVR amino acid sequences listed in Table 4 paired with any of the LCVR amino acid sequences listed in Table 4. According to certain embodiments, the present disclosure provides antibodies, or antigen-binding fragments thereof, comprising an HCVR/LCVR amino acid sequence pair contained within any of the exemplary anti-CD28 antibodies listed in Table 4. In certain embodiments, the HCVR/LCVR amino acid sequence pair is selected from the group consisting of SEQ ID NOs: 10/18 (e.g., mAb3) and 40/48 (e.g., mAb4).

Provided herein are anti-CD28 antibodies, or antigen-binding fragments thereof, comprising a heavy chain CDR1 (HCDR1) comprising an amino acid sequence selected from any of the HCDR1 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising a heavy chain CDR2 (HCDR2) comprising an amino acid sequence selected from any of the HCDR2 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising a heavy chain CDR3 (HCDR3) comprising an amino acid sequence selected from any of the HCDR3 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising a light chain CDR1 (LCDR1) comprising an amino acid sequence selected from any of the LCDR1 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising a light chain CDR2 (LCDR2) comprising an amino acid sequence selected from any of the LCDR2 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising a light chain CDR3 (LCDR3) comprising an amino acid sequence selected from any of the LCDR3 amino acid sequences listed in Table 4 or a substantially similar sequence thereof having at least 90%, at least 95%, at least 98% or at least 99% sequence identity.

Provided herein are anti-CD28 antibodies, or antigen-binding fragments thereof, comprising an HCDR3 and an LCDR3 amino acid sequence pair (HCDR3/LCDR3) comprising any of the HCDR3 amino acid sequences listed in Table 4 paired with any of the LCDR3 amino acid sequences listed in Table 4. According to certain embodiments, the present disclosure provides antibodies, or antigen-binding fragments thereof, comprising an HCDR3/LCDR3 amino acid sequence pair contained within any of the exemplary anti-CD28 antibodies listed in Table 4. In certain embodiments, the HCDR3/LCDR3 amino acid sequence pair is selected from the group consisting of SEQ ID NOs: 16/24 (e.g., mAb3) and 46/54 (e.g., mAb4).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-CD28 antibodies listed in Table 4. In certain embodiments, the HCDR1-HCDR2-HCDR3-LCDR1-LCDR2-LCDR3 amino acid sequences set is selected from the group consisting of SEQ ID NOs: Dec. 14, 2016-20-AAS-24 (e.g., mAb3) and 42-44-46-50-GAS 54 (e.g., mAb4).

In a related embodiment, the present disclosure provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD28 antibodies listed in Table 4. For example, provided herein are antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 10/18 (e.g., mAb3); 40/48 (e.g., mAb4).

In an embodiment provided herein, the anti-CD28 antibody or antigen-binding fragment thereof includes:
an HCDR1 that comprises the amino acid sequence: GFTFSRNN (SEQ ID NO: 12; or a variant thereof); an HCDR2 that comprises the amino acid sequence: ISSNGGRT (SEQ ID NO: 14; or a variant thereof); and an HCDR3 that comprises the amino acid sequence: TRDDELLSFDY (SEQ ID NO: 16; or a variant thereof); and
an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTPPIT (SEQ ID NO: 24; or a variant thereof).

In an embodiment provided herein, the anti-CD28 antibody or antigen-binding fragment thereof includes:
an HCDR1 that comprises the amino acid sequence: GGSISSYY (SEQ ID NO: 42; or a variant thereof); an HCDR2 that comprises the amino acid sequence: IYYSGIT (SEQ ID NO: 44; or a variant thereof); and an HCDR3 that comprises the amino acid sequence: ARWGVRRDYYYYGMDV (SEQ ID NO: 46; or a variant thereof); and
an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof).

In an embodiment provided herein, the anti-CD28 antibody or antigen-binding fragment thereof includes:
an HCVR1 that comprises the amino acid sequence: EVOLVESGGGLVQPGGSLRLS-CAASGFTFSRNNMHWVRQAPGKGLEYVS-GISSNGGRTYYA DSVKGRFTISRDNSKNT-LYLQMGGLRAADMAVYFCTRDDELLSFDYWG QGTLVTVSS (SEQ ID NO: 10; or a variant thereof); and
an LCVR1 that comprises the amino acid sequence: DIQMTQSPSSLSASVGDRVTITCRASQSIS- SYLNWYQQKPGKAPKLLI-YAASSLQSGVPSRFSG SGSGTDFTLTISSLOPED-FATYYCQQSYSTPPITFGQGTRLEIK (SEQ ID NO: 18; or a variant thereof).

In an embodiment provided herein, the anti-CD28 antibody or antigen-binding fragment thereof includes:
an HCVR1 that comprises the amino acid sequence: QVQLQESGPGLVKPSETLSLTCTVSGGSIS-SYYWSWIRQPPGKGLEWIGYIYYSGITHYNPSLK SRVTISVDTSKIQFSLKLSSVTAADTAVYY-CARWGVRRDYYYYGMDVWGQGTTVTVSS (SEQ ID NO: 40; or a variant thereof); and
an LCVR1 that comprises the amino acid sequence: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIK (SEQ ID NO: 48; or a variant thereof).

Also provided herein are nucleic acid molecules encoding anti-CD28 antibodies or portions thereof. For example, the present invention provides nucleic acid molecules encoding any of the HCVR amino acid sequences listed in Table 4; in certain embodiments the nucleic acid molecule comprises a polynucleotide sequence selected from any of the HCVR nucleic acid sequences listed in Table 5, or a substantially similar sequence thereof having at least 90%, at least 95%, at least 98% or at least 99% sequence identity thereto.

Provided herein are nucleic acid molecules encoding any of the LCVR amino acid sequences listed in Table 4; in certain embodiments the nucleic acid molecule comprises a polynucleotide sequence selected from any of the LCVR nucleic acid sequences listed in Table 5, or a substantially similar sequence thereof having at least 90%, at least 95%, at least 98% or at least 99% sequence identity thereto.

Provided herein are nucleic acid molecules encoding any of the HCDR1 amino acid sequences listed in Table 4; in certain embodiments the nucleic acid molecule comprises a polynucleotide sequence selected from any of the HCDR1 nucleic acid sequences listed in Table 5, or a substantially similar sequence thereof having at least 90%, at least 95%, at least 98% or at least 99% sequence identity thereto.

Provided herein are nucleic acid molecules encoding any of the HCDR2 amino acid sequences listed in Table 4; in certain embodiments the nucleic acid molecule comprises a polynucleotide sequence selected from any of the HCDR2 nucleic acid sequences listed in Table 5, or a substantially similar sequence thereof having at least 90%, at least 95%, at least 98% or at least 99% sequence identity thereto.

Provided herein are nucleic acid molecules encoding any of the HCDR3 amino acid sequences listed in Table 4; in certain embodiments the nucleic acid molecule comprises a polynucleotide sequence selected from any of the HCDR3 nucleic acid sequences listed in Table 5, or a substantially similar sequence thereof having at least 90%, at least 95%, at least 98% or at least 99% sequence identity thereto.

Provided herein are nucleic acid molecules encoding any of the LCDR1 amino acid sequences listed in Table 4; in certain embodiments the nucleic acid molecule comprises a polynucleotide sequence selected from any of the LCDR1 nucleic acid sequences listed in Table 5, or a substantially similar sequence thereof having at least 90%, at least 95%, at least 98% or at least 99% sequence identity thereto.

Provided herein are nucleic acid molecules encoding any of the LCDR2 amino acid sequences listed in Table 4; in certain embodiments the nucleic acid molecule comprises a polynucleotide sequence selected from any of the LCDR2 nucleic acid sequences listed in Table 5, or a substantially similar sequence thereof having at least 90%, at least 95%, at least 98% or at least 99% sequence identity thereto.

Provided herein are nucleic acid molecules encoding any of the LCDR3 amino acid sequences listed in Table 4; in certain embodiments the nucleic acid molecule comprises a polynucleotide sequence selected from any of the LCDR3 nucleic acid sequences listed in Table 5, or a substantially similar sequence thereof having at least 90%, at least 95%, at least 98% or at least 99% sequence identity thereto.

Provided herein are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD28 antibodies listed in Table 4.

Provided herein are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CD28 antibodies listed in Table 4.

Provided herein are nucleic acid molecules encoding both an HCVR and an LCVR, wherein the HCVR comprises an amino acid sequence of any of the HCVR amino acid sequences listed in Table 4, and wherein the LCVR comprises an amino acid sequence of any of the LCVR amino acid sequences listed in Table 4. In certain embodiments, the nucleic acid molecule comprises a polynucleotide sequence selected from any of the HCVR nucleic acid sequences listed in Table 5, or a substantially similar sequence thereof having at least 90%, at least 95%, at least 98% or at least 99% sequence identity thereto, and a polynucleotide sequence selected from any of the LCVR nucleic acid sequences listed in Table 5, or a substantially similar sequence thereof having at least 90%, at least 95%, at least 98% or at least 99% sequence identity thereto. In certain embodiments, the nucleic acid molecule encodes an HCVR and LCVR, wherein the HCVR and LCVR are both derived from the same anti-CD28 antibody listed in Table 4.

Provided herein are recombinant expression vectors capable of expressing a polypeptide comprising a heavy or light chain variable region of an anti-CD28 antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 4. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are anti-CD28 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Provided herein is a pharmaceutical composition comprising a recombinant human antibody or fragment thereof which specifically binds CD28 and a pharmaceutically acceptable carrier. In a related aspect, the disclosure features a composition which is a combination of an anti-CD28 antibody and a second therapeutic agent. In one embodiment, the second therapeutic agent is any agent that is advantageously combined with an anti-CD28 antibody. Exemplary agents that may be advantageously combined with an anti-CD28 antibody include, without limitation, other agents that activate or stimulate immune cell activation (including other antibodies or antigen-binding fragments thereof, etc.) and/or agents which do not directly bind CD28 but nonetheless facilitate an anti-tumor response. Additional combination therapies and co-formulations involving the anti-CD28 antibodies of the present disclosure are disclosed elsewhere herein.

In yet another aspect, the provided herein are therapeutic methods for stimulating T cell activation using an anti-CD28 antibody or antigen-binding portion of the antibody, wherein the therapeutic methods comprise administering a therapeutically effective amount of a pharmaceutical composition comprising an antibody or antigen-binding fragment of an anti-CD28 antibody to a subject in need thereof. The disorder treated is any disease or condition which is improved, ameliorated, inhibited or prevented by stimulation of CD28 activity or signaling.

Bispecific Antibodies Comprising Anti-CD38 and Anti-CD28 Antigen Binding Domains According to another aspect, the present disclosure provides bispecific antigen-binding molecules that bind CD28 and a target antigen. According to yet another aspect, the present disclosure provides bispecific antigen-binding molecules that bind CD38 and a costimulatory molecule. According to certain exemplary embodiments, the bispecific antigen-binding molecules bind CD38 and CD28; such bispecific antigen-binding molecules are also referred to herein as "anti-CD38/anti-CD28 bispecific molecules".

The anti-CD38 portion of the anti-CD38/anti-CD28 bispecific molecule is useful for targeting tumor cells that express CD38 (e.g., plasma cells), and the anti-CD28 portion of the bispecific molecule is useful for providing co-stimulation of T cells activated by cognate MHC peptide or tumor targeted CD3 bispecific antibodies. The simultaneous binding of CD38 on a tumor cell and CD28 on a T-cell facilitates directed killing (cell lysis) of the targeted tumor cell by the activated T-cell. The anti-CD38/anti-CD28 bispecific molecules of the invention are therefore useful, inter alia, for treating diseases and disorders related to or caused by CD38-expressing tumors (e.g., lymphomas, leukemias, and multiple myeloma).

The bispecific antigen-binding molecules provided herein comprise a first antigen-binding domain that specifically binds human CD38, and a second antigen-binding domain that specifically binds CD28. The present disclosure includes anti-CD38/anti-CD28 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD38 antigen-binding domain and the anti-CD28 antigen binding domain each comprise different, distinct HCVRs paired with a common LCVR. For example, as illustrated in Example 4 herein, bispecific antibodies were constructed comprising a first antigen-binding domain that specifically binds CD38, wherein the first antigen-binding domain comprises an HCVR/LCVR pair derived from an anti-CD38 antibody; and a second antigen-binding domain that specifically binds CD28, wherein the second antigen-binding domain comprises an HCVR derived from an anti-CD28 antibody paired with an LCVR derived from an anti-CD38 antibody (e.g., the same LCVR that is included in the anti-CD38 antigen-binding domain). In such embodiments, the first and second antigen-binding domains comprise distinct anti-CD38 and anti-CD28 HCVRs but share a common anti-CD38 LCVR.

Provided herein are anti-CD38/anti-CD28 bispecific molecules, wherein the first antigen-binding domain that specifically binds CD38 comprises any of the HCVR amino acid sequences as set forth in Table 1. The first antigen-binding domain that specifically binds CD38 may also comprise any of the LCVR amino acid sequences as set forth in Table 1. According to certain embodiments, the first antigen-binding domain that specifically binds CD38 comprises any of the HCVR/LCVR amino acid sequence pairs as set forth in Table 1. The present disclosure also provides anti-CD38/anti-CD28 bispecific molecules, wherein the first antigen-binding domain that specifically binds CD38 comprises any of the heavy chain CDR1-CDR2-CDR3 amino acid sequences as set forth in Table 1, and/or any of the light chain CDR1-CDR2-CDR3 amino acid sequences as set forth in Table 1.

According to certain embodiments, provided herein are anti-CD38/anti-CD28 bispecific molecules, wherein the first antigen-binding domain that specifically binds CD38 comprises a heavy chain variable region (HCVR) having an amino acid sequence selected from the group consisting of SEQ ID NOs: 2 and 32 or a substantially similar sequence thereof having at least 90%, at least 95%, at least 98% or at least 99% sequence identity.

Provided herein are anti-CD38/anti-CD28 bispecific molecules, wherein the first antigen-binding domain that specifically binds CD38 comprises a light chain variable region (LCVR) having an amino acid sequence selected from the group consisting of SEQ ID NOs: 18 and 48, or a substantially similar sequence thereof having at least 90%, at least 95%, at least 98% or at least 99% sequence identity.

Provided herein are anti-CD38/anti-CD28 bispecific molecules, wherein the first antigen-binding domain that specifically binds CD38 comprises a HCVR and LCVR (HCVR/LCVR) amino acid sequence pair selected from the group consisting of SEQ ID NOs: 2/18 and 32/48.

Provided herein are anti-CD38/anti-CD28 bispecific molecules, wherein the first antigen-binding domain that specifically binds CD38 comprises a heavy chain CDR3 (HCDR3) domain having an amino acid sequence selected from the group consisting of SEQ ID NOs: 8 and 38, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 24 and 54, or a substantially similar sequence thereof having at least 90%, at least 95%, at least 98% or at least 99% sequence identity.

In certain embodiments, the first antigen-binding domain that specifically binds CD38 comprises a HCDR3/LCDR3 amino acid sequence pair selected from the group consisting of SEQ ID NOs: 8/24 and 38/54.

Provided herein are anti-CD38/anti-CD28 bispecific antigen-binding molecules, wherein the first antigen-binding domain that specifically binds CD38 comprises a heavy chain CDR1 (HCDR1) domain having an amino acid sequence selected from the group consisting of SEQ ID NOs: 4 and 34, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 6 and 36, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 20 and 50, or a substantially similar sequence thereof having at least 90%, at least 95%, at least 98% or at least 99% sequence identity; and a light chain CDR2 (LCDR2) domain having an amino acid sequence selected from the group consisting of AAS and GAS, or a substantially similar sequence thereof having at least 90%, at least 95%, at least 98% or at least 99% sequence identity.

Certain non-limiting, exemplary anti-CD38/anti-CD28 bispecific antigen-binding molecules of the invention include a first antigen-binding domain that specifically binds CD38 comprising HCDR1-HCDR2-HCDR3-LCDR1-LCDR2-LCDR3 domains, respectively, having the amino acid sequences selected from the group consisting of: SEQ ID NOs: 4-6-8-20-AAS-24 (e.g. bsAb6031) and 34-36-38-50-GAS-54 (e.g. bsAb7945).

Provided herein are anti-CD38/anti-CD28 bispecific molecules, wherein the second antigen-binding domain that specifically binds CD28 comprises any of the HCVR amino acid sequences as set forth in Table 4. The second antigen-binding domain that specifically binds CD28 may also comprise any of the LCVR amino acid sequences as set forth in Table 4. According to certain embodiments, the second antigen-binding domain that specifically binds CD28 comprises any of the HCVR/LCVR amino acid sequence pairs as set forth in Table 4. The present disclosure also provides anti-CD38/anti-CD28 bispecific molecules, wherein the second antigen-binding domain that specifically binds CD28 comprises any of the heavy chain CDR1-CDR2-CDR3 amino acid sequences as set forth in Table 4, and/or any of the light chain CDR1-CDR2-CDR3 amino acid sequences as set forth in Table 4.

According to certain embodiments, provided herein are anti-CD38/anti-CD28 bispecific molecules, wherein the second antigen-binding domain that specifically binds CD28 comprises a heavy chain variable region (HCVR) having an amino acid sequence selected from the group consisting of SEQ ID NOs: 10 and 40 or a substantially similar sequence thereof having at least 90%, at least 95%, at least 98% or at least 99% sequence identity.

Provided herein are anti-CD38/anti-CD28 bispecific molecules, wherein the second antigen-binding domain that specifically binds CD28 comprises a light chain variable region (LCVR) having an amino acid sequence selected from the group consisting of SEQ ID NOs: 18 and 48, or a substantially similar sequence thereof having at least 90%, at least 95%, at least 98% or at least 99% sequence identity.

Provided herein are anti-CD38/anti-CD28 bispecific molecules, wherein the second antigen-binding domain that specifically binds CD28 comprises a HCVR and LCVR (HCVR/LCVR) amino acid sequence pair selected from the group consisting of SEQ ID NOs: 10/18 and 40/48.

Provided herein are anti-CD38/anti-CD28 bispecific molecules, wherein the second antigen-binding domain that specifically binds CD28 comprises a heavy chain CDR3 (HCDR3) domain having an amino acid sequence selected from the group consisting of SEQ ID NOs: 16 and 46, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 24 and 54, or a substantially similar sequence thereof having at least 90%, at least 95%, at least 98% or at least 99% sequence identity.

In certain embodiments, the second antigen-binding domain that specifically binds CD28 comprises a HCDR3/

LCDR3 amino acid sequence pair selected from the group consisting of SEQ ID NOs: 16/24 and 46/54.

Provided herein are anti-CD38/anti-CD28 bispecific antigen-binding molecules, wherein the second antigen-binding domain that specifically binds CD28 comprises a heavy chain CDR1 (HCDR1) domain having an amino acid sequence selected from the group consisting of SEQ ID NOs: 12 and 42, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 14 and 44, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 20 and 50, or a substantially similar sequence thereof having at least 90%, at least 95%, at least 98% or at least 99% sequence identity; and a light chain CDR2 (LCDR2) domain having an amino acid sequence selected from the group consisting of AAS and GAS, or a substantially similar sequence thereof having at least 90%, at least 95%, at least 98% or at least 99% sequence identity.

Certain non-limiting, exemplary anti-CD38/anti-CD28 bispecific antigen-binding molecules provided herein include a second antigen-binding domain that specifically binds CD28 comprising HCDR1-HCDR2-HCDR3-LCDR1-LCDR2-LCDR3 domains, respectively, having the amino acid sequences selected from the group consisting of: SEQ ID NOs: Dec. 14, 2016-20-AAS-24 (e.g. bsAb6031) and 42-44-46-50-GAS-54 (e.g. bsAb7945).

In an embodiment provided herein, the multispecific (e.g., bi-specific) antigen-binding molecule (e.g., antibody or antigen-binding fragment thereof) that binds CD38 and CD28 includes:

(1)

an anti-CD38 binding arm that comprises:

an HCDR1 that comprises the amino acid sequence: GFTFDDYA (SEQ ID NO: 4; or a variant thereof); an HCDR2 that comprises the amino acid sequence: ISWKSDNI (SEQ ID NO: 6; or a variant thereof); an HCDR3 that comprises the amino acid sequence: AKALGGWKFDYYYGMDV (SEQ ID NO: 8; or a variant thereof); an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTP-PIT (SEQ ID NO: 24; or a variant thereof); and an anti-CD28 binding arm that comprises:

an HCDR1 that comprises the amino acid sequence: GFTFSRNN (SEQ ID NO: 12; or a variant thereof); an HCDR2 that comprises the amino acid sequence: ISSNGGRT (SEQ ID NO: 14; or a variant thereof); an HCDR3 that comprises the amino acid sequence: TRD-DELLSFDY (SEQ ID NO: 16; or a variant thereof); an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTPPIT (SEQ ID NO: 24; or a variant thereof);

(2)

an anti-CD38 binding arm that comprises:

an HCDR1 that comprises the amino acid sequence: GGPFRSSS (SEQ ID NO: 34; or a variant thereof); an HCDR2 that comprises the amino acid sequence: IIPI- LGKT (SEQ ID NO: 36; or a variant thereof); an HCDR3 that comprises the amino acid sequence: VRGSSLFDY (SEQ ID NO: 38; or a variant thereof); an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof); and an anti-CD28 binding arm that comprises:

an HCDR1 that comprises the amino acid sequence: GGSISSYY (SEQ ID NO: 42; or a variant thereof); an HCDR2 that comprises the amino acid sequence: IYYSGIT (SEQ ID NO: 44; or a variant thereof); an HCDR3 that comprises the amino acid sequence: ARWGVRRDYYYYGMDV (SEQ ID NO: 46; or a variant thereof); an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof);

(3)

an anti-CD38 binding arm that comprises:

an HCVR1 that comprises the amino acid sequence: EVOLVESGGGLVQPGRSLRLSCAASGFTFDDYAM-HWVRQAPGKGLEWVSGISWKSDNIGYA DSVKGRFTISRDNAKNSLYLQMNSLRAED-TALYYCAKAL-GGWKFDYYYGMDVWGQGTTVTVS S (SEQ ID NO: 2; or a variant thereof); and an LCVR1 that comprises the amino acid sequence: DIQMTQSPSSL-SASVGDRVTITCRASQSIS-SYLNWYQQKPGKAPKLLI-YAASSLQSGVPSRFSG SGSGTDFTLTISSLOPEDFATYYCQQSYSTP-PITFGQGTRLEIK (SEQ ID NO: 18; or a variant thereof); and an anti-CD28 binding arm that comprises:

an HCVR1 that comprises the amino acid sequence: EVOLVESGGGLVQPGGSLRLS-CAASGFTFSRNNMHWVRQAPGKGLEYVS-GISSNGGRTYYA DSVKGRFTISRDNSKNT-LYLQMGGLRAADMAVYFCTRDDELLSFDYWG QGTLVTVSS (SEQ ID NO: 10; or a variant thereof); and an LCVR1 that comprises the amino acid sequence: DIQMTQSPSSLSASVGDRVTITCRASQ-SISSYLNWYQQKPGKAPKLLI-YAASSLQSGVPSRFSG SGSGTDFTLTISSLOPED-FATYYCQQSYSTPPITFGQGTRLEIK (SEQ ID NO: 18; or a variant thereof);

(4)

an anti-CD38 binding arm that comprises:

an HCVR1 that comprises the amino acid sequence: QVQLVQSGAEVKKPGSSVKVSCKASGGP-FRSSSFSWVRQAPGQGLEWMGGIIPILGKTNYAQ KFQGRITIVTDESTTTVYMELSSLRSED-TAVFYCVRGSSLFDYWGQGTLVTVSS (SEQ ID NO: 32; or a variant thereof); and an LCVR1 that comprises the amino acid sequence: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIK (SEQ ID NO: 48; or a variant thereof); and

an anti-CD28 binding arm that comprises:

an HCVR1 that comprises the amino acid sequence:
QVQLQESGPGLVKPSETLSLTCTVSGGSIS-
SYYWSWIRQPPGKGLEWIGYIYYSGITHYNPSLK
SRVTISVDTSKIQFSLKLSSVTAADTAVYY-
CARWGVRRDYYYYGMDVWGQGTTVTVSS
(SEQ ID NO: 40; or a variant thereof); and an LCVR1
that comprises the amino acid sequence:
EIVLTQSPGTLSLSPGERATLSCRASQSVSSSY-
LAWYQQKPGQAPRLLIYGASSRATGIPDRFS
GSGSGTDFTLTISRLEPED-
FAVYYCQQYGSSPWTFGQGTKVEIK (SEQ ID
NO: 48; or a variant thereof;

(5)

an anti-CD38 binding arm that comprises:

a heavy chain that comprises the amino acid sequence
EVOLVESGGGLVQPGRSLRLSCAASGFTFDDY-
AMHWVRQAPGKGLEWVSGISWKSDNIGYA
DSVKGRFTISRDNAKNSLYLQMNSLRAED-
TALYYCAKAL-
GGWKFDYYYGMDVWGQGTTVTVS SAS-
TKGPSVFPLAPCSRSTSESTAALGCLVKDYFPEP
VTVSWNSGALTSGVHTFPAVLQSSGL
YSLSSVVTVPSSSLGTKTYTCNVDHKPSNTKVD
KRVESKYGPPCPPCPAPPVAGPSVFLFPPK
PKDTLMISRTPEVTCVVVDVSQEDPE-
VQFNWYVDGVEVHNAKTKPREEQFN-
STYRVVSVLTVL
HQDWLNGKEYKCKVSNKGLPSSIEKTISKAKGQ
PREPQVYTLPPSQEEMTKNQVSLTCLVKGF YPS-
DIAVEWESNGQPENNYKTTPPVLDSDGSFFLY-
SRLTVDKSRWQEGNVFSCSVMHEALHN
HYTQKSLSLSLGK* (SEQ ID NO: 26, or a variant
thereof); and a light chain that comprises the amino acid sequence
DIQMTQSPSSLSASVGDRVTITCRASQSIS-
SYLNWYQQKPGKAPKLLI-
YAASSLQSGVPSRFSG SGSGTDFTLTISSLOPED-
FATYYCQQSYSTPPITFGQGTRLEIKRTVAAPSVFI
FPPSDEQLKSG TASVVCLLNNFY-
PREAKVQWKVDNALQSGNSQESVTEQDSKDS-
TYSLSSTLTLSKADYEKHKV YACE-
VTHQGLSSPVTKSFNRGEC* (SEQ ID NO: 30, or a
variant thereof); and an anti-CD28 binding arm that
comprises:

a heavy chain that comprises the amino acid sequence
EVOLVESGGGLVQPGGSLRLS-
CAASGFTFSRNNMHWVRQAPGKGLEYVS-
GISSNGGRTYYA DSVKGRFTISRDNSKNT-
LYLQMGGLRAADMAVYFCTRDDELLSFDYWG
QGTLVTVSSASTKG PSVFPLAPCSRSTSESTAAL-
GCLVKDYFPEPVTVSWNSGALT-
SGVHTFPAVLQSSGLYSLSSV
VTVPSSSLGTKTYTCNVDHKPSNTKVDKRVESKY-
GPPCPPCPAPPVAGPSVFLFPPKPKDTLM ISRTPE-
VTCVVVDVSQEDPE-
VQFNWYVDGVEVHNAKTKPREEQFNSTYRVV
SVLTVLHQDWL
NGKEYKCKVSNKGLPSSIEKTISKAKGQPREPQ
VYTLPPSQEEMTKNQVSLTCLVKGFYPSDIA
VEWESNGQPENNYKTTPPVLDSDGSFFLY-
SRLTVDKSRWQEGNVFSCSVMHEALHNRFTQK
SLSLSPGK* (SEQ ID NO: 28, or a variant thereof);
and a light chain that comprises the amino acid sequence
DIQMTQSPSSLSASVGDRVTITCRASQSIS-
SYLNWYQQKPGKAPKLLI-

18

YAASSLQSGVPSRFSG SGSGTDFTLTISSLOPED-
FATYYCQQSYSTPPITFGQGTRLEIKRTVAAPSV
FIFPPSDEQLKSG TASVVCLLNNFY-
PREAKVQWKVDNALQSGNSQESVTEQDSKDS-
TYSLSSTLTLSKADYEKHKV YACE-
VTHQGLSSPVTKSFNRGEC* (SEQ ID NO: 30, or a
variant thereof); or (6)

an anti-CD38 binding arm that comprises:

a heavy chain that comprises the amino acid sequence
QVQLVQSGAEVKKPGSSVKVSCKASGGP-
FRSSSFSWVRQAPGQGLEWMGGIIPILGKTNYAQ
KFQGRITIVTDESTTTVYMELSSLRSED-
TAVFYCVRGSSLFDYWGQGTLVTVSSAS-
TKGPSVFP LAPCSRSTSESTAALGCLVKDYF-
PEPVTVSWNSGALTSGVHTFPAVLQSSGLYSLSS
VVTVPS
SSLGTKTYTCNVDHKPSNTKVDKRVESKY-
GPPCPPCPAPPVAGPSVFLFPPKPKDTLMISRTP
EVTCVVVDVSQEDPE-
VQFNWYVDGVEVHNAKTKPREEQFN-
STYRVVSVLTVLHQDWLNGKE
YKCKVSNKGLPSSIEKTISKAKGQPREPQVYTL
PPSQEEMTKNQVSLTCLVKGFYPSDIAVEWE
SNGQPENNYKTTPPVLDSDGSFFLY-
SRLTVDKSRWQEGNVFSCSVMHEALHN-
HYTQKSLSLS LGK* (SEQ ID NO: 56, or a variant
thereof); and a light chain that comprises the amino acid sequence
EIVLTQSPGTLSLSPGERATLSCRASQSVSSSY-
LAWYQQKPGQAPRLLIYGASSRATGIPDRFS
GSGSGTDFTLTISRLEPED-
FAVYYCQQYGSSPWTFGQGTKVEIKRTVAAPSV
FIFPPSDEQLKS GTASVVCLLNNFY-
PREAKVQWKVDNALQSGNSQESVTEQDSKDS-
TYSLSSTLTLSKADYEKH KVYACE-
VTHQGLSSPVTKSFNRGEC* (SEQ ID NO: 60, or a
variant thereof); and an anti-CD28 binding arm that
comprises:

a heavy chain that comprises the amino acid sequence
QVQLQESGPGLVKPSETLSLTCTVSGGSIS-
SYYWSWIRQPPGKGLEWIGYIYYSGITHYNPSLK
SRVTISVDTSKIQFSLKLSSVTAADTAVYY-
CARWGVRRDYYYYGMDVWGQGTTVTVSSAS-
TKG PSVFPLAPCSRSTSESTAALGCLVKDYF-
PEPVTVSWNSGALTSGVHTFPAVLQSSGLYSLSSV
VTVPSSSLGTKTYTCNVDHKPSNTKVDKRVESKY-
GPPCPPCPAPPVAGPSVFLFPPKPKDTLM ISRTPE-
VTCVVVDVSQEDPE-
VQFNWYVDGVEVHNAKTKPREEQFNSTYRVVS
VLTVLHQDWL
NGKEYKCKVSNKGLPSSIEKTISKAKGQPREPQ
VYTLPPSQEEMTKNQVSLTCLVKGFYPSDIA
VEWESNGQPENNYKTTPPVLDSDGSFFLY-
SRLTVDKSRWQEGNVFSCSVMHEALHNRFTQK
SLSLSPGK* (SEQ ID NO: 58, or a variant thereof);
and a light chain that comprises the amino acid sequence
EIVLTQSPGTLSLSPGERATLSCRASQSVSSSY-
LAWYQQKPGQAPRLLIYGASSRATGIPDRFS
GSGSGTDFTLTISRLEPED-
FAVYYCQQYGSSPWTFGQGTKVEIKRTVAAPS
VFIFPPSDEQLKS GTASVVCLLNNFY-
PREAKVQWKVDNALQSGNSQESVTEQDSKDS-
TYSLSSTLTLSKADYEKH KVYACE-
VTHQGLSSPVTKSFNRGEC* (SEQ ID NO: 60, or a
variant thereof).

In an embodiment provided herein, the multispecific (e.g., bi-specific) antigen-binding molecule (e.g., antibody or antigen-binding fragment thereof) that binds CD38 and CD28 includes:

(1)

an anti-CD38 binding arm that comprises:

an HCDR1 that comprises the amino acid sequence: GFTFDDYA (SEQ ID NO: 4; or a variant thereof); an HCDR2 that comprises the amino acid sequence: ISWKSDNI (SEQ ID NO: 6; or a variant thereof); an HCDR3 that comprises the amino acid sequence: AKALGGWKFDYYYGMDV (SEQ ID NO: 8; or a variant thereof); an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTP-PIT (SEQ ID NO: 24; or a variant thereof); and an anti-CD28 binding arm that comprises:

an HCDR1 that comprises the amino acid sequence: GGSISSYY (SEQ ID NO: 42; or a variant thereof); an HCDR2 that comprises the amino acid sequence: IYYSGIT (SEQ ID NO: 44; or a variant thereof); an HCDR3 that comprises the amino acid sequence: ARWGVRRDYYYGMDV (SEQ ID NO: 46; or a variant thereof); an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof);

(2)

an anti-CD38 binding arm that comprises:

an HCDR1 that comprises the amino acid sequence: GGPFRSSS (SEQ ID NO: 34; or a variant thereof); an HCDR2 that comprises the amino acid sequence: IIPI-LGKT (SEQ ID NO: 36; or a variant thereof); an HCDR3 that comprises the amino acid sequence: VRGSSLFDY (SEQ ID NO: 38; or a variant thereof); an LCDR1 that comprises the amino acid sequence: QSVSSSY (SEQ ID NO: 50; or a variant thereof); an LCDR2 that comprises the amino acid sequence: GAS (or a variant thereof); and an LCDR3 that comprises the amino acid sequence: QQYGSSPWT (SEQ ID NO: 54; or a variant thereof); and an anti-CD28 binding arm that comprises:

an HCDR1 that comprises the amino acid sequence: GFTFSRNN (SEQ ID NO: 12; or a variant thereof); an HCDR2 that comprises the amino acid sequence: ISSNGGRT (SEQ ID NO: 14; or a variant thereof); an HCDR3 that comprises the amino acid sequence: TRD-DELLSFDY (SEQ ID NO: 16; or a variant thereof); an LCDR1 that comprises the amino acid sequence: QSISSY (SEQ ID NO: 20; or a variant thereof); an LCDR2 that comprises the amino acid sequence: AAS (or a variant thereof); and an LCDR3 that comprises the amino acid sequence: QQSYSTPPIT (SEQ ID NO: 24; or a variant thereof);

(3)

an anti-CD38 binding arm that comprises:

an HCVR1 that comprises the amino acid sequence: EVOLVESGGGLVQPGRSLRLSCAASGFTFDDY-AMHWVRQAPGKGLEWVSGISWKSDNIGYA DSVKGRFTISRDNAKNSLYLQMNSLRAED-TALYYCAKAL-GGWKFDYYYGMDVWGQGTTVTVS S (SEQ ID NO: 2; or a variant thereof); and an LCVR1 that comprises the amino acid sequence: DIQMTQSPSSL-SASVGDRVTITCRASQSIS-SYLNWYQQKPGKAPKLLI-YAASSLQSGVPSRFSG SGSGTDFTLTISSLOPEDFATYYCQQSYSTP-PITFGQGTRLEIK (SEQ ID NO: 18; or a variant thereof); and an anti-CD28 binding arm that comprises:

an HCVR1 that comprises the amino acid sequence: QVQLQESGPGLVKPSETLSLTCTVSGGSIS-SYYWSWIRQPPGKGLEWIGYIYYSGITHYNPSLK SRVTISVDTSKIQFSLKLSSVTAADTAVYY-CARWGVRRDYYYYGMDVWGQGTTVTVSS (SEQ ID NO: 40; or a variant thereof); and an LCVR1 that comprises the amino acid sequence: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIK (SEQ ID NO: 48; or a variant thereof;

(4)

an anti-CD38 binding arm that comprises:

an HCVR1 that comprises the amino acid sequence: QVQLVQSGAEVKKPGSSVKVSCKASGGP-FRSSSFSWVRQAPGQGLEWMGGIIPILGKTNYAQ KFQGRITIVTDESTTTVYMELSSLRSED-TAVFYCVRGSSLFDYWGQGTLVTVSS (SEQ ID NO: 32; or a variant thereof); and an LCVR1 that comprises the amino acid sequence: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIK (SEQ ID NO: 48; or a variant thereof); and an anti-CD28 binding arm that comprises:

an HCVR1 that comprises the amino acid sequence: EVOLVESGGGLVQPGGSLRLS-CAASGFTFSRNNMHWVRQAPGKGLEYVS-GISSNGGRTYYA DSVKGRFTISRDNSKNT-LYLQMGGLRAADMAVYFCTRDDELLSFDYWG QGTLVTVSS (SEQ ID NO: 10; or a variant thereof); and an LCVR1 that comprises the amino acid sequence: DIQMTQSPSSLSASVGDRVTITCRASQ-SISSYLNWYQQKPGKAPKLLI-YAASSLQSGVPSRFSG SGSGTDFTLTISSLOPED-FATYYCQQSYSTPPITFGQGTRLEIK (SEQ ID NO: 18; or a variant thereof);

(5)

an anti-CD38 binding arm that comprises:

a heavy chain that comprises the amino acid sequence EVOLVESGGGLVQPGRSLRLSCAASGFTFDDY-AMHWVRQAPGKGLEWVSGISWKSDNIGYA DSVKGRFTISRDNAKNSLYLQMNSLRAED-TALYYCAKAL-GGWKFDYYYGMDVWGQGTTVTVS SAS-TKGPSVFPLAPCSRSTSESTAALGCLVKDYFPEP VTVSWNSGALTSGVHTFPAVLQSSGL YSLSSVVTVPSSSLGTKTYTCNVDHKPSNTKVD KRVESKYGPPCPPCPAPPVAGPSVFLFPPK PKDTLMISRTPEVTCVVVDVSQEDPE-VQFNWYVDGVEVHNAKTKPREEQFN-STYRVVSVLTVL HQDWLNGKEYKCKVSNKGLPSSIEKTISKAKG QPREPQVYTLPPSQEEMTKNQVSLTCLVKGF YPSDIAVEWESNGQPENNYKTTPPVLDSDGSFF-LYSRLTVDKSRWQEGNVFSCSVMHEALHN HYTQKSLSLSLGK* (SEQ ID NO: 26, or a variant thereof); and a light chain that comprises the amino acid sequence DIQMTQSPSSLSASVGDRVTITCRASQSIS-SYLNWYQQKPGKAPKLLI-YAASSLQSGVPSRFSG SGSGTDFTLTISSLOPED-FATYYCQQSYSTPPITFGQGTRLEIKRTVAAPSVF IFPPSDEQLKSG TASVVCLLNNFY-PREAKVQWKVDNALQSGNSQESVTEQDSKDS-TYSLSSTLTLSKADYEKHKV YACE-VTHQGLSSPVTKSFNRGEC* (SEQ ID NO: 30, or a variant thereof); and an anti-CD28 binding arm that comprises:

a heavy chain that comprises the amino acid sequence QVQLQESGPGLVKPSETLSLTCTVSGGSIS-SYYWSWIRQPPGKGLEWIGYIYYSGITHYNPSLK SRVTISVDTSKIQFSLKLSSVTAADTAVYY-CARWGVRRDYYYYGMDVWGQGTTVTVSSAS-TKG PSVFPLAPCSRSTSESTAALGCLVKDYF-PEPVTVSWNSGALTSGVHTFPAVLQSSGLYSLSSV VTVPSSSLGTKTYTCNVDHKPSNTKVDKRVESKY-GPPCPPCPAPPVAGPSVFLFPPKPKDTLM ISRTPE-VTCVVVDVSQEDPE-VQFNWYVDGVEVHNAKTKPREEQFNSTYRVVS VLTVLHQDWL NGKEYKCKVSNKGLPSSIEKTISKAKGQPREPQ VYTLPPSQEEMTKNQVSLTCLVKGFYPSDIA VEWESNGQPENNYKTTPPVLDSDGSFFLY-SRLTVDKSRWQEGNVFSCSVMHEALHNRFTQK SLSLSPGK* (SEQ ID NO: 58, or a variant thereof); and a light chain that comprises the amino acid sequence EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIKRTVAAPS VFIFPPSDEQLKS GTASVVCLLNNFY-PREAKVQWKVDNALQSGNSQESVTEQDSKDS-TYSLSSTLTLSKADYEKH KVYACE-VTHQGLSSPVTKSFNRGEC* (SEQ ID NO: 60, or a variant thereof); or (6)

an anti-CD38 binding arm that comprises:

a heavy chain that comprises the amino acid sequence QVQLVQSGAEVKKPGSSVKVSCKASGGP-FRSSSFSWVRQAPGQGLEWMGGIIPILGKTNYAQ KFQGRITIVTDESTTTVYMELSSLRSED-TAVFYCVRGSSLFDYWGQGTLVTVSSAS-TKGPSVFP LAPCSRSTSESTAALGCLVKDYF-PEPVTVSWNSGALTSGVHTFPAVLQSSGLYSLSS VVTVPS SSLGTKTYTCNVDHKPSNTKVDKRVESKY-GPPCPPCPAPPVAGPSVFLFPPKPKDTLMISRTP EVTCVVVDVSQEDPE-VQFNWYVDGVEVHNAKTKPREEQFN-STYRVVSVLTVLHQDWLNGKE YKCKVSNKGLPSSIEKTISKAKGQPREPQVYTL PPSQEEMTKNQVSLTCLVKGFYPSDIAVEWE SNGQPENNYKTTPPVLDSDGSFFLY-SRLTVDKSRWQEGNVFSCSVMHEALHN-HYTQKSLSLS LGK* (SEQ ID NO: 56, or a variant thereof); and a light chain that comprises the amino acid sequence EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPWTFGQGTKVEIKRTVAAPSV FIFPPSDEQLKS GTASVVCLLNNFY-PREAKVQWKVDNALQSGNSQESVTEQDSKDS- TYSLSSTLTLSKADYEKH KVYACE-VTHQGLSSPVTKSFNRGEC* (SEQ ID NO: 60, or a variant thereof); and an anti-CD28 binding arm that comprises:

a heavy chain that comprises the amino acid sequence EVOLVESGGGLVQPGGSLRLS-CAASGFTFSRNNMHWVRQAPGKGLEYVS-GISSNGGRTYYA DSVKGRFTISRDNSKNT-LYLQMGGLRAADMAVYFCTRDDELLSFDYWG QGTLVTVSSASTKG PSVFPLAPCSRSTSESTAAL-GCLVKDYFPEPVTVSWNSGALT-SGVHTFPAVLQSSGLYSLSSV VTVPSSSLGTKTYTCNVDHKPSNTKVDKRVES KYGPPCPPCPAPPVAGPSVFLFPPKPKDTLM ISRTPEVTCVVVDVSQEDPE-VQFNWYVDGVEVHNAKTKPREEQFNSTYRVV SVLTVLHQDWL NGKEYKCKVSNKGLPSSIEKTISKAKGQPREPQ VYTLPPSQEEMTKNQVSLTCLVKGFYPSDIA VEWESNGQPENNYKTTPPVLDSDGSFFLY-SRLTVDKSRWQEGNVFSCSVMHEALHNRFTQK SLSLSPGK* (SEQ ID NO: 28, or a variant thereof); and a light chain that comprises the amino acid sequence DIQMTQSPSSLSASVGDRVTITCRASQSIS-SYLNWYQQKPGKAPKLLI-YAASSLQSGVPSRFSG SGSGTDFTLTISSLOPED-FATYYCQQSYSTPPITFGQGTRLEIKRTVAAPSVF IFPPSDEQLKSG TASVVCLLNNFY-PREAKVQWKVDNALQSGNSQESVTEQDSKDS-TYSLSSTLTLSKADYEKHKV YACE-VTHQGLSSPVTKSFNRGEC* (SEQ ID NO: 30, or a variant thereof).

In another aspect, provided herein are nucleic acid molecules encoding any of the HCVR, LCVR or CDR sequences of the anti-CD38/anti-CD28 bispecific antigen-binding molecules disclosed herein, including nucleic acid molecules comprising the polynucleotide sequences as set forth in Table 2 herein, as well as nucleic acid molecules comprising the polynucleotide sequences as set forth in Table 5 herein, in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD38/anti-CD28 bispecific antigen-binding molecules wherein any of the aforementioned antigen-binding domains that specifically bind CD38 is combined, connected or otherwise associated with any of the aforementioned antigen-binding domains that specifically bind CD28 to form a bispecific antigen-binding molecule that binds CD38 and CD28.

Provided herein are anti-CD38/anti-CD28 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, provided herein is a pharmaceutical composition comprising an anti-CD38/anti-CD28 bispecific antigen-binding molecule as disclosed herein and a pharmaceutically acceptable carrier. In a related aspect, the invention features a composition which is a combination of an anti-CD38/anti-CD28 bispecific antigen-binding molecule and a second therapeutic agent. In one embodiment, the second therapeutic agent is any agent that is advantageously combined with an anti-CD38/anti-CD28 bispecific antigen-binding molecule. Exemplary agents that may be advantageously combined with an anti-CD38/anti-CD28 bispecific antigen-binding molecule are discussed in detail elsewhere herein.

In yet another aspect, provided herein are therapeutic methods for targeting/killing tumor cells expressing CD38 using an anti-CD38/anti-CD28 bispecific antigen-binding molecule of the invention, wherein the therapeutic methods comprise administering a therapeutically effective amount of a pharmaceutical composition comprising an anti-CD38/anti-CD28 bispecific antigen-binding molecule provided herein to a subject in need thereof.

The present disclosure also includes the use of an anti-CD38/anti-CD28 bispecific antigen-binding molecule provided herein in the manufacture of a medicament for the treatment of a disease or disorder related to or caused by CD38 expression.

Other embodiments will become apparent from a review of the ensuing detailed description.

BRIEF DESCRIPTION OF THE FIGURES

FIGS. 5-10 show in vivo anti-tumor activity of the costimulatory anti-CD38×CD28 bispecific antibodies bsAb6031 and bsAb7954 alone or in combination with BCMA×CD3 bsAb.

DETAILED DESCRIPTION

Figure 1:
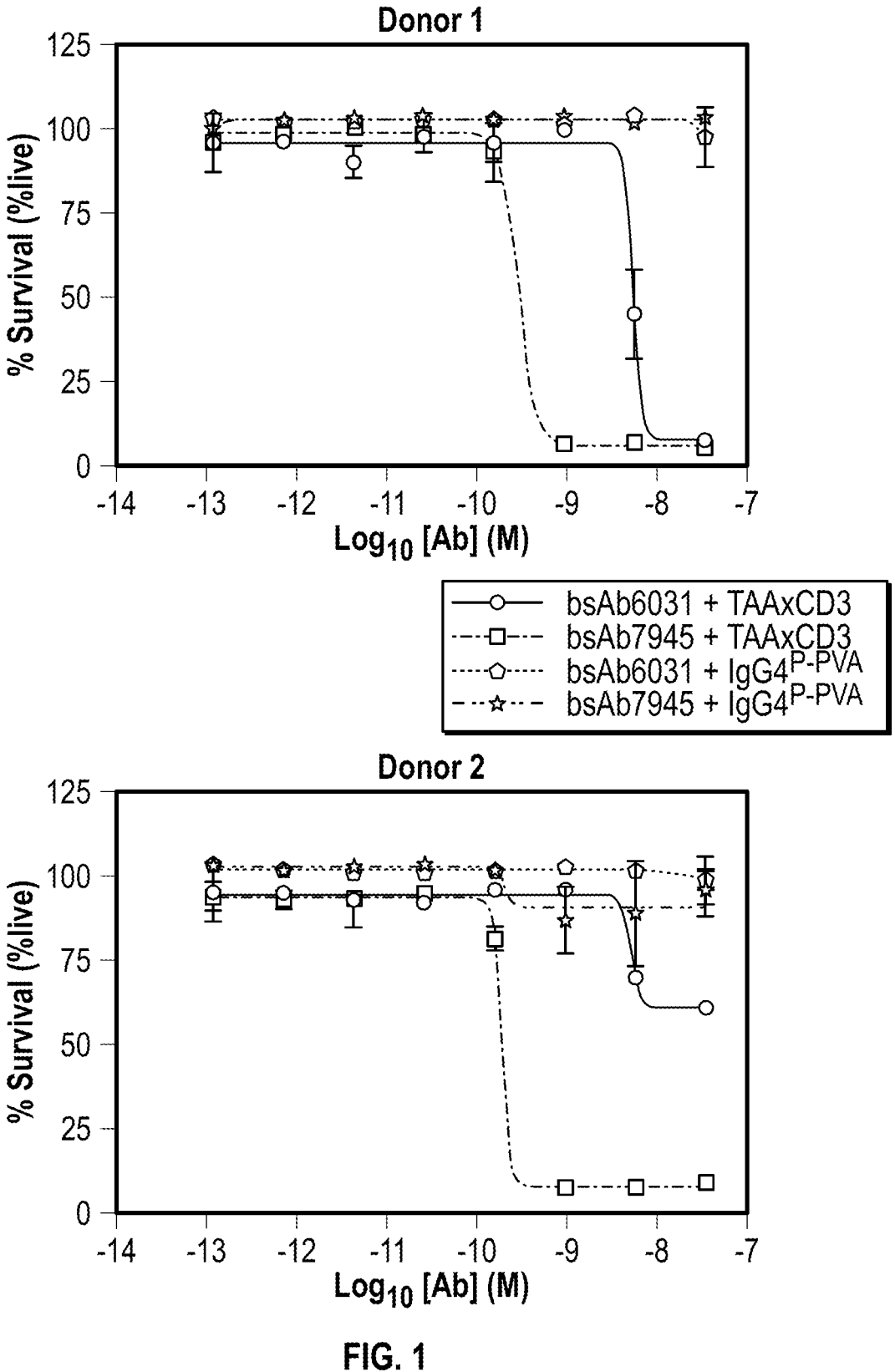
FIGS. 1-4 show cytotoxicity, T cell activation, T cell proliferation, and cytokine release in H929 tumor cells after treatment with the costimulatory anti-CD38×CD28 bispecific antibodies bsAb6031 and bsAb7954.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.
Definitions The expression "CD28", as used herein, refers to an antigen which is expressed on T cells as a homodimer. Human CD28 comprises the amino acid sequence as set forth in SEQ ID NO: 61 (Human CD28 extracellular domain (N19-P152).mFc), and/or having the amino acid sequence as set forth in NCBI accession NM_006139.3, and/or having the amino acid sequence of the Human CD28 >NP_006130.1 T-cell-specific surface glycoprotein CD28 isoform 1 precursor (SEQ ID NO: 63).

```
Human CD28 extracellular domain (N19-P152).mFc
(Immunogen) amino acid sequence
                                    (SEQ ID NO: 61)
NKILVKQSPMLVAYDNAVNLSCKYSYNLFSREFRASLHKGLDSAVEVCVV

YGNYSQQLQVYSKTGFNCDGKLGNESVTFYLQNLYVNQTDIYFCKIEVMY

PPPYLDNEKSNGTIIHVKGKHLCPSPLFPGPSKPEPRGPTIKPCPPCKCP

APNLLGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK*
mFc sequence underlined
```

All references to proteins, polypeptides and protein fragments herein are intended to refer to the human version of the respective protein, polypeptide or protein fragment unless explicitly specified as being from a non-human species. Thus, the expression "CD28" means human CD28 unless specified as being from a non-human species, e.g., "mouse CD28," "monkey CD28," etc.

As used herein, "an antibody that binds CD28" or an "anti-CD28 antibody" includes antibodies and antigen-binding fragments thereof that specifically recognize a single CD28 unit, as well as antibodies and antigen-binding fragments thereof that specifically recognize a dimeric complex of two CD28 subunits. The antibodies and antigen-binding fragments of the present invention may bind soluble CD28 and/or cell surface expressed CD28. Soluble CD28 includes natural CD28 proteins as well as recombinant CD28 protein variants such as, e.g., monomeric and dimeric CD28 constructs, that lack a transmembrane domain or are otherwise unassociated with a cell membrane.

As used herein, the expression "cell surface-expressed CD28" means one or more CD28 protein(s) that is/are expressed on the surface of a cell in vitro or in vivo, such that at least a portion of a CD28 protein is exposed to the extracellular side of the cell membrane and is accessible to an antigen-binding portion of an antibody. "Cell surface-expressed CD28" includes CD28 proteins contained within the context of a functional T cell receptor in the membrane of a cell. The expression "cell surface-expressed CD28" includes CD28 protein expressed as part of a homodimer on the surface of a cell. A "cell surface-expressed CD28" can comprise or consist of a CD28 protein expressed on the surface of a cell which normally expresses CD28 protein. Alternatively, "cell surface-expressed CD28" can comprise or consist of CD28 protein expressed on the surface of a cell that normally does not express human CD28 on its surface but has been artificially engineered to express CD28 on its surface.

The expression "CD38," as used herein, also known as cyclic ADP ribose hydrolase, refers a glycoprotein expressed on malignant plasma cells. CD38 plays a central role in regulating intracellular calcium levels. The protein has an N-terminal cytoplasmic tail, a single membrane-spanning domain, and a C-terminal extracellular region with four N-glycosylation sites.

As used herein, "an antibody that binds CD38" or an "anti-CD38 antibody" includes antibodies and antigen-binding fragments thereof that specifically recognize CD38.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., CD38 or CD28). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD38 antibody or anti-CD28 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$- $C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotox- icity.

In certain embodiments of the invention, the anti-CD38 monospecific antibodies, anti-CD28 monospecific antibod- ies, or anti-CD38 x anti-CD28 bispecific antibodies pro- vided herein are human antibodies. The term "human anti- body", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific muta- genesis in vitro or by somatic mutation in vivo), for example in the CDRs and in particular CDR3. However, the term "human antibody", as used herein, is not intended to include antibodies in which CDR sequences derived from the ger- mline of another mammalian species, such as a mouse, have been grafted onto human framework sequences.

The antibodies of the invention may, in some embodi- ments, be recombinant human antibodies. The term "recom- binant human antibody", as used herein, is intended to include all human antibodies that are prepared, expressed, created or isolated by recombinant means, such as antibod- ies expressed using a recombinant expression vector trans- fected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibod- ies have variable and constant regions derived from human germline immunoglobulin sequences. In certain embodi- ments, however, such recombinant human antibodies are subjected to in vitro mutagenesis (or, when an animal transgenic for human Ig sequences is used, in vivo somatic mutagenesis) and thus the amino acid sequences of the $V_H$ and Vi regions of the recombinant antibodies are sequences that, while derived from and related to human germline $V_H$ and $V_L$ sequences, may not naturally exist within the human antibody germline repertoire in vivo.

Human antibodies can exist in two forms that are asso- ciated with hinge heterogeneity. In one form, an immuno- globulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region iso- type of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibod- ies. An "isolated antibody," as used herein, means an anti- body that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibod- ies are antibodies that have been subjected to at least one purification or isolation step. According to certain embodi- ments, an isolated antibody may be substantially free of other cellular material and/or chemicals.

The present invention also includes one-arm antibodies that bind CD38 or CD28. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1 or Table 4.

The anti-CD38 antibodies, anti-CD28 antibodies, or anti- CD38 x anti-CD28 antibodies disclosed herein may com- prise one or more amino acid substitutions, insertions and/or deletions in the framework and/or CDR regions of the heavy and light chain variable domains as compared to the corre- sponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding frag- ments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

Provided herein are anti-CD38 antibodies, anti-CD28 antibodies, or anti-CD38 x anti-CD28 antibodies comprising variants of any of the HCVR, LCVR, and/or CDR amino acid sequences disclosed herein having one or more conservative substitutions. For example, the present disclosure includes anti-CD38 antibodies, anti-CD28 antibodies, or anti-CD38 x anti-CD28 antibodies having HCVR, LCVR, and/or CDR amino acid sequences with, e.g., 10 or fewer, 8 or fewer, 6 or fewer, 4 or fewer, 3 or fewer, 2, or 1 conservative amino acid substitutions relative to any of the HCVR, LCVR, and/or CDR amino acid sequences set forth in Tables 1, 4, or 7 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Germline Mutations

The anti-CD38 antibodies, anti-CD28 antibodies, and anti-CD38/anti-CD28 bispecific antigen-binding molecules disclosed herein can comprise one or more amino acid substitutions, insertions and/or deletions in the framework and/or CDR regions of the heavy chain variable domains as compared to the corresponding germline sequences from which the antibodies were derived.

Provided herein are antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable binding to a CD38 antigen or a CD28 antigen.

Binding Properties of the Antibodies

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods.* 1997, 201 (2): 223-31; Geuijen, C A, et al. *J Immunol Methods.* 2005, 302 (1-2): 68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present disclosure, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M−1×sec−1 or 1/M/s) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an anti-body or antibody-binding fragment. The association equilibrium constant is obtained by dividing the ka by the ka.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing CD28 or tumor-associated antigen (e.g., CD38), as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Bispecific Antigen-Binding Molecules

The antibodies of the present invention may be mono-specific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD38 monospecific antibodies, anti-CD28 monospecific antibodies, or anti-CD38 x anti-CD28 bispecific antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-CD28 antibody" or "anti-CD38 antibody" herein is intended to include both mono-specific anti-CD28 or anti-CD38 antibodies as well as bispecific antibodies comprising a CD28-binding arm and a CD38-binding arm. Thus, the present disclosure includes bispecific antibodies wherein one arm of an immunoglobulin binds human CD28, and the other arm of the immunoglobulin is specific for human CD38. The CD28-binding arm can comprise any of the HCVR/LCVR or CDR amino acid sequences as set forth in Table 4 herein.

In certain embodiments, the CD28-binding arm binds to human CD28 and facilitates human T cell activation. In certain embodiments, the CD28-binding arm binds to human CD28 and induces human T cell activation. In other embodiments, the CD28-binding arm binds to human CD28 and induces tumor-associated antigen-expressing cell killing in the context of a bispecific or multispecific antibody. The CD38-binding arm can comprise any of the HCVR/LCVR or CDR amino acid sequences as set forth in Table 1 herein.

According to certain exemplary embodiments, the present invention includes bispecific antigen-binding molecules that specifically bind CD28 and CD38. Such molecules may be referred to herein as, e.g., "anti-CD38 x anti-CD28" or "anti-CD38/anti-CD28," or "anti-CD38xCD28" or "CD38xCD28" bispecific molecules, or other similar terminology (e.g., anti-CD28/anti-CD38).

The term "CD38" as used herein, refers to the human CD38 protein unless specified as being from a non-human species (e.g., "mouse CD38", "monkey CD38", etc.). The human CD38 protein has the amino acid sequence shown in SEQ ID NO: 62 (Human CD38 extracellular domain (V43-1300).mFc), and/or having the amino acid sequence as set forth in NCBI accession No. NP_001766.2 or NM_001775.3.

```
Human CD38 extracellular domain (V43-I300).mFc
(Immunogen) amino acid
                                   (SEQ ID NO: 62)
VPRWRQQWSGPGTTKRFPETVLARCVKYTEIHPEMRHVDCQSVWDAFKGA

FISKHPCNITEEDYQPLMKLGTQTVPCNKILLWSRIKDLAHQFTQVQRDM

FTLEDTLLGYLADDLTWCGEFNTSKINYQSCPDWRKDCSNNPVSVFWKTV

SRRFAEAACDVVHVMLNGSRSKIFDKNSTFGSVEVHNLQPEKVQTLEAWV

IHGGREDSRDLCQDPTIKELESIISKRNIQFSCKNIYRPDKFLQCVKNPE

DSSCTSEIEPRGPTIKPCPPCKCPAPNLLGGPSVFIFPPKIKDVLMISLS

PIVTCVVVDVSEDDPDVQISWFVNNVEVHTAQTQTHREDYNSTLRVVSAL

PIQHQDWMSGKEFKCKVNNKDLPAPIERTISKPKGSVRAPQVYVLPPPEE

EMTKKQVTLTCMVTDFMPEDIYVEWTNNGKTELNYKNTEPVLDSDGSYFM

YSKLRVEKKNWVERNSYSCSVVHEGLHNHHTTKSFSRTPGK*
mFc sequence underlined
```

The bispecific antigen-binding molecules that specifically bind CD38 and CD28 may comprise an anti-CD28 antigen-binding molecule which binds to CD28 with a weak binding affinity such as exhibiting a $K_D$ of greater than about 200 uM, as measured by an in vitro affinity binding assay.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD38), and the second antigen-binding domain specifically binds a second, distinct antigen (e.g., CD28).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "D1" and the CDRs of the second antigen-binding domain may be designated with the prefix "D2". Thus, the CDRs of the first antigen-binding domain may be referred to herein as D1-HCDR1, D1-HCDR2, and D1-HCDR3; and the CDRs of the second antigen-binding domain may be referred to herein as D2-HCDR1, D2-HCDR2, and D2-HCDR3.

In certain exemplary embodiments, the isolated bispecific antigen binding molecule comprises a first antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 2; and (b) three light chain complementarity determining regions (LCDR1, LCDR2 and LCDR3) contained within a light chain variable region (LCVR) comprising the amino acid sequence of SEQ ID NO: 18. In some cases, the isolated bispecific antigen binding molecule comprises a first antigen binding domain comprising an HCDR1 comprising the amino acid sequence of SEQ ID NO: 4, a HCDR2 comprising the amino acid sequence of SEQ ID NO: 6, and a HCDR3 comprising the amino acid sequence of SEQ ID NO: 8. In some cases, the isolated bispecific antigen-binding molecule comprises a first antigen binding domain comprising a LCDR1 comprising the amino acid sequence of SEQ ID NO: 20, a LCDR2 comprising the amino acid sequence of AAS, and a LCDR3 comprising the amino acid sequence of SEQ ID NO: 24. In some cases, the first antigen-binding domain comprises a HCVR comprising the amino acid sequence of SEQ ID NO: 2, and a LCVR comprising the amino acid sequence of SEQ ID NO: 18.

In certain exemplary embodiments, the isolated bispecific antigen-binding molecule comprises a second antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 10; and (b) three light chain complementarity determining regions (LCDR1, LCDR2 and LCDR3) contained within a light chain variable region (LCVR) comprising the amino acid sequence of SEQ ID NO: 18. In some cases, the second antigen-binding domain comprises: a HCDR1 comprising the amino acid sequence of SEQ ID NO: 12; a HCDR2 comprising the amino acid sequence of SEQ ID NO: 14; and a HCDR3 comprising the amino acid sequence of SEQ ID NO: 16. In some cases, the second antigen-binding domain comprises a LCDR1 comprising the amino acid sequence of SEQ ID NO: 20, a LCDR2 comprising the amino acid sequence of AAS, and a LCDR3 comprising the amino acid sequence of SEQ ID NO: 24. In some cases, the second antigen-binding domain comprises an HCVR comprising the amino acid sequence of SEQ ID NO: 10, and an LCVR comprising the amino acid sequence of SEQ ID NO: 18.

In certain exemplary embodiments, the isolated bispecific antigen-binding molecule comprises a first antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 32; and (b) three light chain complementarity determining regions (LCDR1, LCDR2 and LCDR3) contained within a light chain variable region (LCVR) comprising the amino acid sequence of SEQ ID NO: 48. In some cases, the isolated bispecific antigen binding molecule comprises a HCDR1 comprising the amino acid sequence of SEQ ID NO: 34, a HCDR2 comprising the amino acid sequence of SEQ ID NO: 36, and a HCDR3 comprising the amino acid sequence of SEQ ID NO: 38. In some cases, the isolated bispecific antigen-binding molecule comprises a LCDR1 comprising the amino acid sequence of SEQ ID NO: 50, a LCDR2 comprising the amino acid sequence of GAS, and a LCDR3 comprising the amino acid sequence of SEQ ID NO: 54. In some cases, the first antigen-binding domain comprises a HCVR comprising the amino acid sequence of SEQ ID NO: 32, and a LCVR comprising the amino acid sequence of SEQ ID NO: 48.

In certain exemplary embodiments, the isolated bispecific antigen-binding molecule comprises a second antigen-binding domain that comprises: (a) three heavy chain complementarity determining regions (HCDR1, HCDR2 and HCDR3) contained within a heavy chain variable region (HCVR) comprising the amino acid sequence of SEQ ID NO: 40; and (b) three light chain complementarity determining regions (LCDR1, LCDR2 and LCDR3) contained within a light chain variable region (LCVR) comprising the amino acid sequence of SEQ ID NO: 48. In some cases, the second antigen-binding domain comprises: a HCDR1 comprising the amino acid sequence of SEQ ID NO: 42; a HCDR2 comprising the amino acid sequence of SEQ ID NO: 44; and a HCDR3 comprising the amino acid sequence of SEQ ID NO: 46. In some cases, the second antigen-binding domain comprises a LCDR1 comprising the amino acid sequence of SEQ ID NO: 50, a LCDR2 comprising the amino acid sequence of GAS, and a LCDR3 comprising the amino acid sequence of SEQ ID NO: 54. In some cases, the second antigen-binding domain comprises: an HCVR comprising the amino acid sequence of SEQ ID NO: 40, and an LCVR comprising the amino acid sequence of SEQ ID NO: 48.

In certain exemplary embodiments, the isolated bispecific antigen-binding molecule comprises: (a) a first antigen-binding domain comprising an HCDR1 amino acid sequence of SEQ ID NO: 4, a HCDR2 amino acid sequence of SEQ ID NO: 6, and a HCDR3 amino acid sequence of SEQ ID NO: 8; and (b) a second antigen binding domain comprising an HCDR1 amino acid sequence of SEQ ID NO: 12; a HCDR2 amino acid sequence of SEQ ID NO: 14; and a HCDR3 amino acid sequence of SEQ ID NO: 16. In some cases, the isolated bispecific antigen-binding molecule comprises a LCDR1 amino acid sequence of SEQ ID NO: 20, a LCDR2 amino acid sequence of AAS, and a LCDR3 amino acid sequence of SEQ ID NO: 24.

In certain exemplary embodiments, the isolated bispecific antigen-binding molecule comprises: (a) a first antigen-binding domain comprising an HCDR1 amino acid sequence of SEQ ID NO: 34, a HCDR2 amino acid sequence of SEQ ID NO: 36, and a HCDR3 amino acid sequence of SEQ ID NO: 38; and (b) a second antigen binding domain comprising an HCDR1 amino acid sequence of SEQ ID NO: 42; a HCDR2 amino acid sequence of SEQ ID NO: 44; and a HCDR3 amino acid sequence of SEQ ID NO: 46. In some cases, the isolated bispecific antigen-binding molecule comprises a LCDR1 amino acid sequence of SEQ ID NO: 50, a LCDR2 amino acid sequence of GAS, and a LCDR3 amino acid sequence of SEQ ID NO: 54.

In certain exemplary embodiments, the isolated bispecific antigen-binding molecule comprises: (a) a first antigen-binding domain that comprises an HCDR1 amino acid sequence of SEQ ID NO: 4, an HCDR2 amino acid sequence of SEQ ID NO: 6, and a HCDR3 amino acid sequence of SEQ ID NO: 8; an LCDR1 amino acid sequence of SEQ ID NO: 20, a LCDR2 amino acid sequence of AAS, and a LCDR3 amino acid sequence of SEQ ID NO: 24; and (b) a second antigen binding domain that comprises an HCDR1 amino acid sequence of SEQ ID NO: 12; an HCDR2 amino acid sequence of SEQ ID NO: 14; and an HCDR3 amino acid sequence of SEQ ID NO: 16; an LCDR1 amino acid sequence of SEQ ID NO: 20, an LCDR2 amino acid sequence of AAS, and an LCDR3 amino acid sequence of SEQ ID NO: 24. In some cases, the isolated bispecific antigen-binding molecule comprises: (a) a first antigen binding domain that comprises an HCVR amino acid sequence of SEQ ID NO: 2, and a LCVR amino acid sequence of SEQ ID NO: 18; and (b) a second antigen binding domain that comprises a HCVR amino acid sequence of SEQ ID NO: 10, and a LCVR amino acid sequence of SEQ ID NO: 18.

In certain exemplary embodiments, the isolated bispecific antigen-binding molecule comprises: (a) a first antigen-binding domain that specifically binds human CD38, and comprises the CDRs of a HCVR comprising an amino acid sequence selected from the group consisting of SEQ ID NOs: 2 and 32, and the CDRs of a LCVR comprising an amino acid sequence selected from the group consisting of SEQ ID NO: 18 and 48; and (b) a second antigen-binding domain that specifically binds human CD28. In some cases, the first antigen-binding domain comprises the CDRs from a HCVR/LCVR amino acid sequence pair selected from the group consisting of SEQ ID NOs: 2/18 and 32/48. In some cases, the first antigen-binding domain comprises HCDR1-HCDR2-HCDR3-LCDR1-LCDR2-LCDR3 domains, respectively, selected from the group consisting of SEQ ID NOs: 4-6-8-20-AAS-24 and 34-36-38-50-GAS-54. In some cases, the first antigen-binding domain comprises an HCVR/LCVR amino acid sequence pair selected from the group consisting of SEQ ID NOs: 2/18 and 32/48. In some cases, the second antigen-binding domain comprises an HCVR/LCVR amino acid sequence pair selected from the group consisting of SEQ ID NOs: 10/18 and 40/48.

In certain exemplary embodiments, the isolated bispecific antigen binding molecule competes for binding to CD38, or binds to the same epitope on CD38 as a reference antibody, wherein the reference antibody comprises an antibody or antigen-binding fragment thereof, or a bispecific anti-CD38/CD28 antibody disclosed herein.

In certain exemplary embodiments, the isolated bispecific antigen binding molecule competes for binding to human CD3, or binds to the same epitope on human CD3 as a reference antibody, wherein the reference antibody comprises an antibody or antigen-binding fragment thereof, or a bispecific anti-CD38/CD28 antibody disclosed herein.

The bispecific antigen-binding molecules discussed above or herein may be bispecific antibodies. In some cases, the bispecific antibody comprises a human IgG heavy chain constant region. In some cases, the human IgG heavy chain constant region is isotype IgG1. In some cases, the human IgG heavy chain constant region is isotype IgG4. In various embodiments, the bispecific antibody comprises a chimeric hinge that reduces Fcγ receptor binding relative to a wild-type hinge of the same isotype.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab2 bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present disclosure also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V821 (by IMGT; D356E, L358M, N384S, K392N, V397M, and V4221 by EU) in the case of IgG1 antibodies; N44S, K52N, and V821 (IMGT; N384S, K392N, and V4221 by EU) in the case of IgG2 antibodies; and Q15R, N44S, K52N, V57M, R69K, E79Q, and V821 (by IMGT; Q355R, N384S, K392N, V397M, R409K, E419Q, and V4221 by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived).

Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

pH-Dependent Binding

The present invention includes anti-CD38 antibodies, anti-CD28 antibodies, and anti-CD38 x anti-CD28 bispecific antigen-binding molecules, with pH-dependent binding characteristics. For example, an anti-CD38 antibody of the present invention may exhibit reduced binding to CD38 at acidic pH as compared to neutral pH. Alternatively, anti-CD38 antibodies of the invention may exhibit enhanced binding to CD38 at acidic pH as compared to neutral pH. The expression "acidic pH" includes pH values less than about 6.2, e.g., about 6.0, 5.95, 5,9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD38 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD38 antibodies, anti-CD28 antibodies, and anti-CD38 x anti-CD28 bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-CD38 antibodies, anti-CD28 antibodies, and anti-CD38 x anti-CD28 bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human CD38 and/or CD28 with high affinity (e.g., nanomolar or sub-nanomolar Ko values).

According to certain embodiments, the present invention includes antibodies, antigen-binding fragments of antibodies, and bispecific antibodies that bind human CD38 (e.g., at 25° C.) with a $K_D$ of less than about 10 nM as measured by surface plasmon resonance, e.g., using an assay format as defined in Example 5 herein. In certain embodiments, the antibodies or antigen-binding fragments of the present invention bind CD38 with a $K_D$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance, e.g., using an assay format as defined in Example 5 herein, or a substantially similar assay.

According to certain embodiments, the present invention includes antibodies, antigen-binding fragments of antibodies, and bispecific antibodies that bind human CD28 (e.g., at 25° C.) with a $K_D$ of less than about 26 nM as measured by surface plasmon resonance, e.g., using an assay format as defined in Example 5 herein. In certain embodiments, the antibodies or antigen-binding fragments of the present invention bind CD28 with a $K_p$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance, e.g., using an assay format as defined in Example 5 herein, or a substantially similar assay. The present disclosure also includes antibodies and antigen-binding fragments thereof that bind CD38 with a dissociative half-life ($t\frac{1}{2}$) of greater than about 8 minutes or greater than about 15 minutes as measured by surface plasmon resonance at 25° C., e.g., using an assay format as defined in Example 5 herein, or a substantially similar assay. In certain embodiments, the antibodies or antigen-binding fragments of the present invention bind CD38 with a $t\frac{1}{2}$ of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C., e.g., using an assay format as defined in Example 5 herein, or a substantially similar assay. The present invention includes bispecific antigen-binding molecules (e.g., bispecific antibodies which bind CD38 with a of greater than about 10 minutes as measured by surface plasmon resonance at 25° C., e.g., using an assay format as defined in Example 5 herein, or a substantially similar assay.

The present disclosure also includes antibodies and antigen-binding fragments thereof that bind CD28 with a dissociative half-life ($t\frac{1}{2}$) of greater than about 5 minutes or greater than about 18 minutes as measured by surface plasmon resonance at 25° C., e.g., using an assay format as defined in Example 5 herein, or a substantially similar assay. In certain embodiments, the antibodies or antigen-binding fragments of the present invention bind CD28 with a t1/2 of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C., e.g., using an assay format as defined in Example 5 herein, or a substantially similar assay. The present invention includes bispecific antigen-binding molecules (e.g., bispecific antibodies which bind CD38 with a of greater than about 10 minutes as measured by surface plasmon resonance at 25° C., e.g., using an assay format as defined in Example 5 herein, or a substantially similar assay.

The present disclosure also includes antibodies and antigen-binding fragments thereof which bind specifically to human cell lines which express endogenous CD38 (e.g., NCI-H929, MOLP-8, or WSU-DLCL2 tumor cells) as determined by the in vivo xenogeneic tumor studies as set forth in Examples 9 through 14 or a substantially similar assay.

The present disclosure also includes anti-CD38 x anti-CD28 bispecific antigen-binding molecules which exhibit one or more characteristics selected from the group consisting of: (a) inhibiting tumor growth in immunocompromised mice bearing human multiple myeloma xenografts; (b) suppressing tumor growth of established tumors in immunocompromised mice bearing human multiple myeloma xenografts (see, e.g., Examples 9 through 14), and (c) suppressing tumor growth of syngeneic melanoma cells engineered to express human CD38 in immunocompetent mice.

The present disclosure includes bispecific antigen-binding molecules (e.g., bispecific antibodies) which are capable of simultaneously binding to human CD38 and a human CD28. The extent to which a bispecific antigen-binding molecule binds cells that express CD38 and/or CD28 can be assessed by fluorescence activated cell sorting (FACS).

For example, the present invention includes antibodies, antigen-binding fragments, and bispecific antibodies thereof which specifically bind human T-cell lines which express CD38 but do not express CD28, and/or BCMA-expressing cells.

The present disclosure includes antibodies, antigen-binding fragments, and bispecific antibodies thereof that bind human CD38 and/or CD28 and induce T cell activation.

The present invention includes anti-CD38 x anti-CD28 bispecific antigen-binding molecules which are capable of depleting or reducing tumor antigen-expressing cells in a subject (see, e.g., Examples 9 through 12, or a substantially similar assay). For example, according to certain embodiments, anti-CD38 x anti-CD28 bispecific antigen-binding molecules are provided, wherein a single administration, or multiple administrations, of 0.04 mg/kg, 0.4 mg/kg, or 4 mg/kg of the bispecific antigen-binding molecule to a subject causes a reduction in the number of CD38-expressing cells in the subject (e.g., tumor growth in the subject is suppressed or inhibited).

Epitope Mapping and Related Technologies

The epitope on CD38 and/or CD28 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD38 or CD28 protein. Alternatively, the epitope may consist of a plurality of non-contiguous amino acids (or amino acid sequences) of CD38 or CD28.

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described in Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267 (2): 252-259; Engen and Smith (2001) *Anal. Chem.* 73: 256A-265A. X-ray crystallography of the antigen/antibody complex may also be used for epitope mapping purposes.

Provided herein are anti-CD38 antibodies that bind to the same epitope as any of the specific exemplary antibodies described herein (e.g. antibodies comprising any of the amino acid sequences as set forth in Table 1 herein). Likewise, the present invention also includes anti-CD38 antibodies that compete for binding to CD38 with any of the specific exemplary antibodies described herein (e.g. antibodies comprising any of the amino acid sequences as set forth in Table 1 herein).

Provided herein are anti-CD28 antibodies that bind to the same epitope as any of the specific exemplary antibodies described herein (e.g. antibodies comprising any of the amino acid sequences as set forth in Table 4 herein). Likewise, the present invention also includes anti-CD28 antibodies that compete for binding to CD28 with any of the specific exemplary antibodies described herein (e.g. antibodies comprising any of the amino acid sequences as set forth in Table 4 herein).

Likewise, the provided herein are bispecific antigen-binding molecules comprising a first antigen-binding domain that specifically binds human CD38, and a second antigen binding domain that specifically binds human CD28, wherein the first antigen-binding domain competes for binding to CD38 with any of the specific exemplary CD38-specific antigen-binding domains described herein, and/or wherein the second antigen-binding domain competes for binding to CD28 with any of the specific exemplary CD28-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD38 (or CD28) as a reference bispecific antigen-binding molecule of the present invention, the reference bispecific molecule is first allowed to bind to a CD38 protein (or CD28 protein). Next, the ability of a test antibody to bind to the CD38 (or CD28) molecule is assessed. If the test antibody is able to bind to CD38 (or CD28) following saturation binding with the reference bispecific antigen-binding molecule, it can be concluded that the test antibody binds to a different epitope of CD38 (or CD28) than the reference bispecific antigen-binding molecule. On the other hand, if the test antibody is not able to bind to the CD38 (or CD28) molecule following saturation binding with the reference bispecific antigen-binding molecule, then the test antibody may bind to the same epitope of CD38 (or CD28) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD38 protein (or CD28 protein) under saturating conditions followed by assessment of binding of the test antibody to the CD38 (or CD28) molecule. In a second orientation, the test antibody is allowed to bind to a CD38 (or CD28) molecule under saturating conditions followed by assessment of binding of the reference antigen-binding molecule to the CD38 (or CD28) molecule. If, in both orientations, only the first (saturating) antigen-binding molecule is capable of binding to the CD38 (or CD28) molecule, then it is concluded that the test antibody and the reference antigen-binding molecule compete for binding to CD38 (or CD28). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD38 and CD28), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD38 or CD28) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind CD38 and/or CD28. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD28 but not to CD28 from other species. Also provided are antigen-binding molecules which bind to human CD38, but not to CD38 from other species. The present invention also includes antigen-binding molecules that bind to human CD28 and to CD38 from one or more non-human species; and/or antigen-binding molecules that bind to human CD28 and to CD28 from one or more non-human species.

According to certain exemplary embodiments of the invention, antigen-binding molecules are provided which bind to human CD38 and/or human CD28 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD38 and/or CD28. For example, in particular exemplary embodiments of the disclosed herein, bispecific antigen-binding molecules are provided comprising a first antigen-binding domain that binds human CD38 and cynomolgus CD38, and a second antigen-binding domain that specifically binds human CD28, or bispecific antigen-binding molecules comprising a first antigen-binding domain that binds human CD38 and cynomolgus CD38, and a second antigen-binding domain that specifically binds human CD28.

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic™ Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPENT, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTART pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD38 antibody, an anti-CD28 antibody, or antigen-binding fragment thereof, or a bispecific antigen-binding molecule that specifically binds CD38 and CD28. The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in CD38 activity or a depletion of CD38+ cells (e.g., multiple myeloma cells).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD38 antibodies, the anti-CD28 antibodies, or the anti-CD38 x anti-CD28 bispecific antigen-binding molecules of the present invention may be used for the treatment, prevention and/or amelioration of any disease or disorder associated with or mediated by CD38 and/or BCMA expression or activity or the proliferation of CD38+ and/or BCMA+ cells. The mechanism of action by which the therapeutic methods of the invention are achieved include killing of the cells expressing CD38 in the presence of effector cells, for example, by CDC, apoptosis, ADCC, phagocytosis, or by a combination of two or more of these mechanisms. Cells expressing CD38 which can be inhibited or killed using the bispecific antigen-binding molecules of the invention include, for example, multiple myeloma cells.

The antibodies and antigen-binding molecules of the present disclosure may be used to treat a disease or disorder associated with CD38 expression including, e.g. multiple myeloma, B-cell leukemia, hepatocellular carcinoma, non-small cell lung cancer, melanoma, pancreatic ductal adenocarcinoma, glioma, or breast cancer, or another cancer characterized in part by having CD38+ cells.

According to certain embodiments, the anti-CD38 x anti-CD28 antibodies or anti-CD38 antibodies or anti-CD28 antibodies are useful for treating tumor cells expressing, for example, BCMA or CD20. The antigen-binding molecules provided herein may also be used to treat a disease or disorder associated with BCMA expression including, e.g., a cancer including multiple myeloma or other B-cell or plasma cell cancers, such as Waldenström's macroglobulinemia, Burkitt lymphoma, and diffuse large B-Cell lymphoma, Non-Hodgkin's lymphoma, chronic lymphocytic leukemia, follicular lymphoma, mantle cell lymphoma, marginal zone lymphoma, lymphoplasmacytic lymphoma, and Hodgkin's lymphoma. According to certain embodiments of the present invention, the anti-CD38 x anti-CD28 antibodies or anti-CD38 antibodies or anti-CD28 antibodies are useful for treating a patient afflicted with multiple myeloma. According to other related embodiments of the invention, methods are provided comprising administering an anti-CD38 x anti-CD28 bispecific antibody provided herein in combination with an anti-BCMA antibody, or an anti-BCMA x anti-CD3 bispecific antigen-binding molecule, or an anti-CD20 x anti-CD3 bispecific antigen-binding molecule as disclosed herein to a patient who is afflicted with cancer cells expressing BCMA or CD20. Analytic/diagnostic methods known in the art, such as tumor scanning, etc., may be used to ascertain whether a patient harbors multiple myeloma or another B-cell lineage cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with CD38 expression (e.g., multiple myeloma) comprising administering one or more of the anti-CD38 antibodies, anti-CD28 antibodies, or bispecific antigen-binding molecules described elsewhere herein to a subject after the subject has been determined to have multiple myeloma. For example, the present invention includes methods for treating multiple myeloma comprising administering an anti-CD38 antibody, an anti-CD28 antibody, or an anti-CD38 x anti-CD28 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject.). In some embodiments, the second therapeutic agent comprises steroids. In some embodiments, the second therapeutic agent comprises targeted therapies including thalidomide, lenalidomide, and bortezomib, which are therapies approved to treat newly diagnosed patients. Lenalidomide, pomalidomide, bortezomib, carfilzomib, panobinostat, ixazomib, elotuzumab, and daratumumab are examples of a second therapeutic agent effective for treating recurrent myeloma.

In some embodiments, the second therapeutic is an anti-BCMAxCD3 bispecific antibody. Illustrative anti-BCMAxCD3 bispecific antibodies are disclosed in U.S. 2020/0024356 incorporated by reference herein. An exemplary anti-BCMAxCD3 bispecific antibody, as disclosed in U.S. 2020/0024356, is REGN5458, which comprises an anti-BCMA binding domain having an HCVR/LCVR of SEQ ID NOs: 66/82 and an anti-CD3 binding domain having an HCVR/LCVR of SEQ ID NOs: 90/82 as provided in the U.S. 2020/0024356 sequence listing. In some embodiments, the second therapeutic is an anti-CD20xCD3 bispecific antibody. Illustrative anti-CD20xCD3 bispecific antibodies are disclosed in U.S. Pat. No. 9,657,102, incorporated by reference herein. An exemplary anti-CD20xCD3 bispecific antibody disclosed in U.S. Pat. No. 9,657,102, is REGN1979, which comprises an anti-CD20 binding domain having an HCVR/LCVR of SEQ ID NOs: 1242/1258 and an anti-CD3 binding domain having an HCVR/LCVR of SEQ ID NOs: 1250/1258 as provided in the U.S. Pat. No. 9,657,102 sequence listing.

In certain embodiments the second therapeutic agent is a regimen comprising radiotherapy or a stem cell transplant. In certain embodiments, the second therapeutic agent may be an immunomodulatory agent. In certain embodiments, the second therapeutic agent may be a proteasome inhibitor. including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD38 x anti-CD28 bispecific antigen-binding molecule as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab (REGN2810; see the PD-1 inhibitor set forth in U.S. Pat. No. 9,987,500, having an HCVR/LCVR pair of SEQ ID NOs: 162/170.). In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvlll, cMet, IGF1R, B-raf, PDGFR-$\alpha$, PDGFR-$\beta$, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD38 antibody, an anti-CD28 antibody, or a bispecific antigen-binding molecule that specifically binds CD38 and CD28) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1 ½, 2, 2 ½, 3, 3 ½, 4, 4 ½, 5, 5 ½, 6, 6 ½, 7, 7 ½, 8, 8 ½, 9, 9 ½, 10, 10 ½, 11, 11 ½, 12, 12 ½, 13, 13 ½, 14, 14 ½, 15, 15 ½, 16, 16 ½, 17, 17 ½, 18, 18 ½, 19, 19 ½, 20, 20 ½, 21, 21 ½, 22, 22 ½, 23, 23 ½, 24, 24 ½, 25, 25 ½, 26, 26 ½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD38 antibody, an anti-CD28 antibody, or a bispecific antigen-binding molecule that specifically binds CD38 and CD28). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-CD38 antibodies disclosed herein may be used to detect and/or measure CD38, or CD38-expressing cells in a sample, e.g., for diagnostic purposes. For example, an anti-CD38 antibody, or fragment thereof, may be used to diagnose a condition or disease characterized by aberrant expression (e.g., over-expression, under-expression, lack of expression, etc.) of CD38. Exemplary diagnostic assays for CD38 may comprise, e.g., contacting a sample, obtained from a patient, with an anti-CD38 antibody disclosed herein, wherein the anti-CD38 antibody is labeled with a detectable label or reporter molecule. Alternatively, an unlabeled anti-CD38 antibody can be used in diagnostic applications in combination with a secondary antibody which is itself detectably labeled. The detectable label or reporter molecule can be a radioisotope, such as $^{3}$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-CD38 antibodies of the invention includes 89Zr-labeled, such as $^{89}$Zr-desferrioxamine-labeled, antibody for the purpose of noninvasive identification and tracking of tumor cells in a subject (e.g. positron emission tomography (PET) imaging). (See, e.g., Tavare, R. et al. Cancer Res. 2016 Jan. 1; 76 (1): 73-82; and Azad, B B. et al. Oncotarget. 2016 Mar. 15; 7 (11): 12344-58.) Specific exemplary assays that can be used to detect or measure CD38 in a sample include enzyme-linked immunosorbent assay (ELISA), radioimmunoassay (RIA), and fluorescence-activated cell sorting (FACS).

Samples that can be used in CD38 diagnostic assays according to the present invention include any tissue or fluid sample obtainable from a patient which contains detectable quantities of CD38 protein, or fragments thereof, under normal or pathological conditions. Generally, levels of CD38 in a particular sample obtained from a healthy patient (e.g., a patient not afflicted with a disease or condition associated with abnormal CD38 levels or activity) will be measured to initially establish a baseline, or standard, level of CD38. This baseline level of CD38 can then be compared against the levels of CD38 measured in samples obtained from individuals suspected of having a CD38 related disease (e.g., a tumor containing CD38-expressing cells) or condition.

Devices

The present invention also provides a vessel (e.g., a vial or chromatography column) or injection device (e.g., syringe, pre-filled syringe or autoinjector) comprising a bispecific antigen binding molecule (e.g., pharmaceutical formulation thereof) set forth herein. The vessel or injection device may be packaged into a kit.

An injection device is a device that introduces a substance into the body of a subject (e.g., a human) via a parenteral route, e.g., intraocular, intravitreal, intramuscular, subcutaneous or intravenous. For example, an injection device may be a syringe (e.g., pre-filled with the pharmaceutical formulation, such as an auto-injector) which, for example, includes a cylinder or barrel for holding fluid to be injected (e.g., comprising the antibody or fragment or a pharmaceutical formulation thereof), a needle for piecing skin, blood vessels or other tissue for injection of the fluid; and a plunger for pushing the fluid out of the cylinder and through the needle bore and into the body of the subject.

A pharmaceutical composition provided herein can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and Ill (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTART pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park III.), to name only a few.

Provided herein are methods for administering a bispecific antigen binding molecule of the present disclosure comprising introducing e.g., injecting, the molecule into the body of the subject, e.g., with an injection device.

Expression Methods

Provided herein are recombinant methods for making a bispecific antigen binding molecule of the present invention, or an immunoglobulin chain thereof, comprising (i) introducing, into a host cell, one or more polynucleotides encoding light and/or heavy immunoglobulin chains of such a bispecific antigen binding molecule, for example, wherein the polynucleotide is in a vector; and/or integrates into the host cell chromosome and/or is operably linked to a promoter; (ii) culturing the host cell (e.g., mammalian, fungal, Chinese hamster ovary (CHO), *Pichia* or *Pichia pastoris*) under conditions favorable to expression of the polynucleotide and, (iii) optionally, isolating the bispecific antigen binding molecule or immunoglobulin chain from the host cell and/or medium in which the host cell is grown. The product of such a method also forms part of the present disclosure along with a pharmaceutical composition thereof.

In an embodiment, a method for making a bispecific antigen binding molecule includes a method of purifying the molecule, e.g., by column chromatography, precipitation and/or filtration. The product of such a method also forms part of the present disclosure along with a pharmaceutical composition thereof.

Host cells comprising a bispecific antigen binding molecule of the present disclosure and/or a polynucleotide encoding immunoglobulin chains of such a molecule (e.g., in a vector) are also part of the present invention. Host cells include, for example, mammalian cells such as Chinese hamster ovary (CHO) cells and fungal cells such as *Pichia* cells (e.g., *P. pastoris*).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Control antibodies used in Examples 9 through 12 include a CD3-binding negative control bispecific Ab (H4sH17664D) and a CD28-binding negative control bispecific Ab (bsAb5671).

Two signals, "signal 1" and "signal 2", are required for proper T cell activation. "Signal 1" is induced by binding of the T cell receptor (TCR) on T cells to peptide-bound major histocompatibility complex (MHC) molecules on antigen presenting cells (APCs). "Signal 2" is provided by engaging the co-stimulatory CD28 receptor on T cells with its ligands cluster of differentiation 80 or 86 (CD80/CD86) present on APCs. Activation of T cells, i.e. "signal 1", can be provided by treatment with a tumor-associated antigen (TAA) xCD3 bispecific antibody such as a CD20xCD3 bispecific antibody (bsAb1979) or a BCMAxCD3 bispecific antibody (bsAb5458).

Isotype controls mentioned throughout include IsoC-1, also referred to as IgG4P-PVA, an isotype control to the CD20xCD3 bispecific antibody (bsAb1979), and IsoC-2, also referred to as IgG4P, an isotype control to cemiplimab.

Example 1. Generation of Anti-CD38 Antibodies and Anti-CD28 Antibodies

Anti-CD38 antibodies were obtained by immunizing a genetically engineered mouse comprising DNA encoding human immunoglobulin heavy and kappa light chain variable regions with cells expressing CD38 or with DNA encoding CD38. The antibody immune response was monitored by a CD38-specific immunoassay. When a desired immune response was achieved splenocytes were harvested and fused with mouse myeloma cells to preserve their viability and form hybridoma cell lines. The hybridoma cell lines were screened and selected to identify cell lines that produce CD38-specific antibodies. Using this technique several anti-CD38 chimeric antibodies (i.e., antibodies possessing human variable domains and mouse constant domains) were obtained. In addition, several fully human anti-CD38 antibodies were isolated directly from antigen-positive B cells without fusion to myeloma cells, as described in US 2007/0280945A1.

Likewise, anti-CD28 antibodies were obtained by immunizing a genetically engineered mouse comprising DNA encoding human immunoglobulin heavy and kappa light chain variable regions with cells expressing CD28 or with DNA encoding CD28. The antibody immune response was monitored by a CD28-specific immunoassay. When a desired immune response was achieved splenocytes were harvested and fused with mouse myeloma cells to preserve their viability and form hybridoma cell lines. The hybridoma cell lines were screened and selected to identify cell lines that produce CD28-specific antibodies. Using this technique several anti-CD28 chimeric antibodies (i.e., antibodies possessing human variable domains and mouse constant domains) were obtained. In addition, several fully human anti-CD28 antibodies were isolated directly from antigen-positive B cells without fusion to myeloma cells, as described in US 2007/0280945A1.

The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-CD38 antibody or fully human anti-CD28 antibody. While the constant region selected may vary according to specific use, high affinity antigen-binding and target specificity characteristics reside in the variable region.

Certain biological properties of the exemplary anti-CD38 antibodies and anti-CD28 antibodies generated in accordance with the methods of this Example, and bispecific antibodies constructed therefrom, are described in detail in the Examples set forth below.

Example 2. Heavy and Light Chain Variable Region Amino Acid and Nucleic Acid Sequences of anti-CD38 Antibodies Table 1 sets forth the amino acid sequence identifiers of the heavy and light chain variable regions and CDRs of selected anti-CD38 antibodies of the invention. The corresponding nucleic acid sequence identifiers are set forth in Table 2. The complete heavy chain and light chain amino acid and nucleic acid sequences are provided in Table 3.

The antibodies provided herein can be of any isotype. For example, anti-CD38 antibodies of the invention may comprise variable domain and CDR sequences as set forth in Tables 1 and 2 and a human Fc domain of isotype IgG4, IgG1, etc. For certain applications or experiments the Fc domain may be a mouse Fc domain. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)-which are indicated by the numerical identifiers shown in Tables 1 and 2-will remain the same, and the binding properties are expected to be identical or substantially similar regardless of the nature of the Fc domain.

TABLE 1

| Anti-CD38 Amino Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb1 | 2 | 4 | 6 | 8 | 18 | 20 | AAS | 24 |
| mAb2 | 32 | 34 | 36 | 38 | 48 | 50 | GAS | 54 |

TABLE 2

| Anti-CD38 Nucleic Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb1 | 1 | 3 | 5 | 7 | 17 | 19 | gctgcatcc | 23 |
| mAb2 | 31 | 33 | 35 | 37 | 47 | 49 | ggggcaagt | 53 |

TABLE 3

| Anti-CD38 Heavy Chain and Light Chain Sequence Identifiers | | | |
|---|---|---|---|
| | SEQ ID NOs: | | |
| Antibody Designation | HC Amino Acid | LC Amino Acid | HC Nucleic Acid | LC Nucleic Acid |
| mAb1 | 26 | 30 | 25 | 29 |
| mAb2 | 56 | 60 | 55 | 59 |

Example 3: Heavy and Light Chain Variable Region Amino Acid and Nucleic Acid Sequences of anti-CD28 Antibodies Table 4 sets forth the amino acid sequence identifiers of the heavy and light chain variable regions and CDRs of selected anti-CD28 antibodies of the invention. The corresponding nucleic acid sequence identifiers are set forth in Table 5. The complete heavy chain and light chain amino acid and nucleic acid sequences are provided in Table 6.

TABLE 4

| Anti-CD28 Amino Acid Sequence Identifiers | | | | | | | |
|---|---|---|---|---|---|---|---|
| Antibody | SEQ ID NOs: | | | | | | |
| Designation | HCVR | HCDR1 | HCDR2 | HCDR3 | LCVR | LCDR1 | LCDR2 | LCDR3 |
| mAb3 | 10 | 12 | 14 | 16 | 18 | 20 | AAS | 24 |
| mAb4 | 40 | 42 | 44 | 46 | 48 | 50 | GAS | 54 |

TABLE 5

| Anti-CD28 Nucleic Acid Sequence Identifiers | | | | | | | |
| Antibody | SEQ ID NOs: | | | | | | |
| Designation | HCVR | HCDR1 | HCDR2 | HCDR3 | LCVR | LCDR1 | LCDR2 | LCDR3 |
|---|---|---|---|---|---|---|---|---|
| mAb3 | 9 | 11 | 13 | 15 | 17 | 19 | gctgcatcc | 23 |
| mAb4 | 39 | 41 | 43 | 45 | 47 | 49 | ggggcaagt | 53 |

TABLE 6

| Anti-CD28 Heavy Chain and Light Chain Sequence Identifiers | | | | |
| | SEQ ID NOs: | | | |
| Antibody Designation | HC Amino Acid | LC Amino Acid | HC Nucleic Acid | LC Nucleic Acid |
|---|---|---|---|---|
| mAb3 | 28 | 30 | 27 | 29 |
| mAb4 | 58 | 60 | 57 | 59 |

The antibodies of the present invention can be of any isotype. For example, anti-CD28 antibodies of the invention may comprise variable domain and CDR sequences as set forth in Tables 4 and 5 and a human Fc domain of isotype IgG4, IgG1, etc. For certain applications or experiments the Fc domain may be a mouse Fc domain. As will be appreciated by a person of ordinary skill in the art, an antibody having a particular Fc isotype can be converted to an antibody with a different Fc isotype (e.g., an antibody with portion of the bispecific molecule is useful for activating T-cells. The simultaneous binding of CD38 on a tumor cell and CD28 on a T-cell facilitates directed killing (cell lysis) of the targeted tumor cell by the activated T-cell.

Bispecific antibodies comprising an anti-CD38-specific binding domain and an anti-CD28-specific binding domain were constructed using standard methodologies wherein a heavy chain and a light chain from an anti-CD38 antibody were combined with a heavy chain from an anti-CD28 antibody. In exemplified bispecific antibodies, the molecules were constructed utilizing a heavy chain from an anti-CD38 antibody, a heavy chain from an anti-CD28 antibody and a common light chain from the anti-CD38 antibody. In other instances, the bispecific antibodies may be constructed utilizing a heavy chain from an anti-CD28 antibody, a heavy chain from an anti-CD38 antibody and an antibody light chain known to be promiscuous or pair effectively with a variety of heavy chain arms.

A summary of the component parts of the antigen-binding domains of the various bispecific antibodies made in accordance with this Example is set forth in Table 7.

TABLE 7

| CD38 × CD28 Bispecific Antibody Components Summary | | | | | | | | | | | | |
| | Anti-CD38 (D1) SEQ ID NOs: | | | | Anti-CD28 (D2) SEQ ID NOs: | | | | Common Light Chain SEQ ID NOs: | | | |
| | HCVR | HCDR1 | HCDR2 | HCDR3 | HCVR | HCDR1 | HCDR2 | HCDR3 | LCVR | LCDR1 | LCDR2 | LCDR3 |
|---|---|---|---|---|---|---|---|---|---|---|---|---|
| | mAb1 | | | | mAb3 | | | | | | | |
| bsAb6031 | 2 | 4 | 6 | 8 | 10 | 12 | 14 | 16 | 18 | 20 | AAS | 24 |
| | mAb2 | | | | mAb4 | | | | | | | |
| bsAb7945 | 32 | 34 | 36 | 38 | 40 | 42 | 44 | 46 | 48 | 50 | GAS | 54 | a mouse IgG4 Fc can be converted to an antibody with a human IgG1, etc.), but in any event, the variable domains (including the CDRs)-which are indicated by the numerical identifiers shown in Tables 4 and 5-will remain the same, and the binding properties are expected to be identical or substantially similar regardless of the nature of the Fc domain.

Example 4: Generation of Bispecific Antibodies that Bind CD38 and CD28

Provided herein are bispecific antigen-binding molecules that bind CD28 and CD38; such bispecific antigen-binding molecules are also referred to herein as "anti-CD38 x anti-CD28" or "anti-CD28xanti-CD38" or "anti-CD38 x anti-CD28 bispecific molecules", or "anti-CD38/anti-CD28", or "CD38xCD28 bispecific molecules", or "CD38xCD28 bsAb". The anti-CD38 portion of the anti-CD38 x anti-CD28 bispecific molecule is useful for targeting tumor cells that express CD38, and the anti-CD28

Example 5: Biacore Binding Kinetics of Anti-CD38 Antibodies and Anti-CD28 Antibodies Surface Plasmon Resonance (SPR) kinetics were performed to determine kinetic parameters for CD38 and CD28 binding to the CD38xCD28 bispecific antibodies.

For CD38 kinetic determinations, SPR experiments were performed using a Biacore 3000 instrument at 25° C. Antibodies were captured for 37 seconds at a flow rate of 8 uL/min on a CM5 anti-humanFc-(bsAb2567)-coupled surface. Approximately 230 RU of each antibody were captured. Monomeric human CD38 with a c-terminal myc-myc-hexahistiine tag (hCD38.mmH, bsAb3305) at concentrations of 90, 30, 10, 3.33, 1.11, or 0.37 nM were injected over this surface for 5 minutes at a flow rate of 50 uL/min. Dissociation was measured for 10 minutes. The $K_D$ and t½ were calculated by fitting the double-referenced sensorgrams to a 1:1 binding model.

For CD28 kinetic determinations, SPR experiments were performed using a Biacore 3000 instrument at 25° C.

Dimeric human CD28 with a c-terminal mouse Fc tag (hCD28.mFc, bsAb2012) were captured for 37 seconds at a flow rate of 8 uL/min on a CM5 anti-mouseFc-(GE)-coupled surface. Approximately 150 RU of hCD28.mFc were captured. CD38xCD28 antibodies (bsAb7945 and bsAb6031) at concentrations of 90, 30, 10, 3.33, 1.11, or 0.37 nM were injected over this surface for 5 minutes at a flow rate of 50 uL/min. Dissociation was measured for 10 minutes. The $K_D$ and $t_{1/2}$ were calculated by fitting the double-referenced sensorgrams to a 1:1 binding model.

Binding kinetics parameters for hCD38.mmH and hCD28.mFc binding to different two CD38 x CD28 bispecific antibodies of the invention at 25° C. are shown in Tables 8 and 9. As shown in Table 8, the two bispecific antibodies bind human CD38 with a $K_D$ of less than about 10 nM; and in Table 9, bind human CD28 with a $K_D$ of less than about 26 nM.

TABLE 8

Binding Kinetics of hCD38.mmH to
CD38 x CD28 Bispecific Antibodies

| | | hCD38.mmH | | |
| bsAb # | ka ($M^{-1}$ $s^{-1}$) | kd ($s^{-1}$) | KD (M) | t1/2 (min) |
| --- | --- | --- | --- | --- |
| bsAb6031 | 1.06E+05 | 7.48E−04 | 7.08E−09 | 15.4 |
| bsAb7945 | 9.57E+05 | 1.44E−03 | 1.50E−09 | 8.0 |

TABLE 9

Binding Kinetics of hCD28.mFc to
CD38 x CD28 Bispecific Antibodies

| | | hCD28.mFc | | |
| bsAb # | ka ($M^{-1}$ $s^{-1}$) | kd ($s^{-1}$) | KD (M) | t1/2 (min) |
| --- | --- | --- | --- | --- |
| bsAb6031 | 5.74E+04 | 1.49E−03 | 2.59E−08 | 7.8 |
| bsAb7945 | 1.78E+05 | 2.36E−03 | 1.33E−08 | 4.9 |

Example 6: T-Cell Activation by CD38 x CD28
Bispecific Antibodies in the Presence of CD38+
HEK93 Cells or MOLP8 Cells Which
Endogenously Express BCMA As mentioned above, two signals, "signal 1" and "signal 2", are required for proper T cell activation. "Signal 1" is induced by binding of the T cell receptor (TCR) on T cells to peptide-bound major histocompatibility complex (MHC) molecules on antigen presenting cells (APCs). "Signal 2" is provided by engaging the co-stimulatory CD28 receptor on T cells with its ligands cluster of differentiation 80 or 86 (CD80/CD86) present on APCs (Martin et al. A 44 kilodalton cell surface homodimer regulates interleukin 2 production by activated human T lymphocytes. Journal of immunology, 1986; 136 (9): 3282-7; June et al. T-cell proliferation involving the CD28 pathway is associated with cyclosporine-resistant interleukin 2 gene expression. Molecular and cellular biology. 1987; 7 (12): 4472-81; Harding et al. CD28-mediated signalling co-stimulates murine T cells and prevents induction of anergy in T-cell clones. Nature. 1992; 356 (6370): 607-9). Therefore, activation of CD28 signaling provides a targeted approach to enhance existing TCR signaling.

CD38xCD28 bispecific antibodies provided herein were designed to mimic the natural ligands of CD28, by bridging CD38+ target cells with CD28+ T cells, to provide "signal 2" in order to enhance the activation of T cells in the presence of a "signal 1" provided by a Tumor-associated antigen (TAA) x CD3 bispecific antibody or an allogeneic response provided by the APC.

In this example, the ability of CD38xCD28 bispecific antibodies to activate human primary T-cells by engaging CD38 and CD28 to deliver "signal 2", as determined by IL2 release, IFNγ release, and T-cell proliferation, was evaluated in the presence of a human embryonic kidney cancer cell line engineered to express hCD20 and hCD38 (HEK293/hCD20/hCD38) using bsAb1979 (CD20xCD3) to serve as "signal 1." HEK293 cells expressing only hCD20 were included as a control to measure activity that may occur in the absence of CD38 on APC's. Additionally, a multiple myeloma cell line that endogenously expresses hCD38, MOLP8, was included in testing CD38xCD28 bispecific antibodies. As MOLP8 cells also endogenously express BCMA, bsAb5458 (BCMAxCD3) was included to serve as "signal 1." Of note, unlike HEK293 cells, MOLP8 cells are able to provide detectable allogeneic stimulation of T-cells, serving as "signal 1", in the absence CD3 stimulation provided by bsAb5458.

Isolation of Human Primary CD3+ T Cells:

Human peripheral blood mononuclear cells (PBMCs) were isolated from a healthy donor leukocyte pack from Precision for Medicine (Donor 555130) using the EasySep™ Direct Human PBMC Isolation Kit, following the manufacturers recommended protocol and frozen down. CD3+ T-cells were isolated from thawed PBMC's using an EasySep™ Human CD3+ T Cell Isolation Kit from StemCell Technologies and following the manufacturer's recommended instructions.

IL2 & IFNγ Release Assay:

Enriched CD3+ T-cells, resuspended in stimulation media, were added into 96-well round bottom plates at a concentration of $1\times10^5$ cells/well. Growth-arrested HEK293/hCD20/hCD38 or HEK293/hCD20 were added to CD3+ T-cells at a final concentration of $1\times10^4$ cells/well. Growth-arrested MOLP8 cells were added to CD3+ T-cells at a final concentration of $5\times10^4$ cells/well. Following addition of cells, a constant of 0.1 nM bsAb1979 or its matched isotype control (IsoC-1) was added to wells containing HEK293/hCD20/hCD38 or HEK293/hCD20. A constant of 0.5 nM bsAb5458 or IsoC-1 was added to wells containing MOLP8 cells. Subsequently, bsAb6031, bsAb7945, and IsoC-1 were titrated from 3 pM to 200 nM in a 1:4 dilution and added to wells. The final point of the 10-point dilution contained no titrated antibody. Plates were incubated for 48 hours at 37° C., 5% $CO_2$ and 5 μL total supernatant was removed and used for measuring IL2. At 72 hours 45 μL total supernatant was removed and 5 μL was used for measuring IFNγ. The amount of cytokine in assay supernatant was determined using AlphaLisa kits from PerkinElmer following the manufacturer's protocol. The cytokine measurements were acquired on Perkin Elmer's multilabel plate reader Envision and values were reported as pg/mL. All serial dilutions were tested in duplicate.

The $EC_{50}$ values of the antibodies were determined from a four-parameter logistic equation over a 10-point dose-response curve using GraphPad Prism™ software. Maximal IL2 & IFNγ is given as the mean max response detected within the tested dose range.

T-Cell Proliferation Assay:

After the final supernatant removal at 72 hours, 0.25 µCi/well of tritiated thymidine was added to wells and plates were incubated for 6 hours. Thymidine, and therefore tritium, will be incorporated at higher amounts into newly synthesized DNA of the dividing cells. After the 6 hour incubation, cells were harvested onto 96-well UniFilter plates and 30 µL of scintillation fluid was added to each well. Tritium incorporation was measured as counts per minute (CPM) using the Microplate Scintillation & Luminescence Counter TopCount NXT instrument. All serial dilutions were tested in duplicate.

The $EC_{50}$ values of the antibodies were determined from a four-parameter logistic equation over a 10-point dose-response curve using GraphPad Prism™ software. Maximal CPM is given as the mean max response detected within the tested dose range.

Results:

HEK293/hCD20 & HEK293/hCD20/hCD38

In the presence of target and "signal 1", provided by bsAb1979, CD38xCD28 antibody treatment (bsAb6031 and bsAb7945) led to a higher cytokine and proliferative response compared to their matched isotype control, IsoC-1.

However, in the absence of either target or "signal 1," CD38xCD28 antibody treatment did not enhance cytokine release from or proliferation of T-cells. See Tables 10, 11, and 12.

MOLP8

In the presence of allogeneic MOLP8 cells, and absence of bsAb5458, CD38xCD28 antibody treatment (bsAb6031 and bsAb7945), in comparison to matched isotype control, led to dose dependent increases in IL2 release and proliferation. While "signal 1" can be provided by allogeneic MOLP8 cells, the addition of bsAb5458, was also evaluated. Under these conditions CD38xCD28 antibody treatment (bsAb6031 and bsAb7945) led to dose dependent increases in IL2 release and IFNg release compared to matched isotype control, IsoC-1. As proliferation is a sensitive read-out, the addition of bsAb5458 in the absence of CD38xCD28, combined with the allogeneic stimulation that MOLP8 cells provide led to saturating signals for proliferation, preventing the impact of CD38xCD28 to be detected. See Tables 10, 11, and 12.

Thus, in the presence of "signal 1", CD38xCD28 bispecific antibodies activate human primary T-cells by delivering "signal 2", as determined by dose dependent increase in IL2 release and IFNγ release and T-cell proliferation.

TABLE 10

| | Maximum IL2 release and Potency values of Antibodies | | | | | |
| | HEK293/hCD20/hCD38 | | HEK293/hCD20 | | MOLP8 | |
| Antibodies | MAX (pg/mL) | $EC_{50}$ [M] | MAX (pg/mL) | $EC_{50}$ [M] | MAX (pg/mL) | $EC_{50}$ [M] |
| --- | --- | --- | --- | --- | --- | --- |
| bsAb6031 + TAAxCD3 | 1642 | 1.99E−10 | 48.01 | ND | 5864 | 1.02E−09 |
| bsAb6031 + IgG4$^{P}$ | 1 | ND | 1 | ND | 2821 | 6.53E−10 |
| bsAb7945 + TAAxCD3 | 3878 | 5.02E−12 | 416.4 | NC | 9109 | NC |
| bsAb7945 + IgG4$^{P}$ | 143.7 | 4.14E−08 | 48.85 | NC | 4880 | 9.71E−12 |
| IgG4$^{P-PVA}$ + TAAxCD3 | 7.221 | ND | 32.16 | ND | 152.3 | ND |
| IgG4$^{P-PVA}$ + IgG4$^{P}$ | 1 | ND | 1 | ND | 715.1 | ND |

Abbreviations:
ND: Not Determined;
NC: Not calculated because the data did not fit a 4-parameter logistic equation.

TABLE 11

| | Maximum IFNγ release and Potency values of Antibodies | | | | | |
| | HEK293/hCD20/hCD38 | | HEK293/hCD20 | | MOLP8 | |
| Antibodies | MAX (pg/mL) | $EC_{50}$ [M] | MAX (pg/mL) | $EC_{50}$ [M] | MAX (pg/mL) | $EC_{50}$ [M] |
| --- | --- | --- | --- | --- | --- | --- |
| bsAb6031 + TAAxCD3 | 1306 | 2.94E−10 | 1 | ND | 1578 | 7.48E−10 |
| bsAb6031 + IgG4$^{P}$ | 1 | ND | 1 | ND | 40.66 | NC |
| bsAb7945 + TAAxCD3 | 3120 | 1.23E−10 | 226.1 | NC | 1759 | 4.24E−12 |
| bsAb7945 + IgG4$^{P}$ | 1 | ND | 1 | ND | 90.52 | NC |
| IgG4$^{P-PVA}$ + TAAxCD3 | 1 | ND | 1 | ND | 1 | ND |
| IgG4$^{P-PVA}$ + IgG4$^{P}$ | 1 | ND | 1 | ND | 715.1 | ND |

Abbreviations:
ND: Not Determined;
NC: Not calculated because the data did not fit a 4-parameter logistic equation.

TABLE 12

| | | | | | | |
|---|---|---|---|---|---|---|
| | HEK293/hCD20/hCD38 | | HEK293/hCD20 | | MOLP8 | |
| Antibodies | MAX (CPM) | $EC_{50}$ [M] | MAX (CPM) | $EC_{50}$ [M] | MAX (CPM) | $EC_{50}$ [M] |
| bsAb6031 + TAAxCD3 | 5543 | 1.43E−10 | 2390 | ND | 6264 | ND |
| bsAb6031 + IgG4$^{P}$ | 86.5 | ND | 97 | ND | 1269 | 4.67E−10 |
| bsAb7945 + TAAxCD3 | 6627 | 8.94E−13 | 4162 | NC | 6682 | ND |
| bsAb7945 + IgG4$^{P}$ | 998 | 4.56E−08 | 245 | ND | 2369 | NC |
| IgG4$^{P\text{-}PVA}$ + TAAxCD3 | 842 | ND | 1825 | ND | 5446 | ND |
| IgG4$^{P\text{-}PVA}$ + IgG4$^{P}$ | 112.5 | ND | 74 | ND | 818.5 | ND |

Abbreviations:
ND: Not Determined;
NC: Not calculated because the data did not fit a 4-parameter logistic equation.

Example 7: Characterization of CD38xCD28 Bispecific Antibodies in Combination with Cemiplimab As mentioned above, CD38xCD28 bispecific antibodies were designed to mimic the natural ligands of CD28, by bridging CD38+target cells with CD28$^{+}$ T cells, to provide a costimulatory "signal 2" in order to enhance the activation of T cells in the presence of an existing "signal 1". In this instance the recognition by T-cells of nonself determinants on the tumor cell line, NALM-6, leads to an allogeneic response, providing 'signal 1'. In addition to costimulatory signals, inhibitory signals also exist that function to decrease T-cell activity. The ligation of programmed cell death protein 1 receptor (PD-1) on T cells to its ligand PD-L1 on APCs leads to the recruitment of phosphatases to CD28 and the TCR complex (Zou and Chen, Inhibitory B7-family molecules in the tumor microenvironment. Nature Reviews Immunology 2008; 8:467-477; Francisco et al., The PD-1 pathway in tolerance and autoimmunity. Immunol Rev 2010; 236:219-242; Hui et al., T cell costimulatory receptor CD28 is a primary target for PD-1-mediated inhibition. Science. 2017; 355 (6332): 1428-33), which in turn counteract TCR signaling and CD28 stimulation. Blockade of the PD-1/PD-L1 interaction with the antagonist antibody cemiplimab in combination with CD38xCD28 bispecific antibodies may potentiate T cell function and promote killing of target cells such as in cancer.

In this example, the ability of CD38xCD28 bispecific antibodies to activate human primary T-cells by engaging CD38 and CD28 to deliver "signal 2", as determined by IL2 & IFNγ release, was evaluated in the presence of the CD38+human acute lymphoblastic leukemia cancer cell line engineered to express PD-L1 (NALM-6/hPD-L1). NALM-6 cells provide an allogeneic TCR response sufficient to serve as "signal 1". The addition of a fixed concentration of the PD-1 antagonist antibody, cemiplimab, was also evaluated.

Isolation of Human Primary CD3$^{+}$ T Cells:

Human peripheral blood mononuclear cells (PBMCs) were isolated from a healthy donor leukocyte pack from Precision for Medicine (Donor 555192) using the Easy-Sep™ Direct Human PBMC Isolation Kit, following the manufacturers recommended protocol and frozen down. CD3$^{+}$ T-cells were isolated by thawing vials of frozen PBMCs. Donor PBMCs were enriched for CD3$^{+}$ T-cells using an EasySep™ Human CD3$^{+}$ T Cell Isolation Kit from StemCell Technologies and following the manufacturer's recommended instructions.

IL2 & IFNγ Release Assay;

Enriched CD3$^{+}$ T-cells, resuspended in stimulation media, were added into 96-well round bottom plates at a concentration of $1 \times 10^{5}$ cells/well. NALM-6 cells or NALM-6 cells engineered to express hPD-L1, were added to CD3$^{+}$ T-cells at a final concentration of $5 \times 10^{4}$ cells/well. Subsequently, bsAb6031, bsAb7945, and Non-TAAxCD28, were titrated from 0.76 pM to 50 nM in a 1:4 dilution and added to wells. The final point of the 10-point dilution contained no titrated antibody. Following addition of titrated antibody, a constant 20 nM of either cemiplimab or its matched isotype control (IsoC-2) was added to wells. Plates were incubated for 72 hours at 37° C., 5% $CO_2$ and 50 μL total supernatant was removed and 5 μL from collected supernatant was used for measuring IL2 and IFNγ. The amount of cytokine in assay supernatant was determined using AlphaLisa kits from PerkinElmer following the manufacturer's protocol. The cytokine measurements were acquired on Perkin Elmer's multilabel plate reader Envision and values were reported as pg/mL. All serial dilutions were tested in triplicate.

The $EC_{50}$ values of the antibodies were determined from a four-parameter logistic equation over a 10-point dose-response curve using GraphPad Prism™ software. Maximal cytokine is given as the mean max response detected within the tested dose range.

Results:

In the presence of allogeneic NALM-6 cells or NALM-6 cells engineered to express PD-L1, CD38xCD28 antibody treatment (bsAb6031 and bsAb7945), in comparison to matched isotype control (IsoC-1), led to dose dependent increases in IL-2 release. The maximum IL-2 release was lower in conditions with NALM-6/PD-L1 cells, compared to NALM-6 (not expressing PD-L1). Addition of cemiplimab did not impact IL-2 release in conditions with NALM-6 cells not expressing PD-L1. However, in the presence of NALM-6 cells expressing PD-L1, the maximum IL-2 release was increased when cemiplimab was added, in comparison to the IL-2 released upon addition of the matched isotype control for cemiplimab, IsoC-2, suggesting that blocking the interaction of PD-1 with PD-L1 may potentiate T cell function.

Thus, in the presence of an allogeneic TCR response provided by the CD38+NALM-6/hPD-L1 cells sufficient to serve as "signal 1", CD38xCD28 bispecific antibodies activate human primary T-cells by engaging CD38 and CD28 to deliver "signal 2", as determined by IL2 and IFNγ release.

TABLE 13

| | NALM-6 | | NALM-6/hPD-L1 | |
|---|---|---|---|---|
| Antibodies | MAX (pg/mL) | EC$_{50}$ [M] | MAX (pg/mL) | EC$_{50}$ [M] |
| bsAb6031 + Cemiplimab | 1216.28 | 2.44E−09 | 614.28 | 4.39E−09 |
| bsAb6031 + IgG4$^P$ | 1219.58 | 1.68E−09 | 240.39 | 2.64E−09 |
| bsAb7945 + Cemiplimab | 3978.67 | 9.81E−11 | 2462.25 | 1.43E−10 |
| bsAb7945 + IgG4$^P$ | 4204.95 | 1.33E−10 | 952.66 | 1.69E−10 |
| Non-TAAxCD28 + Cemiplimab | 134.53 | ND | 101.61 | ND |
| Non-TAAxCD28 + IgG4$^P$ | 125.33 | ND | 31.52 | ND |

Maximum IL2 release and Potency values of Antibodies

Abbreviations:
ND: Not Determined

TABLE 14

| | NALM-6 | | NALM-6/hPD-L1 | |
|---|---|---|---|---|
| Antibodies | MAX (pg/mL) | EC$_{50}$ [M] | MAX (pg/mL) | EC$_{50}$ [M] |
| bsAb6031 + Cemiplimab | 380.19 | NC | 1.00 | NC |
| bsAb6031 + IgG4$^P$ | 288.95 | NC | 1.00 | NC |
| bsAb7945 + Cemiplimab | 1619.64 | NC | 1239.90 | NC |
| bsAb7945 + IgG4$^P$ | 1649.24 | NC | 701.11 | NC |
| Non-TAAxCD28 + Cemiplimab | 332.72 | ND | 14.07 | ND |
| Non-TAAxCD28 + IgG4$^P$ | 85.64 | ND | 1.00 | ND |

Maximum IFNγ release and Potency values of Antibodies

Abbreviations:
ND: Not Determined;
NC: Not calculated because the data did not fit a 4-parameter logistic equation.

Example 8: CD38xCD28 Bispecific Antibody on BCMA and CD38 Expressing Target cells with Human PBMC CD38xCD28 enhancement of BCMAxCD3 targeted killing was evaluated in a 96-hour cytotoxicity assay targeting H929 cells (CD38+ multiple myeloma cell line). Briefly, human PBMCs were plated in supplemented RPMI media at 1×10⁶ cells/mL and incubated overnight at 37° C. in order to enrich for lymphocytes by depleting adherent macrophages, dendritic cells, and some monocytes. The following day, H929 cells were labeled with 1 uM of the fluorescent tracking dye CFDA-SE and the adherent cell-depleted naïve PBMC were labeled with 1 uM of the fluorescent tracking dye CellTrace Violet. Labeled target cells and PBMC (Effector/Target cell 4:1 ratio) were co-incubated a serial dilution of CD38xCD28 bispecific antibodies bsAb6031 or bsAb7945 (concentration range: 33 nM to 0.71 pM) with either a fixed 30 PM concentration of BCMAxCD3 (bsAb5458) or IgG4$^{P-PVA}$ isotype control H4sH10154P3. Wells with BCMAxCD3 or IgG4$^{P-PVA}$ were also included. After incubation for 96 hours at 37° C., cells were harvested from the plates and analyzed by FACS on a FACS BD LSRFortessa-X20. After removing supernatant for cytokine analysis, cells were washed with cold PBS and stained with a LIVE/DEAD Fixable Aqua Dead Cell Stain to identify viable cells. For assessment of NCI-H929 killing, cells were gated on live violet-labeled populations. The percent live population was recorded and used for the calculation of survival. Percent viability was normalized to control condition (target cells in the presence of PBMC only).

T cell activation was assessed by incubating cells with directly conjugated antibodies to CD2, CD4, CD8, and CD25. The median fluorescence intensity (MFI) of CD25 on CD2+/CD4+ or CD2+/CD8+ T cells was reported as the measure of T cell activation. Additionally, as T cells proliferate, CellTraceViolet is diluted, leading to lower MFI as measured by FACS. T cell proliferation was thus reported as a decrease in the MFI of CellTraceViolet on CD2+/CD4+ or CD2+/CD8+ T cells.

Supernatants from this assay were collected for analysis of cytokine levels. Concentrations of IL 17a, IFNγ, TNFα, IL-10, IL-6, IL-4, and IL-2 were analyzed using a Cytometric Bead Array (CBA) kit following the manufacturer's instructions. Cytokine levels were interpolated from the curves generated by the kit standards and reported as pg/mL. EC50 values for target cell killing, T cell activation, proliferation, and cytokine levels, and maximum cytokine levels were calculated using 4-parameter non-linear regression analysis in Prism software.

Results:

Costimulatory anti-CD38xCD28 bispecific antibodies bsAb6031 and bsAb7954 were tested for their ability to enhance H929 target cell killing and T cell activation mediated by the BCMAxCD3 bispecific antibody bsAb5458. Additionally, bsAb6031 and bsAb7954 were evaluated for the ability to mediate target cell and T cell activation in the presence of a non-stimulatory isotype control.

bsAb6031 and bsAb7954 enhanced the cytotoxicity mediated by 30 PM BCMAxCD3 in two donors tested with an average EC50 of 5.2 nM and 0.24 nM respectively, with an average percent increase in maximal cytotoxicity of 64% and 93% respectively over cytotoxicity in the presence of 30 PM BCMAxCD3 alone. In the presence of 30 PM isotype control, bsAb6031 and bsAb7954 mediated modest cytotoxicity with average increase of 4% and 5% respectively over 30 pM isotype control alone (Table 15, FIG. 1).

Figure 2:
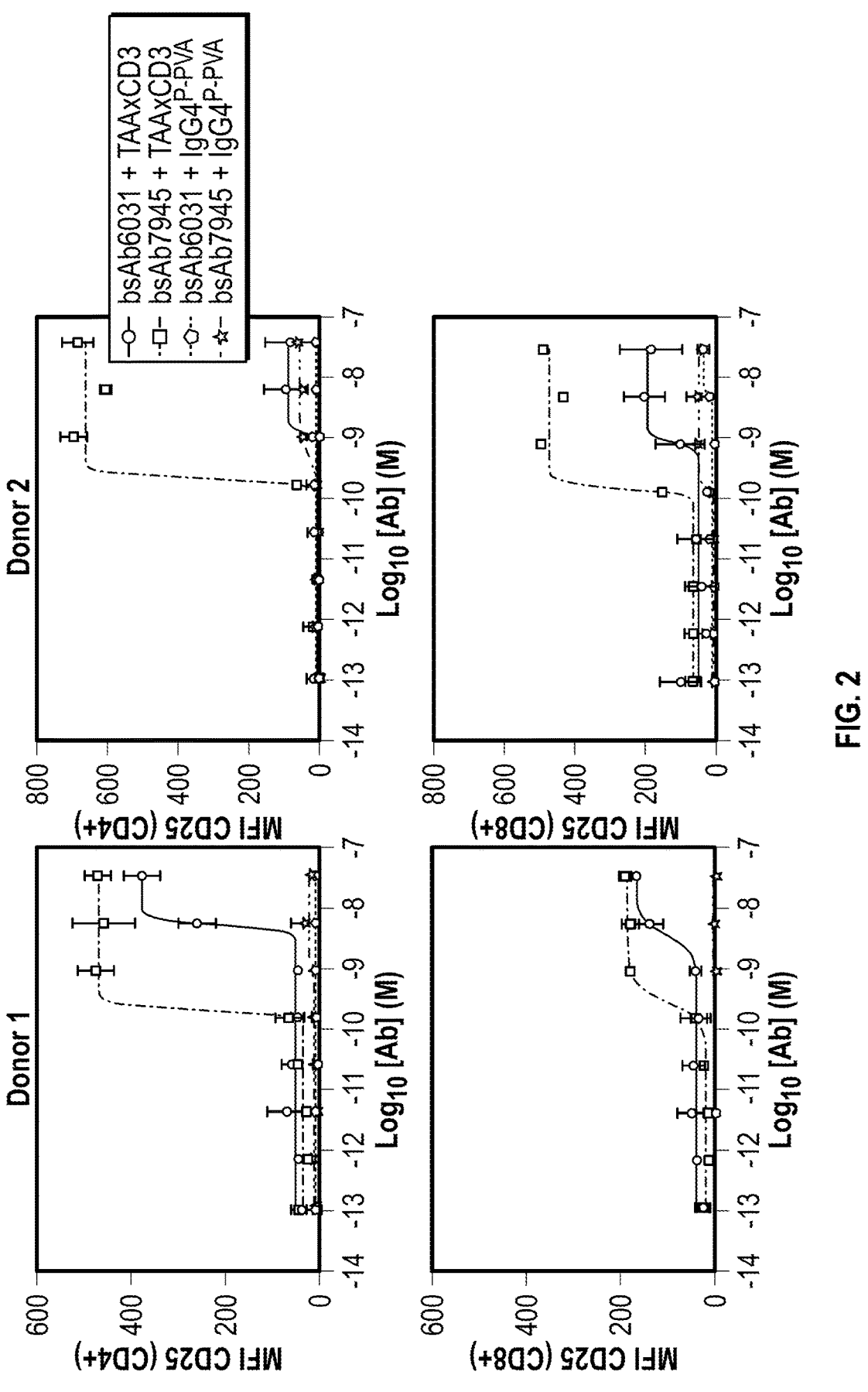

The observed target-cell lysis was associated with T cell activation as measured by CD25 upregulation on CD4+ and CD8+ T cells. bsAb6031 and bsAb7954 enhanced the CD4 T cell activation mediated by 30 PM BCMAxCD3 in two donors tested with an average EC50 of 3.1 nM and 0.20 nM respectively, with an average fold increase in maximal CD25 MFI of 10-fold and 50-fold respectively over CD25 MFI in the presence of 30 pM BCMAxCD3 alone. bsAb6031 and bsAb7954 enhanced the CD8 T cell activation mediated by 30 pM BCMAxCD3 in two donors tested with an average EC50 of 2.3 nM and 0.24 nM respectively, with an average fold increase in maximal CD25 MFI of 5-fold and 8-fold respectively over CD25 MFI in the presence of 30 PM BCMAxCD3 alone. In the presence of 30 pM isotype control, bsAb6031 and bsAb7954 mediated modest CD4+ T cell activation (5-fold and 8-fold respectively) and CD8+ T cell activation (6.5-fold and 10-fold respectively) over 30 pM isotype control alone. EC50 values could not be obtained (Table 16, FIG. 2).

Figure 3:
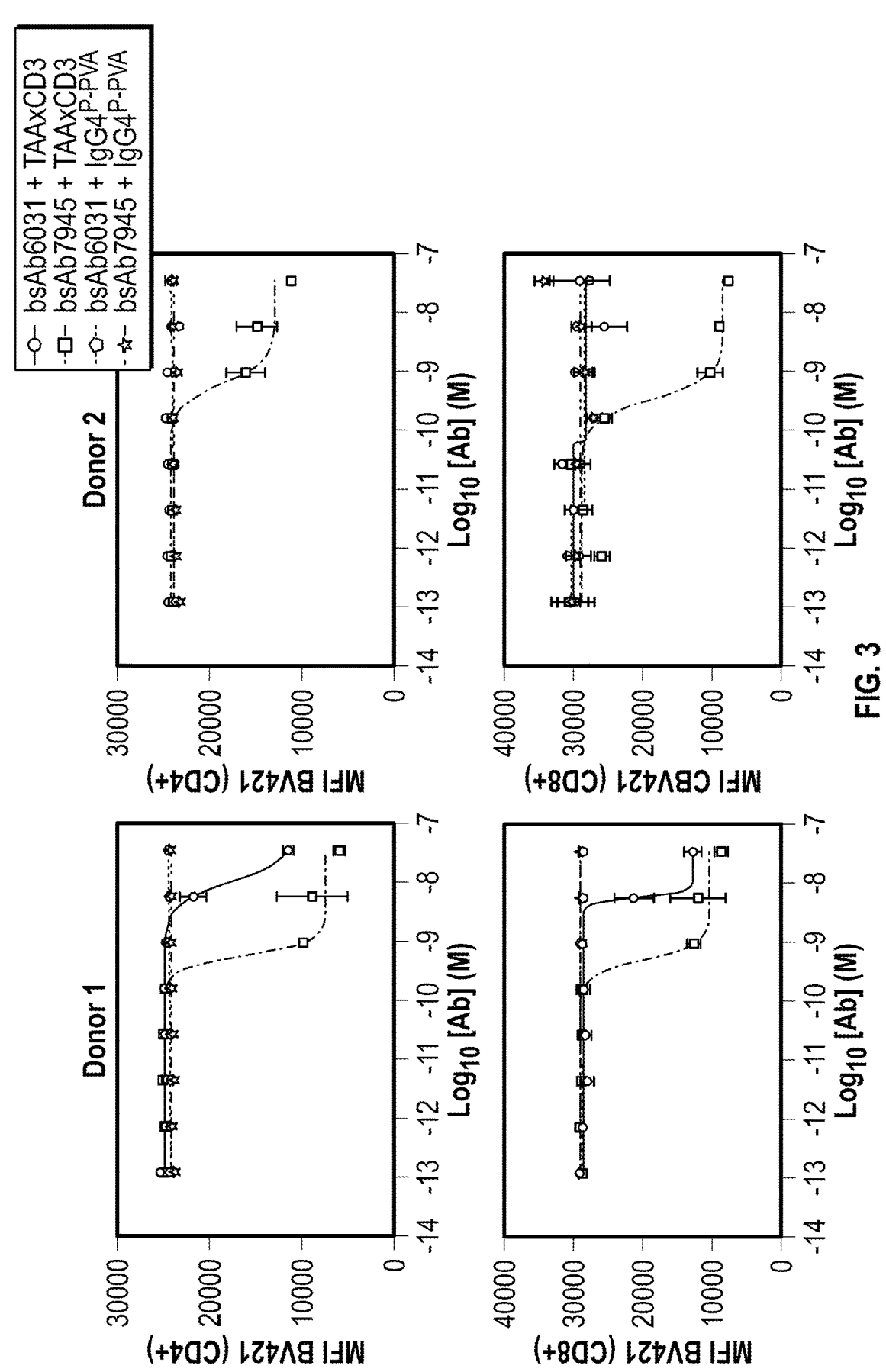

The observed target-cell lysis was associated with T cell proliferation as measured by dilution of CellTrace violet proliferation dye in CD4+ and CD8+ T cells. bsAb6031 enhanced the CD4 T cell and CD8 T cell proliferation mediated by 30 PM BCMAxCD3 in one of two donors tested. bsAb7954 enhanced the CD4 T cell and CD8 T cell proliferation mediated by 30 PM BCMAxCD3 in two donors tested with an average EC50 of 0.59 nM and 0.41 nM respectively, with an average percent increase in proliferation of 62-fold and 69-fold respectively over the proliferation mediated of 30 PM BCMAxCD3 alone.

bsAb6031 and bsAb7945 did not induce proliferation of CD4+ or CD8+ T cells in the presence of 30 pM isotype control (Table 17, FIG. 3).

Figure 4:
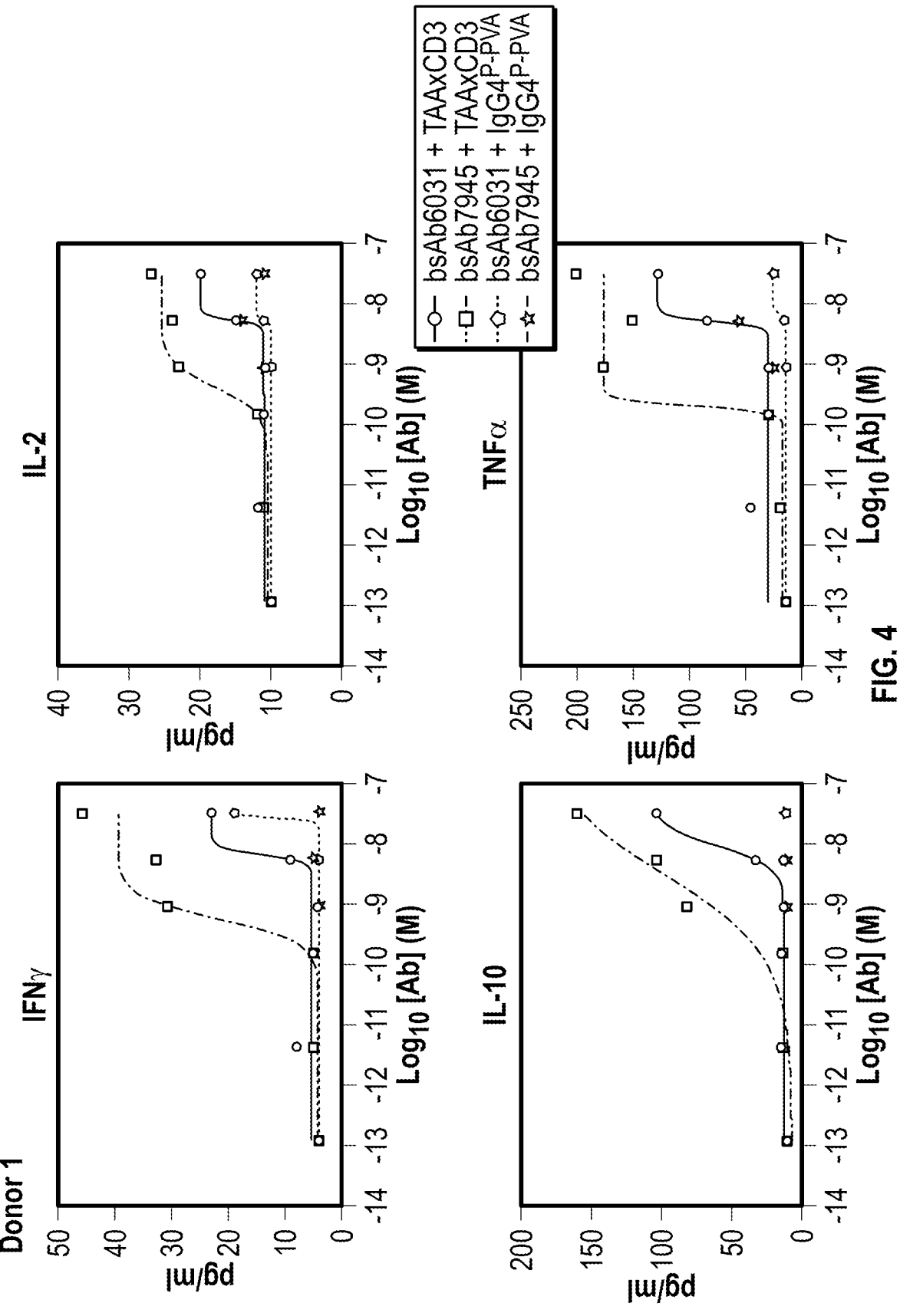
Figure 4:
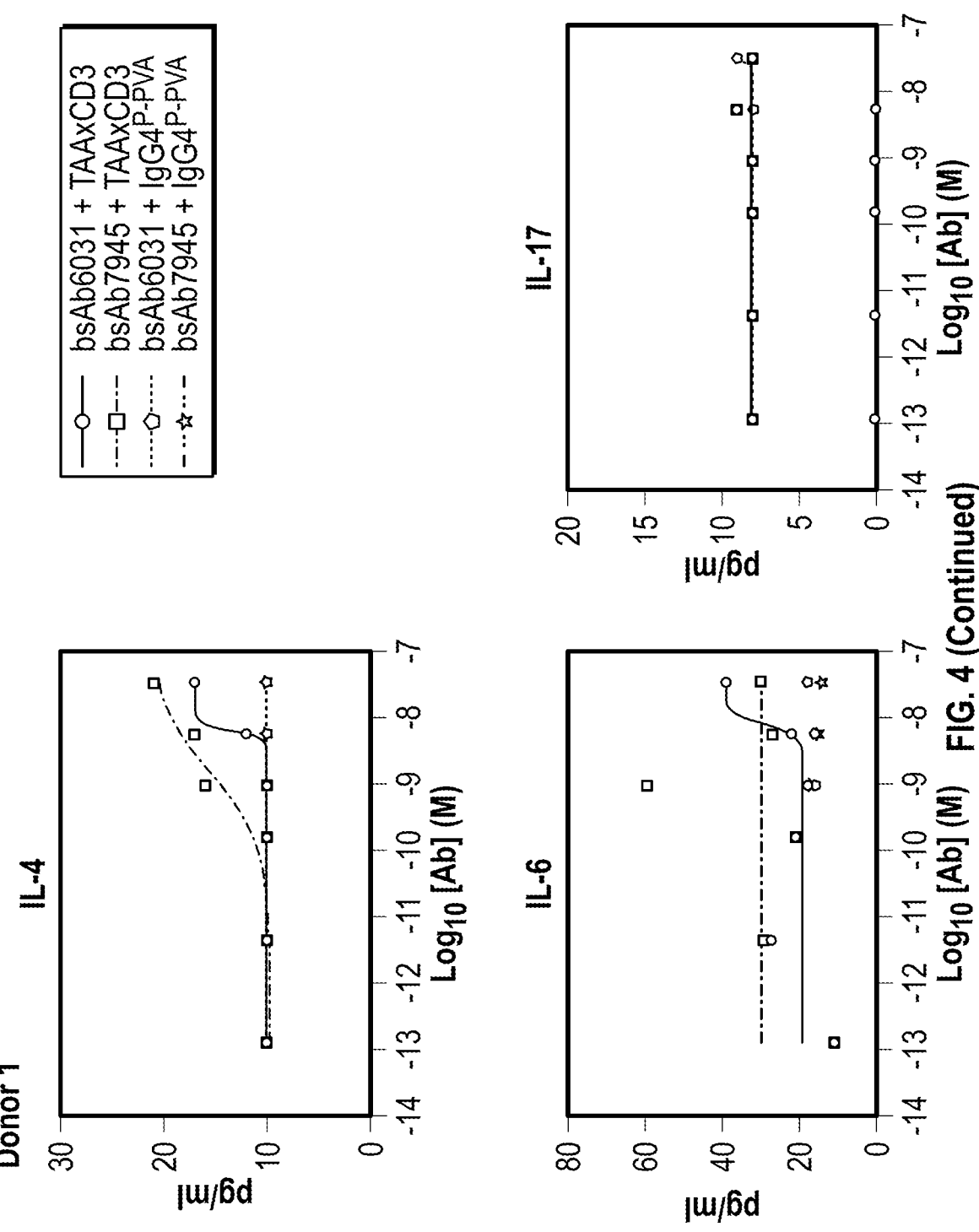

Cytokine release mediated by 30 PM BCMAxCD3 was enhanced in the presence of bsAb6031 and bsAb7945. Specifically, bsAb6031 increased maximal concentrations of IFNg, IL-2, IL-4, IL-10, and TNFa 2-7 fold over 30 PM BCMAxCD3 alone, however EC50s could not be calculated. In the presence of 30 PM isotype control, bsAb6031 increased IFNg and TNFa concentrations 2-fold over 30 PM isotype control only. bsAb7954 increased concentrations of IFNg, IL-2, IL-4, IL-10, and TNFa 2-13 fold at the maximal bsAb7954 concentration, with EC50s, when able to be calculated, of 0.21 nM-1.5 nM. (Table 18, FIG. 4).

In summary, co-stimulation increased the potency of targeted cytotoxicity, T cell activation, and cytokine release when compared to what was observed with BCMAxCD3 alone.

TABLE 15

EC50 values for cytotoxicity with H929 targets

| | Cytotoxicity | | | |
|---|---|---|---|---|
| | Donor 1 | | Donor 2 | |
| | $EC_{50}$ [M] | Max % Increase | $EC_{50}$ [M] | Max % Increase |
| bsAb6031 + TAAxCD3 | 5.37E−09 | 92 | 4.95E−09 | 35 |

TABLE 15-continued

EC50 values for cytotoxicity with H929 targets

| | Cytotoxicity | | | |
|---|---|---|---|---|
| | Donor 1 | | Donor 2 | |
| | $EC_{50}$ [M] | Max % Increase | $EC_{50}$ [M] | Max % Increase |
| bsAb7945 + TAAxCD3 | 2.86E−10 | 94 | 1.87E−10 | 92 |
| bsAb6031 + $IgG4^{P-PVA}$ | ND | 5 | ND | 3 |
| bsAb7945 + $IgG4^{P-PVA}$ | ND | 0 | NC | 11 |

Abbreviations: ND: Not Determined; NC: Not calculated because the data did not fit a 4-parameter logistic equation.

% Increase: 100*((% Survival $_{(SO)}$-% Survival$_{(SC)}$)/% Survival MFI$_{(SO)}$)

Where "SO" 30 pM TAAxCD3 or 30 pM IgG4$^{P-PVA}$ only and "SC" is 30 pM TAAxCD3 or 30 pM IgG4$^{P-PVA}$ with CD38xCD28 costimulation at the highest concentration

TABLE 16

EC50 values for T-cell Activation (Upregulation of CD25)

| | CD4 T cell activation | | | | CD8 T cell activation | | | |
|---|---|---|---|---|---|---|---|---|
| | Donor 1 | | Donor 2 | | Donor 1 | | Donor 2 | |
| | $EC_{50}$ [M] | Fold max (MFI) | $EC_{50}$ [M] | Fold max (MFI) | $EC_{50}$ [M] | Fold max (MFI) | $EC_{50}$ [M] | Fold max (MFI) |
| bsAb6031 + TAAxCD3 | 5.22E−09 | 9 | 1.06E−09 | 11 | 3.63E−09 | 6 | 9.86E−10 | 4 |
| bsAb7945 + TAAxCD3 | 2.03E−10 | 11 | 1.97E−10 | 89 | 2.93E−10 | 6 | 1.78E−10 | 10 |
| bsAb6031 + $IgG4^{P-PVA}$ | ND | 1 | ND | 0 | ND | 0 | ND | 13 |
| bsAb7945 + $IgG4^{P-PVA}$ | ND | 3 | 4.59E−10 | 11 | ND | 1 | NC | 19 |

Abbreviations:
ND: Not Determined;
NC: Not calculated because the data did not fit a 4-parameter logistic equation.
Fold Max: CD25 MFI$_{(SC)}$/CD25 MFI$_{(SO)}$
Where "SO" 30 pM TAAxCD3 or 30 pM IgG4$^{P-PVA}$ only and "SC" $^{is}$ 30 pM TAAxCD3 or 30 pM IgG4$^{P-PVA}$ with CD38xCD28 costimulation at the highest concentration

TABLE 17

EC50 values for T-cell Proliferation (Dilution of CellTrace Violet)

| | CD4 T cell proliferation | | | | CD8 T cell proliferation | | | |
|---|---|---|---|---|---|---|---|---|
| | Donor 1 | | Donor 2 | | Donor 1 | | Donor 2 | |
| | $EC_{50}$ [M] | % Increase | $EC_{50}$ [M] | % Increase | $EC_{50}$ [M] | % Increase | $EC_{50}$ [M] | % Increase |
| bsAb6031 + TAAxCD3 | NC | 56 | ND | 0 | 5.67E−09 | 56 | ND | 5 |

TABLE 17-continued

| | | | | EC50 values for T-cell Proliferation (Dilution of CellTrace Violet) | | | | |
|---|---|---|---|---|---|---|---|---|
| | CD4 T cell proliferation | | | | CD8 T cell proliferation | | | |
| | Donor 1 | | Donor 2 | | Donor 1 | | Donor 2 | |
| | EC$_{50}$ [M] | % Increase | EC$_{50}$ [M] | % Increase | EC$_{50}$ [M] | % Increase | EC$_{50}$ [M] | % Increase |
| bsAb7945 + TAAxCD3 | 5.67E−10 | 70 | 6.20E−10 | 54 | 4.96E−10 | 64 | 3.25E−10 | 74 |
| bsAb6031 + IgG4$^{P-PVA}$ | ND | 1 | ND | −2 | ND | 1 | ND | 8 |
| bsAb7945 + IgG4$^{P-PVA}$ | ND | 1 | ND | 0 | ND | 0 | ND | −14 |

Abbreviations:
ND: Not Determined;
NC: Not calculated because the data did not fit a 4-parameter logistic equation.
% Increase: 100 * ((CellTraceViolet MFI$_{(SO)}$ − CellTraceViolet MFI$_{(SC)}$)/CellTraceViolet MFI$_{(SO)}$)
Where "SO" 30 pM TAAxCD3 or 30 pM IgG4$^{P-PVA}$ only and "SC" $^{is}$ 30 pM TAAxCD3 or 30 pM IgG4$^{P-PVA}$ with CD38xCD28 costimulation at the highest concentration

TABLE 18

| | | Cytokine in Supernatant of H929 Cytotoxicity Assay (donor 1 only) | | | |
|---|---|---|---|---|---|
| | | bsAb6031 + TAAxCD3 | bsAb7945 + TAAxCD3 | bsAb6031 + IgG4$^{P-PVA}$ | bsAb7945 + IgG4$^{P-PVA}$ |
| IFNg | EC50 | NC | 5.79E−10 | NC | ND |
| | Max | 23 | 46 | 19 | 4 |
| | Fold max | 3 | 10 | 4 | 1 |
| IL2 | EC50 | NC | 4.37E−10 | NC | ND |
| | Max | 20 | 27 | 12 | 11 |
| | Fold max | 2 | 2 | 1 | 1 |
| IL4 | EC50 | NC | 1.58E−09 | ND | ND |
| | Max | 17 | 21 | 10 | 10 |
| | Fold max | 2 | 2 | 1 | 1 |
| IL6 | EC50 | ND | ND | ND | ND |
| | Max | 39 | 30 | 18 | 14 |
| | Fold max | 1 | 1 | 1 | 1 |
| IL-10 | EC50 | ND | ND | ND | ND |
| | Max | 104 | 160 | 12 | 12 |
| | Fold max | 7 | 13 | 1 | 1 |
| TNFa | EC50 | NC | 2.11E−10 | NC | ND |
| | Max | 128 | 201 | 26 | 25 |
| | Fold max | 3 | 10 | 2 | 1 |
| IL17 | EC50 | ND | ND | ND | ND |
| | Max | 8 | 8 | 9 | 8 |
| | Fold max | 1 | 1 | 1 | 1 |

Abbreviations: ND: Not Determined; NC: Not calculated because the data did not fit a 4-parameter logistic equation.
Fold Max: Cytokine pg/ml$_{(SC)}$/Cytokine pg/ml$_{(SO)}$
Where "SO" 30 pM TAAxCD3 or 30 pM IgG4$^{P-PVA}$ only and "SC" is 30 pM TAAxCD3 or 30 pM IgG4$^{P-PVA}$ with CD38xCD28 costimulation at the highest concentration

Example 9: In Vivo Efficacy of CD38 x CD28 Bispecific Antibodies in Combination with 4 Mg/Kg BCMA x CD3 Bispecific Antibodies on BCMA$^+$CD38$^+$ MOLP-8 Human Multiple Myeloma Tumor Growth To determine the in vivo anti-tumor efficacy of CD38xCD28 bispecific antibodies (bsAb) in combination with a BCMAxCD3 bsAb, a xenogeneic tumor study was performed. On day-13, immunodeficient NOD.Cg-Prkdc$^{scid}$Il2rg$^{tm1Wjl}$/SzJ (NSG) mice (8-10 Weeks Old, Jackson Labs, CAT #: 005557) were intraperitoneally injected with 4×10$^6$ human peripheral blood mononuclear cells (PBMC) from a normal, healthy donor (Reach Bio, CAT #: 0500-301, Lot #: 0160506). On day 0, the mice were intravenously administered 2×10$^6$ BCMA$^+$CD38$^+$ MOLP-8 human multiple myeloma tumor cells (DSMZ, CAT #: ACC569) that were engineered to also express firefly luciferase (MOLP-8-luciferase cells). The mice (n=5 per group) were then immediately administered either a CD3-binding negative control bispecific Ab (H4sH17664D) or a BCMAxCD3 (bsAb5458) bsAb at 4 mg/kg, in combination with a CD28-binding negative control bispecific Ab or a CD38xCD28 bsAb (either bsAb6031 or bsAb7945) at 4 mg/kg. The mice were administered these antibodies twice more on days 7 and 14, for a total of three doses. Tumor growth was assessed over 52 days by measuring tumor bioluminescence (BLI) in anesthetized animals. As a positive control, a group of mice (n=5) was given only MOLP-8-luciferase cells and PBMCs, but not antibody (PBS-treated group). In order to measure background BLI levels, a group of mice (n=5) were untreated and did not receive tumors, PBMC, or antibody (No Tumor group).

Measurement of Xenogeneic Tumor Growth

BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as total flux (photons/second—p/s).

Results:

Monotherapy of BCMAxCD3 bsAb provides modest anti-tumor efficacy, with mean BLI readings reduced compared to controls. While CD38xCD28 bsAb6031 does not induce any activity as a monotherapy, bsAb7945 does exert monotherapy activity and modestly reduces mean BLI readings compared to controls. However, the combination of BCMAxCD3 bsAb plus either CD38xCD28 bsAb results in mean BLI readings that are lower than any monotherapy. See Tables 19 through 29 and FIG. 5.

Thus, these studies demonstrate that while monotherapy with either BCMAxCD3 bsAb or CD38xCD28 bsAb demonstrates only modest anti-tumor efficacy, combination treatment with BCMAxCD3 bsAb plus CD38xCD28 bsAb results in more potent, combinatorial anti-tumor efficacy that is superior to either therapy alone.

TABLE 19

Tumor Burden and Surviving Mice on Day 9

| Antibody Treatment | Tumor Burden - Mean Total Flux (p/s) on Day 9 | Total flux SEM on Day 9 | Number of mice still alive on day 9 |
|---|---|---|---|
| PBS vehicle | 5.74E+05 | 1.39E+04 | 5 of 5 |
| CD3-binding negative control bsAb (4 mg/kg) + CD28-binding negative control bsAb (4 mg/kg) | 6.70E+05 | 2.94E+04 | 5 of 5 |
| CD3-binding negative control bsAb (4 mg/kg) + bsAb6031 (4 mg/kg) | 6.74E+05 | 3.42E+04 | 5 of 5 |
| CD3-binding negative control bsAb (4 mg/kg) + bsAb7945 (4 mg/kg) | 6.41E+05 | 6.46E+04 | 5 of 5 |
| BCMAxCD3 bsAb (4 mg/kg) + CD28-binding negative control bsAb (4 mg/kg) | 6.55E+05 | 4.61E+04 | 5 of 5 |
| BCMAxCD3 bsAb (4 mg/kg) + CD38xCD28 bsAb6031 (4 mg/kg) | 6.17E+05 | 2.23E+04 | 5 of 5 |
| BCMAxCD3 bsAb (4 mg/kg) + CD38xCD28 bsAb7945 (4 mg/kg) | 5.97E+05 | 2.06E+04 | 5 of 5 |
| No Tumor (Background BLI) | 5.14E+05 | 6.59E+03 | 4 of 4 |

TABLE 20

Tumor Burden and Surviving Mice on Day 13

| Antibody Treatment | Tumor Burden - Mean Total Flux (p/s) on Day 13 | Total Flux SEM on Day 13 | Number of mice still alive on day 13 |
|---|---|---|---|
| PBS vehicle | 1.33E+06 | 2.90E+05 | 5 of 5 |
| CD3-binding negative control bsAb (4 mg/kg) + CD28-binding negative control bsAb (4 mg/kg) | 1.59E+06 | 3.30E+05 | 5 of 5 |
| CD3-binding negative control bsAb (4 mg/kg) + bsAb6031 (4 mg/kg) | 9.76E+05 | 2.01E+05 | 5 of 5 |
| CD3-binding negative control bsAb (4 mg/kg) + bsAb7945 (4 mg/kg) | 6.17E+05 | 4.39E+04 | 5 of 5 |
| BCMAxCD3 bsAb (4 mg/kg) + CD28-binding negative control bsAb (4 mg/kg) | 6.42E+05 | 4.02E+04 | 5 of 5 |
| BCMAxCD3 bsAb (4 mg/kg) + CD38xCD28 bsAb6031 (4 mg/kg) | 6.85E+05 | 5.45E+04 | 5 of 5 |
| BCMAxCD3 bsAb (4 mg/kg) + CD38xCD28 bsAb7945 (4 mg/kg) | 5.55E+05 | 3.26E+04 | 5 of 5 |
| No Tumor (Background BLI) | 5.19E+05 | 4.67E+04 | 4 of 4 |

TABLE 21

Tumor Burden and Surviving Mice on Day 16

| Antibody Treatment | Tumor Burden - Mean Total Flux (p/s) on Day 16 | Total Flux SEM on Day 16 | Number of mice still alive on day 16 |
|---|---|---|---|
| PBS vehicle | 5.12E+06 | 1.68E+06 | 5 of 5 |
| CD3-binding negative control bsAb (4 mg/kg) + CD28-binding negative control bsAb (4 mg/kg) | 7.05E+06 | 1.64E+06 | 5 of 5 |
| CD3-binding negative control bsAb (4 mg/kg) + bsAb6031 (4 mg/kg) | 1.69E+06 | 5.68E+05 | 5 of 5 |
| CD3-binding negative control bsAb (4 mg/kg) + bsAb7945 (4 mg/kg) | 8.81E+05 | 2.70E+05 | 5 of 5 |
| BCMAxCD3 bsAb (4 mg/kg) + CD28-binding negative control bsAb (4 mg/kg) | 6.05E+05 | 4.20E+04 | 5 of 5 |
| BCMAxCD3 bsAb (4 mg/kg) + CD38xCD28 bsAb6031 (4 mg/kg) | 4.78E+05 | 1.30E+04 | 5 of 5 |

TABLE 21-continued

Tumor Burden and Surviving Mice on Day 16

| Antibody Treatment | Tumor Burden - Mean Total Flux (p/s) on Day 16 | Total Flux SEM on Day 16 | Number of mice still alive on day 16 |
|---|---|---|---|
| BCMAxCD3 bsAb (4 mg/kg) + CD38xCD28 bsAb7945 (4 mg/kg) | 6.99E+05 | 5.42E+04 | 5 of 5 |
| No Tumor (Background BLI) | 3.84E+05 | 2.37E+04 | 4 of 4 |

TABLE 22

Tumor Burden and Surviving Mice on Day 20

| Antibody Treatment | Tumor Burden - Mean Total Flux (p/s) on Day 20 | Total Flux SEM on Day 20 | Number of mice still alive on day 20 |
|---|---|---|---|
| PBS vehicle | 1.53E+07 | 3.29E+06 | 5 of 5 |
| CD3-binding negative control bsAb (4 mg/kg) + CD28-binding negative control bsAb (4 mg/kg) | 1.46E+07 | 4.10E+06 | 5 of 5 |
| CD3-binding negative control bsAb (4 mg/kg) + bsAb6031 (4 mg/kg) | 5.19E+06 | 2.21E+06 | 5 of 5 |
| CD3-binding negative control bsAb (4 mg/kg) + bsAb7945 (4 mg/kg) | 1.17E+06 | 3.39E+05 | 5 of 5 |
| BCMAxCD3 bsAb (4 mg/kg) + CD28-binding negative control bsAb (4 mg/kg) | 7.79E+05 | 1.27E+05 | 5 of 5 |
| BCMAxCD3 bsAb (4 mg/kg) + CD38xCD28 bsAb6031 (4 mg/kg) | 5.10E+05 | 1.97E+04 | 5 of 5 |
| BCMAxCD3 bsAb (4 mg/kg) + CD38xCD28 bsAb7945 (4 mg/kg) | 6.56E+05 | 4.70E+04 | 5 of 5 |
| No Tumor (Background BLI) | 5.55E+05 | 2.93E+04 | 4 of 4 |

TABLE 23

Tumor Burden and Surviving Mice on Day 24

| Antibody Treatment | Tumor Burden - Mean Total Flux (p/s) on Day 24 | Total Flux SEM on Day 24 | Number of mice still alive on day 24 |
|---|---|---|---|
| PBS vehicle | 4.36E+07 | 5.76E+06 | 5 of 5 |
| CD3-binding negative control bsAb (4 mg/kg) + CD28-binding negative control bsAb (4 mg/kg) | 4.27E+07 | 2.03E+07 | 4 of 5 |
| CD3-binding negative control bsAb (4 mg/kg) + bsAb6031 (4 mg/kg) | 1.90E+07 | 4.69E+06 | 5 of 5 |
| CD3-binding negative control bsAb (4 mg/kg) + bsAb7945 (4 mg/kg) | 1.78E+06 | 7.82E+05 | 5 of 5 |
| BCMAxCD3 bsAb (4 mg/kg) + CD28-binding negative control bsAb (4 mg/kg) | 1.54E+06 | 6.90E+05 | 5 of 5 |
| BCMAxCD3 bsAb (4 mg/kg) + CD38xCD28 bsAb6031 (4 mg/kg) | 4.27E+05 | 1.83E+04 | 5 of 5 |
| BCMAxCD3 bsAb (4 mg/kg) + CD38xCD28 bsAb7945 (4 mg/kg) | 5.45E+05 | 2.82E+04 | 5 of 5 |
| No Tumor (Background BLI) | 3.52E+05 | 3.36E+04 | 4 of 4 |

TABLE 24

Tumor Burden and Surviving Mice on Day 28

| Antibody Treatment | Tumor Burden - Mean Total Flux (p/s) on Day 28 | Total Flux SEM on Day 28 | Number of mice still alive on day 28 |
|---|---|---|---|
| PBS vehicle | 8.23E+07 | 1.52E+07 | 4 of 5 |
| CD3-binding negative control bsAb (4 mg/kg) + CD28-binding negative control bsAb (4 mg/kg) | 6.63E+06 | 0.00E+00 | 1 of 5 |
| CD3-binding negative control bsAb (4 mg/kg) + bsAb6031 (4 mg/kg) | 6.45E+07 | 1.21E+07 | 5 of 5 |
| CD3-binding negative control bsAb (4 mg/kg) + bsAb7945 (4 mg/kg) | 2.99E+06 | 1.49E+06 | 5 of 5 |
| BCMAxCD3 bsAb (4 mg/kg) + CD28-binding negative control bsAb (4 mg/kg) | 3.99E+06 | 2.11E+06 | 5 of 5 |
| BCMAxCD3 bsAb (4 mg/kg) + CD38xCD28 bsAb6031 (4 mg/kg) | 5.87E+05 | 9.24E+04 | 5 of 5 |
| BCMAxCD3 bsAb (4 mg/kg) + CD38xCD28 bsAb7945 (4 mg/kg) | 6.06E+05 | 8.62E+04 | 5 of 5 |
| No Tumor (Background BLI) | 4.17E+05 | 1.28E+04 | 4 of 4 |

TABLE 25

Tumor Burden and Surviving Mice on Day 31

| Antibody Treatment | Tumor Burden - Mean Total Flux (p/s) on Day 31 | Total Flux SEM on Day 31 | Number of mice still alive on day 31 |
|---|---|---|---|
| PBS vehicle | 1.29E+08 | 4.60E+07 | 3 of 5 |
| CD3-binding negative control bsAb (4 mg/kg) + CD28-binding negative control bsAb (4 mg/kg) | 4.30E+07 | 0.00E+00 | 1 of 5 |
| CD3-binding negative control bsAb (4 mg/kg) + bsAb6031 (4 mg/kg) | 6.94E+07 | 1.54E+07 | 5 of 5 |
| CD3-binding negative control bsAb (4 mg/kg) + bsAb7945 (4 mg/kg) | 9.25E+06 | 5.75E+06 | 5 of 5 |
| BCMAxCD3 bsAb (4 mg/kg) + CD28-binding negative control bsAb (4 mg/kg) | 8.59E+06 | 2.73E+06 | 5 of 5 |
| BCMAxCD3 bsAb (4 mg/kg) + CD38xCD28 bsAb6031 (4 mg/kg) | 7.16E+05 | 1.49E+05 | 5 of 5 |
| BCMAxCD3 bsAb (4 mg/kg) + CD38xCD28 bsAb7945 (4 mg/kg) | 9.85E+05 | 2.07E+05 | 5 of 5 |
| No Tumor (Background BLI) | 4.19E+05 | 6.81E+04 | 4 of 4 |

TABLE 26

Tumor Burden and Surviving Mice on Day 36

| Antibody Treatment | Tumor Burden - Mean Total Flux (p/s) on Day 36 | Total Flux SEM on Day 36 | Number of mice still alive on day 36 |
|---|---|---|---|
| PBS vehicle | | | 0 of 5 |
| CD3-binding negative control bsAb (4 mg/kg) + CD28-binding negative control bsAb (4 mg/kg) | | | 0 of 5 |
| CD3-binding negative control bsAb (4 mg/kg) + bsAb6031 (4 mg/kg) | 2.72E+08 | 2.22E+08 | 3 of 5 |
| CD3-binding negative control bsAb (4 mg/kg) + bsAb7945 (4 mg/kg) | 1.49E+07 | 1.01E+07 | 5 of 5 |
| BCMAxCD3 bsAb (4 mg/kg) + CD28-binding negative control bsAb (4 mg/kg) | 3.76E+07 | 2.51E+07 | 5 of 5 |
| BCMAxCD3 bsAb (4 mg/kg) + CD38xCD28 bsAb6031 (4 mg/kg) | 8.78E+05 | 2.06E+05 | 5 of 5 |

TABLE 26-continued

Tumor Burden and Surviving Mice on Day 36

| Antibody Treatment | Tumor Burden - Mean Total Flux (p/s) on Day 36 | Total Flux SEM on Day 36 | Number of mice still alive on day 36 |
|---|---|---|---|
| BCMAxCD3 bsAb (4 mg/kg) + CD38xCD28 bsAb7945 (4 mg/kg) | 2.25E+06 | 7.72E+05 | 5 of 5 |
| No Tumor (Background BLI) | 4.45E+05 | 1.88E+04 | 4 of 4 |

TABLE 27

Tumor Burden and Surviving Mice on Day 38

| Antibody Treatment | Tumor Burden - Mean Total Flux (p/s) on Day 38 | Total Flux SEM on Day 38 | Number of mice still alive on day 38 |
|---|---|---|---|
| PBS vehicle | | | 0 of 5 |
| CD3-binding negative control bsAb (4 mg/kg) + CD28-binding negative control bsAb (4 mg/kg) | | | 0 of 5 |
| CD3-binding negative control bsAb (4 mg/kg) + bsAb6031 (4 mg/kg) | 4.56E+08 | 3.74E+08 | 3 of 5 |
| CD3-binding negative control bsAb (4 mg/kg) + bsAb7945 (4 mg/kg) | 1.29E+07 | 7.25E+06 | 5 of 5 |
| BCMAxCD3 bsAb (4 mg/kg) + CD28-binding negative control bsAb (4 mg/kg) | 5.80E+07 | 3.35E+07 | 5 of 5 |
| BCMAxCD3 bsAb (4 mg/kg) + CD38xCD28 bsAb6031 (4 mg/kg) | 1.27E+06 | 4.32E+05 | 5 of 5 |
| BCMAxCD3 bsAb (4 mg/kg) + CD38xCD28 bsAb7945 (4 mg/kg) | 5.46E+06 | 2.11E+06 | 5 of 5 |
| No Tumor (Background BLI) | 5.23E+05 | 2.30E+04 | 4 of 4 |

TABLE 28

Tumor Burden and Surviving Mice on Day 45

| Antibody Treatment | Tumor Burden - Mean Total Flux (p/s) on Day 45 | Total Flux SEM on Day 45 | Number of mice still alive on day 45 |
|---|---|---|---|
| PBS vehicle | | | 0 of 5 |
| CD3-binding negative control bsAb (4 mg/kg) + CD28-binding negative control bsAb (4 mg/kg) | | | 0 of 5 |
| CD3-binding negative control bsAb (4 mg/kg) + bsAb6031 (4 mg/kg) | 5.75E+08 | 2.74E+08 | 2 of 5 |
| CD3-binding negative control bsAb (4 mg/kg) + bsAb7945 (4 mg/kg) | 7.04E+06 | 5.64E+06 | 4 of 5 |
| BCMAxCD3 bsAb (4 mg/kg) + CD28-binding negative control bsAb (4 mg/kg) | 8.75E+07 | 3.56E+07 | 4 of 5 |
| BCMAxCD3 bsAb (4 mg/kg) + CD38xCD28 bsAb6031 (4 mg/kg) | 4.84E+06 | 2.62E+06 | 5 of 5 |
| BCMAxCD3 bsAb (4 mg/kg) + CD38xCD28 bsAb7945 (4 mg/kg) | 2.10E+07 | 1.20E+07 | 5 of 5 |
| No Tumor (Background BLI) | 5.11E+05 | 2.68E+04 | 4 of 4 |

TABLE 29

Tumor Burden and Surviving Mice on Day 52

| Antibody Treatment | Tumor Burden - Mean Total Flux (p/s) on Day 52 | Total Flux SEM on Day 52 | Number of mice still alive on day 52 |
|---|---|---|---|
| PBS vehicle | | | 0 of 5 |
| CD3-binding negative control bsAb (4 mg/kg) + CD28-binding negative control bsAb (4 mg/kg) | | | 0 of 5 |
| CD3-binding negative control bsAb (4 mg/kg) + bsAb6031 (4 mg/kg) | 4.47E+08 | 0.00E+00 | 1 of 5 |
| CD3-binding negative control bsAb (4 mg/kg) + bsAb7945 (4 mg/kg) | 1.82E+07 | 1.73E+07 | 4 of 5 |
| BCMAxCD3 bsAb (4 mg/kg) + CD28-binding negative control bsAb (4 mg/kg) | 2.24E+08 | 9.11E+07 | 4 of 5 |
| BCMAxCD3 bsAb (4 mg/kg) + CD38xCD28 bsAb6031 (4 mg/kg) | 1.26E+07 | 7.44E+06 | 5 of 5 |
| BCMAxCD3 bsAb (4 mg/kg) + CD38xCD28 bsAb7945 (4 mg/kg) | 3.60E+07 | 1.92E+07 | 5 of 5 |
| No Tumor (Background BLI) | 4.40E+05 | 4.30E+04 | 4 of 4 |

Example 10: In Vivo Efficacy of CD38 x CD28 Bispecific Antibodies in Combination with 0.4 mg/kg or 0.04 mg/kg BCMA x CD3 Bispecific Antibodies on BCMA+CD38+MOLP-8 Human Multiple Myeloma Tumor Growth To determine the in vivo anti-tumor efficacy of CD38xCD28 bispecific antibodies (bsAb) in combination with a BCMAxCD3 bsAb, a xenogeneic tumor study was performed BCMA+CD38+MOLP-8 human multiple myeloma tumor cells. This experiment was similar to that discussed above in Example 9, except that the dose of BCMAxCD3 bsAb was reduced from 4 mg/kg to 0.4 mg/kg or 0.04 mg/kg. In addition, the length of the experiment was shorter in the present Example, 40 days, versus 52 days in Example 9.

On day-12, immunodeficient NOD.Cg-Prkdc$^{scid}$Il2rg$^{tm1 Wjl}$/SzJ (NSG) mice (8-10 Weeks Old, Jackson Labs, CAT #: 005557) were intraperitoneally injected with 4×10$^6$ human peripheral blood mononuclear cells (PBMC) from a normal, healthy donor (Reach Bio, CAT #: 0500-301, Lot #: 0180821). On day 0, the mice were intravenously administered 2×10$^6$ BCMA$^+$CD38$^+$ MOLP-8 human multiple myeloma tumor cells (DSMZ, CAT #: ACC569) that were engineered to also express firefly luciferase (MOLP-8-luciferase cells). The mice (n=4-5 per group) were then immediately administered either a CD3-binding negative control bispecific Ab (H4sH17664D at 0.4 mg/kg) or a BCMAxCD3 bsAb (bsAb5458; at either 0.4 mg/kg or 0.04 mg/kg), in combination with a CD28-binding negative control bispecific Ab (bsAb5671) or a CD38xCD28 bsAb (either bsAb6031 or bsAb7945) at 4 mg/kg. The mice were administered these Abs twice more on days 7 and 14, for a total of three doses. Tumor growth was assessed over 40 days by measuring tumor bioluminescence (BLI) in anesthetized animals. As a positive control, a group of mice (n=4) was given only MOLP-8-luciferase cells and PBMCs, but not antibody (PBS-treated group). In order to measure background BLI levels, a group of mice (n=5) were untreated and did not receive tumors, PBMC, or antibody (No Tumor group).

Measurement of Xenogeneic Tumor Growth

BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as total flux (photons/second-p/s).

Results:

BCMAxCD3 bsAb (at either 0.4 mg/kg or 0.04 mg/kg) plus CD28-binding negative control bsAb provided modest and significant anti-tumor efficacy, with mean BLI readings reduced compared to mice receiving CD3-binding negative control bsAb plus CD28-binding negative control bsAb (Rows 3 and 10 in Table 30, respectively). Treatment with CD3-binding negative control bsAb plus either CD38xCD28 bsAb (bsAb6031 and bsAb7945) modestly and significantly reduced mean BLI readings compared to mice receiving CD3-binding negative control bsAb plus CD28-binding negative control bsAb (Rows 1 and 2 in Table 30, respectively). However, the combination of BCMAxCD3 bsAb (at either 0.4 mg/kg or 0.04 mg/kg) plus either CD38xCD28 bsAb (bsAb6031 and bsAb7945) resulted in mean BLI readings that were significantly lower than mice receiving BCMAxCD3 bsAb plus CD28-binding negative control bsAb (Rows 8, 9, 15, and 16 in Table 30), mice receiving CD3-binding negative control bsAb plus bsAb6031 (Rows 6 and 13 in Table 30), or mice receiving CD3-binding negative control bsAb plus bsAb7945 (Rows 7 and 14 in Table 30). See also Tables 31 through 39 and FIG. 6.

Thus, these studies demonstrate that while monotherapy with either BCMAxCD3 bsAb or CD38xCD28 bsAb demonstrates only modest anti-tumor efficacy, combination treatment with BCMAxCD3 bsAb plus CD38xCD28 bsAb results in more potent, combinatorial anti-tumor efficacy that is superior to either therapy alone.

TABLE 30

2-way ANOVA statistics at day 29:

| | Comparison | | P value (by 2-way ANOVA) at |
|---|---|---|---|
| | Treatment Group 1 | Treatment Group 2 | day 29 |
| 1 | CD3-binding negative control bsAb (0.4 mg/kg) + CD28-binding negative control bsAb (4 mg/kg) | CD3-binding negative control bsAb (0.4 mg/kg) + bsAb6031 (4 mg/kg) | p = 0.0214 |

TABLE 30-continued 2-way ANOVA statistics at day 29:

| Comparison | | P value (by 2-way ANOVA) at |
|---|---|---|
| Treatment Group 1 | Treatment Group 2 | day 29 |
| 2 CD3-binding negative control bsAb (0.4 mg/kg) + CD28-binding negative control bsAb (4 mg/kg) | CD3-binding negative control bsAb (0.4 mg/kg) + bsAb7945 (4 mg/kg) | P = 0.0024 |
| 3 CD3-binding negative control bsAb (0.4 mg/kg) + CD28-binding negative control bsAb (4 mg/kg) | BCMAxCD3 bsAb (0.4 mg/kg) + CD28-binding negative control bsAb (4 mg/kg) | p = 0.0147 |
| 4 CD3-binding negative control bsAb (0.4 mg/kg) + CD28-binding negative control bsAb (4 mg/kg) | BCMAxCD3 bsAb (0.4 mg/kg) + CD38xCD28 bsAb6031 (4 mg/kg) | p < 0.0001 |
| 5 CD3-binding negative control bsAb (0.4 mg/kg) + CD28-binding negative control bsAb (4 mg/kg) | BCMAxCD3 bsAb (0.4 mg/kg) + CD38xCD28 bsAb7945 (4 mg/kg) | p < 0.0001 |
| 6 CD3-binding negative control bsAb (0.4 mg/kg) + CD38xCD28 bsAb6031 (4 mg/kg) | BCMAxCD3 bsAb (0.4 mg/kg) + CD38xCD28 bsAb6031 (4 mg/kg) | p = 0.0005 |
| 7 CD3-binding negative control bsAb (0.4 mg/kg) + CD38xCD28 bsAb7945 (4 mg/kg) | BCMAxCD3 bsAb (0.4 mg/kg) + CD38xCD28 bsAb7945 (4 mg/kg) | p = 0.0005 |
| 8 BCMAxCD3 bsAb (0.4 mg/kg) + CD28-binding negative control bsAb (4 mg/kg) | BCMAxCD3 bsAb (0.4 mg/kg) + CD38xCD28 bsAb6031 (4 mg/kg) | p = 0.0001 |
| 9 BCMAxCD3 bsAb (0.4 mg/kg) + CD28-binding negative control bsAb (4 mg/kg) | BCMAxCD3 bsAb (0.4 mg/kg) + CD38xCD28 bsAb7945 (4 mg/kg) | p < 0.0001 |
| 10 CD3-binding negative control bsAb (0.4 mg/kg) + CD28-binding negative control bsAb (4 mg/kg) | BCMAxCD3 bsAb (0.04 mg/kg) + CD28-binding negative control bsAb (4 mg/kg) | p = 0.0043 |
| 11 CD3-binding negative control bsAb (0.4 mg/kg) + CD28-binding negative control bsAb (4 mg/kg) | BCMAxCD3 bsAb (0.04 mg/kg) + CD38xCD28 bsAb6031 (4 mg/kg) | p < 0.0001 |
| 12 CD3-binding negative control bsAb (0.4 mg/kg) + CD28-binding negative control bsAb (4 mg/kg) | BCMAxCD3 bsAb (0.04 mg/kg) + CD38xCD28 bsAb7945 (4 mg/kg) | p < 0.0001 |
| 13 CD3-binding negative control bsAb (0.4 mg/kg) + CD38xCD28 bsAb6031 (4 mg/kg) | BCMAxCD3 bsAb (0.04 mg/kg) + CD38xCD28 bsAb6031 (4 mg/kg) | p = 0.0083 |
| 14 CD3-binding negative control bsAb (0.4 mg/kg) + CD38xCD28 bsAb7945 (4 mg/kg) | BCMAxCD3 bsAb (0.04 mg/kg) + CD38xCD28 bsAb7945 (4 mg/kg) | p = 0.0016 |
| 15 BCMAxCD3 bsAb (0.04 mg/kg) + CD28-binding negative control bsAb (4 mg/kg) | BCMAxCD3 bsAb (0.04 mg/kg) + CD38xCD28 bsAb6031 (4 mg/kg) | p = 0.0128 |
| 16 BCMAxCD3 bsAb (0.04 mg/kg) + CD28-binding negative control bsAb (4 mg/kg) | BCMAxCD3 bsAb (0.04 mg/kg) + CD38xCD28 bsAb7945 (4 mg/kg) | P = 0.0008 |

TABLE 31

Tumor Burden and Surviving Mice on Day 6

| Antibody Treatment | Tumor Burden - Mean Total Flux (p/s) on Day 6 | Total Flux SEM on Day 6 | Number of mice still alive on day 6 |
|---|---|---|---|
| PBS vehicle | 4.73E+05 | 3.23E+04 | 4 of 4 |
| CD3-binding negative control bsAb (0.4 mg/kg) + CD28-binding negative control bsAb (4 mg/kg) | 4.59E+05 | 2.29E+04 | 5 of 5 |
| CD3-binding negative control bsAb (0.4 mg/kg) + bsAb6031 (4 mg/kg) | 5.07E+05 | 1.18E+04 | 5 of 5 |
| CD3-binding negative control bsAb (0.4 mg/kg) + bsAb7945 (4 mg/kg) | 4.41E+05 | 1.31E+04 | 5 of 5 |
| BCMAxCD3 bsAb (0.4 mg/kg) + CD28-binding negative control bsAb (4 mg/kg) | 5.65E+05 | 3.84E+04 | 5 of 5 |
| BCMAxCD3 bsAb (0.4 mg/kg) + CD38xCD28 bsAb6031 (4 mg/kg) | 5.02E+05 | 1.47E+04 | 5 of 5 |
| BCMAxCD3 bsAb (0.4 mg/kg) + CD38xCD28 bsAb7945 (4 mg/kg) | 4.45E+05 | 2.80E+04 | 5 of 5 |

TABLE 31-continued

Tumor Burden and Surviving Mice on Day 6

| Antibody Treatment | Tumor Burden - Mean Total Flux (p/s) on Day 6 | Total Flux SEM on Day 6 | Number of mice still alive on day 6 |
|---|---|---|---|
| BCMAxCD3 bsAb (0.04 mg/kg) + CD28-binding negative control bsAb (4 mg/kg) | 5.13E+05 | 2.88E+04 | 5 of 5 |
| BCMAxCD3 bsAb (0.04 mg/kg) + CD38xCD28 bsAb6031 (4 mg/kg) | 3.80E+05 | 2.67E+04 | 5 of 5 |
| BCMAxCD3 bsAb (0.04 mg/kg) + CD38xCD28 bsAb7945 (4 mg/kg) | 3.79E+05 | 1.60E+04 | 4 of 4 |
| No Tumor (Background BLI) | 5.13E+05 | 2.54E+04 | 5 of 5 |

TABLE 32

Tumor Burden and Surviving Mice on Day 9

| Antibody Treatment | Tumor Burden - Mean Total Flux (p/s) on Day 9 | Total Flux SEM on Day 9 | Number of mice still alive on day 9 |
|---|---|---|---|
| PBS vehicle | 5.90E+05 | 5.72E+04 | 4 of 4 |
| CD3-binding negative control bsAb (0.4 mg/kg) + CD28-binding negative control bsAb (4 mg/kg) | 6.06E+05 | 2.51E+04 | 5 of 5 |
| CD3-binding negative control bsAb (0.4 mg/kg) + bsAb6031 (4 mg/kg) | 4.66E+05 | 4.43E+04 | 5 of 5 |
| CD3-binding negative control bsAb (0.4 mg/kg) + bsAb7945 (4 mg/kg) | 3.49E+05 | 2.38E+04 | 5 of 5 |
| BCMAxCD3 bsAb (0.4 mg/kg) + CD28-binding negative control bsAb (4 mg/kg) | 5.44E+05 | 1.96E+04 | 5 of 5 |
| BCMAxCD3 bsAb (0.4 mg/kg) + CD38xCD28 bsAb6031 (4 mg/kg) | 4.56E+05 | 3.44E+04 | 5 of 5 |
| BCMAxCD3 bsAb (0.4 mg/kg) + CD38xCD28 bsAb7945 (4 mg/kg) | 4.19E+05 | 7.67E+03 | 5 of 5 |
| BCMAxCD3 bsAb (0.04 mg/kg) + CD28-binding negative control bsAb (4 mg/kg) | 6.16E+05 | 4.20E+04 | 5 of 5 |
| BCMAxCD3 bsAb (0.04 mg/kg) + CD38xCD28 bsAb6031 (4 mg/kg) | 3.68E+05 | 2.63E+04 | 5 of 5 |
| BCMAxCD3 bsAb (0.04 mg/kg) + CD38xCD28 bsAb7945 (4 mg/kg) | 3.90E+05 | 3.34E+04 | 4 of 4 |
| No Tumor (Background BLI) | 3.73E+05 | 1.23E+04 | 5 of 5 |

TABLE 34

Tumor Burden and Surviving Mice on Day 16

| Antibody Treatment | Tumor Burden - Mean Total Flux (p/s) on Day 16 | Total Flux SEM on Day 16 | Number of mice still alive on day 16 |
|---|---|---|---|
| PBS vehicle | 6.61E+06 | 2.28E+06 | 4 of 4 |
| CD3-binding negative control bsAb (0.4 mg/kg) + CD28-binding negative control bsAb (4 mg/kg) | 9.63E+06 | 1.55E+06 | 5 of 5 |
| CD3-binding negative control bsAb (0.4 mg/kg) + bsAb6031 (4 mg/kg) | 1.66E+06 | 4.59E+05 | 5 of 5 |
| CD3-binding negative control bsAb (0.4 mg/kg) + bsAb7945 (4 mg/kg) | 4.91E+05 | 5.60E+04 | 5 of 5 |
| BCMAxCD3 bsAb (0.4 mg/kg) + CD28-binding negative control bsAb (4 mg/kg) | 1.25E+06 | 2.76E+05 | 5 of 5 |
| BCMAxCD3 bsAb (0.4 mg/kg) + CD38xCD28 bsAb6031 (4 mg/kg) | 4.80E+05 | 2.95E+04 | 5 of 5 |
| BCMAxCD3 bsAb (0.4 mg/kg) + CD38xCD28 bsAb7945 (4 mg/kg) | 4.89E+05 | 6.50E+03 | 5 of 5 |
| BCMAxCD3 bsAb (0.04 mg/kg) + CD28-binding negative control bsAb (4 mg/kg) | 2.95E+06 | 1.17E+06 | 5 of 5 |
| BCMAxCD3 bsAb (0.04 mg/kg) + CD38xCD28 bsAb6031 (4 mg/kg) | 6.21E+05 | 4.07E+04 | 5 of 5 |
| BCMAxCD3 bsAb (0.04 mg/kg) + CD38xCD28 bsAb7945 (4 mg/kg) | 5.54E+05 | 6.14E+04 | 4 of 4 |
| No Tumor (Background BLI) | 4.82E+05 | 3.37E+04 | 5 of 5 |

TABLE 33

Tumor Burden and Surviving Mice on Day 12

| Antibody Treatment | Tumor Burden - Mean Total Flux (p/s) on Day 12 | Total Flux SEM on Day 12 | Number of mice still alive on day 12 |
|---|---|---|---|
| PBS vehicle | 1.58E+06 | 2.88E+05 | 4 of 4 |
| CD3-binding negative control bsAb (0.4 mg/kg) + CD28-binding negative control bsAb (4 mg/kg) | 1.53E+06 | 1.97E+05 | 5 of 5 |
| CD3-binding negative control bsAb (0.4 mg/kg) + bsAb6031 (4 mg/kg) | 6.06E+05 | 3.81E+04 | 5 of 5 |
| CD3-binding negative control bsAb (0.4 mg/kg) + bsAb7945 (4 mg/kg) | 4.23E+05 | 2.23E+04 | 5 of 5 |
| BCMAxCD3 bsAb (0.4 mg/kg) + CD28-binding negative control bsAb (4 mg/kg) | 5.64E+05 | 3.49E+04 | 5 of 5 |
| BCMAxCD3 bsAb (0.4 mg/kg) + CD38xCD28 bsAb6031 (4 mg/kg) | 4.76E+05 | 2.40E+04 | 5 of 5 |
| BCMAxCD3 bsAb (0.4 mg/kg) + CD38xCD28 bsAb7945 (4 mg/kg) | 4.73E+05 | 1.85E+04 | 5 of 5 |
| BCMAxCD3 bsAb (0.04 mg/kg) + CD28-binding negative control bsAb (4 mg/kg) | 6.66E+05 | 1.02E+05 | 5 of 5 |
| BCMAxCD3 bsAb (0.04 mg/kg) + CD38xCD28 bsAb6031 (4 mg/kg) | 4.65E+05 | 1.92E+04 | 5 of 5 |
| BCMAxCD3 bsAb (0.04 mg/kg) + CD38xCD28 bsAb7945 (4 mg/kg) | 5.46E+05 | 3.09E+04 | 4 of 4 |
| No Tumor (Background BLI) | 4.72E+05 | 1.80E+04 | 5 of 5 |

TABLE 35

Tumor Burden and Surviving Mice on Day 21

| Antibody Treatment | Tumor Burden - Mean Total Flux (p/s) on Day 21 | Total Flux SEM on Day 21 | Number of mice still alive on day 21 |
|---|---|---|---|
| PBS vehicle | 2.92E+07 | 1.81E+06 | 3 of 4 |
| CD3-binding negative control bsAb (0.4 mg/kg) + CD28-binding negative control bsAb (4 mg/kg) | 3.47E+07 | 7.52E+06 | 5 of 5 |
| CD3-binding negative control bsAb (0.4 mg/kg) + bsAb6031 (4 mg/kg) | 9.33E+06 | 3.19E+06 | 5 of 5 |
| CD3-binding negative control bsAb (0.4 mg/kg) + bsAb7945 (4 mg/kg) | 8.61E+05 | 3.23E+05 | 5 of 5 |
| BCMAxCD3 bsAb (0.4 mg/kg) + CD28-binding negative control bsAb (4 mg/kg) | 5.97E+06 | 2.50E+06 | 5 of 5 |
| BCMAxCD3 bsAb (0.4 mg/kg) + CD38xCD28 bsAb6031 (4 mg/kg) | 5.97E+05 | 3.55E+04 | 5 of 5 |
| BCMAxCD3 bsAb (0.4 mg/kg) + CD38xCD28 bsAb7945 (4 mg/kg) | 4.90E+05 | 2.85E+04 | 5 of 5 |
| BCMAxCD3 bsAb (0.04 mg/kg) + CD28-binding negative control bsAb (4 mg/kg) | 1.19E+07 | 4.65E+06 | 5 of 5 |
| BCMAxCD3 bsAb (0.04 mg/kg) + CD38xCD28 bsAb6031 (4 mg/kg) | 6.55E+05 | 1.12E+05 | 5 of 5 |
| BCMAxCD3 bsAb (0.04 mg/kg) + CD38xCD28 bsAb7945 (4 mg/kg) | 4.80E+05 | 2.04E+04 | 4 of 4 |
| No Tumor (Background BLI) | 4.27E+05 | 1.17E+04 | 5 of 5 |

TABLE 36

| Tumor Burden and Surviving Mice on Day 26 | | |
| --- | --- | --- |
| Antibody Treatment | Tumor Burden - Mean Total Flux (p/s) on Day 26 | Total Flux SEM on Day 26 | Number of mice still alive on day 26 |
| --- | --- | --- | --- |
| PBS vehicle | 5.14E+07 | 2.24E+07 | 3 of 4 |
| CD3-binding negative control bsAb (0.4 mg/kg) + CD28-binding negative control bsAb (4 mg/kg) | 8.02E+07 | 1.36E+07 | 5 of 5 |
| CD3-binding negative control bsAb (0.4 mg/kg) + bsAb6031 (4 mg/kg) | 3.41E+07 | 1.15E+07 | 5 of 5 |
| CD3-binding negative control bsAb (0.4 mg/kg) + bsAb7945 (4 mg/kg) | 4.59E+06 | 1.82E+06 | 5 of 5 |
| BCMAxCD3 bsAb (0.4 mg/kg) + CD28-binding negative control bsAb (4 mg/kg) | 1.61E+07 | 3.74E+06 | 5 of 5 |
| BCMAxCD3 bsAb (0.4 mg/kg) + CD38xCD28 bsAb6031 (4 mg/kg) | 9.57E+05 | 3.41E+05 | 5 of 5 |
| BCMAxCD3 bsAb (0.4 mg/kg) + CD38xCD28 bsAb7945 (4 mg/kg) | 4.78E+05 | 3.86E+04 | 5 of 5 |
| BCMAxCD3 bsAb (0.04 mg/kg) + CD28-binding negative control bsAb (4 mg/kg) | 3.37E+07 | 1.27E+07 | 5 of 5 |
| BCMAxCD3 bsAb (0.04 mg/kg) + CD38xCD28 bsAb6031 (4 mg/kg) | 2.80E+06 | 1.54E+06 | 5 of 5 |
| BCMAxCD3 bsAb (0.04 mg/kg) + CD38xCD28 bsAb7945 (4 mg/kg) | 6.59E+05 | 6.02E+04 | 4 of 4 |
| No Tumor (Background BLI) | 4.54E+05 | 2.72E+04 | 5 of 5 |

TABLE 37

| Tumor Burden and Surviving Mice on Day 29 | | |
| --- | --- | --- |
| Antibody Treatment | Tumor Burden - Mean Total Flux (p/s)) on Day 29 | Total Flux SEM on Day 29 | Number of mice still alive on day 29 |
| --- | --- | --- | --- |
| PBS vehicle | 4.06E+07 | 7.54E+06 | 3 of 4 |
| CD3-binding negative control bsAb (0.4 mg/kg) + CD28-binding negative control bsAb (4 mg/kg) | 7.93E+07 | 3.61E+07 | 3 of 5 |
| CD3-binding negative control bsAb (0.4 mg/kg) + bsAb6031 (4 mg/kg) | 4.35E+07 | 1.48E+07 | 4 of 5 |
| CD3-binding negative control bsAb (0.4 mg/kg) + bsAb7945 (4 mg/kg) | 3.89E+07 | 2.53E+07 | 5 of 5 |
| BCMAxCD3 bsAb (0.4 mg/kg) + CD28-binding negative control bsAb (4 mg/kg) | 4.39E+07 | 7.99E+06 | 5 of 5 |
| BCMAxCD3 bsAb (0.4 mg/kg) + CD38xCD28 bsAb6031 (4 mg/kg) | 2.73E+06 | 1.80E+06 | 5 of 5 |
| BCMAxCD3 bsAb (0.4 mg/kg) + CD38xCD28 bsAb7945 (4 mg/kg) | 8.08E+05 | 1.78E+05 | 5 of 5 |
| BCMAxCD3 bsAb (0.04 mg/kg) + CD28-binding negative control bsAb (4 mg/kg) | 4.05E+07 | 1.90E+07 | 5 of 5 |
| BCMAxCD3 bsAb (0.04 mg/kg) + CD38xCD28 bsAb6031 (4 mg/kg) | 9.48E+06 | 5.22E+06 | 5 of 5 |
| BCMAxCD3 bsAb (0.04 mg/kg) + CD38xCD28 bsAb7945 (4 mg/kg) | 9.18E+05 | 1.36E+05 | 4 of 4 |
| No Tumor (Background BLI) | 4.99E+05 | 2.05E+04 | 5 of 5 |

TABLE 38

| Tumor Burden and Surviving Mice on Day 33 | | |
| --- | --- | --- |
| Antibody Treatment | Tumor Burden - Mean Total Flux (p/s) on Day 33 | Total Flux SEM on Day 33 | Number of mice still alive on day 33 |
| --- | --- | --- | --- |
| PBS vehicle | | | 0 of 4 |
| CD3-binding negative control bsAb (0.4 mg/kg) + CD28-binding negative control bsAb (4 mg/kg) | | | 0 of 5 |
| CD3-binding negative control bsAb (0.4 mg/kg) + bsAb6031 (4 mg/kg) | 3.76E+07 | 2.11E+07 | 2 of 5 |
| CD3-binding negative control bsAb (0.4 mg/kg) + bsAb7945 (4 mg/kg) | 2.11E+07 | 1.05E+07 | 5 of 5 |
| BCMAxCD3 bsAb (0.4 mg/kg) + CD28-binding negative control bsAb (4 mg/kg) | 7.44E+07 | 1.22E+07 | 5 of 5 |
| BCMAxCD3 bsAb (0.4 mg/kg) + CD38xCD28 bsAb6031 (4 mg/kg) | 8.04E+06 | 6.65E+06 | 5 of 5 |
| BCMAxCD3 bsAb (0.4 mg/kg) + CD38xCD28 bsAb7945 (4 mg/kg) | 1.40E+06 | 6.40E+05 | 5 of 5 |
| BCMAxCD3 bsAb (0.04 mg/kg) + CD28-binding negative control bsAb (4 mg/kg) | 4.15E+07 | 3.50E+07 | 2 of 5 |
| BCMAxCD3 bsAb (0.04 mg/kg) + CD38xCD28 bsAb6031 (4 mg/kg) | 2.58E+07 | 1.15E+07 | 5 of 5 |
| BCMAxCD3 bsAb (0.04 mg/kg) + CD38xCD28 bsAb7945 (4 mg/kg) | 1.12E+06 | 4.20E+05 | 4 of 4 |
| No Tumor (Background BLI) | 4.90E+05 | 3.80E+04 | 5 of 5 |

TABLE 39

| Tumor Burden and Surviving Mice on Day 36 | | |
| --- | --- | --- |
| Antibody Treatment | Tumor Burden - Mean Total Flux (p/s) on Day 36 | Total Flux SEM on Day 36 | Number of mice still alive on day 36 |
| --- | --- | --- | --- |
| PBS vehicle | | | 0 of 4 |
| CD3-binding negative control bsAb (0.4 mg/kg) + CD28-binding negative control bsAb (4 mg/kg) | | | 0 of 5 |
| CD3-binding negative control bsAb (0.4 mg/kg) + bsAb6031 (4 mg/kg) | 6.01E+07 | 3.06E+07 | 2 of 5 |
| CD3-binding negative control bsAb (0.4 mg/kg) + bsAb7945 (4 mg/kg) | 4.21E+07 | 2.08E+07 | 4 of 5 |
| BCMAxCD3 bsAb (0.4 mg/kg) + CD28-binding negative control bsAb (4 mg/kg) | 1.39E+08 | 4.35E+07 | 3 of 5 |
| BCMAxCD3 bsAb (0.4 mg/kg) + CD38xCD28 bsAb6031 (4 mg/kg) | 1.14E+07 | 7.71E+06 | 5 of 5 |
| BCMAxCD3 bsAb (0.4 mg/kg) + CD38xCD28 bsAb7945 (4 mg/kg) | 2.75E+06 | 1.82E+06 | 5 of 5 |
| BCMAxCD3 bsAb (0.04 mg/kg) + CD28-binding negative control bsAb (4 mg/kg) | 9.62E+07 | 5.28E+07 | 2 of 5 |
| BCMAxCD3 bsAb (0.04 mg/kg) + CD38xCD28 bsAb6031 (4 mg/kg) | 9.55E+07 | 4.38E+07 | 5 of 5 |
| BCMAxCD3 bsAb (0.04 mg/kg) + CD38xCD28 bsAb7945 (4 mg/kg) | 2.90E+06 | 9.91E+05 | 4 of 4 |
| No Tumor (Background BLI) | 5.89E+05 | 4.29E+04 | 5 of 5 |

TABLE 40

Tumor Burden and Surviving Mice on Day 40

| Antibody Treatment | Tumor Burden - Mean Total Flux (p/s) on Day 40 | Total Flux SEM on Day 0 | Number of mice still alive on day 40 |
|---|---|---|---|
| PBS vehicle | | | 0 of 4 |
| CD3-binding negative control bsAb (0.4 mg/kg) + CD28-binding negative control bsAb (4 mg/kg) | | | 0 of 5 |
| CD3-binding negative control bsAb (0.4 mg/kg) + bsAb6031 (4 mg/kg) | 1.51E+08 | 9.84E+07 | 2 of 5 |
| CD3-binding negative control bsAb (0.4 mg/kg) + bsAb7945 (4 mg/kg) | 4.85E+07 | 1.59E+07 | 4 of 5 |
| BCMAxCD3 bsAb (0.4 mg/kg) + CD28-binding negative control bsAb (4 mg/kg) | 3.03E+08 | 4.40E+07 | 2 of 5 |
| BCMAxCD3 bsAb (0.4 mg/kg) + CD38xCD28 bsAb6031 (4 mg/kg) | 1.64E+07 | 1.18E+07 | 5 of 5 |
| BCMAxCD3 bsAb (0.4 mg/kg) + CD38xCD28 bsAb7945 (4 mg/kg) | 3.55E+06 | 2.42E+06 | 5 of 5 |
| BCMAxCD3 bsAb (0.04 mg/kg) + CD28-binding negative control bsAb (4 mg/kg) | 5.75E+07 | 1.43E+07 | 2 of 5 |
| BCMAxCD3 bsAb (0.04 mg/kg) + CD38xCD28 bsAb6031 (4 mg/kg) | 1.61E+08 | 7.77E+07 | 5 of 5 |
| BCMAxCD3 bsAb (0.04 mg/kg) + CD38xCD28 bsAb7945 (4 mg/kg) | 4.77E+06 | 2.16E+06 | 4 of 4 |
| No Tumor (Background BLI) | 5.88E+05 | 3.44E+04 | 5 of 5 |

Example 11: In Vivo Anti-Tumor Efficacy of CD38xCD28 Bispecific Antibodies (bsAb) in Combination with a BCMAxCD3 Bispecific Antibodies Against BCMA$^+$CD38$^+$ WSU-DLCL2 Tumor Cells To determine the in vivo anti-tumor efficacy of CD38xCD28 bispecific antibodies (bsAb) in combination with a BCMAxCD3 bsAb, a xenogeneic tumor study was performed. This experiment was similar to Examples 9 and 10 above, except that the tumor cell line used in the present experiment was a diffuse large B-cell Lymphoma cell line, BCMA$^+$CD38$^+$ WSU-DLCL2, and the only CD38/CD28 bsAb tested was bsAb6031.

On day 0, immunodeficient NOD.Cg-Prkdc$^{scid}$Il2rg$^{tm1Wjl}$/SzJ (NSG) mice (8-10 Weeks Old, Jackson Labs, CAT #: 005557) were subcutaneously injected with a 3×10$^6$ WSU-DLCL2 tumor cells (Diffuse Large B Cell Lymphoma Cell Line, DSMZ, CAT #: ACC575) and 0.5×10$^6$ PBMC's from a normal donor (Reach Bio, CAT #: 0500-301, Lot #: 0180821) mixed together in 50% Matrigel. On day 1, the mice (n=5 per group) were administered either a CD3-binding negative control bispecific Ab (H4sH17664D) or a BCMAxCD3 bsAb (bsAb5458), in combination with a CD28-binding negative control bispecific Ab (bsAb5671) or the CD38xCD28 bsAb6031 at 4 mg/kg. The mice were administered these Abs twice more on days 8 and 14, for a total of three doses. Tumor growth was assessed through day 50 by measuring tumor volumes.

Calculation of Xenogeneic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Figure 7:
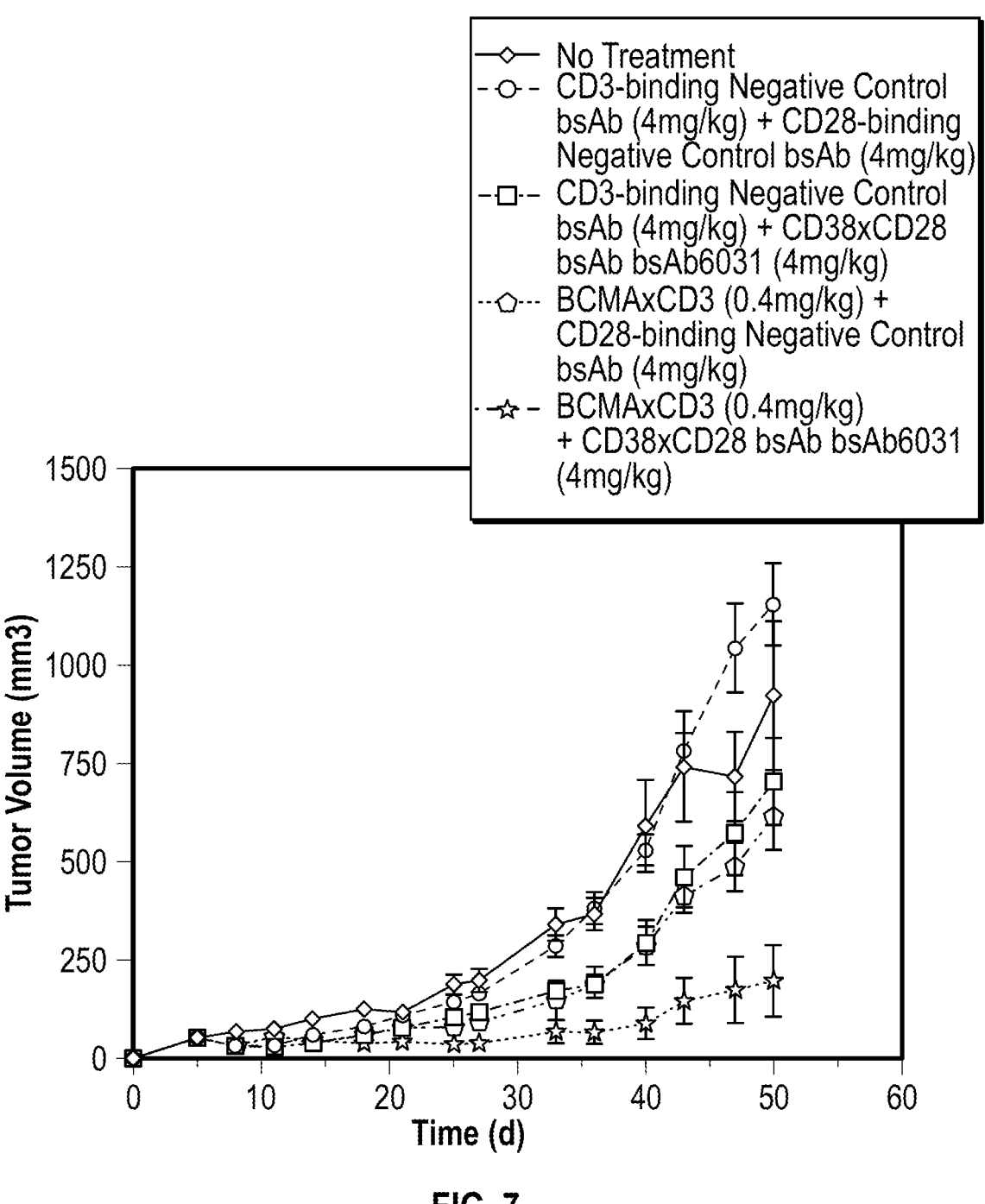

Results:

BCMAxCD3 bsAb plus CD28-binding negative control bsAb provided modest anti-tumor efficacy, with mean tumor sizes reduced compared to mice receiving CD3-binding negative control bsAb plus CD28-binding negative control bsAb (p=0.0004 on day 40 and p<0.0001 on days 43, 47, and 50 by 2-way ANOVA). Treatment with CD38xCD28 bsAb (bsAb6031) plus CD3-binding negative control bsAb modestly reduced mean tumor sizes compared to mice receiving CD3-binding negative control bsAb plus CD28-binding negative control bsAb (p=0.0007 on day 40 and p<0.0001 on days 43, 47, and 50 by 2-way ANOVA). However, the combination of BCMAxCD3 bsAb plus CD38xCD28 bsAb (bsAb6031) resulted in mean tumor sizes that were significantly lower than mice receiving BCMAxCD3 bsAb plus CD28-binding negative control bsAb (p=0.0069 on day 40 and p<0.0001 on days 43, 47, and 50 by 2-way ANOVA), or mice receiving CD3-binding negative control bsAb plus the CD38xCD28 bsAb6031 (p=0.0043 on day 40 and p<0.0001 on days 43, 47, and 50 by 2-way ANOVA). See Tables 41-54 and FIG. 7.

Thus, these studies demonstrate that while monotherapy with either BCMAxCD3 bsAb or CD38xCD28 bsAb demonstrates modest anti-tumor efficacy, combination treatment with BCMAxCD3 bsAb plus CD38xCD28 bsAb results in more potent, combinatorial anti-tumor efficacy that is superior to either therapy alone.

TABLE 41

Tumor Burden on Day 5

| Antibody Treatment | Average Tumor Size (mm$^3$) on Day 5 | Tumor Size SEM on Day 5 |
|---|---|---|
| PBS vehicle | 58.6 | 10.6 |
| CD3-binding negative control bsAb (4 mg/kg) + CD28-binding negative control bsAb (4 mg/kg) | 50.8 | 2.7 |
| CD3-binding negative control bsAb (4 mg/kg) + CD38xCD28 bsAb6031 (4 mg/kg) | 59.2 | 5.4 |
| BCMAxCD3 bsAb (0.4 mg/kg) + CD28-binding negative control bsAb (4 mg/kg) | 53.2 | 7.5 |
| BCMAxCD3 bsAb (0.4 mg/kg) + CD38xCD28 bsAb6031 (4 mg/kg) | 51.8 | 8.1 |

TABLE 42

Tumor Burden on Day 8

| Antibody Treatment | Average Tumor Size (mm$^3$) on Day 8 | Tumor Size SEM on Day 8 |
|---|---|---|
| PBS vehicle | 68.6 | 7.8 |
| CD3-binding negative control bsAb (4 mg/kg) + CD28-binding negative control bsAb (4 mg/kg) | 36.8 | 7.7 |
| CD3-binding negative control bsAb (4 mg/kg) + CD38xCD28 bsAb6031 (4 mg/kg) | 44.6 | 9.5 |
| BCMAxCD3 bsAb (0.4 mg/kg) + CD28-binding negative control bsAb (4 mg/kg) | 29.6 | 2.1 |
| BCMAxCD3 bsAb (0.4 mg/kg) + CD38xCD28 bsAb6031 (4 mg/kg) | 31.8 | 10.2 |

TABLE 43

Tumor Burden on Day 11

| Antibody Treatment | Average Tumor Size (mm³) on Day 11 | Tumor Size SEM on Day 11 |
|---|---|---|
| PBS vehicle | 75.0 | 10.6 |
| CD3-binding negative control bsAb (4 mg/kg) + CD28-binding negative control bsAb (4 mg/kg) | 51.4 | 7.9 |
| CD3-binding negative control bsAb (4 mg/kg) + CD38xCD28 bsAb6031 (4 mg/kg) | 28.8 | 4.9 |
| BCMAxCD3 bsAb (0.4 mg/kg) + CD28-binding negative control bsAb (4 mg/kg) | 35.0 | 5.4 |
| BCMAxCD3 bsAb (0.4 mg/kg) + CD38xCD28 bsAb6031 (4 mg/kg) | 52.8 | 19.7 |

TABLE 44

Tumor Burden on Day 14

| Antibody Treatment | Average Tumor Size (mm³) on Day 14 | Tumor Size SEM on Day 14 |
|---|---|---|
| PBS vehicle | 101.6 | 14.3 |
| CD3-binding negative control bsAb (4 mg/kg) + CD28-binding negative control bsAb (4 mg/kg) | 62.4 | 9.5 |
| CD3-binding negative control bsAb (4 mg/kg) + CD38xCD28 bsAb6031 (4 mg/kg) | 48.0 | 11.5 |
| BCMAxCD3 bsAb (0.4 mg/kg) + CD28-binding negative control bsAb (4 mg/kg) | 37.6 | 6.6 |
| BCMAxCD3 bsAb (0.4 mg/kg) + CD38xCD28 bsAb6031 (4 mg/kg) | 45.8 | 17.1 |

TABLE 45

Tumor Burden on Day 18

| Antibody Treatment | Average Tumor Size (mm³) on Day 18 | Tumor Size SEM on Day 18 |
|---|---|---|
| PBS vehicle | 124.6 | 14.7 |
| CD3-binding negative control bsAb (4 mg/kg) + CD28-binding negative control bsAb (4 mg/kg) | 81.2 | 10.3 |
| CD3-binding negative control bsAb (4 mg/kg) + CD38xCD28 bsAb6031 (4 mg/kg) | 62.6 | 11.8 |
| BCMAxCD3 bsAb (0.4 mg/kg) + CD28-binding negative control bsAb (4 mg/kg) | 47.0 | 5.7 |
| BCMAxCD3 bsAb (0.4 mg/kg) + CD38xCD28 bsAb6031 (4 mg/kg) | 40.4 | 13.4 |

TABLE 46

Tumor Burden on Day 21

| Antibody Treatment | Average Tumor Size (mm³) on Day 21 | Tumor Size SEM on Day 21 |
|---|---|---|
| PBS vehicle | 118.6 | 18.4 |
| CD3-binding negative control bsAb (4 mg/kg) + CD28-binding negative control bsAb (4 mg/kg) | 110.8 | 15.3 |
| CD3-binding negative control bsAb (4 mg/kg) + CD38xCD28 bsAb6031 (4 mg/kg) | 80.4 | 14.7 |
| BCMAxCD3 bsAb (0.4 mg/kg) + CD28-binding negative control bsAb (4 mg/kg) | 76.6 | 17.0 |
| BCMAxCD3 bsAb (0.4 mg/kg) + CD38xCD28 bsAb6031 (4 mg/kg) | 45.0 | 18.6 |

TABLE 47

Tumor Burden on Day 25

| Antibody Treatment | Average Tumor Size (mm³) on Day 25 | Tumor Size SEM on Day 25 |
|---|---|---|
| PBS vehicle | 188.4 | 25.5 |
| CD3-binding negative control bsAb (4 mg/kg) + CD28-binding negative control bsAb (4 mg/kg) | 144.2 | 11.9 |
| CD3-binding negative control bsAb (4 mg/kg) + CD38xCD28 bsAb6031 (4 mg/kg) | 103.6 | 22.9 |
| BCMAxCD3 bsAb (0.4 mg/kg) + CD28-binding negative control bsAb (4 mg/kg) | 75.0 | 15.9 |
| BCMAxCD3 bsAb (0.4 mg/kg) + CD38xCD28 bsAb6031 (4 mg/kg) | 36.6 | 14.9 |

TABLE 48

Tumor Burden on Day 27

| Antibody Treatment | Average Tumor Size (mm³) on Day 27 | Tumor Size SEM on Day 27 |
|---|---|---|
| PBS vehicle | 199.0 | 29.3 |
| CD3-binding negative control bsAb (4 mg/kg) + CD28-binding negative control bsAb (4 mg/kg) | 165.6 | 18.7 |
| CD3-binding negative control bsAb (4 mg/kg) + CD38xCD28 bsAb6031 (4 mg/kg) | 115.8 | 24.6 |
| BCMAxCD3 bsAb (0.4 mg/kg) + CD28-binding negative control bsAb (4 mg/kg) | 88.2 | 19.7 |
| BCMAxCD3 bsAb (0.4 mg/kg) + CD38xCD28 bsAb6031 (4 mg/kg) | 40.0 | 16.8 |

TABLE 49

Tumor Burden on Day 33

| Antibody Treatment | Average Tumor Size (mm³) on Day 33 | Tumor Size SEM on Day 33 |
|---|---|---|
| PBS vehicle | 340.2 | 42.3 |
| CD3-binding negative control bsAb (4 mg/kg) + CD28-binding negative control bsAb (4 mg/kg) | 287.2 | 27.0 |
| CD3-binding negative control bsAb (4 mg/kg) + CD38xCD28 bsAb6031 (4 mg/kg) | 172.2 | 27.6 |

TABLE 49-continued

| Antibody Treatment | Tumor Burden on Day 33 | |
| --- | --- | --- |
| | Average Tumor Size (mm³) on Day 33 | Tumor Size SEM on Day 33 |
| BCMAxCD3 bsAb (0.4 mg/kg) + CD28-binding negative control bsAb (4 mg/kg) | 148.2 | 14.2 |
| BCMAxCD3 bsAb (0.4 mg/kg) + CD38xCD28 bsAb6031 (4 mg/kg) | 68.4 | 29.9 |

TABLE 50

| Antibody Treatment | Tumor Burden on Day 36 | |
| --- | --- | --- |
| | Average Tumor Size (mm³) on Day 36 | Tumor Size SEM on Day 36 |
| PBS vehicle | 366.8 | 40.6 |
| CD3-binding negative control bsAb (4 mg/kg) + CD28-binding negative control bsAb (4 mg/kg) | 381.8 | 40.3 |
| CD3-binding negative control bsAb (4 mg/kg) + CD38xCD28 bsAb6031 (4 mg/kg) | 193.4 | 40.2 |
| BCMAxCD3 bsAb (0.4 mg/kg) + CD28-binding negative control bsAb (4 mg/kg) | 190.0 | 22.6 |
| BCMAxCD3 bsAb (0.4 mg/kg) + CD38xCD28 bsAb6031 (4 mg/kg) | 66.2 | 30.0 |

TABLE 51

| Antibody Treatment | Tumor Burden on Day 40 | |
| --- | --- | --- |
| | Average Tumor Size (mm³) on Day 40 | Tumor Size SEM on Day 40 |
| PBS vehicle | 591.2 | 117.6 |
| CD3-binding negative control bsAb (4 mg/kg) + CD28-binding negative control bsAb (4 mg/kg) | 530.0 | 39.4 |
| CD3-binding negative control bsAb (4 mg/kg) + CD38xCD28 bsAb6031 (4 mg/kg) | 294.8 | 58.4 |
| BCMAxCD3 bsAb (0.4 mg/kg) + CD28-binding negative control bsAb (4 mg/kg) | 286.0 | 48.8 |
| BCMAxCD3 bsAb (0.4 mg/kg) + CD38xCD28 bsAb6031 (4 mg/kg) | 89.6 | 40.8 |

TABLE 52

| Antibody Treatment | Tumor Burden on Day 43 | |
| --- | --- | --- |
| | Average Tumor Size (mm³) on Day 43 | Tumor Size SEM on Day 43 |
| PBS vehicle | 741.0 | 140.3 |
| CD3-binding negative control bsAb (4 mg/kg) + CD28-binding negative control bsAb (4 mg/kg) | 782.0 | 45.3 |
| CD3-binding negative control bsAb (4 mg/kg) + CD38xCD28 bsAb6031 (4 mg/kg) | 461.8 | 79.3 |
| BCMAxCD3 bsAb (0.4 mg/kg) + CD28-binding negative control bsAb (4 mg/kg) | 411.6 | 39.4 |

TABLE 52-continued

| Antibody Treatment | Tumor Burden on Day 43 | |
| --- | --- | --- |
| | Average Tumor Size (mm³) on Day 43 | Tumor Size SEM on Day 43 |
| BCMAxCD3 bsAb (0.4 mg/kg) + CD38xCD28 bsAb6031 (4 mg/kg) | 146.6 | 58.3 |

TABLE 53

| Antibody Treatment | Tumor Burden on Day 47 | |
| --- | --- | --- |
| | Average Tumor Size (mm³) on Day 47 | Tumor Size SEM on Day 47 |
| PBS vehicle | 717.8 | 113.5 |
| CD3-binding negative control bsAb (4 mg/kg) + CD28-binding negative control bsAb (4 mg/kg) | 1043.0 | 113.3 |
| CD3-binding negative control bsAb (4 mg/kg) + CD38xCD28 bsAb6031 (4 mg/kg) | 572.4 | 104.0 |
| BCMAxCD3 bsAb (0.4 mg/kg) + CD28-binding negative control bsAb (4 mg/kg) | 486.8 | 62.2 |
| BCMAxCD3 bsAb (0.4 mg/kg) + CD38xCD28 bsAb6031 (4 mg/kg) | 173.2 | 82.2 |

TABLE 54

| Antibody Treatment | Tumor Burden on Day 50 | |
| --- | --- | --- |
| | Average Tumor Size (mm³) on Day 50 | Tumor Size SEM on Day 50 |
| PBS vehicle | 922.8 | 188.6 |
| CD3-binding negative control bsAb (4 mg/kg) + CD28-binding negative control bsAb (4 mg/kg) | 1155.4 | 105.6 |
| CD3-binding negative control bsAb (4 mg/kg) + CD38xCD28 bsAb6031 (4 mg/kg) | 705.8 | 110.2 |
| BCMAxCD3 bsAb (0.4 mg/kg) + CD28-binding negative control bsAb (4 mg/kg) | 615.2 | 86.4 |
| BCMAxCD3 bsAb (0.4 mg/kg) + CD38xCD28 bsAb6031 (4 mg/kg) | 197.8 | 92.0 |

Example 12: In Vivo Anti-Tumor Efficacy of CD38xCD28 Bispecific Antibodies (bsAb) in Combination with a BCMAxCD3 bsAb against BCMA+CD38+MOLP-8 Human Multiple Myeloma Tumor Cell Growth To determine the in vivo anti-tumor efficacy of CD38xCD28 bispecific antibodies (bsAb) in combination with a BCMAxCD3 bsAb, a xenogeneic tumor study was performed. Like the previous experiments in Examples 9 and 10, this experiment changed the dose of the BCMAxCD3 bsAb from 4 mg/kg to 0.4 mg/kg and the dose of bsAb6031 and bsAb7945 to 0.4 mg/kg. In addition, the length of the experiment was shorter in the present Example, 44 days, versus 52 days in Example 9.

Implantation and Measurement of Xenogeneic Tumors

On day-12, immunodeficient NOD.Cg-Prkdc$^{scid}$Il2rg$^{tm1Wjl}$/SzJ (NSG) mice (8-10 Weeks Old, Jackson Labs, CAT #: 005557) were intraperitoneally injected with $4 \times 10^6$ human peripheral blood mononuclear cells (PBMC) from a normal, healthy donor (Reach Bio, CAT #: 0500-301, Lot #: 0180821). On day 0, the mice were intravenously administered $2 \times 10^6$ BCMA$^+$CD38$^+$ MOLP-8 human multiple myeloma tumor cells (DSMZ, CAT #: ACC569) that were engineered to also express firefly luciferase (MOLP-8-luciferase cells). The mice (n=5 per group) were then immediately administered either a CD3-binding negative control bispecific Ab (H4sH17664D) or a BCMAxCD3 (bsAb5458) bsAb at 0.4 mg/kg, in combination with a CD28-binding negative control bispecific Ab (bsAb5671) at 4 mg/kg or a CD38xCD28 bsAb (either bsAb6031 or bsAb7945) at 0.4 mg/kg. The mice were administered these Abs twice more on days 7 and 15, for a total of three doses. Tumor growth was assessed over 44 days by measuring tumor bioluminescence (BLI) in anesthetized animals. As a positive control, a group of mice (n=5) was given only MOLP-8-luciferase cells and PBMCs, but not antibody (PBS-treated group). In order to measure background BLI levels, a group of mice (n=5) were untreated and did not receive tumors, PBMC, or antibody (No Tumor group).

Measurement of Xenogeneic Tumor Growth

BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as total flux (photons/second—p/s).

Results:

BCMAxCD3 bsAb plus CD28-binding negative control bsAb provided modest anti-tumor efficacy, with mean BLI readings reduced compared to mice receiving CD3-binding negative control bsAb plus CD28-binding negative control bsAb. Treatment with CD3-binding negative control bsAb plus either CD38xCD28 bsAb (bsAb6031 and bsAb7945) modestly reduced mean BLI readings compared to mice receiving CD3-binding negative control bsAb plus CD28-binding negative control bsAb. However, the combination of BCMAxCD3 bsAb plus either CD38xCD28 bsAb (bsAb6031 and bsAb7945) resulted in mean BLI readings that were lower than mice receiving BCMAxCD3 bsAb plus CD28-binding negative control bsAb, mice receiving CD3-binding negative control bsAb plus bsAb6031, or mice receiving CD3-binding negative control bsAb plus bsAb7945. See Tables 55-64 and FIG. 8.

Thus, these studies demonstrate that while monotherapy with either BCMAxCD3 bsAb or CD38xCD28 bsAb demonstrates only modest anti-tumor efficacy, combination treatment with BCMAxCD3 bsAb plus CD38xCD28 bsAb results in more potent, combinatorial anti-tumor efficacy that is superior to either therapy alone.

TABLE 55

| Tumor Burden and Surviving Mice on Day 9 | | | |
| --- | --- | --- | --- |
| Antibody Treatment | Tumor Burden-Mean Total Flux (p/s) on Day 9 | Total Flux SEM on Day 9 | Number of mice still alive on day 9 |
| PBS vehicle | 1.66E+06 | 1.22E+05 | 5 of 5 |
| CD3-binding negative control bsAb (0.4 mg/kg) + CD28-binding negative control bsAb (4 mg/kg) | 1.98E+06 | 3.53E+05 | 5 of 5 |
| CD3-binding negative control bsAb (0.4 mg/kg) + CD38xCD28 bsAb6031 (0.4 mg/kg) | 2.04E+06 | 5.74E+05 | 5 of 5 |
| CD3-binding negative control bsAb (0.4 mg/kg) + CD38xCD28 bsAb7945 (0.4 mg/kg) | 7.65E+05 | 1.49E+05 | 5 of 5 |
| BCMAxCD3 bsAb (0.4 mg/kg) + CD28-binding negative control bsAb (4 mg/kg) | 5.06E+05 | 1.21E+05 | 5 of 5 |
| BCMAxCD3 bsAb (0.4 mg/kg) + CD38xCD28 bsAb6031 (0.4 mg/kg) | 4.52E+05 | 2.71E+04 | 5 of 5 |
| BCMAxCD3 bsAb (0.4 mg/kg) + CD38xCD28 bsAb7945 (0.4 mg/kg) | 3.57E+05 | 2.01E+04 | 4 of 4 |
| No Tumor (Background BLI) | 4.26E+05 | 2.05E+04 | 5 of 5 |

TABLE 56

| Tumor Burden and Surviving Mice on Day 14 | | | |
| --- | --- | --- | --- |
| Antibody Treatment | Tumor Burden-Mean Total Flux (p/s) on Day 14 | Total Flux SEM on Day 14 | Number of mice still alive on day 14 |
| PBS vehicle | 2.98E+07 | 8.54E+06 | 5 of 5 |
| CD3-binding negative control bsAb (0.4 mg/kg) + CD28-binding negative control bsAb (4 mg/kg) | 3.29E+07 | 9.51E+06 | 5 of 5 |
| CD3-binding negative control bsAb (0.4 mg/kg) + CD38xCD28 bsAb6031 (0.4 mg/kg) | 2.74E+07 | 4.37E+06 | 5 of 5 |
| CD3-binding negative control bsAb (0.4 mg/kg) + CD38xCD28 bsAb7945 (0.4 mg/kg) | 9.05E+06 | 2.97E+06 | 5 of 5 |
| BCMAxCD3 bsAb (0.4 mg/kg) + CD28-binding negative control bsAb (4 mg/kg) | 2.48E+06 | 1.93E+06 | 5 of 5 |
| BCMAxCD3 bsAb (0.4 mg/kg) + CD38xCD28 bsAb6031 (0.4 mg/kg) | 5.28E+05 | 4.62E+04 | 5 of 5 |
| BCMAxCD3 bsAb (0.4 mg/kg) + CD38xCD28 bsAb7945 (0.4 mg/kg) | 4.72E+05 | 4.23E+04 | 4 of 4 |
| No Tumor (Background BLI) | 4.15E+05 | 4.91E+03 | 5 of 5 |

TABLE 57

| Tumor Burden and Surviving Mice on Day 17 | | | |
| --- | --- | --- | --- |
| Antibody Treatment | Tumor Burden-Mean Total Flux (p/s) on Day 17 | Total Flux SEM on Day 17 | Number of mice still alive on day 17 |
| PBS vehicle | 4.64E+07 | 1.11E+07 | 5 of 5 |
| CD3-binding negative control bsAb (0.4 mg/kg) + CD28-binding negative control bsAb (4 mg/kg) | 5.90E+07 | 9.00E+06 | 5 of 5 |
| CD3-binding negative control bsAb (0.4 mg/kg) + CD38xCD28 bsAb6031 (0.4 mg/kg) | 4.81E+07 | 4.48E+06 | 5 of 5 |
| CD3-binding negative control bsAb (0.4 mg/kg) + CD38xCD28 bsAb7945 (0.4 mg/kg) | 2.25E+07 | 6.35E+06 | 5 of 5 |

TABLE 57-continued

| | Tumor Burden- Mean Total Flux (p/s) on Day 17 | Total Flux SEM on Day 17 | Number of mice still alive on day 17 |
|---|---|---|---|
| Antibody Treatment | | | |
| BCMAxCD3 bsAb (0.4 mg/kg) + CD28-binding negative control bsAb (4 mg/kg) | 9.49E+06 | 8.38E+06 | 5 of 5 |
| BCMAxCD3 bsAb (0.4 mg/kg) + CD38xCD28 bsAb6031 (0.4 mg/kg) | 7.14E+05 | 1.16E+05 | 5 of 5 |
| BCMAxCD3 bsAb (0.4 mg/kg) + CD38xCD28 bsAb7945 (0.4 mg/kg) | 5.40E+05 | 4.87E+04 | 4 of 4 |
| No Tumor (Background BLI) | 4.78E+05 | 1.75E+04 | 5 of 5 |

TABLE 58

Tumor Burden and Surviving Mice on Day 21

| Antibody Treatment | Tumor Burden- Mean Total Flux (p/s) on Day 21 | Total Flux SEM on Day 21 | Number of mice still alive on day 21 |
|---|---|---|---|
| PBS vehicle | 7.45E+07 | 3.12E+07 | 5 of 5 |
| CD3-binding negative control bsAb (0.4 mg/kg) + CD28-binding negative control bsAb (4 mg/kg) | 7.45E+07 | 2.70E+07 | 5 of 5 |
| CD3-binding negative control bsAb (0.4 mg/kg) + CD38xCD28 bsAb6031 (0.4 mg/kg) | 5.99E+07 | 1.05E+07 | 5 of 5 |
| CD3-binding negative control bsAb (0.4 mg/kg) + CD38xCD28 bsAb7945 (0.4 mg/kg) | 2.62E+07 | 9.18E+06 | 4 of 5 |
| BCMAxCD3 bsAb (0.4 mg/kg) + CD28-binding negative control bsAb (4 mg/kg) | 1.57E+07 | 1.22E+07 | 5 of 5 |
| BCMAxCD3 bsAb (0.4 mg/kg) + CD38xCD28 bsAb6031 (0.4 mg/kg) | 9.49E+05 | 3.50E+05 | 5 of 5 |
| BCMAxCD3 bsAb (0.4 mg/kg) + CD38xCD28 bsAb7945 (0.4 mg/kg) | 4.49E+05 | 1.14E+04 | 4 of 4 |
| No Tumor (Background BLI) | 4.30E+05 | 1.56E+04 | 5 of 5 |

TABLE 59

Tumor Burden and Surviving Mice on Day 24

| Antibody Treatment | Tumor Burden- Mean Total Flux (p/s) on Day 24 | Total Flux SEM on Day 24 | Number of mice still alive on day 24 |
|---|---|---|---|
| PBS vehicle | | | 0 of 5 |
| CD3-binding negative control bsAb (0.4 mg/kg) + CD28-binding negative control bsAb (4 mg/kg) | 7.38E+06 | 0.00E+00 | 1 of 5 |
| CD3-binding negative control bsAb (0.4 mg/kg) + CD38xCD28 bsAb6031 (0.4 mg/kg) | 2.02E+07 | 0.00E+00 | 1 of 5 |
| CD3-binding negative control bsAb (0.4 mg/kg) + CD38xCD28 bsAb7945 (0.4 mg/kg) | 4.19E+07 | 2.01E+07 | 2 of 5 |
| BCMAxCD3 bsAb (0.4 mg/kg) + CD28-binding negative control bsAb (4 mg/kg) | 1.02E+07 | 5.05E+06 | 4 of 5 |
| BCMAxCD3 bsAb (0.4 mg/kg) + CD38xCD28 bsAb6031 (0.4 mg/kg) | 2.49E+06 | 1.59E+06 | 5 of 5 |
| BCMAxCD3 bsAb (0.4 mg/kg) + CD38xCD28 bsAb7945 (0.4 mg/kg) | 6.60E+05 | 9.94E+04 | 4 of 4 |
| No Tumor (Background BLI) | 5.72E+05 | 3.29E+04 | 5 of 5 |

TABLE 60

Tumor Burden and Surviving Mice on Day 28

| Antibody Treatment | Tumor Burden- Mean Total Flux (p/s) on Day 28 | Total Flux SEM on Day 28 | Number of mice still alive on day 28 |
|---|---|---|---|
| PBS vehicle | | | 0 of 5 |
| CD3-binding negative control bsAb (0.4 mg/kg) + CD28-binding negative control bsAb (4 mg/kg) | 1.13E+07 | 0.00E+00 | 1 of 5 |
| CD3-binding negative control bsAb (0.4 mg/kg) + CD38xCD28 bsAb6031 (0.4 mg/kg) | | | 0 of 5 |
| CD3-binding negative control bsAb (0.4 mg/kg) + CD38xCD28 bsAb7945 (0.4 mg/kg) | 3.94E+07 | 0.00E+00 | 1 of 5 |
| BCMAxCD3 bsAb (0.4 mg/kg) + CD28-binding negative control bsAb (4 mg/kg) | 4.01E+07 | 2.14E+07 | 4 of 5 |
| BCMAxCD3 bsAb (0.4 mg/kg) + CD38xCD28 bsAb6031 (0.4 mg/kg) | 7.74E+06 | 5.60E+06 | 5 of 5 |
| BCMAxCD3 bsAb (0.4 mg/kg) + CD38xCD28 bsAb7945 (0.4 mg/kg) | 6.73E+05 | 1.97E+05 | 4 of 4 |
| No Tumor (Background BLI) | 3.46E+05 | 1.10E+04 | 5 of 5 |

TABLE 61

Tumor Burden and Surviving Mice on Day 31

| Antibody Treatment | Tumor Burden- Mean Total Flux (p/s) on Day 31 | Total Flux SEM on Day 31 | Number of mice still alive on day 31 |
|---|---|---|---|
| PBS vehicle | | | 0 of 5 |
| CD3-binding negative control bsAb (0.4 mg/kg) + CD28-binding negative control bsAb (4 mg/kg) | 5.59E+07 | 0.00E+00 | 1 of 5 |
| CD3-binding negative control bsAb (0.4 mg/kg) + CD38xCD28 bsAb6031 (0.4 mg/kg) | | | 0 of 5 |
| CD3-binding negative control bsAb (0.4 mg/kg) + CD38xCD28 bsAb7945 (0.4 mg/kg) | 7.43E+07 | 0.00E+00 | 1 of 5 |
| BCMAxCD3 bsAb (0.4 mg/kg) + CD28-binding negative control bsAb (4 mg/kg) | 5.53E+07 | 3.02E+07 | 4 of 5 |
| BCMAxCD3 bsAb (0.4 mg/kg) + CD38xCD28 bsAb6031 (0.4 mg/kg) | 3.52E+07 | 2.13E+07 | 5 of 5 |
| BCMAxCD3 bsAb (0.4 mg/kg) + CD38xCD28 bsAb7945 (0.4 mg/kg) | 1.01E+06 | 4.56E+05 | 3 of 4 |
| No Tumor (Background BLI) | 4.53E+05 | 2.11E+04 | 5 of 5 |

TABLE 62

Tumor Burden and Surviving Mice on Day 34

| Antibody Treatment | Tumor Burden-Mean Total Flux (p/s) on Day 34 | Total Flux SEM on Day 34 | Number of mice still alive on day 34 |
|---|---|---|---|
| PBS vehicle | | | 0 of 5 |
| CD3-binding negative control bsAb (0.4 mg/kg) + CD28-binding negative control bsAb (4 mg/kg) | 7.79E+07 | 0.00E+00 | 1 of 5 |
| CD3-binding negative control bsAb (0.4 mg/kg) + CD38xCD28 bsAb6031 (0.4 mg/kg) | | | 0 of 5 |
| CD3-binding negative control bsAb (0.4 mg/kg) + CD38xCD28 bsAb7945 (0.4 mg/kg) | 1.37E+08 | 0.00E+00 | 1 of 5 |
| BCMAxCD3 bsAb (0.4 mg/kg) + CD28-binding negative control bsAb (4 mg/kg) | 2.80E+08 | 1.40E+08 | 3 of 5 |
| BCMAxCD3 bsAb (0.4 mg/kg) + CD38xCD28 bsAb6031 (0.4 mg/kg) | 4.41E+07 | 2.79E+07 | 5 of 5 |
| BCMAxCD3 bsAb (0.4 mg/kg) + CD38xCD28 bsAb7945 (0.4 mg/kg) | 1.68E+06 | 1.10E+06 | 3 of 4 |
| No Tumor (Background BLI) | 5.90E+05 | 3.29E+04 | 5 of 5 |

TABLE 63

Tumor Burden and Surviving Mice on Day 38

| Antibody Treatment | Tumor Burden-Mean Total Flux (p/s) on Day 38 | Total Flux SEM on Day 38 | Number of mice still alive on day 38 |
|---|---|---|---|
| PBS vehicle | | | 0 of 5 |
| CD3-binding negative control bsAb (0.4 mg/kg) + CD28-binding negative control bsAb (4 mg/kg) | 2.64E+08 | 0.00E+00 | 1 of 5 |
| CD3-binding negative control bsAb (0.4 mg/kg) + CD38xCD28 bsAb6031 (0.4 mg/kg) | | | 0 of 5 |
| CD3-binding negative control bsAb (0.4 mg/kg) + CD38xCD28 bsAb7945 (0.4 mg/kg) | | | 0 of 5 |
| BCMAxCD3 bsAb (0.4 mg/kg) + CD28-binding negative control bsAb (4 mg/kg) | 7.07E+08 | 4.05E+08 | 3 of 5 |
| BCMAxCD3 bsAb (0.4 mg/kg) + CD38xCD28 bsAb6031 (0.4 mg/kg) | 7.12E+07 | 6.96E+07 | 4 of 5 |
| BCMAxCD3 bsAb (0.4 mg/kg) + CD38xCD28 bsAb7945 (0.4 mg/kg) | 4.37E+06 | 3.87E+06 | 3 of 4 |
| No Tumor (Background BLI) | 4.86E+05 | 1.15E+04 | 5 of 5 |

TABLE 64

Tumor Burden and Surviving Mice on Day 44

| Antibody Treatment | Tumor Burden-Mean Total Flux (p/s) on Day 44 | Total Flux SEM on Day 44 | Number of mice still alive on day 44 |
|---|---|---|---|
| PBS vehicle | | | 0 of 5 |
| CD3-binding negative control bsAb (0.4 mg/kg) + CD28-binding negative control bsAb (4 mg/kg) | 1.27E+09 | 0.00E+00 | 1 of 5 |
| CD3-binding negative control bsAb (0.4 mg/kg) + CD38xCD28 bsAb6031 (0.4 mg/kg) | | | 0 of 5 |
| CD3-binding negative control bsAb (0.4 mg/kg) + CD38xCD28 bsAb7945 (0.4 mg/kg) | | | 0 of 5 |

TABLE 64-continued

Tumor Burden and Surviving Mice on Day 44

| Antibody Treatment | Tumor Burden-Mean Total Flux (p/s) on Day 44 | Total Flux SEM on Day 44 | Number of mice still alive on day 44 |
|---|---|---|---|
| BCMAxCD3 bsAb (0.4 mg/kg) + CD28-binding negative control bsAb (4 mg/kg) | 2.33E+08 | 1.33E+08 | 3 of 5 |
| BCMAxCD3 bsAb (0.4 mg/kg) + CD38xCD28 bsAb6031 (0.4 mg/kg) | 2.49E+08 | 2.39E+08 | 3 of 5 |
| BCMAxCD3 bsAb (0.4 mg/kg) + CD38xCD28 bsAb7945 (0.4 mg/kg) | 1.88E+07 | 1.79E+07 | 2 of 4 |
| No Tumor (Background BLI) | 6.22E+05 | 7.86E+04 | 5 of 5 |

Example 13: CD38 Cross Competition Analysis

A competition binding assay was performed to assess the ability of CD38xCD28 bispecific antibodies, CD38 parental antibodies, and CD38 comparator antibodies to compete with one another for binding to hCD38.mmh.

The entire experiment was performed at 25° C. with the flow rate of 1000 rpm in Octet HBS-EP buffer (pH 7.4 plus 1 mg/mL BSA). To assess whether 2 antibodies were able to compete with one another for binding to their respective epitopes on recombinant human CD38 expressed with a C-terminal myc-myc-hexahistidine tag (hCD38-mmH), around 0.27 nm of hCD38.mmH was captured by dipping high density anti-His1K coated Octet tips in wells containing 50 ug/mL (300 nM) of hCD38.mmh for 5 min. The antigen coated sensor tips were then placed into wells containing 50 ug/mL solution of a first anti-CD38 monoclonal antibody or bispecific antibody for 5 minutes to saturate the hCD38.mmH surface. The sensor tips were then subsequently dipped into wells containing 50 ug/mL solution of a second anti-CD38 monoclonal antibody or bispecific antibody. The sensor tips were washed in Octet HBS-EP buffer in between every step of the experiment. The real-time binding response was monitored during the course of the experiment and the binding response at the end of every step was recorded. The response of antibody binding to hCD38.mmH pre-complexed with the first antibody was compared and competitive/non-competitive behavior of different anti-CD38 monoclonal and bispecific antibodies was determined.

Results: The data, not shown, indicate that the CD38xCD28 bsAb7945 and bsAb6031 bi-directionally compete with each other for binding to hCD38.mmh. The parental anti-CD38 antibodies also showed bi-directional cross-competition for binding to hCD38.mmh.

Example 14: In Vivo Anti-Tumor Efficacy of CD38xCD28 Bispecific Antibodies (bsAb) in Combination with a BCMAxCD3 bsAb against BCMA⁺CD38⁺ WSU-DLCL2 Tumor Cell Growth To determine the in vivo anti-tumor efficacy of CD38xCD28 bispecific antibodies (bsAb) in combination with a BCMAxCD3 bsAb, the following xenogeneic tumor study was performed. This example is like the previous experiment in Example 11, however this experiment also examined 0.4 mg/kg and 0.04 mg/kg dosages of bsAb6031 and bsAb7945. Implantation and measurement of xenogeneic tumors.

On day 0, immunodeficient NOD.Cg-Prkdc$^{scid}$Il2rg$^{tm1Wjl}$/ SzJ (NSG) mice were subcutaneously injected with a 3×10$^6$ BCMA$^+$CD38$^+$ WSU-DLCL2 tumor cells and 0.5×10$^6$ PBMC's from a normal donor mixed together in 50% Matrigel. On day 1, the mice (n=5 per group) were administered either a CD3-binding negative control bispecific Ab (H4sH17664D) or a BCMAxCD3 bsAb (bsAb5458) at 0.4 mg/kg, in combination with a CD28-binding negative control bispecific Ab (bsAb5671) at 4 mg/kg or a CD38xCD28 bsAb (either bsAb6031 or bsAb7945) at either 4 mg/kg, 0.4 mg/kg, or 0.04 mg/kg. The mice were administered these Abs twice more on days 8 and 15, for a total of three doses. Tumor growth was assessed through day 50 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/ 2.

Results:

BCMAxCD3 bsAb plus CD28-binding negative control bsAb provided modest anti-tumor efficacy, with mean tumor sizes reduced compared to mice receiving CD3-binding negative control bsAb plus CD28-binding negative control bsAb (p<0.0001 on day 50 by 2-way ANOVA). Treatment with CD38xCD28 bsAb6031 plus CD3-binding negative control bsAb modestly reduced mean tumor sizes compared to mice receiving CD3-binding negative control bsAb plus CD28-binding negative control bsAb (p=0.0089 on day 50 by 2-way ANOVA). Treatment with CD38xCD28 bsAb7945 plus CD3-binding negative control bsAb also modestly reduced mean tumor sizes compared to mice receiving CD3-binding negative control bsAb plus CD28-binding negative control bsAb (p<0.0001 on day 50 by 2-way ANOVA). However, the combination of BCMAxCD3 bsAb plus CD38xCD28 bsAb6031 at 4 mg/kg resulted in mean tumor sizes that were significantly lower than mice receiving BCMAxCD3 bsAb plus CD28-binding negative control bsAb (p<0.0001 on day 50 by 2-way ANOVA), or mice receiving CD3-binding negative control bsAb plus the CD38xCD28 bsAb6031 (p<0.0001 on day 50 by 2-way ANOVA). Further, the combination of BCMAxCD3 bsAb plus CD38xCD28 bsAb7945 at 4 mg/kg and 0.4 mg/kg resulted in mean tumor sizes that were significantly lower than mice receiving BCMAxCD3 bsAb plus CD28-binding negative control bsAb (p<0.0001 on day 50 by 2-way ANOVA for both doses), or mice receiving CD3-binding negative control bsAb plus the CD38xCD28 bsAb6031 (p<0.0001 on day 50 by 2-way ANOVA for both doses). See FIG. 9 and Tables 65-78.

These studies confirm that while monotherapy with either BCMAxCD3 bsAb or CD38xCD28 bsAb demonstrates modest anti-tumor efficacy, combination treatment with BCMAxCD3 bsAb plus CD38xCD28 bsAb results in more potent, combinatorial anti-tumor efficacy that is superior to either therapy alone.

TABLE 65

| Tumor Burden on Day 4 | | |
|---|---|---|
| Antibody Treatment | Average Tumor Size (mm$^3$) on Day 4 | Tumor Size SEM on Day 4 |
| PBS vehicle | 85.50 | 16.18 |
| CD3-binding negative control bsAb (0.4 mg/kg) + CD28-binding negative control bsAb (4 mg/kg) | 66.10 | 5.19 |
| BCMAxCD3 bsAb (0.4 mg/kg) + CD28-binding negative control bsAb (4 mg/kg) | 56.82 | 4.05 |
| CD3-binding negative control bsAb (0.4 mg/kg) + CD38xCD28 bsAb6031 (4 mg/kg) | 66.45 | 6.01 |
| CD3-binding negative control bsAb (0.4 mg/kg) + CD38xCD28 bsAb7945 (4 mg/kg) | 74.71 | 3.16 |
| BCMAxCD3 bsAb (0.4 mg/kg) + CD38xCD28 bsAb6031 (4 mg/kg) | 51.39 | 5.57 |
| BCMAxCD3 bsAb (0.4 mg/kg) + CD38xCD28 bsAb6031 (0.4 mg/kg) | 50.11 | 6.03 |
| BCMAxCD3 bsAb (0.4 mg/kg) + CD38xCD28 bsAb6031 (0.04 mg/kg) | 83.73 | 9.58 |
| BCMAxCD3 bsAb (0.4 mg/kg) + CD38xCD28 bsAb7945 (4 mg/kg) | 64.12 | 6.04 |
| BCMAxCD3 bsAb (0.4 mg/kg) + CD38xCD28 bsAb7945 (0.4 mg/kg) | 54.57 | 3.77 |
| BCMAxCD3 bsAb (0.4 mg/kg) + CD38xCD28 bsAb7945 (0.04 mg/kg) | 63.14 | 3.11 |

TABLE 66

| Tumor Burden on Day 8 | | |
|---|---|---|
| Antibody Treatment | Average Tumor Size (mm$^3$) on Day 8 | Tumor Size SEM on Day 8 |
| PBS vehicle | 55.83 | 2.38 |
| CD3-binding negative control bsAb (0.4 mg/kg) + CD28-binding negative control bsAb (4 mg/kg) | 71.47 | 6.67 |
| BCMAxCD3 bsAb (0.4 mg/kg) + CD28-binding negative control bsAb (4 mg/kg) | 51.44 | 3.02 |
| CD3-binding negative control bsAb (0.4 mg/kg) + CD38xCD28 bsAb6031 (4 mg/kg) | 56.85 | 5.01 |
| CD3-binding negative control bsAb (0.4 mg/kg) + CD38xCD28 bsAb7945 (4 mg/kg) | 53.51 | 6.15 |
| BCMAxCD3 bsAb (0.4 mg/kg) + CD38xCD28 bsAb6031 (4 mg/kg) | 42.03 | 4.38 |
| BCMAxCD3 bsAb (0.4 mg/kg) + CD38xCD28 bsAb6031 (0.4 mg/kg) | 57.05 | 5.82 |
| BCMAxCD3 bsAb (0.4 mg/kg) + CD38xCD28 bsAb6031 (0.04 mg/kg) | 73.74 | 4.07 |
| BCMAxCD3 bsAb (0.4 mg/kg) + CD38xCD28 bsAb7945 (4 mg/kg) | 50.21 | 5.48 |
| BCMAxCD3 bsAb (0.4 mg/kg) + CD38xCD28 bsAb7945 (0.4 mg/kg) | 53.78 | 3.73 |
| BCMAxCD3 bsAb (0.4 mg/kg) + CD38xCD28 bsAb7945 (0.04 mg/kg) | 56.03 | 3.47 |

TABLE 67

| Antibody Treatment | Average Tumor Size (mm³) on Day 12 | Tumor Size SEM on Day 12 |
|---|---|---|
| PBS vehicle | 85.78 | 12.07 |
| CD3-binding negative control bsAb (0.4 mg/kg) + CD28-binding negative control bsAb (4 mg/kg) | 83.84 | 8.78 |
| BCMAxCD3 bsAb (0.4 mg/kg) + CD28-binding negative control bsAb (4 mg/kg) | 80.34 | 4.68 |
| CD3-binding negative control bsAb (0.4 mg/kg) + CD38xCD28 bsAb6031 (4 mg/kg) | 85.66 | 8.35 |
| CD3-binding negative control bsAb (0.4 mg/kg) + CD38xCD28 bsAb7945 (4 mg/kg) | 82.00 | 3.62 |
| BCMAxCD3 bsAb (0.4 mg/kg) + CD38xCD28 bsAb6031 (4 mg/kg) | 63.97 | 7.77 |
| BCMAxCD3 bsAb (0.4 mg/kg) + CD38xCD28 bsAb6031 (0.4 mg/kg) | 99.11 | 12.46 |
| BCMAxCD3 bsAb (0.4 mg/kg) + CD38xCD28 bsAb6031 (0.04 mg/kg) | 97.39 | 3.49 |
| BCMAxCD3 bsAb (0.4 mg/kg) + CD38xCD28 bsAb7945 (4 mg/kg) | 71.13 | 6.31 |
| BCMAxCD3 bsAb (0.4 mg/kg) + CD38xCD28 bsAb7945 (0.4 mg/kg) | 74.53 | 8.22 |
| BCMAxCD3 bsAb (0.4 mg/kg) + CD38xCD28 bsAb7945 (0.04 mg/kg) | 96.15 | 6.91 |

TABLE 68

Tumor Burden on Day 15

| Antibody Treatment | Average Tumor Size (mm³) on Day 15 | Tumor Size SEM on Day 15 |
|---|---|---|
| PBS vehicle | 96.13 | 6.95 |
| CD3-binding negative control bsAb (0.4 mg/kg) + CD28-binding negative control bsAb (4 mg/kg) | 108.55 | 9.12 |
| BCMAxCD3 bsAb (0.4 mg/kg) + CD28-binding negative control bsAb (4 mg/kg) | 77.60 | 4.77 |
| CD3-binding negative control bsAb (0.4 mg/kg) + CD38xCD28 bsAb6031 (4 mg/kg) | 95.61 | 4.30 |
| CD3-binding negative control bsAb (0.4 mg/kg) + CD38xCD28 bsAb7945 (4 mg/kg) | 107.35 | 3.75 |
| BCMAxCD3 bsAb (0.4 mg/kg) + CD38xCD28 bsAb6031 (4 mg/kg) | 77.48 | 7.64 |
| BCMAxCD3 bsAb (0.4 mg/kg) + CD38xCD28 bsAb6031 (0.4 mg/kg) | 111.19 | 5.43 |
| BCMAxCD3 bsAb (0.4 mg/kg) + CD38xCD28 bsAb6031 (0.04 mg/kg) | 131.37 | 6.27 |
| BCMAxCD3 bsAb (0.4 mg/kg) + CD38xCD28 bsAb7945 (4 mg/kg) | 85.93 | 11.39 |
| BCMAxCD3 bsAb (0.4 mg/kg) + CD38xCD28 bsAb7945 (0.4 mg/kg) | 90.88 | 9.25 |
| BCMAxCD3 bsAb (0.4 mg/kg) + CD38xCD28 bsAb7945 (0.04 mg/kg) | 122.56 | 8.22 |

TABLE 69

Tumor Burden on Day 18

| Antibody Treatment | Average Tumor Size (mm³) on Day 18 | Tumor Size SEM on Day 18 |
|---|---|---|
| PBS vehicle | 106.35 | 12.16 |
| CD3-binding negative control bsAb (0.4 mg/kg) + CD28-binding negative control bsAb (4 mg/kg) | 120.82 | 10.41 |
| BCMAxCD3 bsAb (0.4 mg/kg) + CD28-binding negative control bsAb (4 mg/kg) | 104.88 | 9.04 |
| CD3-binding negative control bsAb (0.4 mg/kg) + CD38xCD28 bsAb6031 (4 mg/kg) | 116.50 | 4.33 |
| CD3-binding negative control bsAb (0.4 mg/kg) + CD38xCD28 bsAb7945 (4 mg/kg) | 121.23 | 6.49 |
| BCMAxCD3 bsAb (0.4 mg/kg) + CD38xCD28 bsAb6031 (4 mg/kg) | 79.21 | 6.63 |
| BCMAxCD3 bsAb (0.4 mg/kg) + CD38xCD28 bsAb6031 (0.4 mg/kg) | 118.88 | 13.24 |
| BCMAxCD3 bsAb (0.4 mg/kg) + CD38xCD28 bsAb6031 (0.04 mg/kg) | 148.63 | 12.24 |
| BCMAxCD3 bsAb (0.4 mg/kg) + CD38xCD28 bsAb7945 (4 mg/kg) | 70.63 | 6.89 |
| BCMAxCD3 bsAb (0.4 mg/kg) + CD38xCD28 bsAb7945 (0.4 mg/kg) | 83.16 | 6.72 |
| BCMAxCD3 bsAb (0.4 mg/kg) + CD38xCD28 bsAb7945 (0.04 mg/kg) | 143.53 | 22.02 |

TABLE 70

Tumor Burden on Day 22

| Antibody Treatment | Average Tumor Size (mm³) on Day 22 | Tumor Size SEM on Day 22 |
|---|---|---|
| PBS vehicle | 146.39 | 17.98 |
| CD3-binding negative control bsAb (0.4 mg/kg) + CD28-binding negative control bsAb (4 mg/kg) | 192.17 | 15.35 |
| BCMAxCD3 bsAb (0.4 mg/kg) + CD28-binding negative control bsAb (4 mg/kg) | 130.06 | 14.28 |
| CD3-binding negative control bsAb (0.4 mg/kg) + CD38xCD28 bsAb6031 (4 mg/kg) | 160.92 | 12.52 |
| CD3-binding negative control bsAb (0.4 mg/kg) + CD38xCD28 bsAb7945 (4 mg/kg) | 168.61 | 10.10 |
| BCMAxCD3 bsAb (0.4 mg/kg) + CD38xCD28 bsAb6031 (4 mg/kg) | 108.90 | 12.96 |
| BCMAxCD3 bsAb (0.4 mg/kg) + CD38xCD28 bsAb6031 (0.4 mg/kg) | 148.48 | 16.02 |
| BCMAxCD3 bsAb (0.4 mg/kg) + CD38xCD28 bsAb6031 (0.04 mg/kg) | 189.83 | 14.62 |
| BCMAxCD3 bsAb (0.4 mg/kg) + CD38xCD28 bsAb7945 (4 mg/kg) | 74.83 | 2.85 |
| BCMAxCD3 bsAb (0.4 mg/kg) + CD38xCD28 bsAb7945 (0.4 mg/kg) | 71.89 | 8.02 |
| BCMAxCD3 bsAb (0.4 mg/kg) + CD38xCD28 bsAb7945 (0.04 mg/kg) | 140.61 | 20.63 |

Tumor Burden on Day 12

TABLE 71

| | Tumor Burden on Day 26 | |
| --- | --- | --- |
| Antibody Treatment | Average Tumor Size (mm$^3$) on Day 26 | Tumor Size SEM on Day 26 |
| PBS vehicle | 204.12 | 26.45 |
| CD3-binding negative control bsAb (0.4 mg/kg) + CD28-binding negative control bsAb (4 mg/kg) | 267.72 | 31.94 |
| BCMAxCD3 bsAb (0.4 mg/kg) + CD28-binding negative control bsAb (4 mg/kg) | 190.92 | 13.67 |
| CD3-binding negative control bsAb (0.4 mg/kg) + CD38xCD28 bsAb6031 (4 mg/kg) | 244.00 | 27.60 |
| CD3-binding negative control bsAb (0.4 mg/kg) + CD38xCD28 bsAb7945 (4 mg/kg) | 218.67 | 5.28 |
| BCMAxCD3 bsAb (0.4 mg/kg) + CD38xCD28 bsAb6031 (4 mg/kg) | 144.50 | 13.44 |
| BCMAxCD3 bsAb (0.4 mg/kg) + CD38xCD28 bsAb6031 (0.4 mg/kg) | 266.65 | 24.05 |
| BCMAxCD3 bsAb (0.4 mg/kg) + CD38xCD28 bsAb6031 (0.04 mg/kg) | 323.35 | 28.97 |
| BCMAxCD3 bsAb (0.4 mg/kg) + CD38xCD28 bsAb7945 (4 mg/kg) | 79.75 | 4.75 |
| BCMAxCD3 bsAb (0.4 mg/kg) + CD38xCD28 bsAb7945 (0.4 mg/kg) | 81.49 | 17.70 |
| BCMAxCD3 bsAb (0.4 mg/kg) + CD38xCD28 bsAb7945 (0.04 mg/kg) | 209.38 | 42.42 |

TABLE 72

| | Tumor Burden on Day 29 | |
| --- | --- | --- |
| Antibody Treatment | Average Tumor Size (mm$^3$) on Day 29 | Tumor Size SEM on Day 29 |
| PBS vehicle | 240.89 | 20.67 |
| CD3-binding negative control bsAb (0.4 mg/kg) + CD28-binding negative control bsAb (4 mg/kg) | 340.58 | 33.04 |
| BCMAxCD3 bsAb (0.4 mg/kg) + CD28-binding negative control bsAb (4 mg/kg) | 226.09 | 16.33 |
| CD3-binding negative control bsAb (0.4 mg/kg) + CD38xCD28 bsAb6031 (4 mg/kg) | 300.95 | 45.46 |
| CD3-binding negative control bsAb (0.4 mg/kg) + CD38xCD28 bsAb7945 (4 mg/kg) | 220.35 | 8.48 |
| BCMAxCD3 bsAb (0.4 mg/kg) + CD38xCD28 bsAb6031 (4 mg/kg) | 146.60 | 15.78 |
| BCMAxCD3 bsAb (0.4 mg/kg) + CD38xCD28 bsAb6031 (0.4 mg/kg) | 358.00 | 34.85 |
| BCMAxCD3 bsAb (0.4 mg/kg) + CD38xCD28 bsAb6031 (0.04 mg/kg) | 408.27 | 29.03 |
| BCMAxCD3 bsAb (0.4 mg/kg) + CD38xCD28 bsAb7945 (4 mg/kg) | 91.00 | 6.00 |
| BCMAxCD3 bsAb (0.4 mg/kg) + CD38xCD28 bsAb7945 (0.4 mg/kg) | 87.99 | 15.00 |
| BCMAxCD3 bsAb (0.4 mg/kg) + CD38xCD28 bsAb7945 (0.04 mg/kg) | 237.40 | 53.41 |

TABLE 73

| | Tumor Burden on Day 33 | |
| --- | --- | --- |
| Antibody Treatment | Average Tumor Size (mm$^3$) on Day 33 | Tumor Size SEM on Day 33 |
| PBS vehicle | 322.30 | 26.49 |
| CD3-binding negative control bsAb (0.4 mg/kg) + CD28-binding negative control bsAb (4 mg/kg) | 476.53 | 27.19 |
| BCMAxCD3 bsAb (0.4 mg/kg) + CD28-binding negative control bsAb (4 mg/kg) | 340.84 | 40.81 |
| CD3-binding negative control bsAb (0.4 mg/kg) + CD38xCD28 bsAb6031 (4 mg/kg) | 406.59 | 51.88 |
| CD3-binding negative control bsAb (0.4 mg/kg) + CD38xCD28 bsAb7945 (4 mg/kg) | 351.79 | 16.97 |
| BCMAxCD3 bsAb (0.4 mg/kg) + CD38xCD28 bsAb6031 (4 mg/kg) | 208.14 | 28.76 |
| BCMAxCD3 bsAb (0.4 mg/kg) + CD38xCD28 bsAb6031 (0.4 mg/kg) | 464.58 | 54.13 |
| BCMAxCD3 bsAb (0.4 mg/kg) + CD38xCD28 bsAb6031 (0.04 mg/kg) | 590.23 | 56.94 |
| BCMAxCD3 bsAb (0.4 mg/kg) + CD38xCD28 bsAb7945 (4 mg/kg) | 123.92 | 21.27 |
| BCMAxCD3 bsAb (0.4 mg/kg) + CD38xCD28 bsAb7945 (0.4 mg/kg) | 103.05 | 12.96 |
| BCMAxCD3 bsAb (0.4 mg/kg) + CD38xCD28 bsAb7945 (0.04 mg/kg) | 318.65 | 74.12 |

TABLE 74

| | Tumor Burden on Day 36 | |
| --- | --- | --- |
| Antibody Treatment | Average Tumor Size (mm$^3$) on Day 36 | Tumor Size SEM on Day 36 |
| PBS vehicle | 409.05 | 30.64 |
| CD3-binding negative control bsAb (0.4 mg/kg) + CD28-binding negative control bsAb (4 mg/kg) | 619.65 | 42.22 |
| BCMAxCD3 bsAb (0.4 mg/kg) + CD28-binding negative control bsAb (4 mg/kg) | 383.08 | 61.14 |
| CD3-binding negative control bsAb (0.4 mg/kg) + CD38xCD28 bsAb6031 (4 mg/kg) | 446.97 | 48.15 |
| CD3-binding negative control bsAb (0.4 mg/kg) + CD38xCD28 bsAb7945 (4 mg/kg) | 445.04 | 29.21 |
| BCMAxCD3 bsAb (0.4 mg/kg) + CD38xCD28 bsAb6031 (4 mg/kg) | 280.56 | 34.13 |
| BCMAxCD3 bsAb (0.4 mg/kg) + CD38xCD28 bsAb6031 (0.4 mg/kg) | 557.24 | 78.00 |
| BCMAxCD3 bsAb (0.4 mg/kg) + CD38xCD28 bsAb6031 (0.04 mg/kg) | 648.82 | 81.16 |
| BCMAxCD3 bsAb (0.4 mg/kg) + CD38xCD28 bsAb7945 (4 mg/kg) | 127.30 | 24.04 |
| BCMAxCD3 bsAb (0.4 mg/kg) + CD38xCD28 bsAb7945 (0.4 mg/kg) | 111.12 | 14.87 |
| BCMAxCD3 bsAb (0.4 mg/kg) + CD38xCD28 bsAb7945 (0.04 mg/kg) | 400.33 | 103.59 |

TABLE 75

| | Tumor Burden on Day 39 | |
| --- | --- | --- |
| Antibody Treatment | Average Tumor Size (mm³) on Day 39 | Tumor Size SEM on Day 39 |
| PBS vehicle | 502.34 | 28.84 |
| CD3-binding negative control bsAb (0.4 mg/kg) + CD28-binding negative control bsAb (4 mg/kg) | 799.34 | 58.49 |
| BCMAxCD3 bsAb (0.4 mg/kg) + CD28-binding negative control bsAb (4 mg/kg) | 499.98 | 49.70 |
| CD3-binding negative control bsAb (0.4 mg/kg) + CD38xCD28 bsAb6031 (4 mg/kg) | 605.29 | 69.33 |
| CD3-binding negative control bsAb (0.4 mg/kg) + CD38xCD28 bsAb7945 (4 mg/kg) | 579.16 | 38.09 |
| BCMAxCD3 bsAb (0.4 mg/kg) + CD38xCD28 bsAb6031 (4 mg/kg) | 297.89 | 36.15 |
| BCMAxCD3 bsAb (0.4 mg/kg) + CD38xCD28 bsAb6031 (0.4 mg/kg) | 719.36 | 47.93 |
| BCMAxCD3 bsAb (0.4 mg/kg) + CD38xCD28 bsAb6031 (0.04 mg/kg) | 925.08 | 99.40 |
| BCMAxCD3 bsAb (0.4 mg/kg) + CD38xCD28 bsAb7945 (4 mg/kg) | 159.10 | 35.59 |
| BCMAxCD3 bsAb (0.4 mg/kg) + CD38xCD28 bsAb7945 (0.4 mg/kg) | 126.81 | 16.92 |
| BCMAxCD3 bsAb (0.4 mg/kg) + CD38xCD28 bsAb7945 (0.04 mg/kg) | 468.32 | 127.47 |

TABLE 76

| | Tumor Burden on Day 43 | |
| --- | --- | --- |
| Antibody Treatment | Average Tumor Size (mm³) on Day 43 | Tumor Size SEM on Day 43 |
| PBS vehicle | 704.71 | 71.69 |
| CD3-binding negative control bsAb (0.4 mg/kg) + CD28-binding negative control bsAb (4 mg/kg) | 1138.42 | 65.21 |
| BCMAxCD3 bsAb (0.4 mg/kg) + CD28-binding negative control bsAb (4 mg/kg) | 731.60 | 53.59 |
| CD3-binding negative control bsAb (0.4 mg/kg) + CD38xCD28 bsAb6031 (4 mg/kg) | 867.05 | 101.16 |
| CD3-binding negative control bsAb (0.4 mg/kg) + CD38xCD28 bsAb7945 (4 mg/kg) | 684.22 | 17.96 |
| BCMAxCD3 bsAb (0.4 mg/kg) + CD38xCD28 bsAb6031 (4 mg/kg) | 427.12 | 57.21 |
| BCMAxCD3 bsAb (0.4 mg/kg) + CD38xCD28 bsAb6031 (0.4 mg/kg) | 956.84 | 102.11 |
| BCMAxCD3 bsAb (0.4 mg/kg) + CD38xCD28 bsAb6031 (0.04 mg/kg) | 1197.95 | 138.72 |
| BCMAxCD3 bsAb (0.4 mg/kg) + CD38xCD28 bsAb7945 (4 mg/kg) | 204.36 | 51.71 |
| BCMAxCD3 bsAb (0.4 mg/kg) + CD38xCD28 bsAb7945 (0.4 mg/kg) | 176.31 | 27.26 |
| BCMAxCD3 bsAb (0.4 mg/kg) + CD38xCD28 bsAb7945 (0.04 mg/kg) | 666.85 | 192.44 |

TABLE 77

| | Tumor Burden on Day 48 | |
| --- | --- | --- |
| Antibody Treatment | Average Tumor Size (mm³) on Day 48 | Tumor Size SEM on Day 48 |
| PBS vehicle | 769.26 | 65.08 |
| CD3-binding negative control bsAb (0.4 mg/kg) + CD28-binding negative control bsAb (4 mg/kg) | 1640.91 | 122.90 |
| BCMAxCD3 bsAb (0.4 mg/kg) + CD28-binding negative control bsAb (4 mg/kg) | 1008.89 | 43.06 |
| CD3-binding negative control bsAb (0.4 mg/kg) + CD38xCD28 bsAb6031 (4 mg/kg) | 1278.26 | 154.03 |
| CD3-binding negative control bsAb (0.4 mg/kg) + CD38xCD28 bsAb7945 (4 mg/kg) | 958.84 | 72.53 |
| BCMAxCD3 bsAb (0.4 mg/kg) + CD38xCD28 bsAb6031 (4 mg/kg) | 606.92 | 75.49 |
| BCMAxCD3 bsAb (0.4 mg/kg) + CD38xCD28 bsAb6031 (0.4 mg/kg) | 1506.77 | 251.49 |
| BCMAxCD3 bsAb (0.4 mg/kg) + CD38xCD28 bsAb6031 (0.04 mg/kg) | 1737.78 | 234.10 |
| BCMAxCD3 bsAb (0.4 mg/kg) + CD38xCD28 bsAb7945 (4 mg/kg) | 264.67 | 74.97 |
| BCMAxCD3 bsAb (0.4 mg/kg) + CD38xCD28 bsAb7945 (0.4 mg/kg) | 198.78 | 30.83 |
| BCMAxCD3 bsAb (0.4 mg/kg) + CD38xCD28 bsAb7945 (0.04 mg/kg) | 899.61 | 263.60 |

TABLE 78

| | Tumor Burden on Day 50 | |
| --- | --- | --- |
| Antibody Treatment | Average Tumor Size (mm³) on Day 50 | Tumor Size SEM on Day 50 |
| PBS vehicle | 934.63 | 48.33 |
| CD3-binding negative control bsAb (0.4 mg/kg) + CD28-binding negative control bsAb (4 mg/kg) | 1829.70 | 151.42 |
| BCMAxCD3 bsAb (0.4 mg/kg) + CD28-binding negative control bsAb (4 mg/kg) | 1245.51 | 46.95 |
| CD3-binding negative control bsAb (0.4 mg/kg) + CD38xCD28 bsAb6031 (4 mg/kg) | 1445.19 | 155.75 |
| CD3-binding negative control bsAb (0.4 mg/kg) + CD38xCD28 bsAb7945 (4 mg/kg) | 1023.52 | 81.70 |
| BCMAxCD3 bsAb (0.4 mg/kg) + CD38xCD28 bsAb6031 (4 mg/kg) | 730.89 | 179.00 |
| BCMAxCD3 bsAb (0.4 mg/kg) + CD38xCD28 bsAb6031 (0.4 mg/kg) | 1591.50 | 286.71 |
| BCMAxCD3 bsAb (0.4 mg/kg) + CD38xCD28 bsAb6031 (0.04 mg/kg) | 1855.56 | 272.36 |
| BCMAxCD3 bsAb (0.4 mg/kg) + CD38xCD28 bsAb7945 (4 mg/kg) | 260.42 | 60.39 |
| BCMAxCD3 bsAb (0.4 mg/kg) + CD38xCD28 bsAb7945 (0.4 mg/kg) | 262.05 | 30.60 |
| BCMAxCD3 bsAb (0.4 mg/kg) + CD38xCD28 bsAb7945 (0.04 mg/kg) | 1038.47 | 330.97 |

Example 15: In Vivo Anti-Tumor Efficacy of CD38xCD28 Bispecific Antibodies (bsAb) in Combination with a BCMAxCD3 bsAb against BCMA+CD38+MOLP-8 Human Multiple Myeloma Tumor Cell Growth To determine the in vivo anti-tumor efficacy of CD38xCD28 bispecific antibodies (bsAb) in combination with a BCMAxCD3 bsAb, a xenogeneic tumor study was performed. This example is similar to the experiment in Example 12, however this experiment tested more mice (10-13 per group versus 5 mice per group in Example 12) and the duration of the present study was longer (48 days versus 44 days in Example 12).

Implantation and Measurement of Xenogeneic Tumors

On day-12, immunodeficient NOD.Cg-Prkdc$^{scid}$Il2rg$^{tm1\,Wjl}$/SzJ (NSG) mice were intraperitoneally injected with $4\times10^6$ human peripheral blood mononuclear cells (PBMC) from a normal, healthy donor. On day 0, the mice were intravenously administered $2\times10^6$ BCMA$^+$ CD38$^+$ MOLP-8 human multiple myeloma tumor cells that were engineered to also express firefly luciferase (MOLP-8-luciferase cells). The mice (n=10-13 per group) were then immediately administered either a CD3-binding negative control bispecific Ab (H4sH17664D) or a BCMAxCD3 (bsAb5458) bsAb at 0.4 mg/kg, in combination with a CD28-binding negative control bispecific Ab (bsAb5671) or a CD38xCD28 bsAb (either bsAb6031 or bsAb7945) at 0.4 mg/kg. The mice were administered these Abs twice more on days 7 and 14, for a total of three doses. Tumor growth was assessed over 48 days by measuring tumor bioluminescence (BLI) in anesthetized animals. As a positive control, a group of mice (n=5) was given only MOLP-8-luciferase cells and PBMCs, but not antibody (PBS-treated group). In order to measure background BLI levels, a group of mice (n=5) were untreated and did not receive tumors, PBMC, or antibody (No Tumor group).

Measurement of Xenogeneic Tumor Growth

BLI imaging was used to measure tumor burden. Mice were injected IP with 150 mg/kg of the luciferase substrate D-luciferin suspended in PBS. Five minutes after this injection, BLI imaging of the mice was performed under isoflurane anesthesia using the Xenogen IVIS system. Image acquisition was carried out with the field of view at D, subject height of 1.5 cm, and medium binning level with automatic exposure time determined by the Living Image Software. BLI signals were extracted using Living Image software: regions of interest were drawn around each tumor mass and photon intensities were recorded as total flux (photons/second-p/s).

Figure 10:
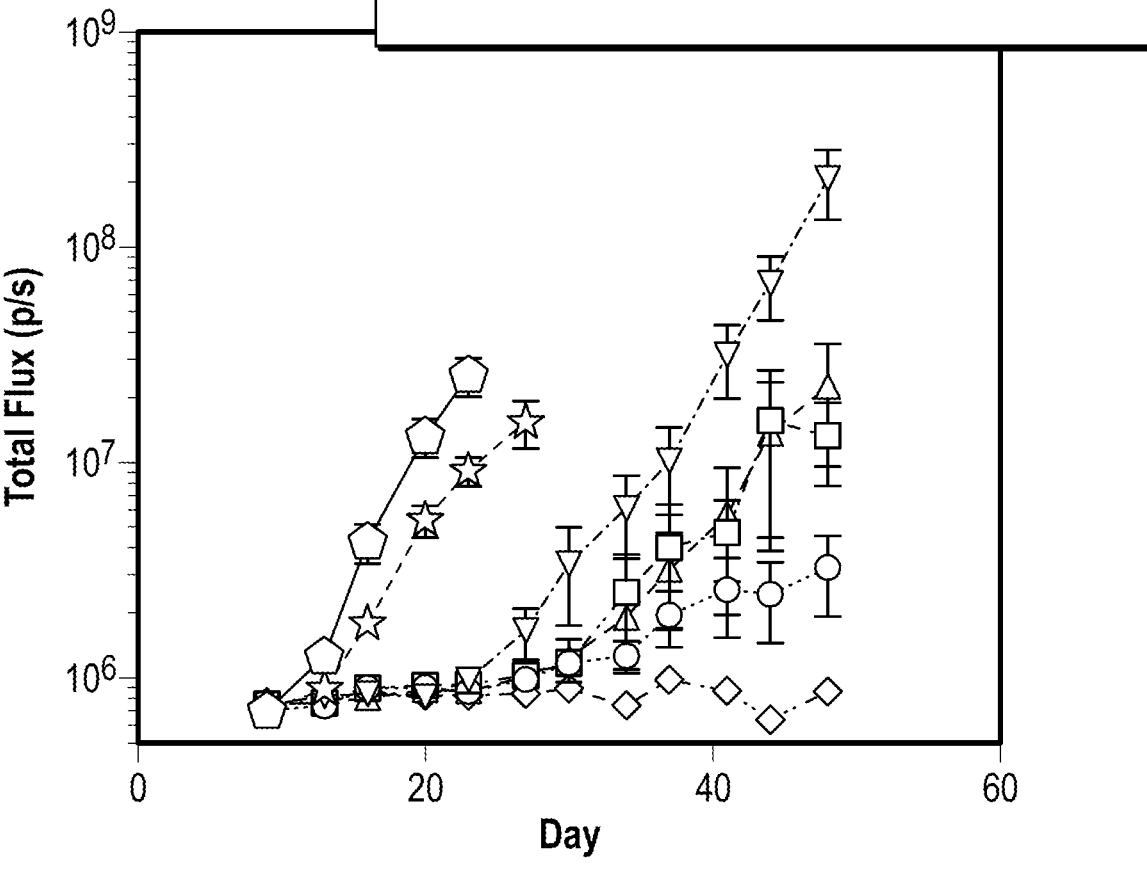

Results:

BCMAxCD3 bsAb plus CD28-binding negative control bsAb provided some anti-tumor efficacy, with mean BLI readings reduced compared to mice receiving CD3-binding negative control bsAb plus CD28-binding negative control bsAb (p<0.0001 on days 20, 23, and 27 by 2-way ANOVA analysis). Treatment with CD3-binding negative control bsAb plus CD38xCD28 bsAb (bsAb7945) modestly reduced mean BLI readings compared to mice receiving CD3-binding negative control bsAb plus CD28-binding negative control bsAb (p<0.0001 on day 23 by 2-way ANOVA analysis). However, the combination of BCMAxCD3 bsAb plus CD38xCD28 bsAb (bsAb7945) at all three doses resulted in mean BLI readings that were lower than mice receiving BCMAxCD3 bsAb plus CD28-binding negative control bsAb (Day 44 2-way ANOVA analysis: p<0.0001 for 4 mg/kg dose of bsAb7945, 0=0.0007 for 0.4 mg/kg dose of bsAb7945, and p=0.0018 for 0.04 mg/kg dose of bsAb7945; p<0.0001 for all 3 doses of bsAb7945 on day 48 by 2-way ANOVA analysis). See FIG. 10 and Tables 79-90 below.

Thus, these studies demonstrate that while monotherapy with either BCMAxCD3 bsAb or CD38xCD28 bsAb demonstrates only modest anti-tumor efficacy, combination treatment with BCMAxCD3 bsAb plus CD38xCD28 bsAb results in more potent, combinatorial anti-tumor efficacy that is superior to either therapy alone.

TABLE 79

Tumor Burden and Surviving Mice on Day 9

| Antibody Treatment | Tumor Burden - Mean Total Flux (p/s) on Day 9 | Total Flux SEM on Day 9 | Number of mice still alive on day 9 |
|---|---|---|---|
| PBS vehicle | 7.13E+05 | 2.30E+04 | 10 of 10 |
| CD3-binding negative control bsAb (0.4 mg/kg) + CD28-binding negative control bsAb (4 mg/kg) | 7.03E+05 | 2.63E+04 | 10 of 10 |
| BCMAxCD3 bsAb (0.4 mg/kg) + CD28-binding negative control bsAb (4 mg/kg) | 7.51E+05 | 2.55E+04 | 10 of 10 |
| CD3-binding negative control bsAb (0.4 mg/kg) + CD38xCD28 bsAb7945 (4 mg/kg) | 7.15E+05 | 1.75E+04 | 10 of 10 |
| BCMAxCD3 bsAb (0.4 mg/kg) + CD38xCD28 bsAb7945 (4 mg/kg) | 7.09E+05 | 2.28E+04 | 13 of 13 |
| BCMAxCD3 bsAb (0.4 mg/kg) + CD38xCD28 bsAb7945 (0.4 mg/kg) | 7.55E+05 | 2.39E+04 | 12 of 12 |
| BCMAxCD3 bsAb (0.4 mg/kg) + CD38xCD28 bsAb7945 (0.04 mg/kg) | 7.57E+05 | 3.17E+04 | 10 of 10 |
| No Tumor (Background BLI) | 7.69E+05 | 3.56E+04 | 5 of 5 |

TABLE 80

Tumor Burden and Surviving Mice on Day 13

| Antibody Treatment | Tumor Burden - Mean Total Flux (p/s) on Day 13 | Total Flux SEM on Day 13 | Number of mice still alive on day 13 |
|---|---|---|---|
| PBS vehicle | 1.41E+06 | 2.00E+05 | 10 of 10 |
| CD3-binding negative control bsAb (0.4 mg/kg) + CD28-binding negative control bsAb (4 mg/kg) | 1.25E+06 | 1.32E+05 | 10 of 10 |
| BCMAxCD3 bsAb (0.4 mg/kg) + CD28-binding negative control bsAb (4 mg/kg) | 8.27E+05 | 2.25E+04 | 10 of 10 |
| CD3-binding negative control bsAb (0.4 mg/kg) + CD38xCD28 bsAb7945 (4 mg/kg) | 8.83E+05 | 2.62E+04 | 10 of 10 |
| BCMAxCD3 bsAb (0.4 mg/kg) + CD38xCD28 bsAb7945 (4 mg/kg) | 7.43E+05 | 1.83E+04 | 13 of 13 |
| BCMAxCD3 bsAb (0.4 mg/kg) + CD38xCD28 bsAb7945 (0.4 mg/kg) | 7.68E+05 | 2.12E+04 | 12 of 12 |
| BCMAxCD3 bsAb (0.4 mg/kg) + CD38xCD28 bsAb7945 (0.04 mg/kg) | 7.65E+05 | 2.98E+04 | 10 of 10 |
| No Tumor (Background BLI) | 7.68E+05 | 4.85E+04 | 5 of 5 |

TABLE 81

Tumor Burden and Surviving Mice on Day 16

| Antibody Treatment | Tumor Burden - Mean Total Flux (p/s) on Day 16 | Total Flux SEM on Day 16 | Number of mice still alive on day 16 |
|---|---|---|---|
| PBS vehicle | 6.55E+06 | 1.63E+06 | 10 of 10 |
| CD3-binding negative control bsAb (0.4 mg/kg) + CD28-binding negative control bsAb (4 mg/kg) | 4.28E+06 | 8.89E+05 | 10 of 10 |
| BCMAxCD3 bsAb (0.4 mg/kg) + CD28-binding negative control bsAb (4 mg/kg) | 8.44E+05 | 2.50E+04 | 10 of 10 |

TABLE 81-continued

Tumor Burden and Surviving Mice on Day 16

| Antibody Treatment | Tumor Burden - Mean Total Flux (p/s) on Day 16 | Total Flux SEM on Day 16 | Number of mice still alive on day 16 |
|---|---|---|---|
| CD3-binding negative control bsAb (0.4 mg/kg) + CD38xCD28 bsAb7945 (4 mg/kg) | 1.79E+06 | 1.79E+05 | 9 of 10 |
| BCMAxCD3 bsAb (0.4 mg/kg) + CD38xCD28 bsAb7945 (4 mg/kg) | 8.98E+05 | 4.57E+04 | 13 of 13 |
| BCMAxCD3 bsAb (0.4 mg/kg) + CD38xCD28 bsAb7945 (0.4 mg/kg) | 8.96E+05 | 2.07E+04 | 12 of 12 |
| BCMAxCD3 bsAb (0.4 mg/kg) + CD38xCD28 bsAb7945 (0.04 mg/kg) | 8.11E+05 | 2.86E+04 | 10 of 10 |
| No Tumor (Background BLI) | 8.64E+05 | 4.19E+04 | 5 of 5 |

TABLE 82

Tumor Burden and Surviving Mice on Day 20

| Antibody Treatment | Tumor Burden - Mean Total Flux (p/s) on Day 20 | Total Flux SEM on Day 20 | Number of mice still alive on day 20 |
|---|---|---|---|
| PBS vehicle | 1.70E+07 | 3.68E+06 | 9 of 10 |
| CD3-binding negative control bsAb (0.4 mg/kg) + CD28-binding negative control bsAb (4 mg/kg) | 1.32E+07 | 2.66E+06 | 10 of 10 |
| BCMAxCD3 bsAb (0.4 mg/kg) + CD28-binding negative control bsAb (4 mg/kg) | 8.16E+05 | 5.11E+04 | 10 of 10 |
| CD3-binding negative control bsAb (0.4 mg/kg) + CD38xCD28 bsAb7945 (4 mg/kg) | 5.41E+06 | 9.13E+05 | 9 of 10 |
| BCMAxCD3 bsAb (0.4 mg/kg) + CD38xCD28 bsAb7945 (4 mg/kg) | 9.05E+05 | 3.30E+04 | 13 of 13 |
| BCMAxCD3 bsAb (0.4 mg/kg) + CD38xCD28 bsAb7945 (0.4 mg/kg) | 9.25E+05 | 3.90E+04 | 12 of 12 |
| BCMAxCD3 bsAb (0.4 mg/kg) + CD38xCD28 bsAb7945 (0.04 mg/kg) | 8.83E+05 | 3.98E+04 | 10 of 10 |
| No Tumor (Background BLI) | 8.26E+05 | 4.69E+04 | 5 of 5 |

TABLE 83

Tumor Burden and Surviving Mice on Day 23

| Antibody Treatment | Tumor Burden - Mean Total Flux (p/s) on Day 23 | Total Flux SEM on Day 23 | Number of mice still alive on day 23 |
|---|---|---|---|
| PBS vehicle | 2.87E+07 | 4.94E+06 | 8 of 10 |
| CD3-binding negative control bsAb (0.4 mg/kg) + CD28-binding negative control bsAb (4 mg/kg) | 2.54E+07 | 5.18E+06 | 10 of 10 |
| BCMAxCD3 bsAb (0.4 mg/kg) + CD28-binding negative control bsAb (4 mg/kg) | 9.78E+05 | 1.26E+05 | 10 of 10 |
| CD3-binding negative control bsAb (0.4 mg/kg) + CD38xCD28 bsAb7945 (4 mg/kg) | 9.16E+06 | 1.39E+06 | 9 of 10 |
| BCMAxCD3 bsAb (0.4 mg/kg) + CD38xCD28 bsAb7945 (4 mg/kg) | 8.65E+05 | 4.55E+04 | 13 of 13 |
| BCMAxCD3 bsAb (0.4 mg/kg) + CD38xCD28 bsAb7945 (0.4 mg/kg) | 9.32E+05 | 2.37E+04 | 12 of 12 |
| BCMAxCD3 bsAb (0.4 mg/kg) + CD38xCD28 bsAb7945 (0.04 mg/kg) | 8.71E+05 | 4.66E+04 | 10 of 10 |
| No Tumor (Background BLI) | 8.29E+05 | 2.83E+04 | 5 of 5 |

TABLE 84

Tumor Burden and Surviving Mice on Day 27

| Antibody Treatment | Tumor Burden - Mean Total Flux (p/s) on Day 27 | Total Flux SEM on Day 27 | Number of mice still alive on day 27 |
|---|---|---|---|
| PBS vehicle | 3.68E+07 | 4.83E+06 | 6 of 10 |
| CD3-binding negative control bsAb (0.4 mg/kg) + CD28-binding negative control bsAb (4 mg/kg) | 1.66E+07 | 5.05E+06 | 4 of 10 |
| BCMAxCD3 bsAb (0.4 mg/kg) + CD28-binding negative control bsAb (4 mg/kg) | 1.66E+06 | 4.36E+05 | 10 of 10 |
| CD3-binding negative control bsAb (0.4 mg/kg) + CD38xCD28 bsAb7945 (4 mg/kg) | 1.55E+07 | 3.85E+06 | 8 of 10 |
| BCMAxCD3 bsAb (0.4 mg/kg) + CD38xCD28 bsAb7945 (4 mg/kg) | 9.86E+05 | 7.69E+04 | 13 of 13 |
| BCMAxCD3 bsAb (0.4 mg/kg) + CD38xCD28 bsAb7945 (0.4 mg/kg) | 1.03E+06 | 4.51E+04 | 12 of 12 |
| BCMAxCD3 bsAb (0.4 mg/kg) + CD38xCD28 bsAb7945 (0.04 mg/kg) | 1.02E+06 | 1.07E+05 | 10 of 10 |
| No Tumor (Background BLI) | 8.44E+05 | 2.71E+04 | 5 of 5 |

TABLE 85

Tumor Burden and Surviving Mice on Day 30

| Antibody Treatment | Tumor Burden - Mean Total Flux (p/s) on Day 30 | Total Flux SEM on Day 30 | Number of mice still alive on day 30 |
|---|---|---|---|
| PBS vehicle | | | 0 of 10 |
| CD3-binding negative control bsAb (0.4 mg/kg) + CD28-binding negative control bsAb (4 mg/kg) | 5.50E+07 | 0.00E+00 | 1 of 10 |
| BCMAxCD3 bsAb (0.4 mg/kg) + CD28-binding negative control bsAb (4 mg/kg) | 3.38E+06 | 1.63E+06 | 10 of 10 |
| CD3-binding negative control bsAb (0.4 mg/kg) + CD38xCD28 bsAb7945 (4 mg/kg) | 5.46E+07 | 2.30E+07 | 5 of 10 |
| BCMAxCD3 bsAb (0.4 mg/kg) + CD38xCD28 bsAb7945 (4 mg/kg) | 1.17E+06 | 1.45E+05 | 13 of 13 |
| BCMAxCD3 bsAb (0.4 mg/kg) + CD38xCD28 bsAb7945 (0.4 mg/kg) | 1.18E+06 | 1.34E+05 | 12 of 12 |
| BCMAxCD3 bsAb (0.4 mg/kg) + CD38xCD28 bsAb7945 (0.04 mg/kg) | 1.23E+06 | 2.79E+05 | 10 of 10 |
| No Tumor (Background BLI) | 8.94E+05 | 2.91E+04 | 5 of 5 |

TABLE 86

Tumor Burden and Surviving Mice on Day 34

| Antibody Treatment | Tumor Burden - Mean Total Flux (p/s) on Day 34 | Total Flux SEM on Day 34 | Number of mice still alive on day 34 |
|---|---|---|---|
| PBS vehicle | | | 0 of 10 |
| CD3-binding negative control bsAb (0.4 mg/kg) + CD28-binding negative control bsAb (4 mg/kg) | | | 0 of 10 |
| BCMAxCD3 bsAb (0.4 mg/kg) + CD28-binding negative control bsAb (4 mg/kg) | 6.14E+06 | 2.55E+06 | 10 of 10 |

TABLE 86-continued

Tumor Burden and Surviving Mice on Day 34

| Antibody Treatment | Tumor Burden - Mean Total Flux (p/s) on Day 34 | Total Flux SEM on Day 34 | Number of mice still alive on day 34 |
|---|---|---|---|
| CD3-binding negative control bsAb (0.4 mg/kg) + CD38xCD28 bsAb7945 (4 mg/kg) | 6.54E+07 | 2.84E+07 | 2 of 10 |
| BCMAxCD3 bsAb (0.4 mg/kg) + CD38xCD28 bsAb7945 (4 mg/kg) | 1.27E+06 | 2.15E+05 | 13 of 13 |
| BCMAxCD3 bsAb (0.4 mg/kg) + CD38xCD28 bsAb7945 (0.4 mg/kg) | 2.50E+06 | 1.24E+06 | 12 of 12 |
| BCMAxCD3 bsAb (0.4 mg/kg) + CD38xCD28 bsAb7945 (0.04 mg/kg) | 1.91E+06 | 8.17E+05 | 9 of 10 |
| No Tumor (Background BLI) | 7.45E+05 | 1.33E+04 | 5 of 5 |

TABLE 87

Tumor Burden and Surviving Mice on Day 37

| Antibody Treatment | Tumor Burden - Mean Total Flux (p/s) on Day 37 | Total Flux SEM on Day 37 | Number of mice still alive on day 37 |
|---|---|---|---|
| PBS vehicle | | | 0 of 10 |
| CD3-binding negative control bsAb (0.4 mg/kg) + CD28-binding negative control bsAb (4 mg/kg) | | | 0 of 10 |
| BCMAxCD3 bsAb (0.4 mg/kg) + CD28-binding negative control bsAb (4 mg/kg) | 1.02E+07 | 4.44E+06 | 10 of 10 |
| CD3-binding negative control bsAb (0.4 mg/kg) + CD38xCD28 bsAb7945 (4 mg/kg) | | | 0 of 10 |
| BCMAxCD3 bsAb (0.4 mg/kg) + CD38xCD28 bsAb7945 (4 mg/kg) | 1.96E+06 | 5.75E+05 | 13 of 13 |
| BCMAxCD3 bsAb (0.4 mg/kg) + CD38xCD28 bsAb7945 (0.4 mg/kg) | 4.04E+06 | 2.34E+06 | 12 of 12 |
| BCMAxCD3 bsAb (0.4 mg/kg) + CD38xCD28 bsAb7945 (0.04 mg/kg) | 3.20E+06 | 1.53E+06 | 8 of 10 |
| No Tumor (Background BLI) | 9.82E+05 | 3.75E+04 | 5 of 5 |

TABLE 88

Tumor Burden and Surviving Mice on Day 41

| Antibody Treatment | Tumor Burden - Mean Total Flux (p/s) on Day 41 | Total Flux SEM on Day 41 | Number of mice still alive on day 41 |
|---|---|---|---|
| PBS vehicle | | | 0 of 10 |
| CD3-binding negative control bsAb (0.4 mg/kg) + CD28-binding negative control bsAb (4 mg/kg) | | | 0 of 10 |
| BCMAxCD3 bsAb (0.4 mg/kg) + CD28-binding negative control bsAb (4 mg/kg) | 3.17E+07 | 1.18E+07 | 10 of 10 |
| CD3-binding negative control bsAb (0.4 mg/kg) + CD38xCD28 bsAb7945 (4 mg/kg) | | | 0 of 10 |
| BCMAxCD3 bsAb (0.4 mg/kg) + CD38xCD28 bsAb7945 (4 mg/kg) | 2.57E+06 | 1.03E+06 | 13 of 13 |
| BCMAxCD3 bsAb (0.4 mg/kg) + CD38xCD28 bsAb7945 (0.4 mg/kg) | 4.74E+06 | 1.93E+06 | 12 of 12 |
| BCMAxCD3 bsAb (0.4 mg/kg) + CD38xCD28 bsAb7945 (0.04 mg/kg) | 5.72E+06 | 3.76E+06 | 8 of 10 |
| No Tumor (Background BLI) | 8.72E+05 | 4.59E+04 | 5 of 5 |

TABLE 89

Tumor Burden and Surviving Mice on Day 44

| Antibody Treatment | Tumor Burden - Mean Total Flux (p/s) on Day 44 | Total Flux SEM on Day 44 | Number of mice still alive on day 44 |
|---|---|---|---|
| PBS vehicle | | | 0 of 10 |
| CD3-binding negative control bsAb (0.4 mg/kg) + CD28-binding negative control bsAb (4 mg/kg) | | | 0 of 10 |
| BCMAxCD3 bsAb (0.4 mg/kg) + CD28-binding negative control bsAb (4 mg/kg) | 6.82E+07 | 2.25E+07 | 10 of 10 |
| CD3-binding negative control bsAb (0.4 mg/kg) + CD38xCD28 bsAb7945 (4 mg/kg) | | | 0 of 10 |
| BCMAxCD3 bsAb (0.4 mg/kg) + CD38xCD28 bsAb7945 (4 mg/kg) | 2.45E+06 | 9.91E+05 | 13 of 13 |
| BCMAxCD3 bsAb (0.4 mg/kg) + CD38xCD28 bsAb7945 (0.4 mg/kg) | 1.57E+07 | 1.12E+07 | 12 of 12 |
| BCMAxCD3 bsAb (0.4 mg/kg) + CD38xCD28 bsAb7945 (0.04 mg/kg) | 1.37E+07 | 9.85E+06 | 8 of 10 |
| No Tumor (Background BLI) | 6.41E+05 | 2.20E+04 | 5 of 5 |

TABLE 90

Tumor Burden and Surviving Mice on Day 48

| Antibody Treatment | Tumor Burden - Mean Total Flux (p/s) on Day 48 | Total Flux SEM on Day 48 | Number of mice still alive on day 48 |
|---|---|---|---|
| PBS vehicle | | | 0 of 10 |
| CD3-binding negative control bsAb (0.4 mg/kg) + CD28-binding negative control bsAb (4 mg/kg) | | | 0 of 10 |
| BCMAxCD3 bsAb (0.4 mg/kg) + CD28-binding negative control bsAb (4 mg/kg) | 2.08E+08 | 7.43E+07 | 9 of 10 |
| CD3-binding negative control bsAb (0.4 mg/kg) + CD38xCD28 bsAb7945 (4 mg/kg) | | | 0 of 10 |
| BCMAxCD3 bsAb (0.4 mg/kg) + CD38xCD28 bsAb7945 (4 mg/kg) | 3.26E+06 | 1.33E+06 | 13 of 13 |
| BCMAxCD3 bsAb (0.4 mg/kg) + CD38xCD28 bsAb7945 (0.4 mg/kg) | 1.34E+07 | 5.57E+06 | 11 of 12 |
| BCMAxCD3 bsAb (0.4 mg/kg) + CD38xCD28 bsAb7945 (0.04 mg/kg) | 2.26E+07 | 1.29E+07 | 8 of 10 |
| No Tumor (Background BLI) | 8.63E+05 | 4.83E+04 | 5 of 5 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 91

Informal Sequence Listing

| SEQ ID NO. | SEQUENCE | Description |
|---|---|---|
| 1. | gaagtgcagctggtggagtctggggggaggcttggtacagcctggcaggtccctgagactctcctgtgcagcctctggat tcacctttgatgattatgccatgcactgggtccggcaagctccaggggaaggggcctggagtgggtctcaggtattagttgg aaaagtgataacataggctatgcggactctgtgaagggccgattcaccatttccagagacaacgccaagaactccct gtatctgcaaatgaacagtctgagagctgaggacacggccttgtattactgtgcaaaagcccttggggggctggaagttc gactactattacggtatggacgtttgggggccaagggaccacggtcaccgtctcctca | DNA sequence |
| 2. | EVQLVESGGGLVQPGRSLRLSCAASGFTFDDYAMHWVRQAPGKGLEWVSGISWK SDNIGYADSVKGRFTISRDNAKNSLYLQMNSLRAEDTALYYCAKALGGWKFDYYYG MDVWGQGTTVTVSS | Amino Acid sequence |
| 3. | ggattcacctttgatgattatgcc | DNA sequence |
| 4. | GFTFDDYA | Amino Acid sequence |
| 5. | attagttggaaaagtgataacata | DNA sequence |
| 6. | ISWKSDNI | Amino Acid sequence |
| 7. | gcaaaagcccttggggggctggaagttcgactactattacggtatggacgtt | DNA sequence |
| 8. | AKALGGWKFDYYYGMDV | Amino Acid sequence |
| 9. | gaggtgcagctggtggagtctggggggaggcttggtccagcctggggggtccctgagactctcctgtgcagcctccgga ttcaccttcagtaggaataatatgcactgggtccgccaggctccagggaagggactggaatatgtttcaggtattagtag taatggggggtcgcacatattatgcagactctgtgaagggcagattcaccatctccagagacaattccaagaacacgct gtatctcaaatgggcggcctgagagctgcggacatggctgtgtatttctgtacgagagatgacgagctgctttcctttg actactggggccagggaaccctggtcactgtctcctca | DNA sequence |
| 10. | EVQLVESGGGLVQPGGSLRLSCAASGFTFSRNNMHWVRQAPGKGLEYVSGISSNG GRTYYADSVKGRFTISRDNSKNTLYLQMGGLRAADMAVYFCTRDDELLSFDYWGQ GTLVTVSS | Amino Acid sequence |
| 11. | ggattcaccttcagtaggaataat | DNA sequence |
| 12. | GFTFSRNN | Amino Acid sequence |
| 13. | attagtagtaatggggggtcgcaca | DNA sequence |
| 14. | ISSNGGRT | Amino Acid sequence |
| 15. | acgagagatgacgagctgctttcctttgactac | DNA sequence |
| 16. | TRDDELLSFDY | Amino Acid sequence |
| 17. | gacatccagatgacccagtctccatcctccctgtctgcatctgtaggagacagagtcaccatcacttgccgggcaagtc agagcattagcagctatttaaattggtatcagcagaaaccagggaaagcccctaagctcctgatctatgctgcatccag tttgcaaagtggggtcccgtcaaggttcagtggcagtggatctgggacagatttcactctcaccatcagcagtctgcaac ctgaagattttgcaacttactactgtcaacagagttacagtacccctccgatcaccttcggccaagggacacgactgga gattaaa | DNA sequence |
| 18. | DIQMTQSPSSLSASVGDRVTITCRASQSISSYLNWYQQKPGKAPKLLIYAASSLQSG VPSRFSGSGSGTDFTLTISSLQPEDFATYYCQQSYSTPPITFGQGTRLEIK | Amino Acid sequence |
| 19. | cagagcattagcagctat | DNA sequence |
| 20. | QSISSY | Amino Acid sequence |
| 21. | gctgcatcc | DNA sequence |

TABLE 91-continued

Informal Sequence Listing

| SEQ ID NO. | SEQUENCE | Description |
|---|---|---|
| 22. | AAS | Amino Acid sequence |
| 23. | caacagagttacagtacccctccgatcacc | DNA sequence |
| 24. | QQSYSTPPIT | Amino Acid sequence |
| 25. | gaagtgcagctggtggagtctgggggaggcttggtacagcctggcaggtccctgagactctcctgtgcagcctctggat tcacctttgatgattatgccatgcactgggtccggcaagctccagggaaggggcctggagtgggtctcaggtattagttgg aaaagtgataacataggctatgcggactctgtgaagggccgattcaccatttccagagacaacgccaagaactccct gtatctgcaaatgaacagtctgagagctgaggacacggccttgtattactgtgcaaaagcccttggggggctggaagttc gactactattacggtatggacgtttgggggccaagggaccacggtcaccgtctcctcagcctccaccaagggcccatcg gtcttccccctggcgccctgctccaggagcacctccgagagcacagccgccctgggctgcctggtcaaggactacttc cccgaaccggtgacggtgtcgtggaactcaggcgccctgaccagcggcgtgcacaccttcccggctgtcctacagtc ctcaggactctactccctcagcagcgtggtgaccgtgccctccagcagcttgggcacgaagacctacacctgcaacgt agatcacaagcccagcaacaccaaggtggacaagagagttgagtccaaatatggtcccccatgcccaccgtgccc agcaccacctgtggcaggaccatcagtcttcctgttcccccaaaacccaaggacactctcatgatctcccggacccct gaggtcacgtgcgtggtggtggacgtgagccaggaagaccccgaggtccagttcaactggtacgtggatggcgtgga ggtgcataatgccaagacaaagccgcgggaggagcagttcaacagcacgtaccgtgtggtcagcgtcctcaccgtc ctgcaccaggactggctgaacggcaaggagtacaagtgcaaggtctccaacaaaggcctcccgtcctccatcgaga aaccatctccaaagccaaagggcagccccgagaaccacaggtgtacaccctgcccccatcccaggaggagatg accaagaaccaggtcagcctgacctgcctggtcaaaggcttctacccagcgacatcgccgtggagtgggagagca atgggcagccggagaacaactacaagaccacgcctcccgtgctggactccgacggctccttcttcctctacagcagg ctcaccgtggacaagagcaggtggcaggaggggaatgtcttctcatgctccgtgatgcatgaggctctgcacaaccac tacacacagaagtccctctccctgtctctgggtaaatga | DNA sequence |
| 26. | EVQLVESGGGLVQPGRSLRLSCAASGFTFDDYAMHWVRQAPGKGLEWVSGISWK SDNIGYADSVKGRFTISRDNAKNSLYLQMNSLRAEDTALYYCAKALGGWKFDYYYG MDVWGQGTTVTVSSASTKGPSVFPLAPCSRSTSESTAALGCLVKDYFPEPVTVSW NSGALTSGVHTFPAVLQSSGLYSLSSVVTVPSSSLGTKTYTCNVDHKPSNTKVDKRV ESKYGPPCPPCPAPPVAGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSL SLGK | Amino Acid sequence |
| 27. | gaggtgcagctggtggagtctgggggaggcttggtccagcctggggggtccctgagactctcctgtgcagcctccgga ttcacctttcagtaggaataatatgcactgggtccgccaggctccagggaaggggactggaatatgtttcaggtattagtag taatgggggtcgcacatattatgcagactctgtgaagggcagattcaccatctccagagacaattccaagaacacgct gtatcttcaaatgggcggcctgagagctgcggacatggctgtgtatttctgtacgagagatgacgagctgctttccttga ctactggggccagggaaccctggtcactgtctcctcagcctctacaaagggaccttctgtgtttcctctggctccttgttc tagatctacatctacagctgctctgggatgtctggtgaagtgattatttttcctgaacctgtgacagtgtcttggaa ttctggagctctgacatctggagtgcatacatttcctgctgtgctgcagtcttctggactgtattctctgtcttctgtggt gacagtgccttcttcttctctgggaacaaagacatatacatgtaatgtggatcataagccttctaatacaaaggtggataa gagagtggaatctaagtatggacctccttgtcctccttgtcctgctcctcctgtggctggaccttctgtgtttctgtttcc tcctaagcctaaggatacactgatgatctctagaacacctgaagtgacatgtgtggtggtggatgtgtctcaggaagatcc tgaagtgcagtttaattggtatgtggatggagtggaagtgcataatgctaagacaaagcctagagaagaacagtttaattc tacatatagagtggtgtctgtgctgacagtgctgcatcaggattggctgaatggaaaggaataaagtgtaaggtgtctaa taagggactgccttcttcatcgaaaagacaatctctaaggctaagggacagcctagagaacctcaggtgtatacactgcc tccttctcaggaagaaatgacaaagaatcaggtgtctctgacatgtctggtgaagggatttttatccttctgatatcgctgt ggaatgggaatctaatggacagcctgaaaataattataagacaacacctcctgtgctggattctgatggatctttttttct gtattctagactgacagtggataagtctagatggcaggaaggaaatgtgtttttcttgttctgtgatgcatgaagctctgca taatagatttacacagaagtctctgtctctgtcctggaaagtag | DNA sequence |
| 28. | EVQLVESGGGLVQPGGSLRLSCAASGFTFSRNNMHWVRQAPGKGLEYVSGISSNG GRTYYADSVKGRFTISRDNSKNTLYLQMGGLRAADMAVYFCTRDDELLSFDYWGQ GTLVTVSSASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVESKYGPP CPPCPAPPVAGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTISKA KGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNRFTQKSLSLSPGK | Amino Acid sequence |
| 29. | gacatccagatgacccagtctccatcctccctgtctgcatctgtaggagacagagtcaccatcacttgccgggcaagtc agagcattagcagctatttaaattggtatcagcagaaaccagggaaagcccctaagctcctgatctatgctgcatccag tttgcaaagtggggtcccgtcaaggttcagtggcagtggatctgggacagatttcactctcaccatcagcagtctgcaac ctgaagattttgcaacttactactgtcaacagagttacagtacccctccgatcaccttcggccaagggacacgactgga gattaaacgaactgtggctgcaccatctgtcttcatcttcccgccatctgatgagcagttgaaatctggaactgcctctgt tgtgtgcctgctgaataacttctatcccagagaggccaaagtacagtggaaggtggataacgccctccaatcgggtaact cccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagag cttcaacaggggagagtgttag | DNA sequence |

TABLE 91-continued

Informal Sequence Listing

| SEQ ID NO. | SEQUENCE | Description |
|---|---|---|
| 30. | DIQMTQSPSSLSASVGDRVTITCRASQSISSYLNWYQQKPGKAPKLLIYAASSLQSG VPSRFSGSGSGTDFTLTISSLQPEDFATYYCQQSYSTPPITFGQGTRLEIKRTVAAPS VFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | Amino Acid sequence |
| 31. | caggtgcagctggtgcagtctggggctgaagtgaagaagcctgggtcctcggtgaaggtctcctgtaaggcttctggag gccccttcagaagttcttctttcagctgggtgcgacaggccccaggacaagggcttgaatggatgggagggatcatccc tattttaggtaaaacaaactatgcacagaagttccagggcagaatcacgattgtcacggacgaatccacgaccacagt ctacatggaactgagcagcctgagatctgaggacacggccgtttttttactgtgtgagaggcagctcgctctttgactattg gggccagggaaccctggtcaccgtctcctca | DNA sequence |
| 32. | QVQLVQSGAEVKKPGSSVKVSCKASGGPFRSSSFSWVRQAPGQGLEWMGGIIPIL GKTNYAQKFQGRITIVTDESTTTVYMELSSLRSEDTAVFYCVRGSSLFDYWGQGTLV TVSS | Amino Acid sequence |
| 33. | ggaggcccccttcagaagttcttct | DNA sequence |
| 34. | GGPFRSSS | Amino Acid sequence |
| 35. | atcatccctattttaggtaaaaca | DNA sequence |
| 36. | IIPILGKT | Amino Acid sequence |
| 37. | gtgagaggcagctcgctctttgactat | DNA sequence |
| 38. | VRGSSLFDY | Amino Acid sequence |
| 39. | caggtgcagctgcaggagtcgggcccaggactggtgaagccttcggagaccctgtccctcacctgcactgtctctggt ggctccatcagtagttactactggagctggatccggcagcccccagggaagggactggagtggattgggtatatctatt acagtgggatcacccactacaacccctccctcaagagtcgagtcaccatatcagtagacacgtccaagatccagttct ccctgaagctgagttctgtgaccgctgcggacacggccgtgtattactgtgcgagatggggggggttcggagggactacta ctactacggtatggacgtctgggggccaagggaccacggtcaccgtctcctca | DNA sequence |
| 40. | QVQLQESGPGLVKPSETLSLTCTVSGGSISSYYWSWIRQPPGKGLEWIGYIYYSGIT HYNPSLKSRVTISVDTSKIQFSLKLSSVTAADTAVYYCARWGVRRDYYYYGMDVWG QGTTVTVSS | Amino Acid sequence |
| 41. | ggtggctccatcagtagttactac | DNA sequence |
| 42. | GGSISSYY | Amino Acid sequence |
| 43. | atctattacagtgggatcacc | DNA sequence |
| 44. | IYYSGIT | Amino Acid sequence |
| 45. | gcgagatggggggggttcggagggactactactactacggtatggacgtc | DNA sequence |
| 46. | ARWGVRRDYYYYGMDV | Amino Acid sequence |
| 47. | gaaatagttttgacacagagtcccggcacactgtcactctctcccggggaaagagccaccttgtcatgtagagcaagtc agtcagtctctagctcttatctcgcctggtaccagcagaagccgggacaggcccctagactgctgatctacggggcaa gttccagggccaccggaatccccgaccggttcagtggaagcggaagcggaaccgattttactttgacgatttctagact ggagccagaggatttcgccgtttactattgtcaacagtacggaagcagcccgtggacgtttggccagggcacgaaggt agaaatcaag | DNA sequence |
| 48. | EIVLTQSPGTLSLSPGERATLSCRASQSVSSSYLAWYQQKPGQAPRLLIYGASSRAT GIPDRFSGSGSGTDFTLTISRLEPEDFAVYYCQQYGSSPWTFGQGTKVEIK | Amino Acid sequence |
| 49. | cagtcagtctctagctcttat | DNA sequence |

TABLE 91-continued

Informal Sequence Listing

| SEQ ID NO. | SEQUENCE | Description |
|---|---|---|
| 50. | QSVSSSY | Amino Acid sequence |
| 51. | ggggcaagt | DNA sequence |
| 52. | GAS | Amino Acid sequence |
| 53. | caacagtacggaagcagcccgtggacg | DNA sequence |
| 54. | QQYGSSPWT | Amino Acid sequence |
| 55. | caggtgcagctggtgcagtctggggctgaagtgaagaagcctgggtcctcggtgaaggtctcctgtaaggcttctggag gcccccttcagaagttcttctttcagctgggtgcgacaggcccccaggacaagggcttgaatggatgggagggatcatccc tattttaggtaaaacaaactatgcacagaagttccagggcagaatcacgattgtcacggacgaatccacgaccacagt ctacatggaactgagcagcctgagatctgaggacacggccgtttttactgtgtgagaggcagctcgctctttgactattg gggccagggaaccctggtcaccgtctcctcagcctccaccaagggcccatcggtcttccccctggcgccctgctccag gagcacctccgagagcacagccgccctgggctgcctggtcaaggactacttccccgaaccggtgacggtgtcgtgga actcaggcgccctgaccagcggcgtgcacaccttcccggctgtcctacagtcctcaggactctactccctcagcagcgt ggtgaccgtgccctccagcagcttgggcacgaagacctacacctgcaacgtagatcacaagcccagcaacaccaa ggtggacaagagagttgagtccaaatatggtcccccatgcccaccgtgcccagcaccacctgtggcaggaccatca gtcttcctgttccccccaaaaaacccaaggacactctcatgatctcccggacccctgaggtcacgtgcgtggtggtggacgt gagccaggaagacccgaggtccagttcaactggtacgtggatggcgtggaggtgcataatgccaagacaaagcc gcgggaggagcagttcaacagcacgtaccgtgtggtcagcgtcctcaccgtcctgcaccaggactggctgaacggc aaggagtacaagtgcaaggtctccaacaaaggcctcccgtcctccatctccaaagccaaaggg cagccccgagagccacaggtgtacaccctgcccccatcccaggaggagatgaccaagaaccaggtcagcctgac ctgcctggtcaaaggcttctaccccagcgacatcgccgtggagtgggagagcaatgggcagccggagaacaactac aagaccacgcctcccgtgctggactccgacggctccttcttcctctacagcaggctcaccgtggacaagagcaggtgg caggaggggaatgtcttctcatgctccgtgatgcatgaggctctgcacaaccactacacacagaagtccctctccctgtc tctgggtaaatga | DNA sequence |
| 56. | QVQLVQSGAEVKKPGSSVKVSCKASGGPFRSSSFSWVRQAPGQGLEWMGGIIPIL GKTNYAQKFQGRITIVTDESTTTVYMELSSLRSEDTAVFYCVRGSSLFDYWGQGTLV TVSSASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPCPPC PAPPVAGPSVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLD SDGSFFLYSRLTVDKSRWQEGNVFSCSVMHEALHNHYTQKSLSLSLGK | Amino Acid sequence |
| 57. | caggtgcagctgcaggagtcgggcccaggactggtgaagccttcggagaccctgtccctcacctgcactgtctctggt ggctccatcagtagttactactggagctggatccggcagcccccagggaagggactggagtggattgggtatatctatt acagtgggatcacccactacaaccccctccctcaagagtcgagtcaccatatcagtagacacgtccaagatccagttct ccctgaagctgagttctgtgaccgctgcggacacggccgtgtattactgtgcgagatgggggggttcggagggactacta ctactacggtatggacgtctggggccaagggaccacggtcaccgtctcctcagcctctacaaagggccattctgtgtttc ctctggcctccttgttctagatctacatctgaatctacagctgctctgggatgtctctggtgaaggatcttattttcctgaacctg tgacagtgtcttggaattctggagctctgacatctggagtgcatacatttcctgctgtgctgcagtcttctggactgtatt ctctgtcttctgtggtgacagtgccttcttcttctctgggaacaaagacatatacatgtaatgtggatcataagccttcta atacaaaggtggataagagagtggaatctaagtatggacctccttgtcctccttgtcctgctcctcctgtggctggacctt ctgtgtttctgtttcctcctaaagcctaaggatacactgatgatctctagacacctgaagtgacatgtgtggtggtggatg tgtctcaggaagatcctgaagtgcagtttaattggtatgtggatggtgaggtggaagtgcataatgcctaagacaaagcctagag aagaacagtttaattctacatatagagtggtgtctgtgctgacagtgctgcatcaggattggctgaatggaaaggaatata agtgtaaggtgtctaataaggggactgccttcttctatcgaaaagacaatctctaaggctaagggacagcctagagaacctc aggtgtatacactgcctcccttctcaggaagaaatgacaaagaatcaggtgtctctgacatgtctggtgaagggatttttatc cttctgatatcgctgtggaatgggaatctaatggacagcctgaaaataattataagacaacacctcctgtgctggattctg atggatctttttttctgtattctagactgacagtggataagtctagatggcaggaaggaaatgtgtttttcttgttctgtga tgcatgaagctctgcataatagatttacacagaagtctctgtctctgtctcctggaaagtag | DNA sequence |
| 58. | QVQLQESGPGLVKPSETLSLTCTVSGGSISSYYWSWIRQPPGKGLEWIGYIYYSGIT HYNPSLKSRVTISVDTSKIQFSLKLSSVTAADTAVYYCARWGVRRDYYYGMDVWG QGTTVTVSSASTKGPSVFPLAPCSRSTSESTAALGCLVKDYFPEPVTVSWNSGALT SGVHTFPAVLQSSGLYSLSSVVTVPSSSLGTKTYTCNVDHKPSNTKVDKRVESKYG PPCPPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIEKTIS KAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNRFTQKSLSLSPGK | Amino Acid sequence |
| 59. | gaaatagttttgacacagagtcccggcacactgtcactctctcccggggaaagagccacccttgtcatgtagagcaagtc agtcagtctctagctcttatctcgcctggtaccagcagaagccgggacaggcccctagactgctgatctacggggcaa gttccaggccaccggaatccccgaccggttcagtggaagcggaagcggaaccgattttacttttgacgatttctagact ggagccagaggatttcgccgtttactattgtcaacagtacggaagcagcccgtggacgtttggccagggcacgaaggt | DNA sequence |

TABLE 91-continued

Informal Sequence Listing

| SEQ ID NO. | SEQUENCE | Description |
|---|---|---|
| | agaaatcaagcgaactgtggctgcaccatctgtcttcatcttcccgccatctgatgagcagttgaaatctggaactgcctc<br>tgttgtgtgcctgctgaataacttctatcccagagaggccaaagtacagtggaaggtggataacgccctccaatcgggt<br>aactcccaggagagtgtcacagagcaggacagcaaggacagcacctacagcctcagcagcaccctgacgctgag<br>caaagcagactacgagaaacacaaagtctacgcctgcgaagtcacccatcagggcctgagctcgcccgtcacaaa<br>gagcttcaacaggggggagagtgttag | |
| 60. | EIVLTQSPGTLSLSPGERATLSCRASQSVSSSYLAWYQQKPGQAPRLLIYGASSRAT<br>GIPDRFSGSGSGTDFTLTISRLEPEDFAVYYCQQYGSSPWTFGQGTKVEIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC | Amino Acid sequence |
| 61. | NKILVKQSPMLVAYDNAVNLSCKYSYNLFSREFRASLHKGLDSAVEVCVVYGNYSQ<br>QLQVYSKTGFNCDGKLGNESVTFYLQNLYVNQTDIYFCKIEVMYPPPYLDNEKSNGT<br>IIHVKGKHLCPSPLFPGPSKPEPRGPTIKPCPPCKCPAPNLLGGPSVFIFPPKIKDVLM<br>ISLSPIVTCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKKQVTLT<br>CMVTDFMPEDIYVEWTNNGKTELNYKNTEPVLDSDGSYFMYSKLRVEKKNWVERN<br>SYSCSVVHEGLHNHHTTKSFSRTPGK | Amino Acid sequence |
| 62. | VPRWRQQWSGPGTTKRFPETVLARCVKYTEIHPEMRHVDCQSVWDAFKGAFISKH<br>PCNITEEDYQPLMKLGTQTVPCNKILLWSRIKDLAHQFTQVQRDMFTLEDTLLGYLA<br>DDLTWCGEFNTSKINYQSCPDWRKDCSNNPVSVFWKTVSRRFAEAACDVVHVMLN<br>GSRSKIFDKNSTFGSVEVHNLQPEKVQTLEAWVIHGGREDSRDLCQDPTIKELESIIS<br>KRNIQFSCKNIYRPDKFLQCVKNPEDSSCTSEIEPRGPTIKPCPPCKCPAPNLLGGPS<br>VFIFPPKIKDVLMISLSPIVTCVVVDVSEDDPDVQISWFVNNVEVHTAQTQTHREDYN<br>STLRVVSALPIQHQDWMSGKEFKCKVNNKDLPAPIERTISKPKGSVRAPQVYVLPPP<br>EEEMTKKQVTLTCMVTDFMPEDIYVEWTNNGKTELNYKNTEPVLDSDGSYFMYSKL<br>RVEKKNWVERNSYSCSVVHEGLHNHHTTKSFSRTPGK | Amino Acid sequence |
| 63. | MLRLLLALNLFPSIQVTGNKILVKQSPMLVAYDNAVNLSCKYSYNLFSREFRASLHKG<br>LDSAVEVCVVYGNYSQQLQVYSKTGFNCDGKLGNESVTFYLQNLYVNQTDIYFCKIE<br>VMYPPPYLDNEKSNGTIIHVKGKHLCPSPLFPGPSKPFWVLVVVGGVLACYSLLVTV<br>AFIIFWVRSKRSRLLHSDYMNMTPRRPGPTRKHYQPYAPPRDFAAYRS | Amino Acid sequence |

What it claimed is:

1. A nucleic acid molecule comprising a polynucleotide sequence that encodes a heavy chain variable region (HCVR) and/or a polynucleotide sequence that encodes a light chain variable region (LCVR) of an isolated antibody or antigen-binding fragment thereof that binds to human CD38, wherein the antibody or antigen-binding fragment thereof comprises:

(a) three heavy chain complementarity determining regions (CDRs) (HCDR1, HCDR2 and HCDR3) contained within the HCVR amino acid sequence set forth in SEQ ID NO: 2; and three light chain CDRs (LCDR1, LCDR2 and LCDR3) contained within the LCVR amino acid sequence set forth in SEQ ID NO: 18; or (b) three heavy chain CDRs (HCDR1, HCDR2, and HCDR3) contained within the HCVR amino acid sequence set forth in SEQ ID NO: 32 and three light chain CDRs (LCDR1, LCDR2, and LCDR3) contained within the LCVR amino acid sequence set forth in SEQ ID NO: 48.

2. The nucleic acid molecule of claim 1 comprising:

a polynucleotide sequence that encodes an HCVR comprising an HCDR1 comprising the amino acid sequence of SEQ ID NO: 4; an HCDR2 comprising the amino acid sequence of SEQ ID NO: 6; and an HCDR3 comprising the amino acid sequence of SEQ ID NO: 8; or a polynucleotide sequence that encodes an HCVR comprising an HCDR1 comprising the amino acid sequence of SEQ ID NO: 34; an HCDR2 comprising the amino acid sequence of SEQ ID NO: 36; and an HCDR3 comprising the amino acid sequence of SEQ ID NO: 38.

3. The nucleic acid molecule of claim 2, wherein the polynucleotide encodes an HCVR comprising the amino acid sequence of SEQ ID NO: 2.

4. The nucleic acid molecule of claim 3 comprising a nucleotide sequence as set forth in SEQ ID NO: 1 or a substantially identical sequence having at least 95% homology thereto.

5. The nucleic acid molecule of claim 3, wherein the polynucleotide encodes a heavy chain comprising the amino acid sequence of SEQ ID NO: 26.

6. The nucleic acid molecule of claim 5 comprising a nucleotide sequence as set forth in SEQ ID NO: 25 or a substantially identical sequence having at least 95% homology thereto.

7. The nucleic acid molecule of claim 2, wherein the polynucleotide encodes an HCVR comprising the amino acid sequence of SEQ ID NO: 32.

8. The nucleic acid molecule of claim 7 comprising a nucleotide sequence as set forth in SEQ ID NO: 31 or a substantially identical sequence having at least 95% homology thereto.

9. The nucleic acid molecule of claim 2, wherein the polynucleotide encodes a heavy chain comprising the amino acid sequence of SEQ ID NO: 56.

10. The nucleic acid molecule of claim 9 comprising a nucleotide sequence as set forth in SEQ ID NO: 55 or a substantially identical sequence having at least 95% homology thereto.

11. The nucleic acid molecule of claim 1 comprising:

a polynucleotide sequence that encodes an LCVR comprising an LCDR1 comprising the amino acid sequence of SEQ ID NO: 20; an LCDR2 comprising the amino acid sequence of AAS; and an LCDR3 comprising the amino acid sequence of SEQ ID NO: 24; or a polynucleotide sequence that encodes an LCVR comprising an LCDR1 comprising the amino acid sequence of SEQ ID NO: 50; an LCDR2 comprising the amino acid sequence of GAS; and an LCDR3 comprising the amino acid sequence of SEQ ID NO: 54.

12. The nucleic acid molecule of claim 11, wherein the polynucleotide encodes an LCVR comprising the amino acid sequence of SEQ ID NO: 18.

13. The nucleic acid molecule of claim 12 comprising a nucleotide sequence as set forth in SEQ ID NO: 17 or a substantially identical sequence having at least 95% homology thereto.

14. The nucleic acid molecule of claim 12, wherein the polynucleotide encodes a light chain comprising the amino acid sequence of SEQ ID NO: 30.

15. The nucleic acid molecule of claim 14 comprising a nucleotide sequence as set forth in SEQ ID NO: 29 or a substantially identical sequence having at least 95% homology thereto.

16. The nucleic acid molecule of claim 11, wherein the polynucleotide encodes an LCVR comprising the amino acid sequence of SEQ ID NO: 48.

17. The nucleic acid molecule of claim 16 comprising a nucleotide sequence as set forth in SEQ ID NO: 47 or a substantially identical sequence having at least 95% homology thereto.

18. The nucleic acid molecule of claim 16, wherein the polynucleotide encodes a light chain comprising the amino acid sequence of SEQ ID NO: 60.

19. The nucleic acid molecule of claim 18 comprising a nucleotide sequence as set forth in SEQ ID NO: 59 or a substantially identical sequence having at least 95% homology thereto.

20. The nucleic acid molecule of claim 1 comprising a polynucleotide sequence that encodes (i) an HCVR comprising an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8; and (ii) an LCVR comprising an LCDR1 comprising the amino acid sequence of SEQ ID NO: 20, an LCDR2 comprising the amino acid sequence of AAS, and an LCDR3 comprising the amino acid sequence of SEQ ID NO: 24.

21. The nucleic acid molecule of claim 1 comprising a polynucleotide sequence that encodes (i) an HCVR comprising an HCDR1 comprising the amino acid sequence of SEQ ID NO: 34, an HCDR2 comprising the amino acid sequence of SEQ ID NO: 36, and an HCDR3 comprising the amino acid sequence of SEQ ID NO: 38; and (ii) an LCVR comprising an LCDR 1 comprising the amino acid sequence of SEQ ID NO: 50, an LCDR2 comprising the amino acid sequence of GAS, and an LCDR3 comprising the amino acid sequence of SEQ ID NO: 54.

22. A composition comprising a first nucleic acid molecule and a second nucleic acid molecule, wherein:

a) the first nucleic acid molecule comprises a polynucleotide sequence encoding an HCVR of an isolated antibody or antigen-binding fragment thereof that binds to human CD38, wherein the HCVR comprises an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8; and the second nucleic acid molecule comprises a polynucleotide sequence encoding an LCVR of the antibody or antigen-binding fragment thereof that binds to human CD38, wherein the LCVR comprises an LCDR1 comprising the amino acid sequence of SEQ ID NO: 20, an LCDR2 comprising the amino acid sequence of AAS, and an LCDR3 comprising the amino acid sequence of SEQ ID NO: 24; or b) the first nucleic acid molecule comprises a polynucleotide sequence encoding an HCVR of an isolated antibody or antigen-binding fragment thereof that binds to human CD38, wherein the HCVR comprises an HCDR1 comprising the amino acid sequence of SEQ ID NO: 34, an HCDR2 comprising the amino acid sequence of SEQ ID NO: 36, and an HCDR3 comprising the amino acid sequence of SEQ ID NO: 38; and the second nucleic acid molecule comprises a polynucleotide sequence encoding an LCVR of the antibody or antigen-binding fragment thereof that binds to human CD38, wherein the LCVR comprises an LCDR1 comprising the amino acid sequence of SEQ ID NO: 50, an LCDR2 comprising the amino acid sequence of GAS, and an LCDR3 comprising the amino acid sequence of SEQ ID NO: 54.

23. An expression vector comprising the nucleic acid molecule of claim 1.

24. An isolated host cell comprising the expression vector of claim 23.

25. A method of producing an anti-CD38 antibody or antigen-binding fragment thereof, the method comprising growing the host cell of claim 24 under conditions permitting production of the antibody or antigen-binding fragment thereof, and optionally recovering the antibody or antigen-binding fragment thereof so produced.

26. A set of expression vectors comprising a first expression vector, a second expression vector, and a third expression vector, wherein:

the first expression vector comprises a polynucleotide sequence encoding a first HCVR of a bispecific antigen binding molecule comprising an HCDR1 comprising the amino acid sequence of SEQ ID NO: 4, an HCDR2 comprising the amino acid sequence of SEQ ID NO: 6, and an HCDR3 comprising the amino acid sequence of SEQ ID NO: 8;

the second expression vector comprises a polynucleotide sequence encoding a second HCVR of the bispecific antigen binding molecule comprising an HCDR1 comprising the amino acid sequence of SEQ ID NO: 12, an HCDR2 comprising the amino acid sequence of SEQ ID NO: 14, and an HCDR3 comprising the amino acid sequence of SEQ ID NO: 16; and the third expression vector comprises a polynucleotide sequence encoding an LCVR of the bispecific antigen binding molecule comprising an LCDR1 comprising the amino acid sequence of SEQ ID NO: 20, an LCDR2 comprising the amino acid sequence of AAS, and an LCDR3 comprising the amino acid sequence of SEQ ID NO: 24.

27. The set of expression vectors of claim 26, wherein:

the first expression vector comprises a polynucleotide sequence encoding the first HCVR of the bispecific antigen binding molecule, wherein the HCVR comprises the amino acid sequence of SEQ ID NO: 2; and the second expression vector comprises a polynucleotide sequence encoding the second HCVR of the bispecific antigen binding molecule, wherein the HCVR comprises the amino acid sequence of SEQ ID NO: 10.

28. The set of expression vectors of claim 26, wherein the third expression vector comprises a polynucleotide sequence encoding an LCVR of the bispecific antigen binding molecule, wherein the LCVR comprises the amino acid sequence of SEQ ID NO: 18.

29. An isolated host cell comprising the set of expression vectors of claim 26.

30. A method of producing a bispecific antibody or antigen binding molecule that specifically binds human CD38 and human CD28, the method comprising growing the host cell of claim 29 under conditions permitting production of the antibody or antigen-binding molecule, and optionally recovering the antibody or antigen-binding molecule so produced.

31. A set of expression vectors comprising a first expression vector, a second expression vector, and a third expression vector, wherein:

the first expression vector comprises a polynucleotide sequence encoding a first HCVR of a bispecific antigen binding molecule comprising an HCDR1 comprising the amino acid sequence of SEQ ID NO: 34, an HCDR2 comprising the amino acid sequence of SEQ ID NO: 36, and an HCDR3 comprising the amino acid sequence of SEQ ID NO: 38;

the second expression vector comprises a polynucleotide sequence encoding a second HCVR of the bispecific antigen binding molecule comprising an HCDR1 comprising the amino acid sequence of SEQ ID NO: 42, an HCDR2 comprising the amino acid sequence of SEQ ID NO: 44, and an HCDR3 comprising the amino acid sequence of SEQ ID NO: 46; and the third expression vector comprises a polynucleotide sequence encoding an LCVR of the bispecific antigen binding molecule comprising an LCDR1 comprising the amino acid sequence of SEQ ID NO: 50, an LCDR2 comprising the amino acid sequence of GAS, and an LCDR3 comprising the amino acid sequence of SEQ ID NO: 54.

32. The set of expression vectors of claim 31, wherein:

the first expression vector comprises a polynucleotide sequence encoding the first HCVR of the bispecific antigen binding molecule, wherein the HCVR comprises the amino acid sequence of SEQ ID NO: 32; and the second expression vector comprises a polynucleotide sequence encoding the second HCVR of the bispecific antigen binding molecule, wherein the HCVR comprises the amino acid sequence of SEQ ID NO: 40.

33. The set of expression vectors of claim 31, wherein:

the third expression vector comprises a polynucleotide sequence encoding an LCVR of the bispecific antigen binding molecule, wherein the LCVR comprises the amino acid sequence of SEQ ID NO: 48.

34. An isolated host cell comprising the set of expression vectors of claim 31.

35. A method of producing a bispecific antibody or antigen binding molecule that specifically binds human CD38 and human CD28, the method comprising growing the host cell of claim 34 under conditions permitting production of the antibody or antigen-binding molecule, and optionally recovering the antibody or antigen-binding molecule so produced.

* * * * *

SEQUENCE LISTING

Sequence total quantity: 63
SEQ ID NO: 1              moltype = DNA   length = 372
FEATURE                   Location/Qualifiers
misc_feature              1..372
                          note = Synthetic
source                    1..372
                          mol_type = other DNA
                          organism = synthetic construct
SEQUENCE: 1
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagtggta aaagtgataa cataggctat   180
gcggactctg tgaagggccg attcaccatt tccagagaca acgccaagaa ctccctgtat   240
ctgcaaatga acagtctgag agctgaggac acggccttgt attactgtgc aaaagccctt   300
gggggctgga agttcgacta ctattacggt atggacgttt ggggccaagg gaccacggtc   360
accgtctcct ca                                                       372

SEQ ID NO: 2              moltype = AA   length = 124
FEATURE                   Location/Qualifiers
REGION                    1..124
                          note = Synthetic
source                    1..124
                          mol_type = protein
                          organism = synthetic construct
SEQUENCE: 2
EVQLVESGGG LVQPGRSLRL SCAASGFTFD DYAMHWVRQA PGKGLEWVSG ISWKSDNIGY    60
ADSVKGRFTI SRDNAKNSLY LQMNSLRAED TALYYCAKAL GGWKFDYYYG MDVWGQGTTV   120
TVSS                                                                124

SEQ ID NO: 3              moltype = DNA   length = 24
FEATURE                   Location/Qualifiers
misc_feature              1..24
                          note = Synthetic -continued

```
source                      1..24
                            mol_type = other DNA
                            organism = synthetic construct
SEQUENCE: 3
ggattcacct ttgatgatta tgcc                                              24

SEQ ID NO: 4       moltype = AA   length = 8
FEATURE            Location/Qualifiers
REGION             1..8
                   note = Synthetic
source             1..8
                   mol_type = protein
                   organism = synthetic construct
SEQUENCE: 4
GFTFDDYA                                                                8

SEQ ID NO: 5       moltype = DNA   length = 24
FEATURE            Location/Qualifiers
misc_feature       1..24
                   note = Synthetic
source             1..24
                   mol_type = other DNA
                   organism = synthetic construct
SEQUENCE: 5
attagttgga aaagtgataa cata                                              24

SEQ ID NO: 6       moltype = AA   length = 8
FEATURE            Location/Qualifiers
REGION             1..8
                   note = Synthetic
source             1..8
                   mol_type = protein
                   organism = synthetic construct
SEQUENCE: 6
ISWKSDNI                                                                8

SEQ ID NO: 7       moltype = DNA   length = 51
FEATURE            Location/Qualifiers
misc_feature       1..51
                   note = Synthetic
source             1..51
                   mol_type = other DNA
                   organism = synthetic construct
SEQUENCE: 7
gcaaaagccc ttgggggctg gaagttcgac tactattacg gtatggacgt t               51

SEQ ID NO: 8       moltype = AA   length = 17
FEATURE            Location/Qualifiers
REGION             1..17
                   note = Synthetic
source             1..17
                   mol_type = protein
                   organism = synthetic construct
SEQUENCE: 8
AKALGGWKFD YYYGMDV                                                      17

SEQ ID NO: 9       moltype = DNA   length = 354
FEATURE            Location/Qualifiers
misc_feature       1..354
                   note = Synthetic
source             1..354
                   mol_type = other DNA
                   organism = synthetic construct
SEQUENCE: 9
gaggtgcagc tggtggagtc tggggggaggc ttggtccagc ctggggggtc cctgagactc   60
tcctgtgcag cctccggatt caccttcagt aggaataata tgcactgggt ccgccaggct  120
ccagggaagg gactggaata tgtttcaggt attagtagta tgggggtcg cacatattat  180
gcagactctg tgaagggcag attcaccatc tccagagaca attccaagaa cacgctgtat  240
cttcaaatgg gcggcctgag agctgcggac atggctgtgt atttctgtac gagagatgac  300
gagctgcttt cctttgacta ctggggccag ggaaccctgg tcactgtctc ctca         354

SEQ ID NO: 10      moltype = AA   length = 118
FEATURE            Location/Qualifiers
REGION             1..118
                   note = Synthetic
source             1..118
                   mol_type = protein
                   organism = synthetic construct
SEQUENCE: 10
```

-continued

```
EVQLVESGGG LVQPGGSLRL SCAASGFTFS RNNMHWVRQA PGKGLEYVSG ISSNGGRTYY  60
ADSVKGRFTI SRDNSKNTLY LQMGGLRAAD MAVYFCTRDD ELLSFDYWGQ GTLVTVSS    118

SEQ ID NO: 11          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 11
ggattcacct tcagtaggaa taat                                         24

SEQ ID NO: 12          moltype = AA  length = 8
FEATURE                Location/Qualifiers
REGION                 1..8
                       note = Synthetic
source                 1..8
                       mol_type = protein
                       organism = synthetic construct
SEQUENCE: 12
GFTFSRNN                                                           8

SEQ ID NO: 13          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 13
attagtagta atgggggtcg caca                                         24

SEQ ID NO: 14          moltype = AA  length = 8
FEATURE                Location/Qualifiers
REGION                 1..8
                       note = Synthetic
source                 1..8
                       mol_type = protein
                       organism = synthetic construct
SEQUENCE: 14
ISSNGGRT                                                           8

SEQ ID NO: 15          moltype = DNA  length = 33
FEATURE                Location/Qualifiers
misc_feature           1..33
                       note = Synthetic
source                 1..33
                       mol_type = other DNA
                       organism = synthetic construct
SEQUENCE: 15
acgagagatg acgagctgct ttcctttgac tac                               33

SEQ ID NO: 16          moltype = AA  length = 11
FEATURE                Location/Qualifiers
REGION                 1..11
                       note = Synthetic
source                 1..11
                       mol_type = protein
                       organism = synthetic construct
SEQUENCE: 16
TRDDELLSFD Y                                                       11

SEQ ID NO: 17          moltype = DNA  length = 324
FEATURE                Location/Qualifiers
misc_feature           1..324
                       note = Synthetic
source                 1..324
                       mol_type = other DNA
                       organism = synthetic construct
SEQUENCE: 17
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 18          moltype = AA  length = 108
```

-continued

```
FEATURE                Location/Qualifiers
REGION                 1..108
                       note = Synthetic
source                 1..108
                       mol_type = protein
                       organism = synthetic construct
SEQUENCE: 18
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 19          moltype = DNA   length = 18
FEATURE                Location/Qualifiers
misc_feature           1..18
                       note = Synthetic
source                 1..18
                       mol_type = other DNA
                       organism = synthetic construct
SEQUENCE: 19
cagagcatta gcagctat                                               18

SEQ ID NO: 20          moltype = AA   length = 6
FEATURE                Location/Qualifiers
REGION                 1..6
                       note = Synthetic
source                 1..6
                       mol_type = protein
                       organism = synthetic construct
SEQUENCE: 20
QSISSY                                                            6

SEQ ID NO: 21          moltype =    length =
SEQUENCE: 21
000

SEQ ID NO: 22          moltype =    length =
SEQUENCE: 22
000

SEQ ID NO: 23          moltype = DNA   length = 30
FEATURE                Location/Qualifiers
misc_feature           1..30
                       note = Synthetic
source                 1..30
                       mol_type = other DNA
                       organism = synthetic construct
SEQUENCE: 23
caacagagtt acagtacccc tccgatcacc                                  30

SEQ ID NO: 24          moltype = AA   length = 10
FEATURE                Location/Qualifiers
REGION                 1..10
                       note = Synthetic
source                 1..10
                       mol_type = protein
                       organism = synthetic construct
SEQUENCE: 24
QQSYSTPPIT                                                        10

SEQ ID NO: 25          moltype = DNA   length = 1353
FEATURE                Location/Qualifiers
misc_feature           1..1353
                       note = Synthetic
source                 1..1353
                       mol_type = other DNA
                       organism = synthetic construct
SEQUENCE: 25
gaagtgcagc tggtggagtc tggggggaggc ttggtacagc ctggcaggtc cctgagactc  60
tcctgtgcag cctctggatt caccttttgat gattatgcca tgcactgggt ccggcaagct  120
ccagggaagg gcctggagtg ggtctcaggt attagttgga aaagtgataa cataggctat  180
gcggactctg tgaagggccg attcaccatt tccagagaca acgccaagaa ctccctgtat  240
ctgcaaatga acagtctgag agctgaggac acggccttgt attactgtgc aaaagccctt  300
gggggctgga agttcgacta ctattacggt atggacgttt ggggccaagg gaccacggtc  360
accgtctcct cagcctccac caagggccca tcggtcttcc cctggcgcc ctgctccagg  420
agcacctccg agagcacagc cgccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacgaaga cctacacctg caacgtagat cacaagccca gcaacaccaa ggtggacaag  660
agagttgagt ccaaatatgg tcccccatgc ccaccgtgcc cagcaccacc tgtggcagga  720
ccatcagtct tcctgttccc cccaaaaccc aaggacactc tcatgatctc ccggacccct  780
```

-continued

```
gaggtcacgt gcgtggtggt ggacgtgagc caggaagacc ccgaggtcca gttcaactgg   840
tacgtggatg gcgtggaggt gcataatgcc aagacaaagc cgcggggagga gcagttcaac   900
agcacgtacc gtgtggtcag cgtcctcacc gtcctgcacc aggactggct gaacggcaag   960
gagtacaagt gcaaggtctc caacaaaggc ctcccgtcct ccatcgagaa aaccatctcc  1020
aaagccaaag ggcagccccg agagccacag gtgtacacac tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctca ccgtggacaa gagcaggtgg  1260
caggagggga atgtcttctc atgctccgtg atgcatgagg ctctgcacaa ccactacaca  1320
cagaagtccc tctccctgtc tctgggtaaa tga                               1353
```

```
SEQ ID NO: 26              moltype = AA   length = 450
FEATURE                    Location/Qualifiers
REGION                     1..450
                           note = Synthetic
source                     1..450
                           mol_type = protein
                           organism = synthetic construct
SEQUENCE: 26
EVQLVESGGG LVQPGRSLRL SCAASGFTFD DYAMHWVRQA PGKGLEWVSG ISWKSDNIGY   60
ADSVKGRFTI SRDNAKNSLY LQMNSLRAED TALYYCAKAL GGWKFDYYYG MDVWGQGTTV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPPVAG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                                   450
```

```
SEQ ID NO: 27              moltype = DNA   length = 1335
FEATURE                    Location/Qualifiers
misc_feature               1..1335
                           note = Synthetic
source                     1..1335
                           mol_type = other DNA
                           organism = synthetic construct
SEQUENCE: 27
gaggtgcagc tggtggagtc tgggggaggc ttggtccagc ctggggggtc cctgagactc   60
tcctgtgcag cctccggatt caccttcagt aggaataata tgcactgggt ccgccaggct  120
ccaggggaagg gactggaata tgtttcaggt attagtagta atggggggtcg cacatattat  180
gcagactctg tgaagggcag attcaccatc tccagagaca attccaagaa cacgctgtat  240
cttcaaatgg cgcgcctgag agctgcggac atggctgtgt atttctgtac gagagatgac  300
gagctgcttt cctttgacta ctggggccag ggaaccctgg tcactgtctc ctcagcctct  360
acaaagggac cttctgtgtt tcctctggct ccttgttcta gatctacatc tgaatctaca  420
gctgctctgg gatgtctggt gaaggattat tttcctgaac ctgtgacagt gtcttggaat  480
tctgagctc tgacatctgg agtgcataca tttcctgctg tgctgcagtc ttctggactg  540
tattctctgt cttctgtggt gacagtgcct tcttcttctc tgggaacaaa gacatataca  600
tgtaatgtgg atcataagcc ttctaataca aaggtgataa agagagtgga atctaagtat  660
ggacctcctt gtcctccttg tcctgctcct cctgtggctg gaccttctgt gtttctgttt  720
cctcctaagc ctaaggatac actgatgatc tctagaacac ctgaagtgac atgtgtggtg  780
gtggatgtgt ctcaggaaga tcctgaagtg cagtttaatt ggtatgtgga tggagtggaa  840
gtgcataatg ctaagacaaa gcctagagaa gaacagttta attctacata tagagtggtg  900
tctgtgctga cagtgctgca tcaggattgg ctgaatggaa aggaaatataa gtgtaaggtg  960
tctaataagg gactgccttc ttctatcgaa aagacaatct ctaaggctaa gggacagcct  1020
agagaacctc aggtgtatac actgcctcct tctcaggaag aaatgacaaa gaatcaggtg  1080
tctctgacat gtctggtgaa gggatttat ccttctgata tcgctgtgga tgggaatct  1140
aatggacagc ctgaaaataa ttataagaca cacctcctg tgctggattc tgatggatct  1200
tttttctgt attctagact gacagtggat aagtctagat ggcaggaagg aaatgtgttt  1260
tcttgttctg tgatgcatga agctctgcat aatagattta cacagaagtc tctgtctctg  1320
tctcctggaa agtag                                                   1335
```

```
SEQ ID NO: 28              moltype = AA   length = 444
FEATURE                    Location/Qualifiers
REGION                     1..444
                           note = Synthetic
source                     1..444
                           mol_type = protein
                           organism = synthetic construct
SEQUENCE: 28
EVQLVESGGG LVQPGGSLRL SCAASGFTFS RNNMHWVRQA PGKGLEYVSG ISSNGGRTYY   60
ADSVKGRFTI SRDNSKNTLY LQMGGLRAAD MAVYFCTRDD ELLSFDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP PVAGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NRFTQKSLSL SPGK                                         444
```

```
SEQ ID NO: 29              moltype = DNA   length = 648
FEATURE                    Location/Qualifiers
```

-continued

```
misc_feature             1..648
                         note = Synthetic
source                   1..648
                         mol_type = other DNA
                         organism = synthetic construct
SEQUENCE: 29
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 30          moltype = AA   length = 215
FEATURE                Location/Qualifiers
REGION                 1..215
                       note = Synthetic
source                 1..215
                       mol_type = protein
                       organism = synthetic construct
SEQUENCE: 30
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 31          moltype = DNA   length = 348
FEATURE                Location/Qualifiers
misc_feature           1..348
                       note = Synthetic
source                 1..348
                       mol_type = other DNA
                       organism = synthetic construct
SEQUENCE: 31
caggtgcagc tggtgcagtc tggggctgaa gtgaagaagc ctgggtcctc ggtgaaggtc   60
tcctgtaagg cttctggagg ccccttcaga agttcttctt tcagctgggt gcgacaggcc  120
ccaggacaag ggcttgaatg gatgggaggg atcatcccta tttttaggta a aacaaactat  180
gcacagaagt tccagggcag aatcacgatt gtcacgaacg aatccagtca cacagtcac  240
atggaactga gcagcctgag atctgaggac acggccgttt tttactgtgt gagaggcagc  300
tcgctctttg actattgggg ccagggaacc ctggtcaccg tctcctca            348

SEQ ID NO: 32          moltype = AA   length = 116
FEATURE                Location/Qualifiers
REGION                 1..116
                       note = Synthetic
source                 1..116
                       mol_type = protein
                       organism = synthetic construct
SEQUENCE: 32
QVQLVQSGAE VKKPGSSVKV SCKASGGPFR SSSFSWVRQA PGQGLEWMGG IIPILGKTNY   60
AQKFQGRITI VTDESTTTVY MELSSLRSED TAVFYCVRGS SLFDYWGQGT LVTVSS      116

SEQ ID NO: 33          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 33
ggaggcccct tcagaagttc ttct                                         24

SEQ ID NO: 34          moltype = AA   length = 8
FEATURE                Location/Qualifiers
REGION                 1..8
                       note = Synthetic
source                 1..8
                       mol_type = protein
                       organism = synthetic construct
SEQUENCE: 34
GGPFRSSS                                                            8

SEQ ID NO: 35          moltype = DNA   length = 24
FEATURE                Location/Qualifiers
```

-continued

```
misc_feature          1..24
                      note = Synthetic
source                1..24
                      mol_type = other DNA
                      organism = synthetic construct
SEQUENCE: 35
atcatcccta ttttaggtaa aaca                                              24

SEQ ID NO: 36          moltype = AA   length = 8
FEATURE                Location/Qualifiers
REGION                 1..8
                       note = Synthetic
source                 1..8
                       mol_type = protein
                       organism = synthetic construct
SEQUENCE: 36
IIPILGKT                                                                8

SEQ ID NO: 37          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 37
gtgagaggca gctcgctctt tgactat                                           27

SEQ ID NO: 38          moltype = AA   length = 9
FEATURE                Location/Qualifiers
REGION                 1..9
                       note = Synthetic
source                 1..9
                       mol_type = protein
                       organism = synthetic construct
SEQUENCE: 38
VRGSSLFDY                                                               9

SEQ ID NO: 39          moltype = DNA   length = 366
FEATURE                Location/Qualifiers
misc_feature           1..366
                       note = Synthetic
source                 1..366
                       mol_type = other DNA
                       organism = synthetic construct
SEQUENCE: 39
caggtgcagc tgcaggagtc gggcccagga ctggtgaagc cttcggagac cctgtccctc      60
acctgcactg tctctggtgg ctccatcagt agttactact ggagctggat ccggcagccc      120
ccagggaagg gactggagtg gattgggtat atctattaca gtgggatcac ccactacaac      180
ccctccctca agagtcgagt caccatatca gtagacacgt ccaagatcca gttctccctg      240
aagctgagtt ctgtgaccgc tgcggacacg gccgtgtatt actgtgcgag atggggggtt      300
cggagggact actactacta cggtatggac gtctggggc aagggaccac ggtcaccgtc      360
tcctca                                                                 366

SEQ ID NO: 40          moltype = AA   length = 122
FEATURE                Location/Qualifiers
REGION                 1..122
                       note = Synthetic
source                 1..122
                       mol_type = protein
                       organism = synthetic construct
SEQUENCE: 40
QVQLQESGPG LVKPSETLSL TCTVSGGSIS SYYWSWIRQP PGKGLEWIGY IYYSGITHYN      60
PSLKSRVTIS VDTSKIQFSL KLSSVTAADT AVYYCARWGV RRDYYYYGMD VWGQGTTVTV      120
SS                                                                     122

SEQ ID NO: 41          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 41
ggtggctcca tcagtagtta ctac                                             24

SEQ ID NO: 42          moltype = AA   length = 8
FEATURE                Location/Qualifiers
REGION                 1..8
```

-continued

```
                            note = Synthetic
source                      1..8
                            mol_type = protein
                            organism = synthetic construct
SEQUENCE: 42
GGSISSYY                                                                           8

SEQ ID NO: 43               moltype = DNA  length = 21
FEATURE                     Location/Qualifiers
misc_feature                1..21
                            note = Synthetic
source                      1..21
                            mol_type = other DNA
                            organism = synthetic construct
SEQUENCE: 43
atctattaca gtgggatcac c                                                            21

SEQ ID NO: 44               moltype = AA  length = 7
FEATURE                     Location/Qualifiers
REGION                      1..7
                            note = Synthetic
source                      1..7
                            mol_type = protein
                            organism = synthetic construct
SEQUENCE: 44
IYYSGIT                                                                            7

SEQ ID NO: 45               moltype = DNA  length = 48
FEATURE                     Location/Qualifiers
misc_feature                1..48
                            note = Synthetic
source                      1..48
                            mol_type = other DNA
                            organism = synthetic construct
SEQUENCE: 45
gcgagatggg gggttcggag ggactactac tactacggta tggacgtc                              48

SEQ ID NO: 46               moltype = AA  length = 16
FEATURE                     Location/Qualifiers
REGION                      1..16
                            note = Synthetic
source                      1..16
                            mol_type = protein
                            organism = synthetic construct
SEQUENCE: 46
ARWGVRRDYY YYGMDV                                                                  16

SEQ ID NO: 47               moltype = DNA  length = 324
FEATURE                     Location/Qualifiers
misc_feature                1..324
                            note = Synthetic
source                      1..324
                            mol_type = other DNA
                            organism = synthetic construct
SEQUENCE: 47
gaaatagttt tgacacagag tcccggcaca ctgtcactct ctcccgggga aagagccacc   60
ttgtcatgta gagcaagtca gtcagtctct agctcttatc tcgcctggta ccagcagaag   120
ccgggacagg cccctagact gctgatctac ggggcaagtt ccagggccac cggaatcccc   180
gaccggttca gtgtgaagcgg aagcggaacc gattttactt tgacgatttc tagactggag   240
ccagaggatt tcgccgttta ctattgtcaa cagtacggaa gcagcccgtg gacgtttggc   300
cagggcacga aggtagaaat caag                                          324

SEQ ID NO: 48               moltype = AA  length = 108
FEATURE                     Location/Qualifiers
REGION                      1..108
                            note = Synthetic
source                      1..108
                            mol_type = protein
                            organism = synthetic construct
SEQUENCE: 48
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIK                 108

SEQ ID NO: 49               moltype = DNA  length = 21
FEATURE                     Location/Qualifiers
misc_feature                1..21
                            note = Synthetic
source                      1..21
                            mol_type = other DNA
```

```
                    organism = synthetic construct
SEQUENCE: 49
cagtcagtct ctagctctta t                                                 21

SEQ ID NO: 50            moltype = AA   length = 7
FEATURE                  Location/Qualifiers
REGION                   1..7
                         note = Synthetic
source                   1..7
                         mol_type = protein
                         organism = synthetic construct
SEQUENCE: 50
QSVSSSY                                                                  7

SEQ ID NO: 51            moltype =    length =
SEQUENCE: 51
000

SEQ ID NO: 52            moltype =    length =
SEQUENCE: 52
000

SEQ ID NO: 53            moltype = DNA   length = 27
FEATURE                  Location/Qualifiers
misc_feature             1..27
                         note = Synthetic
source                   1..27
                         mol_type = other DNA
                         organism = synthetic construct
SEQUENCE: 53
caacagtacg gaagcagccc gtggacg                                           27

SEQ ID NO: 54            moltype = AA   length = 9
FEATURE                  Location/Qualifiers
REGION                   1..9
                         note = Synthetic
source                   1..9
                         mol_type = protein
                         organism = synthetic construct
SEQUENCE: 54
QQYGSSPWT                                                                9

SEQ ID NO: 55            moltype = DNA   length = 1329
FEATURE                  Location/Qualifiers
misc_feature             1..1329
                         note = Synthetic
source                   1..1329
                         mol_type = other DNA
                         organism = synthetic construct
SEQUENCE: 55
caggtgcagc tggtgcagtc tgggggctgaa gtgaagaagc ctgggtcctc ggtgaaggtc   60
tcctgtaagg cttctggagg cccccttcaga agttcttctt tcagctgggt gcgacaggcc  120
ccaggacaag ggcttgaatg gatgggaggg atcatccctta ttttaggtaa aacaaactat  180
gcacagaagt tccagggcag aatcacgatt gtcacggacg aatccacgac cacagtctac  240
atggaactga gcagcctgag atctgaggac acggccgttt tttactgtgt gagaggcagc  300
tcgctctttg actattgggg ccagggaacc ctggtcaccg tctcctcagc ctccaccaag  360
ggcccatcgg tcttcccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca gcccagcaa caccaaggtg gacaagagag ttgagtccaa atatggtccc  660
ccatgcccac cgtgcccagc accacctgtg gcaggaccat cagtcttcct gttccccca  720
aaacccaagg acactctcat gatctcccgg accctgagg tcacgtgcgt ggtggtggac  780
gtgagccagg aagaccccga ggtccagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag 1020
ccacaggtgt acaccctgcc cccatcccag gaggagatga ccaagaacca ggtcagcctg 1080
acctgcctgg tcaaaggctt ctaccccagc gacatcgccg tggagtggga gagcaatggg 1140
cagccggaga acaactacaa gaccacgcct cccgtgctgg actccgacgg ctccttcttc 1200
ctctacagca ggctcaccgt ggacaagagc aggtggcagg aggggaatgt cttctcatgc 1260
tccgtgatgc atgaggctct gcacaaccac tacacacaga gtccctctc cctgtctctg 1320
ggtaaatga                                                            1329

SEQ ID NO: 56            moltype = AA   length = 442
FEATURE                  Location/Qualifiers
REGION                   1..442
                         note = Synthetic
source                   1..442
```

-continued

```
                        mol_type = protein
                        organism = synthetic construct
SEQUENCE: 56
QVQLVQSGAE VKKPGSSVKV SCKASGGPFR SSSFSWVRQA PGQGLEWMGG IIPILGKTNY   60
AQKFQGRITI VTDESTTTVY MELSSLRSED TAVFYCVRGS SLFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPPV AGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GK                                           442

SEQ ID NO: 57          moltype = DNA   length = 1347
FEATURE                Location/Qualifiers
misc_feature           1..1347
                       note = Synthetic
source                 1..1347
                       mol_type = other DNA
                       organism = synthetic construct SEQUENCE: 57
caggtgcagc tgcaggagtc gggcccagga ctggtgaagc cttcggagac cctgtccctc   60
acctgcactg tctctggtgg ctccatcagt agttactacc ggagctggat ccggcagccc  120
ccagggaagg gactggagtg gattgggtat atctattaca gtgggatcac ccactacaac  180
ccctccctca agagtcgagt caccatatca gtagacacgt ccaagatcca gttctccctg  240
aagctgagtt ctgtgaccgc tgcggacacg gccgtgtatt actgtgcgag atggggggtt  300
cggagggact actactacta cggtatggac gtctggggcc aagggaccac ggtcaccgtc  360
tcctcagcct ctacaaaggg accttctgtg tttcctctgg ctccttgttc tagatctaca  420
tctgaatcta cagctgctct gggatgtctg gtgaaggatt attttcctga acctgtgaca  480
gtgtcttgga attctggagc tctgacatct ggagtgcata catttcctgc tgtgctgcag  540
tcttctggac tgtattctct gtcttctgtg gtgacagtgc cttcttcttc tctgggaaca  600
aagacatata catgtaatgt ggatcataag ccttctaata caaaggtgga taagagagtg  660
gaatctaagt atggacctcc ttgtcctcct tgtcctgctc ctcctgtggc tggaccttct  720
gtgtttctgt ttcctcctaa gcctaaggat acactgatga tctctagaac acctgaagtg  780
acatgtgtgg tggtggatgt gtctcaggaa gatcctgaag tgcagtttaa ttggtatgtg  840
gatggagtgg aagtgcataa tgctaagaca aagcctagag aagaacagtt taattctaca  900
tatagagtgg tgtctgtgct gacagtgctg catcaggatt ggctgaatgg aaaggaatat  960
aagtgtaagg tgtctaataa gggactgcct tcttctatcg aaaagacaat ctctaaggct 1020
aagggacagc ctagagaacc tcaggtgtat acactgcctc cttctcagga gaaatgaca 1080
aagaatcagg tgtctctgac atgtctggtg aagggattt atccttctga tatcgctgtg 1140
gaatgggaat ctaatggaca gcctgaaaat aattataaga caacacctcc tgtgctggat 1200
tctgatggat ctttttttct gtattctaga ctgacagtgg ataagtctag atggcaggaa 1260
ggaaatgtgt tttcttgttc tgtgatgcat gaagctctgc ataatagatt tacacagaag 1320
tctctgtctc tgtctcctgg aaagtag                                    1347

SEQ ID NO: 58          moltype = AA   length = 448
FEATURE                Location/Qualifiers
REGION                 1..448
                       note = Synthetic
source                 1..448
                       mol_type = protein
                       organism = synthetic construct
SEQUENCE: 58
QVQLQESGPG LVKPSETLSL TCTVSGGSIS SYYWSWIRQP PGKGLEWIGY IYYSGITHYN   60
PSLKSRVTIS VDTSKIQFSL KLSSVTAADT AVYYCARWGV RRDYYYYGMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPPVAGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNRFTQK SLSLSPGK                                     448

SEQ ID NO: 59          moltype = DNA   length = 648
FEATURE                Location/Qualifiers
misc_feature           1..648
                       note = Synthetic
source                 1..648
                       mol_type = other DNA
                       organism = synthetic construct
SEQUENCE: 59
gaaatagttt tgacacagag tcccggcaca ctgtcactct ctcccgggga aagagccacc   60
ttgtcatgta gagcaagtca gtcagtctct agctcttatc tcgcctggta ccagcagaag  120
ccgggacagg cccctagact gctgatctac ggggcaagtt ccagggccac cggaatcccc  180
gaccggttca gtggaagcgg aagcggaacc gattttactt tgacgatttc tagactggag  240
ccagaggatt tcgccgttta ctattgtcaa cagtacggaa gcagcccgtg gacgtttggc  300
cagggcacga aggtagaaat caagcgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
```

-continued

```
ggcctgagct cgcccgtcac aaagagcttc aacaggggag agtgttag              648

SEQ ID NO: 60              moltype = AA  length = 215
FEATURE                    Location/Qualifiers
REGION                     1..215
                           note = Synthetic
source                     1..215
                           mol_type = protein
                           organism = synthetic construct
SEQUENCE: 60
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 61              moltype = AA  length = 367
FEATURE                    Location/Qualifiers
REGION                     1..367
                           note = Synthetic
source                     1..367
                           mol_type = protein
                           organism = synthetic construct
SEQUENCE: 61
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKPEPRGPT IKPCPPCKCP APNLLGGPSV FIFPPKIKDV LMISLSPIVT  180
CVVVDVSEDD PDVQISWFVN NVEVHTAQTQ THREDYNSTL RVVSALPIQH QDWMSGKEFK  240
CKVNNKDLPA PIERTISKPK GSVRAPQVYV LPPPEEEMTK KQVTLTCMVT DFMPEDIYVE  300
WTNNGKTELN YKNTEPVLDS DGSYFMYSKL RVEKKNWVER NSYSCSVVHE GLHNHHTTKS  360
FSRTPGK                                                           367

SEQ ID NO: 62              moltype = AA  length = 491
FEATURE                    Location/Qualifiers
REGION                     1..491
                           note = Synthetic
source                     1..491
                           mol_type = protein
                           organism = synthetic construct
SEQUENCE: 62
VPRWRQQWSG PGTTKRFPET VLARCVKYTE IHPEMRHVDC QSVWDAFKGA FISKHPCNIT   60
EEDYQPLMKL GTQTVPCNKI LLWSRIKDLA HQFTQVQRDM FTLEDTLLGY LADDLTWCGE  120
FNTSKINYQS CPDWRKDCSN NPVSVFWKTV SRRFAEAACD VVHVMLNGSR SKIFDKNSTF  180
GSVEVHNLQP EKVQTLEAWV IHGGREDSRD LCQDPTIKEL ESIISKRNIQ FSCKNIYRPD  240
KFLQCVKNPE DSSCTSEIEP RGPTIKPCPP CKCPAPNLLG GPSVFIFPPK IKDVLMISLS  300
PIVTCVVVDV SEDDPDVQIS WFVNNVEVHT AQTQTHREDY NSTLRVVSAL PIQHQDWMSG  360
KEFKCKVNNK DLPAPIERTI SKPKGSVRAP QVYVLPPPEE EMTKKQVTLT CMVTDFMPED  420
IYVEWTNNGK TELNYKNTEP VLDSDGSYFM YSKLRVEKKN WVERNSYSCS VVHEGLHNHH  480
TTKSFSRTPG K                                                      491

SEQ ID NO: 63              moltype = AA  length = 220
FEATURE                    Location/Qualifiers
REGION                     1..220
                           note = Synthetic
source                     1..220
                           mol_type = protein
                           organism = synthetic construct
SEQUENCE: 63
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220
```